United States Patent
Bounaud et al.

(10) Patent No.: US 8,507,489 B2
(45) Date of Patent: Aug. 13, 2013

(54) BICYCLIC TRIAZOLES AS PROTEIN KINASE MODULATORS

(75) Inventors: Pierre-Yves Bounaud, San Diego, CA (US); Christopher Ronald Smith, San Diego, CA (US); Elizabeth Anne Jefferson, La Jolla, CA (US)

(73) Assignee: SGX Pharmaceuticals, Inc., San Diego, CA (US)

( * ) Notice: Subject to any disclaimer, the term of this patent is extended or adjusted under 35 U.S.C. 154(b) by 631 days.

(21) Appl. No.: 12/442,566

(22) PCT Filed: Oct. 18, 2007

(86) PCT No.: PCT/US2007/081841
§ 371 (c)(1),
(2), (4) Date: Mar. 24, 2009

(87) PCT Pub. No.: WO2008/051808
PCT Pub. Date: May 2, 2008

(65) Prior Publication Data
US 2009/0258855 A1    Oct. 15, 2009

Related U.S. Application Data

(60) Provisional application No. 60/952,840, filed on Jul. 30, 2007, provisional application No. 60/913,766, filed on Apr. 24, 2007, provisional application No. 60/870,309, filed on Dec. 15, 2006, provisional application No. 60/862,552, filed on Oct. 23, 2006.

(51) Int. Cl.
*A61K 31/50* (2006.01)
*C07D 487/00* (2006.01)

(52) U.S. Cl.
USPC ............. 514/252.03; 514/248; 544/236

(58) Field of Classification Search
USPC ............... 544/236; 514/248, 252.03
See application file for complete search history.

(56) References Cited

FOREIGN PATENT DOCUMENTS

| | | |
|---|---|---|
| EP | 0 228 061 | 7/1987 |
| WO | WO 02/083139 | 10/2002 |
| WO | WO 02/083675 | 10/2002 |

OTHER PUBLICATIONS

Pinedo et al, "Translational Research . . . ", The Oncologist 2000; 5(suppl1); 1-2. [www.The Oncologist.com].*
McMahon, G., VEGF Receptor Signaling in Tumor Angiogenisis. The Oncologist 2000;5(suppl 1):3-10. [www.The Oncologist.com].*
International Search Report, PCT/US2007/081841, WO 2008/051808, pub. May 2, 2008.
Petrovanu, et al., "Synthese et proprietes de quelques nouveaux derives de la 3-p-cumyl-pyridazine," Revista Medico-Chirurgicala, vol. 81, 1977, pp. 659-664.
Gafitanu et al., "Nouveaux derives pyridaziniques doues de activites physiologiques," Revista Medico-Chirurgicala, vol. 81, 1977, pp. 469-474.
Basu, N.K. et al., "s-Triazolopyridazines: Synthesis as Potential Therapeutic Agents," Journal of the Chemical Society, Chemical Society, Letchworth, GB Jan. 1, 1963, pp. 5660-5664.

* cited by examiner

*Primary Examiner* — Paul V. Ward
(74) *Attorney, Agent, or Firm* — James J. Sales

(57) ABSTRACT

The present disclosure provides bicyclic triazole protein kinase modulators and methods of using these compounds to treat diseases mediated by kinase activity.

10 Claims, 6 Drawing Sheets

BICYCLIC TRIAZOLES AS PROTEIN KINASE MODULATORS

CROSS-REFERENCES TO RELATED APPLICATIONS

This application claims the benefit of U.S. Provisional Patent Application Ser. Nos. 60/952,840, 60/913,766, and 60/870,309, entitled: BICYCLIC TRIAZOLES AS PROTEIN KINASE MODULATORS", filed Jul. 30, 2007, Apr. 24, 2007, and Dec. 15, 2006, respectively, and U.S. Provisional Patent Application Ser. No. 60/862,552, entitled "TRIAZALOPYRIDAZINE PROTEIN KINASE MODULATORS", filed Oct. 23, 2006. Priority of these filing dates is hereby claimed, and the disclosure of each of these applications is hereby incorporated by reference in their entirety for all purposes.

FIELD OF THE DISCLOSURE

The present disclosure relates to bicyclic triazole protein kinase modulators, pharmaceutical compositions containing the same, and methods of making and using these compounds and compositions to treat diseases mediated by kinase activity.

BACKGROUND OF THE DISCLOSURE

Mammalian protein kinases are important regulators of cellular functions. Because disfunctions in protein kinase activity have been associated with several diseases and disorders, protein kinases are targets for drug development. The Tyrosine kinase family, and particularly the subset of receptor tyrosine kinases, is enriched with proven and putative cancer targets. Receptor tyrosine kinases (RTKs) such as EGFR, HER2, KIT and KDR are well characterized proteins with a clearly established role in cancer. Drugs targeting these RTKs, such as Gleevec, Iressa, and Tarceva, have been approved for the treatment of certain cancers. Other RTKs are less well characterized but have also been implicated in cancer. For example, emerging data suggests that inhibitors of TRKC, ROS, CSF1R/FMS and ALK may be useful in the treatment of cancer. MET and RON are two particularly attractive RTK targets for the development of new agents to treat cancer.

Hepatocyte growth factor (HGF), also known as scatter factor, is a multi-functional growth factor that enhances transformation and tumor development by inducing mitogenesis and cell motility. Further, HGF promotes metastasis by stimulating cell motility and invasion through various signaling pathways. In order to produce cellular effects, HGF must bind to its receptor, MET, a receptor tyrosine kinase. MET, a widely expressed heterodimeric protein comprising of a 50 kilodalton (kDa)α-subunit and a 145 kDa β-subunit (Maggiora et al., J. Cell Physiol., 173:183-186, 1997), is overexpressed in a significant percentage of human cancers and is amplified during the transition between primary tumors and metastasis. The various cancers in which MET overexpression is implicated include, but are not limited to, gastric adenocarcinoma, renal cancer, small cell lung carcinoma, colorectal cancer, prostate cancer, brain cancer, liver cancer, pancreatic cancer, and breast cancer. MET is also implicated in atherosclerosis and lung fibrosis.

MET was first identified as a transforming DNA rearrangement (TPR-MET) in a human osteosarcoma cell line that had been treated with N-methyl-N'-nitro-nitrosoguanidine (Cooper et al. 1984). The MET receptor tyrosine kinase (also known as hepatocyte growth factor receptor, HGFR, MET or c-Met) and its ligand hepatocyte growth factor ("HGF") have numerous biological activities including the stimulation of proliferation, survival, differentiation and morphogenesis, branching tubulogenesis, cell motility and invasive growth. Pathologically, MET has been implicated in the growth, invasion and metastasis of many different forms of cancer including kidney cancer, gastric cancer, lung cancer, ovarian cancer, liver cancer and breast cancer. Somatic, activating mutations in MET have been found in human carcinoma metastases and in sporadic cancers such as papillary renal cell carcinoma. There is also evidence the MET signaling pathway can play an important role in resistance to cancer therapies. For example, the MET gene has been found to be amplified in lung cancer patients that have relapsed after initial response to EGFR inhibitors such as gefitinib and erlotininb. In addition to cancer there is evidence that MET inhibition may have value in the treatment of various indications including: *Listeria* invasion, osteolysis associated with multiple myeloma, malaria infection, diabetic retinopathies, psoriasis, and arthritis. Mutations in the MET coding sequence are relatively uncommon in human cancers. However, based on the precedent of the selection of BCR-ABL mutations in chronic myelogenous leukemia patients treated with imatinib and EGFR mutations in cancer patients treated with erlotinib and gefitinib, these and/or perhaps additional MET mutations that might confer drug resistance are predicted to become increasingly prevalent if MET inhibitors become widely use in cancer. Therefore drugs that effectively inhibit some of these MET mutations could become very important tools in future cancer therapies.

MET is closely related to a group of five receptor tyrosine kinases which have not been as thoroughly studied as MET itself. These include Tyro3/Sky, MER, AXL, RYK and RON. The tyrosine kinase RON is the receptor for the macrophage stimulating protein and is the closest relative of MET, belonging to the MET family of receptor tyrosine kinases. Like MET, RON is implicated in growth, invasion and metastasis of several different forms of cancer including colorectal cancer and bladder cancer. There is also evidence that deregulated AXL and MER can play important roles in cancer. MER has many properties consistent with activity as an oncogene. Transgenic mice expressing MER in the hematopoietic lineage develop symptoms similar to T-cell lymphoblastic leukemia/lymphoma and it is expressed in most T cell acute lymphoblastic leukemia (T-ALL) patients. Studies in mouse models suggested that AXL is important for the growth of breast cancer where AXL appeared to regulate both angiogenic and tumorigenic processes. Additional studies with human cancer cell lines suggest that AXL is involved in NSCLC metastasis and drug resistance. Although very little is known of the normal and pathological roles of Tyro3/Sky this receptor tyrosine kinase shares certain properties and functions with its better studied relatives and may also eventually prove to have an important role in cancer. RYK is also expressed in certain cancers but it is an atypical orphan receptor tyrosine kinase that lacks detectable kinase activity and thus its tractability as a target for small molecule cancer therapeutics is currently uncertain.

Because kinases have been implicated in numerous diseases and conditions, such as cancer, there is a need to develop new and potent protein kinase inhibitors that can be used for treatment. The present invention fulfills these and other needs in the art. Although certain protein kinases are specifically named herein, the present invention is not limited to inhibitors of these kinases, and, includes, within its scope, inhibitors of related protein kinases, and inhibitors of homologous proteins.

BRIEF SUMMARY OF THE DISCLOSURE

It has been discovered that the bicyclic triazole compounds of the present disclosure may be used to modulate kinase activity and to treat diseases mediated by kinase activity. In particular, the compounds of the present disclosure may be used to modulate and/or inhibit tyrosine kinases, including MET. Further, the compounds of the present disclosure may be used to reduce or inhibit kinase activity of MET in a cell or subject, and to modulate MET expression in a cell or subject. The disclosed compounds are also useful for preventing or treating in a subject a cell proliferative disorder and/or disorders related to MET. The disclosed bicyclic triazole kinase modulators are described in detail below. In addition, inhibitory activities of selected compounds are disclosed herein.

In one aspect, the disclosure provides compounds having formula I:

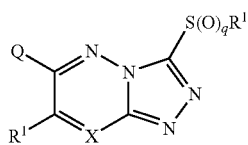

(I)

or an enantiomer, diastereomer, racemate or pharmaceutically acceptable salt or solvate thereof, wherein:

Q is independently hydrogen, halogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, wherein Q is optionally independently substituted with 1 to 3 $R^{22}$;

X is N or $CR^2$;

q is independently an integer from 0 to 2;

$R^1$ and $R^2$ are each optionally independently hydrogen, halogen, nitro, cyano, hydroxyl, substituted or unsubstituted alkyl, perfluoroalkyl, —$(CH_2)_j$CN, —$(CH_2)_j$O$R^3$, —$(CH_2)_j$C(O)$R^3$, —$(CH_2)_j$C(O)O$R^3$, —$(CH_2)_j$N$R^4R^5$, —$(CH_2)_j$C(O)N$R^4R^5$, —$(CH_2)_j$OC(O)N$R^4R^5$, —$(CH_2)_j$N$R^6$C(O)$R^3$, —$(CH_2)_j$N$R^6$C(O)O$R^3$, —$(CH_2)_j$N$R^6$C(O)N$R^4R^5$, —$(CH_2)_j$ S(O)$_m R^7$, —$(CH_2)_j$N$R^6$S(O)$_2 R^7$, —$(CH_2)_j$S(O)$_2$ N$R^4R^5$, wherein each j is independently an integer from 0 to 6, and m is independently an integer from 0 to 2, or $R^1$ and $R^2$ form substituted or unsubstituted cycloalkyl, substituted or unsubstituted heterocycloalkyl, substituted or unsubstituted aryl, or substituted or unsubstituted heteroaryl;

$R^3$, $R^4$, $R^5$, $R^6$, and $R^7$ are each independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, or $R^3$, $R^6$ and $R^7$ are as described above, and $R^4$ and $R^5$, together with the N atom to which they are attached, form substituted or unsubstituted heterocycloalkyl, or substituted or unsubstituted heteroaryl;

$R^{10}$ is independently hydrogen, substituted or unsubstituted aryl or substituted or unsubstituted heteroaryl, wherein $R^{10}$ is optionally independently substituted with 1 to 6 $R^{28}$;

$R^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, substituted or unsubstituted heteroarylalkyl, —$(CH_2)_j$CN, —$(CH_2)_j$O$R^{23}$, —$(CH_2)_j$C(O) $R^{23}$, —$(CH_2)_j$C(O)O$R^{23}$, —$(CH_2)_j$N$R^{24}R^{25}$, —$(CH_2)_j$C(O) N$R^{24}R^{25}$, —$(CH_2)_j$OC(O)N$R^{24}R^{25}$, —$(CH_2)_j$N$R^{26}$C(O)$R^{23}$, —$(CH_2)_j$N$R^{26}$C(O)O$R^{23}$, —$(CH_2)_j$N$R^{26}$C(O)N$R^{24}R^{25}$, —$(CH_2)_j$S(O)$_m R^{27}$, —$(CH_2)_j$S(O)$_2$N$R^{24}R^{25}$, or —$(CH_2)_j$ N$R^{26}$S(O)$_2 R^{27}$, wherein each j is independently an integer from 0 to 6, and each m is independently an integer from 0 to 2;

$R^{23}$, $R^{24}$, $R^{25}$, $R^{26}$, and $R^{27}$ are each independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, or $R^{23}$, $R^{26}$, and $R^{27}$ are as described above, and $R^{24}$ and $R^{25}$, together with the N atom to which they are attached, form substituted or unsubstituted heterocycloalkyl, or substituted or unsubstituted heteroaryl;

$R^{28}$ is independently a covalent bond, hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, substituted or unsubstituted heteroarylalkyl, —$(CH_2)_j$CN, —$(CH_2)_j$ O$R^{30}$, —$(CH_2)_j$C(O)$R^{30}$, —$(CH_2)_j$C(O)O$R^{30}$, —$(CH_2)_j$ N$R^{31}R^{32}$, —$(CH_2)_j$C(O)N$R^{31}R^{32}$, —$(CH_2)_j$OC(O) N$R^{31}R^{32}$, —$(CH_2)_j$N$R^{33}$C(O)$R^{30}$, —$(CH_2)_j$N$R^{33}$C(O) O$R^{30}$, —$(CH_2)_j$N$R^{33}$C(O)N$R^{31}R^{32}$, —$(CH_2)_j$S(O)$_m R^{34}$, —$(CH_2)_j$S(O)$_2$N$R^{31}R^{32}$, or —$(CH_2)_j$N$R^{33}$S(O)$_2 R^{34}$, wherein each j is independently an integer from 0 to 6, and m is independently an integer from 0 to 2, and wherein $R^{28}$ is optionally independently substituted with 1 to 3 $R^{35}$;

$R^{30}$, $R^{31}$, $R^{32}$, $R^{33}$, and $R^{34}$ are each independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, or $R^{30}$, $R^{33}$, and $R^{34}$ are as described above, and $R^{31}$ and $R^{32}$, together with the N atom to which they are attached, form substituted or unsubstituted heterocycloalkyl, or substituted or unsubstituted heteroaryl;

$R^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, substituted or unsubstituted heteroarylalkyl, —$(CH_2)_j$CN, —$(CH_2)_j$O$R^{30}$, —$(CH_2)_j$C(O)$R^{30}$, —$(CH_2)_j$C(O)O$R^{30}$, —$(CH_2)_j$N$R^{31}R^{32}$, —$(CH_2)_j$C(O)N$R^{31}R^{32}$, —$(CH_2)_j$N$R^{33}$C(O)$R^{30}$, —$(CH_2)_j$N$R^{33}$C(O)O$R^{30}$, —$(CH_2)_j$N$R^{33}$C(O)N$R^{31}R^{32}$, —$(CH_2)_j$S(O)$_m$$R^{34}$, —$(CH_2)_j$S(O)$_2$N$R^{31}R^{32}$, or —$(CH_2)_j$N$R^{33}$S(O)$_2$$R^{34}$, wherein each j is independently an integer from 0 to 6, and m is independently an integer from 0 to 2; and wherein $R^1$, $R^2$, $R^3$, $R^4$, $R^5$, $R^6$, $R^7$, $R^{10}$, $R^{22}$, $R^{23}$, $R^{24}$, $R^{25}$, $R^{26}$, $R^{27}$, $R^{28}$, $R^{30}$, $R^{31}$, $R^{32}$, $R^{33}$, $R^{34}$, and $R^{35}$ are each optionally independently substituted with 1 to 3 groups, each group independently selected from hydrogen, halogen, hydroxyl, amino, aminomonoalkyl, aminodialkyl, cyano, nitro, difluoromethyl, trifluoromethyl, oxo, alkyl, —O-alkyl, and —S-alkyl.

In other aspects, the disclosure relates to methods for modulating the activity of protein kinases; methods for treating cancer, pharmaceutical compositions and methods for preparing and using a compound of formula I.

DETAILED DESCRIPTION OF THE DISCLOSURE

Definitions

Figure 1:
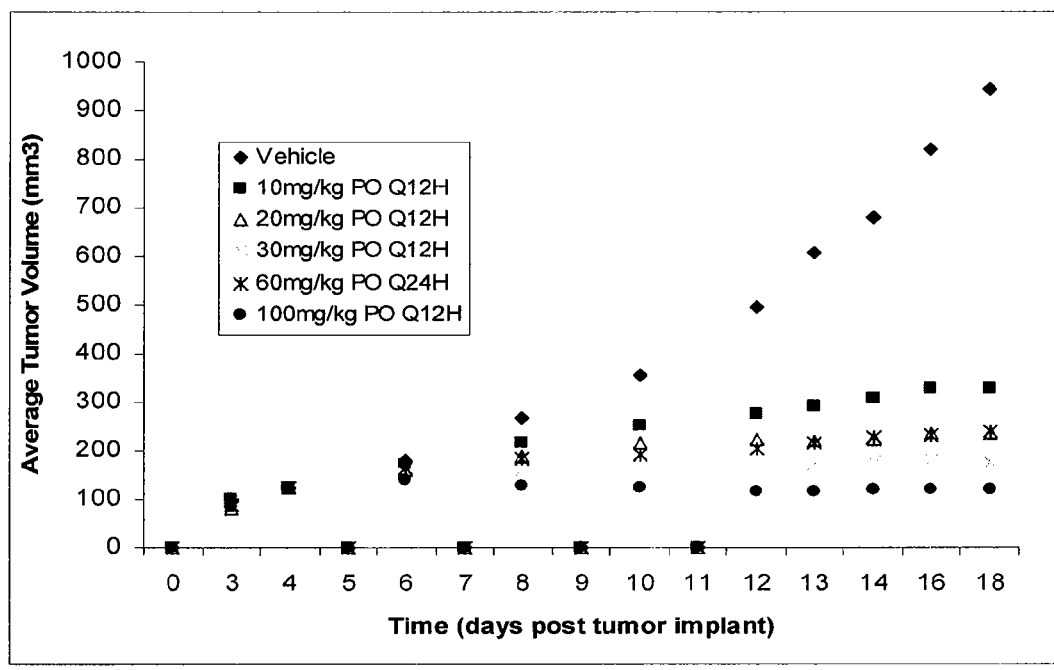
FIG. 1 illustrates the decrease in mean tumor volume after administration of compound 4 compared to the mean tumor volume of the vehicle treated group.

Abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —$CH_2$O— is equivalent to —O$CH_2$—; —C(O)O— is equivalent to —OC(O)—; and —C(O)NR— is equivalent to —NRC(O)—, and the like.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The term "cycloalkyl" or "cycloalkylalkyl" also refers to a 3 to 7 membered cycloalkyl group attached to the remainder of the molecule via an unsubstituted alkylene group. Recitation of a specific number of carbon atoms (e.g. $C_1$-$C_{10}$ cycloalkylalkyl) refers to the number of carbon atoms in the alkylene group.

The term "heterocycloalkyl" or "heterocycloalkylalkyl" also refers to a 3 to 7 membered heterocycloalkyl group attached to the remainder of the molecule via an unsubstituted alkylene group. Recitation of a specific number of carbon atoms (e.g. $C_1$-$C_{10}$ hetero-cycloalkylalkyl) refers to the number of carbon atoms in the alkylene group.

The term "alkylene" by itself or as part of another substituent means a divalent radical derived from an alkyl, as exemplified, but not limited, by —$CH_2CH_2CH_2CH_2$—. Typically, an alkyl (or alkylene) group will have from 1 to 24 carbon atoms, with those groups having 10 or fewer carbon atoms being preferred in the present disclosure. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein nitrogen and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Included within the definition of heteroalkyl compounds are alkoxy, thioalkoxy, aminoalkyl, aminodialkyl and the like. Other examples include, but are not limited to, —O—$CH_2$—$CH_3$, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH═CH—O—$CH_3$, —Si($CH_3$)$_3$, —$CH_2$—CH═N—O$CH_3$, —CH═CH—N($CH_3$)—$CH_3$, O—$CH_3$, —O—$CH_2$—$CH_3$, and —CN. Up to two heteroatoms may be consecutive, such as, for example, —$CH_2$—NH—O$CH_3$ and —$CH_2$—O—Si($CH_3$)$_3$. Similarly, the term "heteroalkylene"

by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

An "alkylesteryl," as used herein, refers to a moiety having the formula R'—C(O)O—R", wherein R' is an alkylene moiety and R" is an alkyl moiety.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydro-pyridinyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The term "cycloalkylalkyl" refers to a 3 to 7 membered cycloalkyl group attached to the remainder of the molecule via an unsubstituted alkylene group. Recitation of a specific number of carbon atoms (e.g. C$_1$-C$_{10}$ cycloalkylalkyl) refers to the number of carbon atoms in the alkylene group.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridinyl, 3-pyridinyl, 4-pyridinyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent derivatives of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridinylmethyl and the like) including those alkyl groups in which a carbon atom (e.g., a methylene group) has been replaced by, for example, an oxygen atom (e.g., phenoxymethyl, 2-pyridinyloxymethyl, 3-(1-naphthyloxy)propyl, and the like). Similarly, the term "heteroarylalkyl" is meant to include those radicals in which a heteroaryl group is attached to an alkyl group (e.g., pyridinylmethyl, quinolinylmethyl, 1,2,4-triazolyl[4,3-b]pyridazinyl-methyl, 1H-benzotriazolylmethyl, benzothiazolylmethyl, and the like. However, the term "haloaryl," as used herein is meant to cover only aryls substituted with one or more halogens.

The term "oxo" as used herein means an oxygen that is double bonded to a carbon atom.

Each of above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical. Preferred substituents for each type of radical are provided below.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the disclosure includes more than one R group, for example, each of the R groups is independently selected as are each R', R", R''' and R'''' groups when more than one of these groups is present. When R' and R" are attached to the same nitrogen atom, they can be combined with the nitrogen atom to form 4-, 5-, 6-, or 7-membered ring. For example, —NR'R" is meant to include, but not be limited to, 1-pyrrolidinyl and 4-morpholinyl. From above discussion of substituents, one of skill in art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R"', —OC(O)R', —C(O)R', —CO$_2$R', —C(O)NR'R", —OC(O)NR'R", —NR"C(O)R', —NR'—C(O)NR"R"', —NR"C(O)OR', —NR—C (NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro (C$_1$-C$_4$)alkyl, in a number ranging from zero to the total number of open valences on aromatic ring system; and where R', R", R"' and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R"' and R"" groups when more than one of these groups is present.

Two of the substituents on adjacent atoms of aryl or heteroaryl ring may optionally form ring of the formula -T-C (O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'— (C"R"')$_d$—, where s and d are independently integers of from 0 to 3, and X' is —O—, —NR'—, —S—, —S(O)—, —S(O)$_2$—, or —S(O)$_2$NR'—. The substituents R, R', R" and R"' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogen-phosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Certain compounds of the present disclosure possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

The term "pharmaceutically acceptable salts" is meant to include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, physiological conditions.

The terms "treating" or "treatment" in reference to a particular disease includes prevention of the disease.

The symbol ~~~ denotes the point of attachment of a moiety to the remainder of the molecule.

Bicyclic Triazole Compounds

In one aspect, the disclosure provides compounds having formula I:

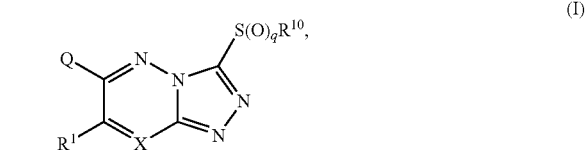

(I)

or an enantiomer, diastereomer, racemate or pharmaceutically acceptable salt or solvate thereof, wherein:

Q is independently hydrogen, halogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, wherein Q is optionally independently substituted with 1 to 3 $R^{22}$;

X is N or $CR^2$;

q is independently an integer from 0 to 2;

$R^1$ and $R^2$ are each optionally independently hydrogen, halogen, nitro, cyano, hydroxyl, substituted or unsubstituted alkyl, perfluoroalkyl, —$(CH_2)_j$CN, —$(CH_2)_j$OR$^3$, —$(CH_2)_j$C(O)R$^3$, —$(CH_2)_j$C(O)OR$^3$, —$(CH_2)_j$NR$^4$R$^5$, —$(CH_2)_j$C(O)NR$^4$R$^5$, —$(CH_2)_j$OC(O)NR$^4$R$^5$, —$(CH_2)_j$NR$^6$C(O)R$^3$, —$(CH_2)_j$NR$^6$C(O)OR$^3$, —$(CH_2)_j$NR$^6$C(O)NR$^4$R$^5$, —$(CH_2)_j$S(O)$_m$R$^7$, —$(CH_2)_j$NR$^6$S(O)$_2$R$^7$, —$(CH_2)_j$S(O)$_2$NR$^4$R$^5$, wherein each j is independently an integer from 0 to 6, and m is independently an integer from 0 to 2, or $R^1$ and $R^2$ form substituted or unsubstituted cycloalkyl, substituted or unsubstituted heterocycloalkyl, substituted or unsubstituted aryl, or substituted or unsubstituted heteroaryl;

$R^3$, $R^4$, $R^5$, $R^6$, and $R^7$ are each independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, or $R^3$, $R^6$ and $R^7$ are as described above, and $R^4$ and $R^5$, together with the N atom to which they are attached, form substituted or unsubstituted heterocycloalkyl, or substituted or unsubstituted heteroaryl;

$R^{10}$ is independently hydrogen, substituted or unsubstituted aryl or substituted or unsubstituted heteroaryl, wherein $R^{10}$ is optionally independently substituted with 1 to 6 $R^{28}$;

$R^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, substituted or unsubstituted heteroarylalkyl, —$(CH_2)_j$CN, —$(CH_2)_j$OR$^{23}$, —$(CH_2)_j$C(O)R$^{23}$, —$(CH_2)_j$C(O)OR$^{23}$, —$(CH_2)_j$NR$^{24}$R$^{25}$, —$(CH_2)_j$C(O)NR$^{24}$R$^{25}$, —$(CH_2)_j$OC(O)NR$^{24}$R$^{25}$, —$(CH_2)_j$NR$^{26}$C(O)

$R^{23}$, —$(CH_2)_jNR^{26}C(O)OR^{23}$, —$(CH_2)_jNR^{26}C(O)NR^{24}R^{25}$, —$(CH_2)_jS(O)_mR^{27}$, —$(CH_2)_jS(O)_2NR^{24}R^{25}$, or —$(CH_2)_jNR^{26}S(O)_2R^{27}$, wherein each j is independently an integer from 0 to 6, and each m is independently an integer from 0 to 2;

$R^{23}$, $R^{24}$, $R^{25}$, $R^{26}$, and $R^{27}$ are each independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, or $R^{23}$, $R^{26}$, and $R^{27}$ are as described above, and $R^{24}$ and $R^{25}$, together with the N atom to which they are attached, form substituted or unsubstituted heterocycloalkyl, or substituted or unsubstituted heteroaryl;

$R^{28}$ is independently a covalent bond, hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, substituted or unsubstituted heteroarylalkyl, —$(CH_2)_jCN$, —$(CH_2)_j$ $OR^{30}$, —$(CH_2)_jC(O)R^{30}$, —$(CH_2)_jC(O)OR^{30}$, —$(CH_2)_jNR^{31}R^{32}$, —$(CH_2)_jC(O)NR^{31}R^{32}$, —$(CH_2)_jOC(O)NR^{31}R^{32}$, —$(CH_2)_jNR^{33}C(O)R^{30}$, —$(CH_2)_jNR^{33}C(O)OR^{30}$, —$(CH_2)_jNR^{33}C(O)NR^{31}R^{32}$, —$(CH_2)_jS(O)_mR^{34}$, —$(CH_2)_jS(O)_2NR^{31}R^{32}$, or —$(CH_2)_jNR^{33}S(O)_2R^{34}$, wherein each j is independently an integer from 0 to 6, and m is independently an integer from 0 to 2, and wherein $R^{28}$ is optionally independently substituted with 1 to 3 $R^{35}$;

$R^{30}$, $R^{31}$, $R^{32}$, $R^{33}$, and $R^{34}$ are each independently hydrogen, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, or substituted or unsubstituted heteroarylalkyl, or $R^{30}$, $R^{33}$, and $R^{34}$ are as described above, and $R^{31}$ and $R^{32}$, together with the N atom to which they are attached, form substituted or unsubstituted heterocycloalkyl, or substituted or unsubstituted heteroaryl;

$R^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted aryl, substituted or unsubstituted —O-aryl, substituted or unsubstituted arylalkyl, substituted or unsubstituted heteroaryl, substituted or unsubstituted —O-heteroaryl, substituted or unsubstituted heteroarylalkyl, —$(CH_2)_jCN$, —$(CH_2)_jOR^{30}$, —$(CH_2)_jC(O)R^{30}$, —$(CH_2)_jC(O)OR^{30}$, —$(CH_2)_jNR^{31}R^{32}$, —$(CH_2)_jC(O)NR^{31}R^{32}$ $(CH_2)OC(O)NR^{31}R^{32}$, —$(CH_2)_jNR^{33}C(O)R^{30}$, $(CH_2)NR^{33}C(O)OR^{30}$, —$(CH_2)_jNR^{33}C(O)NR^{31}R^{32}$, —$(CH_2)_jS(O)_mR^{34}$, —$(CH_2)_jS(O)_2NR^{31}R^{32}$, or —$(CH_2)_jNR^{33}S(O)_2R^{34}$, wherein each j is independently an integer from 0 to 6; and m is independently an integer from 0 to 2; and wherein $R^1$, $R^2$, $R^3$, $R^4$, $R^5$, $R^6$, $R^7$, $R^{10}$, $R^{22}$, $R^{23}$, $R^{24}$, $R^{25}$, $R^{26}$, $R^{27}$, $R^{28}$, $R^{30}$, $R^{31}$, $R^{32}$, $R^{33}$, $R^{34}$, and $R^{35}$ are each optionally independently substituted with 1 to 3 groups, each group independently selected from hydrogen, halogen, hydroxyl, amino, aminomonoalkyl, aminodialkyl, cyano, nitro, difluoromethyl, trifluoromethyl, oxo, alkyl, —O-alkyl, and —S-alkyl.

In another aspect, the disclosure provides compounds having formula I, wherein:

Q is independently hydrogen, halogen, substituted or unsubstituted alkyl, perfluoroalkyl, amino, substituted or unsubstituted aminomonoalkyl, substituted or unsubstituted aminodialkyl, substituted or unsubstituted phenyl, substituted or unsubstituted phenoxy, substituted or unsubstituted piperidinyl, substituted or unsubstituted piperazinyl, substituted or unsubstituted pyrrolidinyl, substituted or unsubstituted morpholinyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, substituted or unsubstituted —O-pyridinyl, substituted or unsubstituted isoxazolyl, substituted or unsubstituted isothiazolyl, or substituted or unsubstituted triazolyl;

q is independently 0;

$R^1$ and $R^2$ are each optionally independently hydrogen, halogen, nitro, cyano, hydroxyl, substituted or unsubstituted alkyl, perfluoroalkyl, —$(CH_2)_jCN$, —$(CH_2)_jOR^3$, —$(CH_2)_jC(O)R^3$, —$(CH_2)_jC(O)OR^3$, —$(CH_2)_jNR^4R^5$, —$(CH_2)_jC(O)NR^4R^5$, —$(CH_2)_jOC(O)NR^4R^5$, —$(CH_2)_jNR^6C(O)R^3$, —$(CH_2)_jNR^6C(O)OR^3$, —$(CH_2)_jNR^6C(O)NR^4R^5$, —$(CH_2)_jS(O)_mR^7$, —$(CH_2)_jNR^6S(O)_2R^7$, or —$(CH_2)_jS(O)_2NR^4R^5$;

$R^{10}$ is independently substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl;

$R^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, —$(CH_2)_j$CN, —$(CH_2)_j$OR$^{23}$, —$(CH_2)_j$C(O)R$^{23}$, —$(CH_2)_j$C(O)OR$^{23}$, —$(CH_2)_j$NR$^{24}$R$^{25}$, —$(CH_2)_j$C(O)NR$^{24}$R$^{25}$, —$(CH_2)_j$OC(O)NR$^{24}$R$^{25}$, —$(CH_2)_j$NR$^{26}$C(O)R$^{23}$, —$(CH_2)_j$NR$^{26}$C(O)OR$^{23}$, —$(CH_2)_j$NR$^{26}$C(O)NR$^{24}$R$^{25}$, —$(CH_2)_j$S(O)$_m$R$^{27}$, —$(CH_2)_j$S(O)$_2$NR$^{24}$R$^{25}$, or —$(CH_2)_j$NR$^{26}$S(O)$_2$R$^{27}$;

R$^{28}$ is independently a covalent bond, hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, —$(CH_2)_j$CN, —$(CH_2)_j$OR$^{30}$, —$(CH_2)_j$C(O)R$^{30}$, —$(CH_2)_j$C(O)OR$^{30}$, —$(CH_2)_j$NR$^{31}$R$^{32}$, —$(CH_2)_j$C(O)NR$^{31}$R$^{32}$, —$(CH_2)_j$OC(O)NR$^{31}$R$^{32}$, —$(CH_2)_j$NR$^{33}$C(O)R$^{30}$, —$(CH_2)_j$NR$^{33}$C(O)NR$^{31}$R$^{32}$, —$(CH_2)_j$S(O)$_m$R$^{34}$, —$(CH_2)_j$S(O)$_2$NR$^{31}$R$^{32}$, or —$(CH_2)_j$NR$^{33}$S(O)$_2$R$^{34}$; and R$^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted azetidinyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, —$(CH_2)_j$CN, —$(CH_2)_j$OR$^{30}$, —$(CH_2)_j$C(O)R$^{30}$, —$(CH_2)_j$C(O)OR$^{30}$, —$(CH_2)_j$NR$^{31}$R$^{32}$, —$(CH_2)_j$C(O)NR$^{31}$R$^{32}$, —$(CH_2)_j$OC(O)NR$^{31}$R$^{32}$, —$(CH_2)_j$NR$^{33}$C(O)R$^{30}$, —$(CH_2)_j$NR$^{33}$C(O)OR$^{30}$, —$(CH_2)_j$NR$^{33}$C(O)NR$^{31}$R$^{32}$, —$(CH_2)_j$S(O)$_m$R$^{34}$, —$(CH_2)_j$S(O)$_2$NR$^{31}$R$^{32}$, or —$(CH_2)_j$NR$^{33}$S(O)$_2$R$^{34}$.

In another aspect, the disclosure provides compounds having formula I, wherein:

Q is independently hydrogen, halogen, substituted or unsubstituted alkyl, perfluoroalkyl, amino, substituted or unsubstituted aminomonoalkyl, substituted or unsubstituted aminodialkyl, substituted or unsubstituted phenyl, substituted or unsubstituted phenoxy, substituted or unsubstituted piperidinyl, substituted or unsubstituted piperazinyl, substituted or unsubstituted pyrrolidinyl, substituted or unsubstituted morpholinyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, or substituted or unsubstituted —O-pyridinyl;

R$^1$ and R$^2$ are each independently hydrogen, halogen, nitro, cyano, hydroxyl, substituted or unsubstituted alkyl, or perfluoroalkyl;

X is CR$^2$;

R$^{10}$ is independently:

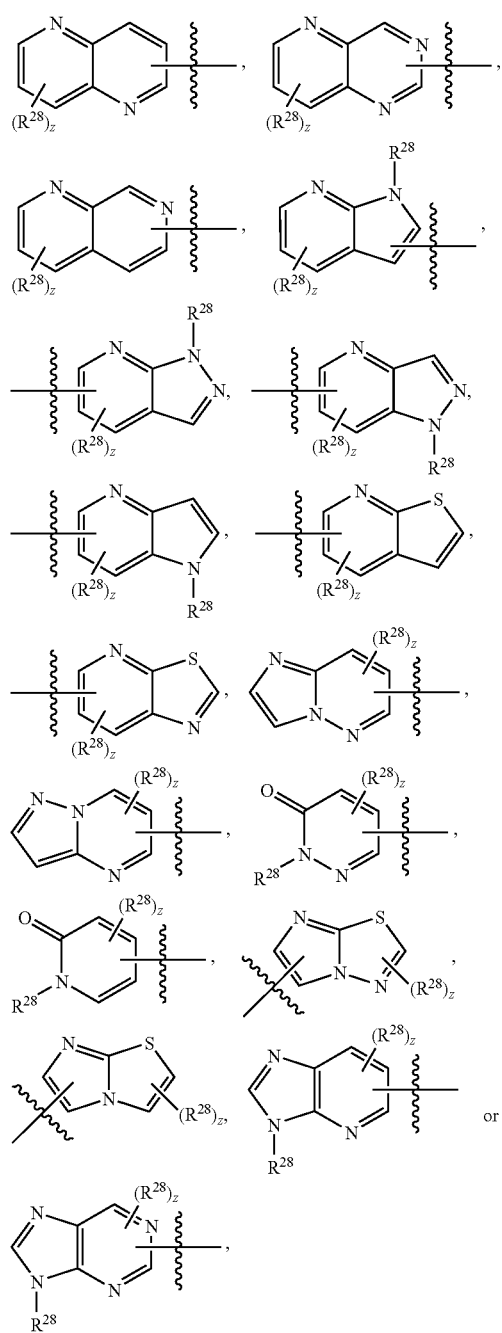

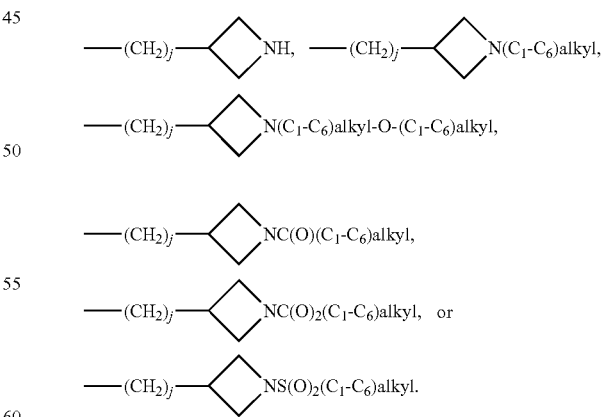

wherein z is independently an integer from 0 to 6;

$R^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, —$(CH_2)_j$CN, —$(CH_2)_j$OR$^{23}$, —$(CH_2)_j$C(O)R$^{23}$, —$(CH_2)_j$C(O)OR$^{23}$, —$(CH_2)_j$NR$^{24}$R$^{25}$, —$(CH_2)_j$C(O)NR$^{24}$R$^{25}$, —$(CH_2)_j$OC(O)NR$^{24}$R$^{25}$, —$(CH_2)_j$NR$^{26}$C(O)R$^{23}$, —$(CH_2)_j$NR$^{26}$C(O)OR$^{23}$, —$(CH_2)_j$NR$^{26}$C(O)NR$^{24}$R$^{25}$, —$(CH_2)_j$S(O)$_m$R$^{27}$, —$(CH_2)_j$S(O)$_2$NR$^{24}$R$^{25}$, or —$(CH_2)_j$NR$^{26}$S(O)$_2$R$^{27}$;

$R^{28}$ is independently a covalent bond, hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl; and $R^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, —$(CH_2)_j$CN, —$(CH_2)_j$OR$^{30}$, —$(CH_2)_j$C(O)R$^{30}$, —$(CH_2)_j$C(O)OR$^{30}$, —$(CH_2)_j$NR$^{31}$R$^{32}$, —$(CH_2)_j$C(O)NR$^{31}$R$^{32}$, —$(CH_2)_j$OC(O)NR$^{31}$R$^{32}$, —$(CH_2)_j$NR$^{33}$C(O)R$^{30}$, —$(CH_2)_j$NR$^{33}$C(O)OR$^{30}$, —$(CH_2)_j$NR$^{33}$C(O)NR$^{31}$R$^{32}$, —$(CH_2)_j$S(O)$_m$R$^{34}$, —$(CH_2)_j$S(O)$_2$NR$^{31}$R$^{32}$, —$(CH_2)_j$NR$^{33}$S(O)$_2$R$^{34}$, In another aspect, the disclosure provides compounds having formula I, wherein:

Q is independently hydrogen, chloro, substituted or unsubstituted alkyl, perfluoroalkyl, —$NH_2$, —NH($C_1$-$C_6$)alkyl or —N[($C_1$-$C_6$)alkyl]$_2$,

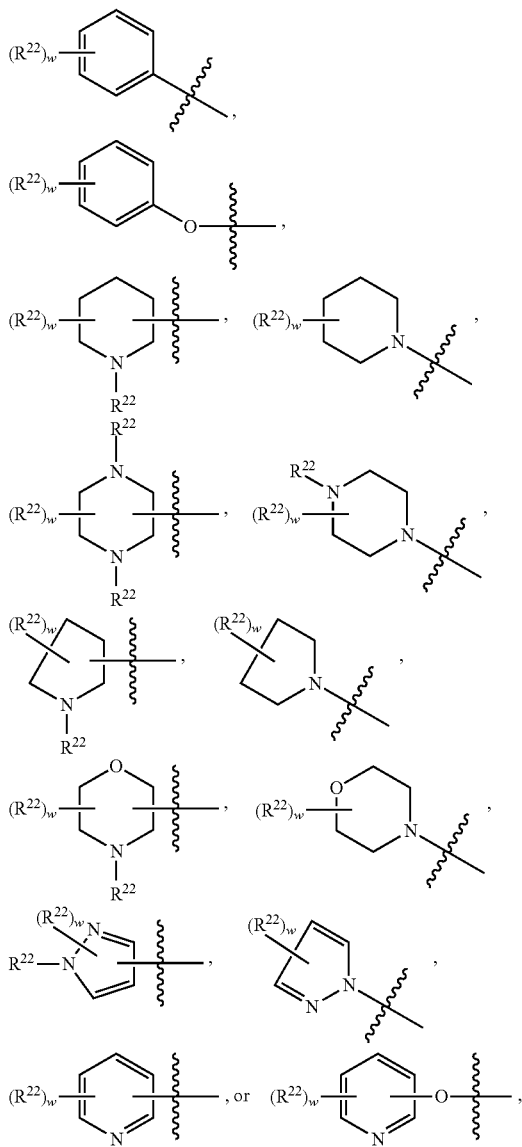

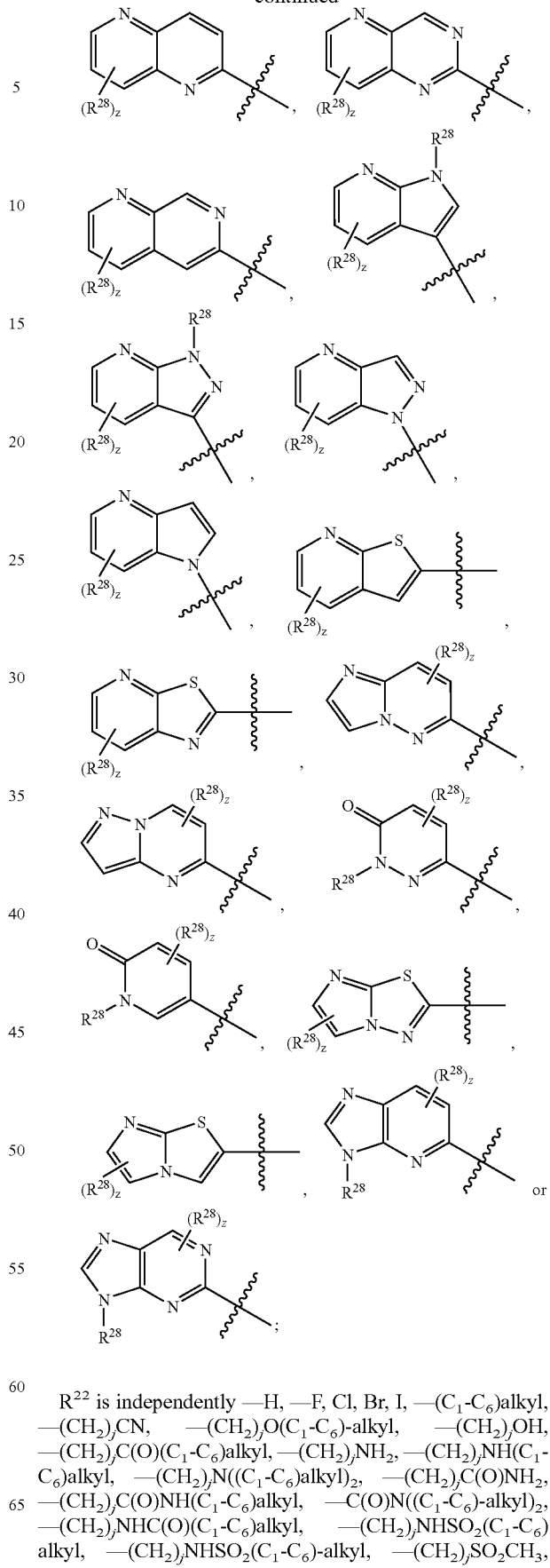

wherein each alkyl is optionally independently substituted with 1 to 3 $R^{22}$, and wherein w is independently an integer from 0 to 3; or wherein two $R^{22}$ optionally form a cyclic structure with —O(CH$_2$CH$_2$)O—;

$R^1$ and $R^2$ are each independently hydrogen;

$R^{10}$ is independently:

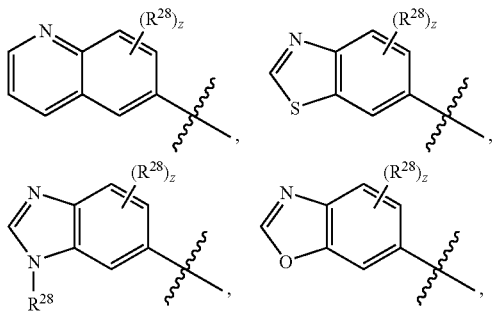

$R^{22}$ is independently —H, —F, Cl, Br, I, —(C$_1$-C$_6$)alkyl, —(CH$_2$)$_j$CN, —(CH$_2$)$_j$O(C$_1$-C$_6$)-alkyl, —(CH$_2$)$_j$OH, —(CH$_2$)$_j$C(O)(C$_1$-C$_6$)alkyl, —(CH$_2$)$_j$NH$_2$, —(CH$_2$)$_j$NH(C$_1$-C$_6$)alkyl, —(CH$_2$)$_j$N((C$_1$-C$_6$)alkyl)$_2$, —(CH$_2$)$_j$C(O)NH$_2$, —(CH$_2$)$_j$C(O)NH(C$_1$-C$_6$)alkyl, —C(O)N((C$_1$-C$_6$)-alkyl)$_2$, —(CH$_2$)$_j$NHC(O)(C$_1$-C$_6$)alkyl, —(CH$_2$)$_j$NHSO$_2$(C$_1$-C$_6$) alkyl, —(CH$_2$)$_j$NHSO$_2$(C$_1$-C$_6$)-alkyl, —(CH$_2$)$_j$SO$_2$CH$_3$, —(CH$_2$)$_j$SO$_2$NH$_2$, —(CH$_2$)$_j$SO$_2$NH(C$_1$-C$_6$)-alkyl, —(CH$_2$)$_j$SO$_2$N((C$_1$-C$_6$)-alkyl)$_2$, —(CH$_2$)$_j$SO$_2$NH(C$_1$-C$_6$)alkyl(OH), phenyl,

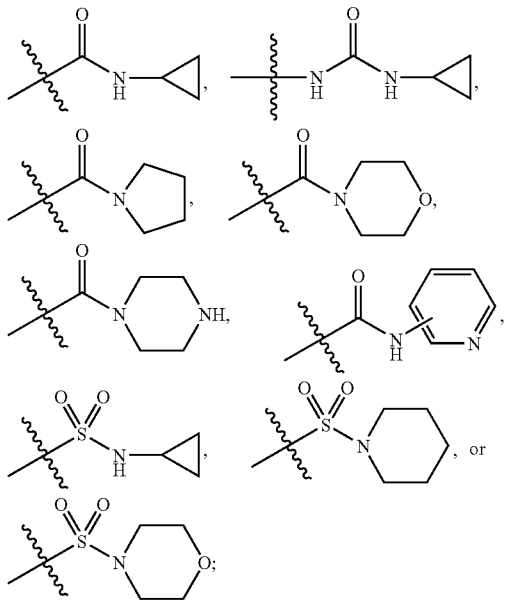

R$^{28}$ is independently:

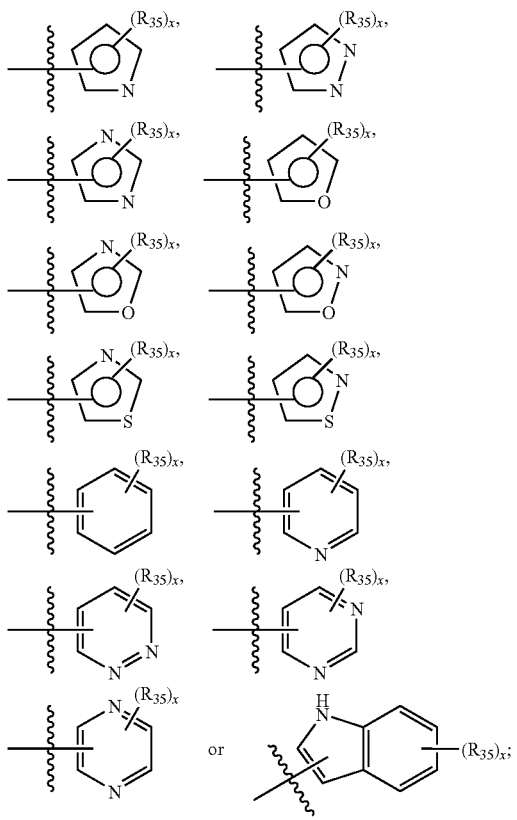

x is independently an integer from 0 to 6; and
R$^{35}$ is independently hydrogen, halogen, nitro, cyano, hydroxyl, (C$_1$-C$_6$)alkyl, cyclo(C$_3$-C$_{10}$)alkyl, perfluoro(C$_1$-C$_6$)alkyl, —(CH$_2$)$_j$CN, —(CH$_2$)$_j$O(C$_1$-C$_6$)alkyl, —(CH$_2$)$_j$C(O)(C$_1$-C$_6$)alkyl, —(CH$_2$)$_j$C(O)O(C$_1$-C$_6$)alkyl, —(CH$_2$)$_j$NH$_2$, —(CH$_2$)$_j$NH(C$_1$-C$_6$)alkyl), —(CH$_2$)$_j$N((C$_1$-C$_6$)alkyl)$_2$, —(CH$_2$)$_j$C(O)NH$_2$, —(CH$_2$)$_j$C(O)NH(C$_1$-C$_6$)alkyl), —(CH$_2$)$_j$C(O)N—((C$_1$-C$_6$)alkyl)$_2$, —(CH$_2$)$_j$OC(O)NH$_2$, —(CH$_2$)$_j$OC(O)NH(C$_1$-C$_6$)alkyl), —(CH$_2$)$_j$OC(O)N((C$_1$-C$_6$)-alkyl)$_2$, —(CH$_2$)$_j$NHC(O)(C$_1$-C$_6$)alkyl, —(CH$_2$)$_j$N((C$_1$-C$_6$)alkyl)C(O)(C$_1$-C$_6$)alkyl, —(CH$_2$)$_j$NHC(O)O(C$_1$-C$_6$)alkyl, —(CH$_2$)$_j$N((C$_1$-C$_6$)alkyl)C(O)O(C$_1$-C$_6$)alkyl, —(CH$_2$)$_j$NHC(O)NH$_2$, —(CH$_2$)$_j$NHC(O)NH(C$_1$-C$_6$)alkyl), —(CH$_2$)$_j$NHC(O)N((C$_1$-C$_6$)alkyl)$_2$, —(CH$_2$)$_j$N((C$_1$-C$_6$)alkyl)C(O)NH(C$_1$-C$_6$)alkyl), —(CH$_2$)$_j$N((C$_1$-C$_6$)alkyl)C(O)N((C$_1$-C$_6$)alkyl)$_2$, —(CH$_2$)$_j$S(O)$_m$(C$_1$-C$_6$)alkyl, —(CH$_2$)$_j$S(O)$_2$NH$_2$, —(CH$_2$)$_j$S(O)$_2$NH(C$_1$-C$_6$)alkyl), —(CH$_2$)$_j$S(O)$_2$N((C$_1$-C$_6$)alkyl)$_2$, —(CH$_2$)$_j$NHS(O)$_2$(C$_1$-C$_6$)alkyl, —(CH$_2$)$_j$N((C$_1$-C$_6$)alkyl)-S(O)$_2$(C$_1$-C$_6$)alkyl,

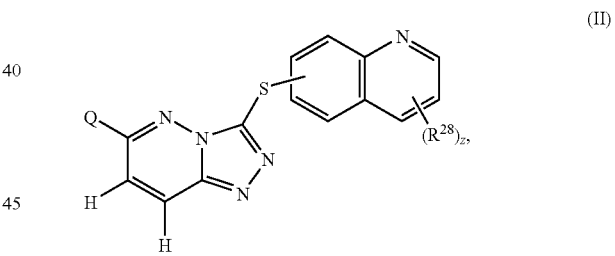

In another aspect, the disclosure provides compounds having formula II:

(II)

[Structure of formula II showing Q, R$^{28}$, and (R$^{28}$)$_z$ substituents on a triazolopyridazine-thio-quinoline scaffold]

wherein:
Q is independently hydrogen, halogen, substituted or unsubstituted alkyl, perfluoroalkyl, amino, substituted or unsubstituted aminomonoalkyl, substituted or unsubstituted aminodialkyl, substituted or unsubstituted phenyl, substituted or unsubstituted phenoxy, substituted or unsubstituted piperidinyl, substituted or unsubstituted piperazinyl, substituted or unsubstituted pyrrolidinyl, substituted or unsubstituted morpholinyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, substituted or unsubstituted —O-pyridinyl, substituted or unsubstituted isoxazolyl, substituted or unsubstituted isothiazolyl, or substituted or unsubstituted triazolyl;
R$^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, $-(CH_2)_jCN$, $-(CH_2)_jOR^{23}$, $-(CH_2)_jC(O)R^{23}$, $-(CH_2)_jC(O)OR^{23}$, $-(CH_2)_jNR^{24}R^{25}$, $-(CH_2)_jC(O)NR^{24}R^{25}$, $-(CH_2)_jOC(O)NR^{24}R^{25}$, $-(CH_2)_jNR^{26}C(O)R^{23}$, $-(CH_2)_jNR^{26}C(O)OR^{23}$, $-(CH_2)_jNR^{26}C(O)NR^{24}R^{25}$, $-(CH_2)_jS(O)_mR^{27}$, $-(CH_2)_jS(O)_2NR^{24}R^{25}$, or $-(CH_2)_jNR^{26}S(O)_2R^{27}$;

$R^{28}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, $-(CH_2)_jCN$, $-(CH_2)_jOR^{30}$, $-(CH_2)_jC(O)R^{30}$, $-(CH_2)_jC(O)OR^{30}$, $-(CH_2)_jNR^{31}R^{32}$, $-(CH_2)_jC(O)NR^{31}R^{32}$, $-(CH_2)_jOC(O)NR^{31}R^{32}$, $-(CH_2)_jNR^{33}C(O)R^{30}$, $-(CH_2)_jNR^{33}C(O)OR^{30}$, $-(CH_2)_jNR^{33}C(O)NR^{31}R^{32}$, $-(CH_2)_jS(O)_mR^{34}$, $-(CH_2)_jS(O)_2NR^{31}R^{32}$, or $-(CH_2)_jNR^{33}S(O)_2R^{34}$; and $R^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted azetidinyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, $-(CH_2)_jCN$, $-(CH_2)_jOR^{30}$, $-(CH_2)_jC(O)R^{30}$, $-(CH_2)_jC(O)OR^{30}$, $-(CH_2)_jNR^{31}R^{32}$, $-(CH_2)_jC(O)NR^{31}R^{32}$, $-(CH_2)_jOC(O)NR^{31}R^{32}$, $-(CH_2)_jNR^{33}C(O)R^{30}$, $-(CH_2)_jNR^{31}C(O)OR^{32}$, $-(CH_2)_jNR^{33}C(O)NR^{31}R^{32}$, $-(CH_2)_jS(O)_mR^{34}$, $-(CH_2)_jS(O)_2NR^{31}R^{32}$, or $-(CH_2)_jNR^{33}S(O)_2R^{34}$.

In another aspect, the disclosure provides compounds having formula II, wherein:

Q is independently hydrogen, halogen, substituted or unsubstituted alkyl, perfluoroalkyl, amino, substituted or unsubstituted aminomonoalkyl, substituted or unsubstituted aminodialkyl, substituted or unsubstituted phenyl, substituted or unsubstituted phenoxy, substituted or unsubstituted piperidinyl, substituted or unsubstituted piperazinyl, substituted or unsubstituted pyrrolidinyl, substituted or unsubstituted morpholinyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, or substituted or unsubstituted —O-pyridinyl;

$R^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, $-(CH_2)_jCN$, $-(CH_2)_jOR^{23}$, $-(CH_2)_jC(O)$ $R^{23}$, —$(CH_2)_jC(O)OR^{23}$, —$(CH_2)_jNR^{24}R^{25}$, —$(CH_2)_jC(O)$
$NR^{24}R^{25}$, —$(CH_2)_jOC(O)NR^{24}R^{25}$, —$(CH_2)_jNR^{26}C(O)$
$R^{23}$, —$(CH_2)_jNR^{26}C(O)OR^{23}$, —$(CH_2)_jNR^{26}C(O)$
$NR^{24}R^{25}$, —$(CH_2)_jS(O)_mR^{27}$, —$(CH_2)_jS(O)_2NR^{24}R^{25}$, or
—$(CH_2)_jNR^{26}S(O)_2R^{27}$;

$R^{28}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl; and $R^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, —$(CH_2)_jCN$, —$(CH_2)_jOR^{30}$, —$(CH_2)_jC(O)$ $R^{30}$, —$(CH_2)_jC(O)OR^{30}$, —$(CH_2)_jNR^{31}R^{32}$, —$(CH_2)_jC(O)$ $NR^{31}R^{32}$, —$(CH_2)_jOC(O)NR^{31}R^{32}$, —$(CH_2)_jNR^{33}C(O)$ $R^{30}$, —$(CH_2)_jNR^{33}C(O)OR^{30}$, —$(CH_2)_jNR^{33}C(O)$ $NR^{31}R^{32}$, —$(CH_2)_jS(O)_mR^{34}$, —$(CH_2)_jS(O)_2NR^{31}R^{32}$, —$(CH_2)_jNR^{33}S(O)_2R^{34}$,

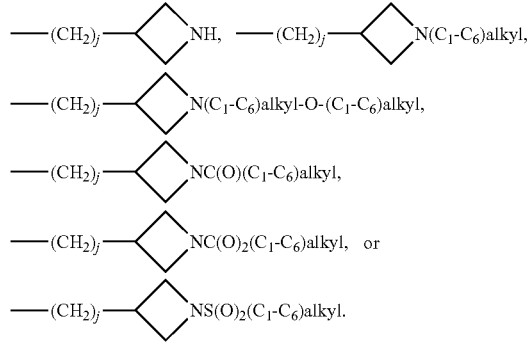

In another aspect, the disclosure provides compounds having formula II, wherein:

Q is independently hydrogen, chloro, substituted or unsubstituted alkyl, perfluoroalkyl, —$NH_2$, —$NH(C_1-C_6)alkyl$ or —$N[(C_1-C_6)alkyl]_2$,

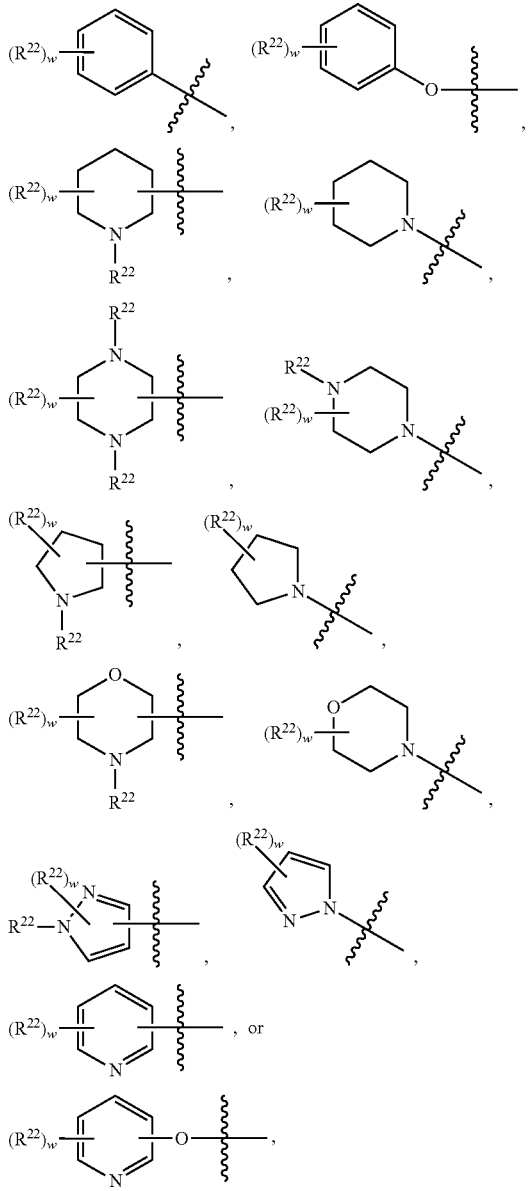

wherein each alkyl is optionally independently substituted with 1 to 3 $R^{22}$, and wherein w is independently an integer from 0 to 3; or wherein two $R^{22}$ optionally form a cyclic structure with —$O(CH_2CH_2)O$—;

$R^{22}$ is independently —H, —F, Cl, Br, I, —$(C_1-C_6)alkyl$, —$(CH_2)_jCN$, —$(CH_2)_jO(C_1-C_6)-alkyl$, —$(CH_2)_jOH$, —$(CH_2)_jC(O)(C_1-C_6)alkyl$, —$(CH_2)_jNH_2$, —$(CH_2)_jNH(C_1-C_6)alkyl$, —$(CH_2)_jN((C_1-C_6)alkyl)_2$, —$(CH_2)_jC(O)NH_2$, —$(CH_2)_jC(O)NH(C_1-C_6)alkyl$, —$C(O)N((C_1-C_6)-alkyl)_2$, —$(CH_2)_jNHC(O)(C_1-C_6)alkyl$, —$(CH_2)_jNHSO_2(C_1-C_6)alkyl$, —$(CH_2)_jNHSO_2(C_1-C_6)-alkyl$, —$(CH_2)_jSO_2CH_3$, —$(CH_2)_jSO_2NH_2$, —$(CH_2)_jSO_2NH(C_1-C_6)-alkyl$, —$(CH_2)_jSO_2N((C_1-C_6)-alkyl)_2$, —$(CH_2)_jSO_2NH(C_1-C_6)alkyl(OH)$, phenyl,

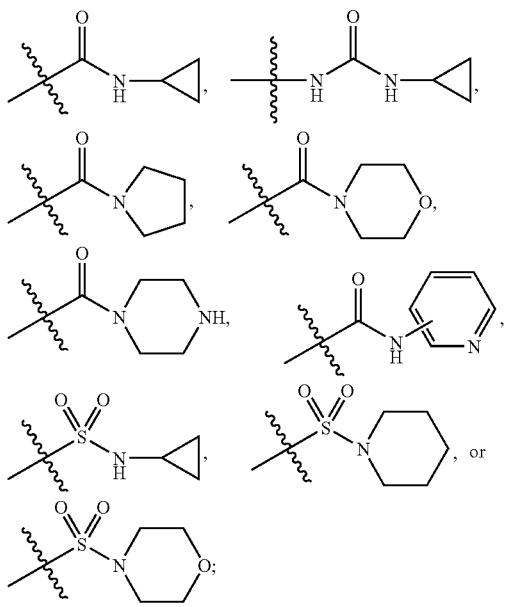

$R^{28}$ is independently:

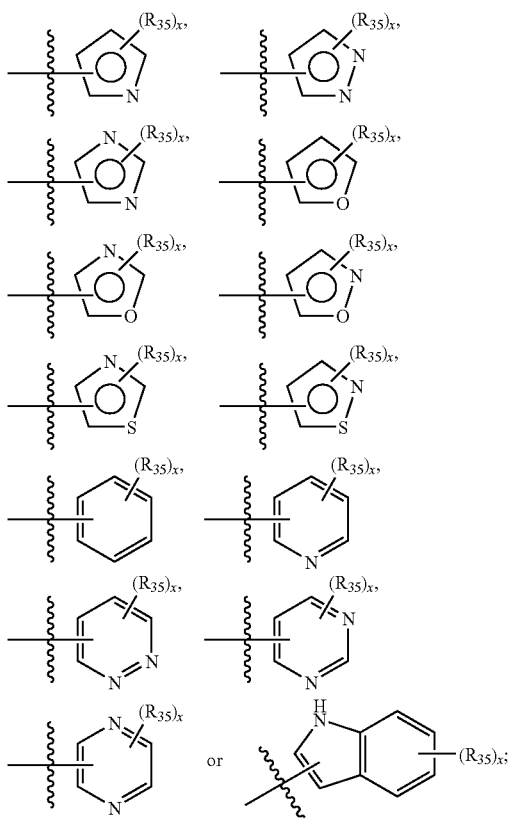

x is independently an integer from 0 to 6; and
$R^{35}$ is independently hydrogen, halogen, nitro, cyano, hydroxyl, $(C_1\text{-}C_6)$alkyl, cyclo$(C_3\text{-}C_{10})$alkyl, perfluoro$(C_1\text{-}C_6)$alkyl, —$(CH_2)_j$CN, —$(CH_2)_j$O$(C_1\text{-}C_6)$alkyl, —$(CH_2)_j$C(O)$(C_1\text{-}C_6)$alkyl, —$(CH_2)_j$C(O)O$(C_1\text{-}C_6)$alkyl, —$(CH_2)_j$NH$_2$, —$(CH_2)_j$NH$(C_1\text{-}C_6)$alkyl, —$(CH_2)_j$N$((C_1\text{-}C_6)$alkyl$)_2$, —$(CH_2)_j$C(O)NH$_2$, —$(CH_2)_j$C(O)NH$(C_1\text{-}C_6)$alkyl), —$(CH_2)_j$C(O)N$((C_1\text{-}C_6)$alkyl$)_2$, —$(CH_2)_j$OC(O)NH$_2$, —$(CH_2)_j$OC(O)NH$(C_1\text{-}C_6)$alkyl), —$(CH_2)_j$OC(O)N$((C_1\text{-}C_6)$-alkyl$)_2$, —$(CH_2)_j$NHC(O)$(C_1\text{-}C_6)$alkyl, —$(CH_2)_j$N$((C_1\text{-}C_6)$alkyl)C(O)$(C_1\text{-}C_6)$alkyl, —$(CH_2)_j$NHC(O)O$(C_1\text{-}C_6)$alkyl, —$(CH_2)_j$N$((C_1\text{-}C_6)$alkyl)C(O)O$(C_1\text{-}C_6)$alkyl, —$(CH_2)_j$NHC(O)NH$_2$, —$(CH_2)_j$NHC(O)NH$(C_1\text{-}C_6)$alkyl), —$(CH_2)_j$NHC(O)N$((C_1\text{-}C_6)$alkyl$)_2$, —$(CH_2)_j$N$((C_1\text{-}C_6)$alkyl)C(O)NH$(C_1\text{-}C_6)$alkyl, —$(CH_2)_j$N$((C_1\text{-}C_6)$alkyl)C(O)N$((C_1\text{-}C_6)$alkyl$)_2$, —$(CH_2)_j$S(O)$_m(C_1\text{-}C_6)$alkyl, —$(CH_2)_j$S(O)$_2$NH$_2$, —$(CH_2)_j$S(O)$_2$NH$(C_1\text{-}C_6)$alkyl), —$(CH_2)_j$S(O)$_2$N$((C_1\text{-}C_6)$alkyl$)_2$, —$(CH_2)_j$NHS(O)$_2(C_1\text{-}C_6)$alkyl, —$(CH_2)_j$N$((C_1\text{-}C_6)$alkyl)-S(O)$_2(C_1\text{-}C_6)$alkyl,

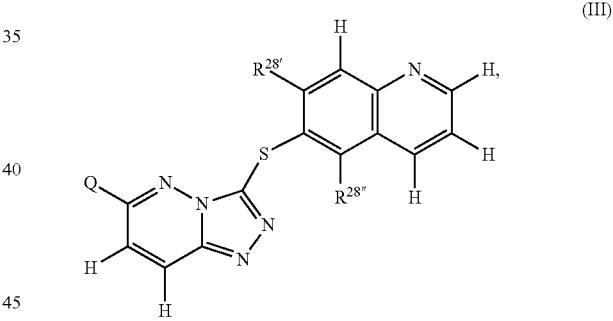

In another aspect, the disclosure provides compounds having formula III:

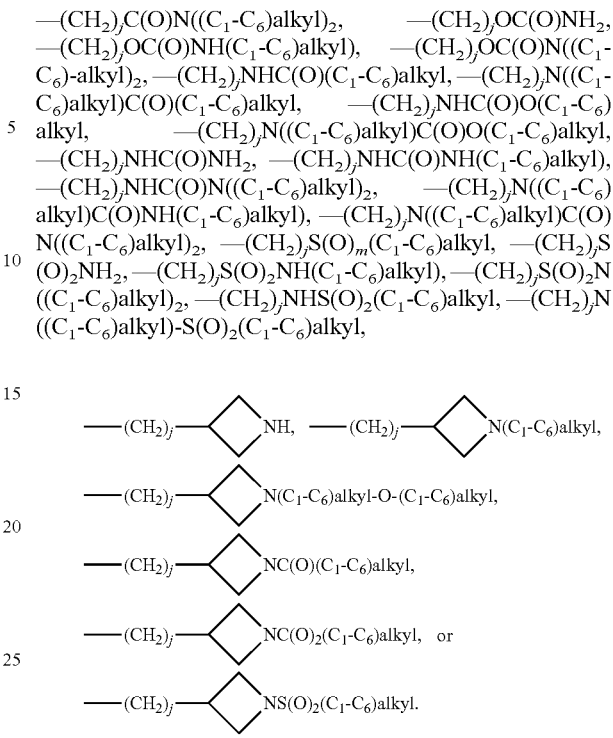

(III)

wherein:

Q is independently hydrogen, halogen, substituted or unsubstituted alkyl, perfluoroalkyl, amino, substituted or unsubstituted aminomonoalkyl, substituted or unsubstituted aminodialkyl, substituted or unsubstituted phenyl, substituted or unsubstituted phenoxy, substituted or unsubstituted piperidinyl, substituted or unsubstituted piperazinyl, substituted or unsubstituted pyrrolidinyl, substituted or unsubstituted morpholinyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, substituted or unsubstituted —O-pyridinyl, substituted or unsubstituted isoxazolyl, substituted or unsubstituted isothiazolyl, or substituted or unsubstituted triazolyl;

$R^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, —(CH$_2$)$_j$CN, —(CH$_2$)$_j$OR$^{23}$, —(CH$_2$)$_j$C(O)R$^{23}$, —(CH$_2$)$_j$C(O)OR$^{23}$, —(CH$_2$)$_j$NR$^{24}$R$^{25}$, —(CH$_2$)$_j$C(O)NR$^{24}$R$^{25}$, —(CH$_2$)$_j$OC(O)NR$^{24}$R$^{25}$, —(CH$_2$)$_j$NR$^{26}$C(O)R$^{23}$, —(CH$_2$)$_j$NR$^{26}$C(O)OR$^{23}$, —(CH$_2$)$_j$NR$^{26}$C(O)NR$^{24}$R$^{25}$, —(CH$_2$)$_j$S(O)$_m$R$^{27}$, —(CH$_2$)$_j$S(O)$_2$NR$^{24}$R$^{25}$, or —(CH$_2$)$_j$NR$^{26}$S(O)$_2$R$^{27}$;

R$^{28'}$ and R$^{28''}$ are each independently hydrogen, halogen, nitro, cyano, hydroxyl, substituted or unsubstituted alkyl, substituted or unsubstituted cycloalkyl, perfluoroalkyl, substituted or unsubstituted alkoxy, amino, aminomonoalkyl, or aminodialkyl, wherein R$^{28'}$ and R$^{28''}$ are each optionally independently substituted with 1 to 3 R$^{35}$; and R$^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted azetidinyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, —(CH$_2$)$_j$CN, —(CH$_2$)$_j$OR$^{30}$, —(CH$_2$)$_j$C(O)R$^{30}$, —(CH$_2$)$_j$C(O)OR$^{30}$, —(CH$_2$)$_j$NR$^{31}$R$^{32}$, —(CH$_2$)$_j$C(O)NR$^{31}$R$^{32}$, —(CH$_2$)$_j$OC(O)NR$^{31}$R$^{32}$, —(CH$_2$)$_j$NR$^{33}$C(O)R$^{30}$, —(CH$_2$)$_j$NR$^{33}$C(O)OR$^{30}$, —(CH$_2$)$_j$NR$^{33}$C(O)NR$^{31}$R$^{32}$, —(CH$_2$)$_j$S(O)$_m$R$^{34}$, —(CH$_2$)$_j$S(O)$_2$NR$^{31}$R$^{32}$, or —(CH$_2$)$_j$NR$^{33}$S(O)$_2$R$^{34}$.

In another aspect, the disclosure provides compounds having formula III, wherein:

Q is independently hydrogen, halogen, substituted or unsubstituted alkyl, perfluoroalkyl, amino, substituted or unsubstituted aminomonoalkyl, substituted or unsubstituted aminodialkyl, substituted or unsubstituted phenyl, substituted or unsubstituted phenoxy, substituted or unsubstituted piperidinyl, substituted or unsubstituted piperazinyl, substituted or unsubstituted pyrrolidinyl, substituted or unsubstituted morpholinyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, or substituted or unsubstituted —O-pyridinyl;

R$^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, —(CH$_2$)$_j$CN, —(CH$_2$)$_j$OR$^{23}$, —(CH$_2$)$_j$C(O)R$^{23}$, —(CH$_2$)$_j$C(O)OR$^{23}$, —(CH$_2$)$_j$NR$^{24}$R$^{25}$, —(CH$_2$)$_j$C(O)NR$^{24}$R$^{25}$, —(CH$_2$)$_j$OC(O)NR$^{24}$R$^{25}$, —(CH$_2$)$_j$NR$^{26}$C(O)R$^{23}$, —(CH$_2$)$_j$NR$^{26}$C(O)OR$^{23}$, —(CH$_2$)$_j$NR$^{26}$C(O)NR$^{24}$R$^{25}$, —(CH$_2$)$_j$S(O)$_m$R$^{27}$, —(CH$_2$)$_j$S(O)$_2$NR$^{24}$R$^{25}$, or —(CH$_2$)$_j$NR$^{26}$S(O)$_2$R$^{27}$;

R$^{28'}$ and R$^{28''}$ are each independently hydrogen, halogen, cyano, hydroxyl, substituted or unsubstituted alkyl, or perfluoroalkyl; and R$^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, —(CH$_2$)$_j$CN, —(CH$_2$)$_j$OR$^{30}$, —(CH$_2$)$_j$C(O)R$^{30}$, —(CH$_2$)$_j$C(O)OR$^{30}$, —(CH$_2$)$_j$NR$^{31}$R$^{32}$, —(CH$_2$)$_j$C(O)NR$^{31}$R$^{32}$, —(CH$_2$)$_j$OC(O)NR$^{31}$R$^{32}$, (CH$_2$)$_j$NR$^{33}$C(O)R$^{30}$, —(CH$_2$)$_j$NR$^{33}$C(O)OR$^{30}$, —(CH$_2$)$_j$NR$^{33}$C(O)NR$^{31}$R$^{32}$, —(CH$_2$)$_j$S(O)$_m$R$^{34}$, —(CH$_2$)$_j$S(O)$_2$NR$^{31}$R$^{32}$, —(CH$_2$)$_j$NR$^{33}$S(O)$_2$R$^{34}$,

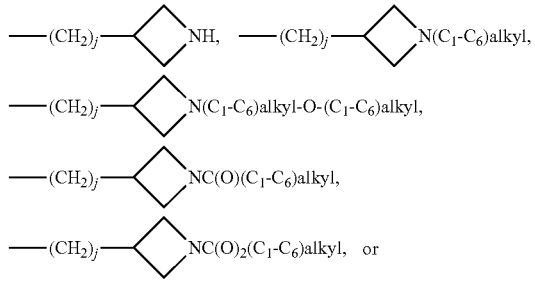

-continued

In another aspect, the disclosure provides compounds having formula III, wherein:

Q is independently hydrogen, chloro, substituted or unsubstituted alkyl, perfluoroalkyl, —$NH_2$, —$NH(C_1-C_6)$alkyl or —$N[(C_1-C_6)$alkyl$]_2$,

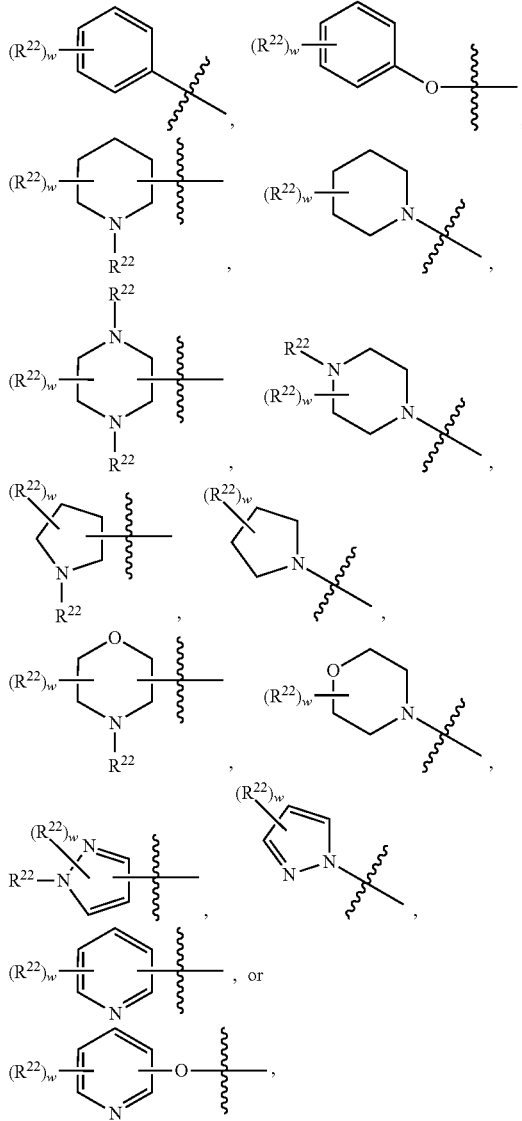

wherein each alkyl is optionally independently substituted with 1 to 3 $R^{22}$, and wherein w is independently an integer from 0 to 3; or wherein two $R^{22}$ optionally form a cyclic structure with —$OCH_2CH_2O$—;

$R^{22}$ is independently —H, —F, Cl, Br, I, —$(C_1-C_6)$alkyl, —$(CH_2)_j$CN, —$(CH_2)_j$O$(C_1-C_6)$-alkyl, —$(CH_2)_j$OH, —$(CH_2)_j$C(O)$(C_1-C_6)$alkyl, —$(CH_2)_j$NH$_2$, —$(CH_2)_j$NH$(C_1-C_6)$alkyl, —$(CH_2)_j$N$((C_1-C_6)$alkyl$)_2$, —$(CH_2)_j$C(O)NH$_2$, —$(CH_2)_j$C(O)NH$(C_1-C_6)$alkyl, —C(O)N$((C_1-C_6)$-alkyl$)_2$, —$(CH_2)_j$NHC(O)$(C_1-C_6)$alkyl, —$(CH_2)_j$NHSO$_2$$(C_1-C_6)$alkyl, —$(CH_2)_j$NHSO$_2$$(C_1-C_6)$-alkyl, —$(CH_2)_j$SO$_2$CH$_3$, —$(CH_2)_j$SO$_2$NH$_2$, —$(CH_2)_j$SO$_2$NH$(C_1-C_6)$-alkyl, —$(CH_2)_j$SO$_2$N$((C_1-C_6)$-alkyl$)_2$, —$(CH_2)_j$SO$_2$NH$(C_1-C_6)$alkyl(OH), phenyl,

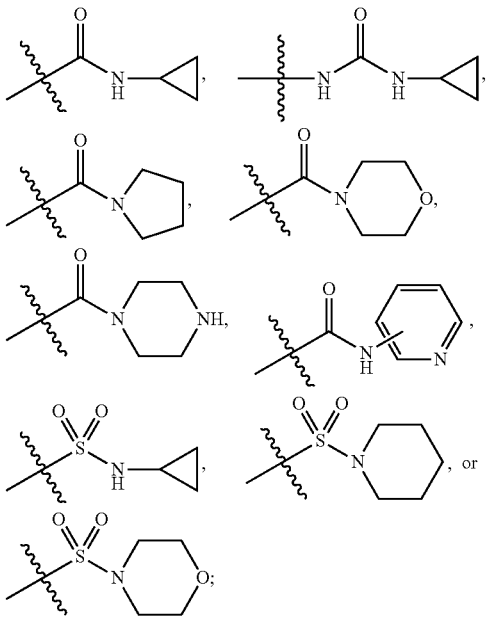

$R^{28'}$ and $R^{28''}$ are each independently hydrogen, halogen, hydroxyl, alkyl, or perfluoroalkyl; and $R^{35}$ is independently hydrogen, halogen, nitro, cyano, hydroxyl, $(C_1-C_6)$alkyl, cyclo$(C_3-C_{10})$alkyl, perfluoro$(C_1-C_6)$alkyl, —$(CH_2)_j$CN, —$(CH_2)_j$O$(C_1-C_6)$alkyl, —$(CH_2)_j$C(O)$(C_1-C_6)$alkyl, —$(CH_2)_j$C(O)O$(C_1-C_6)$alkyl, —$(CH_2)_j$NH$_2$, —$(CH_2)_j$NH$(C_1-C_6)$alkyl), —$(CH_2)_j$N$((C_1-C_6)$alkyl$)_2$, —$(CH_2)_j$C(O)NH$_2$, —$(CH_2)_j$C(O)NH$(C_1-C_6)$alkyl), —$(CH_2)_j$C(O)N—$((C_1-C_6)$alkyl$)_2$, —$(CH_2)_j$OC(O)NH$_2$, —$(CH_2)_j$OC(O)NH$(C_1-C_6)$alkyl), —$(CH_2)_j$OC(O)N$((C_1-C_6)$-alkyl$)_2$, —$(CH_2)_j$NHC(O)$(C_1-C_6)$alkyl, —$(CH_2)_j$N$((C_1-C_6)$alkyl)C(O)O$(C_1-C_6)$alkyl, —$(CH_2)_j$NHC(O)O$(C_1-C_6)$alkyl, —$(CH_2)_j$N$((C_1-C_6)$alkyl)C(O)O$(C_1-C_6)$alkyl, —$(CH_2)_j$NHC(O)NH$_2$, —$(CH_2)_j$NHC(O)NH$(C_1-C_6)$alkyl), —$(CH_2)_j$NHC(O)N$((C_1-C_6)$alkyl$)_2$, —$(CH_2)_j$N$((C_1-C_6)$alkyl)C(O)NH$(C_1-C_6)$alkyl), —$(CH_2)_j$N$((C_1-C_6)$alkyl)C(O)N$((C_1-C_6)$alkyl$)_2$, —$(CH_2)_j$S(O)$_m$$(C_1-C_6)$alkyl, —$(CH_2)_j$S(O)$_2$NH$_2$, —$(CH_2)_j$S(O)$_2$NH$(C_1-C_6)$alkyl), —$(CH_2)_j$S(O)$_2$N$((C_1-C_6)$alkyl$)_2$, —$(CH_2)_j$NHS(O)$_2$$(C_1-C_6)$alkyl, —$(CH_2)_j$N$((C_1-C_6)$-alkyl)S(O)$_2$$(C_1-C_6)$alkyl,

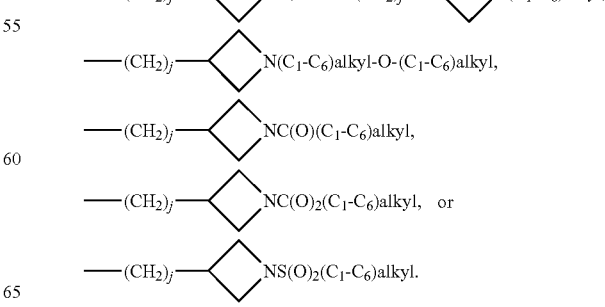

In another aspect, the disclosure provides compounds having formula III, wherein:

Q is independently —NH$_2$, —NH(C$_1$-C$_6$)alkyl or —N[(C$_1$-C$_6$)alkyl]$_2$,

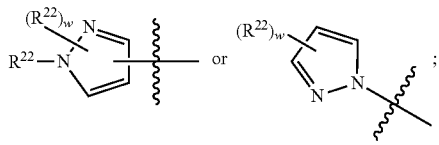

R$^{28'}$ and R$^{28''}$ are each independently hydrogen, halogen, hydroxyl, (C$_1$-C$_6$)alkyl, or trifluoromethyl; and R$^{35}$ is independently hydrogen, halogen, cyano, hydroxyl, (C$_1$-C$_6$)alkyl, trifluoromethyl,

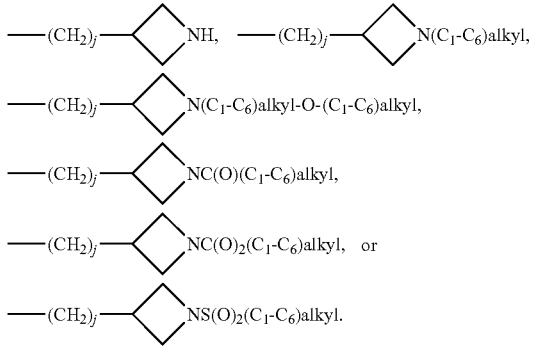

In another aspect, the disclosure provides compounds having formula IV:

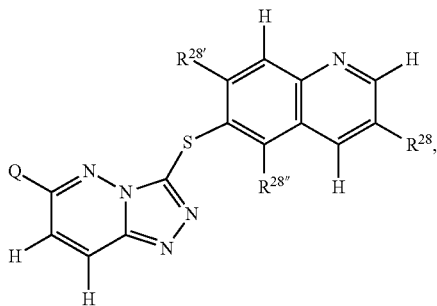

(IV)

wherein:

Q is independently hydrogen, halogen, substituted or unsubstituted alkyl, perfluoroalkyl, amino, substituted or unsubstituted aminomonoalkyl, substituted or unsubstituted aminodialkyl, substituted or unsubstituted phenyl, substituted or unsubstituted phenoxy, substituted or unsubstituted piperidinyl, substituted or unsubstituted piperazinyl, substituted or unsubstituted pyrrolidinyl, substituted or unsubstituted morpholinyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, substituted or unsubstituted —O-pyridinyl, substituted or unsubstituted isoxazolyl, substituted or unsubstituted isothiazolyl, or substituted or unsubstituted triazolyl;

R$^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, —(CH$_2$)$_j$CN, —(CH$_2$)$_j$OR$^{23}$, —(CH$_2$)$_j$C(O)R$^{23}$, —(CH$_2$)$_j$C(O)OR$^{23}$, —(CH$_2$)$_j$NR$^{24}$R$^{25}$, —(CH$_2$)$_j$C(O)NR$^{24}$R$^{25}$, —(CH$_2$)$_j$OC(O)NR$^{24}$R$^{25}$, —(CH$_2$)$_j$NR$^{26}$C(O)R$^{23}$, —(CH$_2$)$_j$NR$^{26}$C(O)OR$^{23}$, —(CH$_2$)$_j$NR$^{26}$C(O)NR$^{24}$R$^{25}$, —(CH$_2$)$_j$S(O)$_m$R$^{27}$, —(CH$_2$)$_j$S(O)$_2$NR$^{24}$R$^{25}$, or —(CH$_2$)$_j$NR$^{26}$S(O)$_2$R$^{27}$;

R$^{28}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, —(CH$_2$)$_j$CN, —(CH$_2$)$_j$OR$^{30}$, —(CH$_2$)$_j$C(O)R$^{30}$, —(CH$_2$)$_j$C(O)OR$^{30}$, —(CH$_2$)$_j$NR$^{31}$R$^{32}$, —(CH$_2$)$_j$C(O)NR$^{31}$R$^{32}$, —(CH$_2$)$_j$OC(O)NR$^{31}$R$^{32}$, —(CH$_2$)$_j$NR$^{33}$C(O)R$^{30}$, —(CH$_2$)$_j$NR$^{33}$C(O)OR$^{30}$, —(CH$_2$)$_j$NR$^{33}$C(O)NR$^{31}$R$^{32}$, —(CH$_2$)$_j$S(O)$_m$R$^{34}$, —(CH$_2$)$_j$S(O)$_2$NR$^{31}$R$^{32}$, or —(CH$_2$)$_j$NR$^{33}$S(O)$_2$R$^{34}$;

R$^{28'}$ and R$^{28''}$ are each independently hydrogen, halogen, nitro, cyano, hydroxyl, substituted or unsubstituted alkyl, substituted or unsubstituted cycloalkyl, or perfluoroalkyl, wherein R$^{28}$, R$^{28'}$, and R$^{28''}$ are each optionally independently substituted with 1 to 3 R$^{35}$; and R$^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted azetidinyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl, —(CH$_2$)$_j$CN, —(CH$_2$)$_j$OR$^{30}$, —(CH$_2$)$_j$C(O)R$^{30}$, —(CH$_2$)$_j$C(O)OR$^{30}$, —(CH$_2$)$_j$NR$^{31}$R$^{32}$, —(CH$_2$)$_j$C(O)NR$^{31}$R$^{32}$, (CH$_2$)$_j$OC(O)NR$^{31}$R$^{32}$, (CH$_2$)$_j$NR$^{33}$C(O)R$^{30}$, —(CH$_2$)$_j$NR$^{33}$C(O)OR$^{30}$, —(CH$_2$)$_j$NR$^{33}$C(O)NR$^{31}$R$^{32}$, —(CH$_2$)$_j$S(O)$_m$R$^{34}$, —(CH$_2$)$_j$S(O)$_2$NR$^{31}$R$^{32}$, or —(CH$_2$)$_j$NR$^{33}$S(O)$_2$R$^{34}$.

In another aspect, the disclosure provides compounds having formula IV, wherein:

Q is independently hydrogen, halogen, substituted or unsubstituted alkyl, perfluoroalkyl, amino, substituted or unsubstituted aminomonoalkyl, substituted or unsubstituted aminodialkyl, substituted or unsubstituted phenyl, substituted or unsubstituted phenoxy, substituted or unsubstituted piperidinyl, substituted or unsubstituted piperazinyl, substituted or unsubstituted pyrrolidinyl, substituted or unsubstituted morpholinyl, substituted or unsubstituted pyrrolyl, substituted or unsubstituted furyl, substituted or unsubstituted thienyl, substituted or unsubstituted oxazolyl, substituted or unsubstituted thiazolyl, substituted or unsubstituted imidazolyl, substituted or unsubstituted pyrazolyl, substituted or unsubstituted pyridinyl, or substituted or unsubstituted —O-pyridinyl;

R$^{22}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, —(CH$_2$)$_j$CN, —(CH$_2$)$_j$OR$^{23}$, —(CH$_2$)$_j$C(O)R$^{23}$, —(CH$_2$)$_j$C(O)OR$^{23}$, —(CH$_2$)$_j$NR$^{24}$R$^{25}$, —(CH$_2$)$_j$C(O)NR$^{24}$R$^{25}$, —(CH$_2$)$_j$OC(O)NR$^{24}$R$^{25}$, —(CH$_2$)$_j$NR$^{26}$C(O)R$^{23}$, —(CH$_2$)$_j$NR$^{26}$C(O)OR$^{23}$, —(CH$_2$)$_j$NR$^{26}$C(O)NR$^{24}$R$^{25}$, —(CH$_2$)$_j$S(O)$_m$R$^{27}$, —(CH$_2$)$_j$S(O)$_2$NR$^{24}$R$^{25}$, or —(CH$_2$)$_j$NR$^{26}$S(O)$_2$R$^{27}$;

R$^{28}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, substituted or unsubstituted phenyl, substituted or unsubstituted naphthyl, substituted or unsubstituted biphenyl, substituted or unsubstituted pyrrolyl, substituted or unsubstituted imidazolyl, substituted or unsubstituted pyrazolyl, substituted or unsubstituted furyl, substituted or unsubstituted thienyl, substituted or unsubstituted oxazolyl, substituted or unsubstituted isooxazolyl, substituted or unsubstituted thiazolyl, substituted or unsubstituted pyridinyl, substituted or unsubstituted pyrazinyl, substituted or unsubstituted pyrimidinyl, substituted or unsubstituted benzothiazolyl, substituted or unsubstituted purinyl, substituted or unsubstituted benzimidazolyl, substituted or unsubstituted indolyl, substituted or unsubstituted isoquinolinyl, substituted or unsubstituted quinoxalinyl, substituted or unsubstituted quinolinyl, substituted or unsubstituted benzooxazolyl, substituted or unsubstituted [1,5]naphthyridinyl, substituted or unsubstituted pyrido[3,2-d]pyrimidinyl, substituted or unsubstituted [1,7]naphthyridinyl, substituted or unsubstituted 1H-pyrrolo[2,3-b]pyridinyl, substituted or unsubstituted pyrazolo[4,3-b]pyridinyl, substituted or unsubstituted pyrrolo[2,3-b]pyridinyl, substituted or unsubstituted thieno[2,3-b]pyridinyl, substituted or unsubstituted thiazolo[5,4-b]pyridinyl, substituted or unsubstituted pyridinyl-2-one, substituted or unsubstituted imidazo[1,2-b]pyridazinyl, substituted or unsubstituted pyrazolo[1,5-a]pyrimidinyl, substituted or unsubstituted pyridazinyl-3-one, substituted or unsubstituted imidazo[2,1-b][1,3,4]thiaciazolyl, substituted or unsubstituted imidazo[2,1-b]thiazolyl, or substituted or unsubstituted imidazo[4,5-b]pyridinyl;

R$^{28'}$ and R$^{28''}$ are each independently hydrogen, halogen, cyano, hydroxyl, substituted or unsubstituted alkyl, or perfluoroalkyl; and R$^{35}$ is independently hydrogen, halogen, nitro, cyano, hydroxyl, substituted or unsubstituted alkyl, substituted or unsubstituted cycloalkyl, perfluoroalkyl, substituted or unsubstituted heteroalkyl, substituted or unsubstituted heterocycloalkyl, —(CH$_2$)$_j$CN, —(CH$_2$)$_j$OR$^{30}$, —(CH$_2$)$_j$C(O)R$^{30}$, —(CH$_2$)$_j$C(O)OR$^{30}$, —(CH$_2$)$_j$NR$^{31}$R$^{32}$, —(CH$_2$)$_j$C(O)NR$^{31}$R$^{32}$, —(CH$_2$)$_j$OC(O)NR$^{31}$R$^{32}$, —(CH$_2$)$_j$NR$^{33}$C(O)R$^{30}$, —(CH$_2$)$_j$NR$^{33}$C(O)OR$^{30}$, —(CH$_2$)$_j$NR$^{33}$C(O)NR$^{31}$R$^{32}$, —(CH$_2$)$_j$S(O)$_m$R$^{34}$, —(CH$_2$)$_j$S(O)$_2$NR$^{31}$R$^{32}$, —(CH$_2$)$_j$NR$^{33}$S(O)$_2$R$^{34}$,

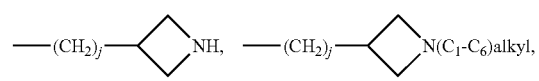

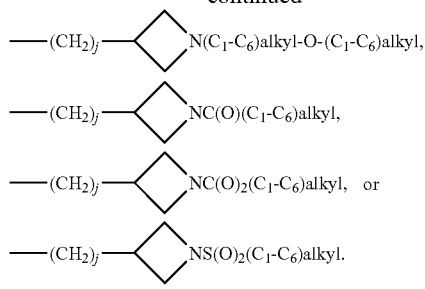

In another aspect, the disclosure provides compounds having formula IV, wherein:

Q is independently hydrogen, chloro, substituted or unsubstituted alkyl, perfluoroalkyl, —$NH_2$, —$NH(C_1$-$C_6)$alkyl or —$N[(C_1$-$C_6)$alkyl$]_2$,

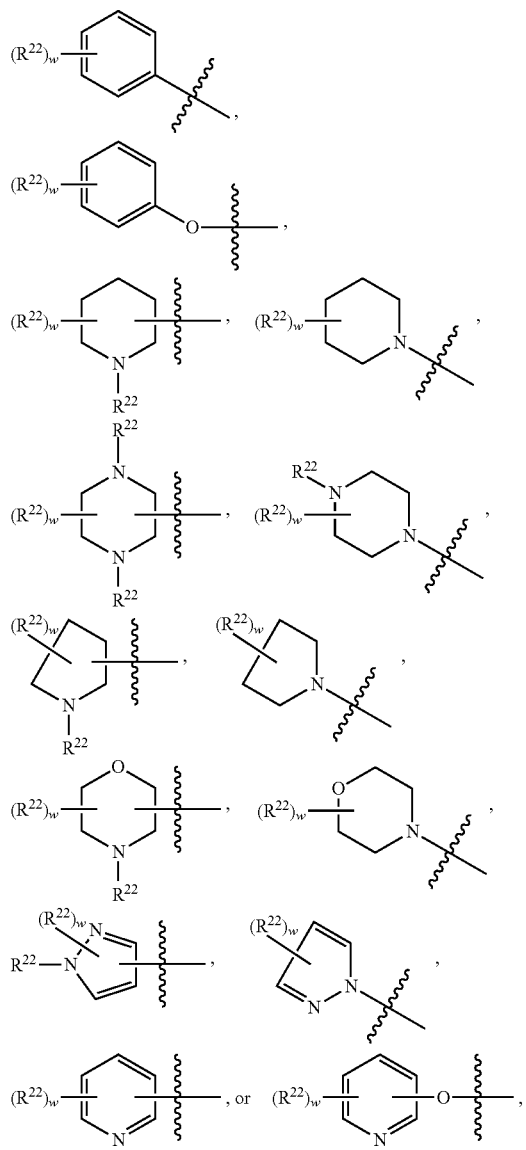

wherein each alkyl is optionally independently substituted with 1 to 3 $R^{22}$, and wherein w is independently an integer from 0 to 3; or wherein two $R^{22}$ optionally form a cyclic structure with —$O(CH_2CH_2)O$—;

$R^{22}$ is independently —H, —F, Cl, Br, I, —$(C_1$-$C_6)$alkyl, —$(CH_2)_jCN$, —$(CH_2)_jO(C_1$-$C_6)$-alkyl, —$(CH_2)_jOH$, —$(CH_2)_jC(O)(C_1$-$C_6)$alkyl, —$(CH_2)_jNH_2$, —$(CH_2)_jNH(C_1$-$C_6)$alkyl, —$(CH_2)_jN((C_1$-$C_6)$alkyl$)_2$, —$(CH_2)_jC(O)NH_2$, —$(CH_2)_jC(O)NH(C_1$-$C_6)$alkyl, —$C(O)N((C_1$-$C_6)$-alkyl$)_2$, —$(CH_2)_jNHC(O)(C_1$-$C_6)$alkyl, —$(CH_2)_jNHSO_2(C_1$-$C_6)$ alkyl, —$(CH_2)_jNHSO_2(C_1$-$C_6)$-alkyl, —$(CH_2)_jSO_2CH_3$, —$(CH_2)_jSO_2NH_2$, —$(CH_2)_jSO_2NH(C_1$-$C_6)$-alkyl, —$(CH_2)_jSO_2N((C_1$-$C_6)$-alkyl$)_2$, —$(CH_2)_jSO_2NH(C_1$-$C_6)$alkyl$(OH)$, phenyl,

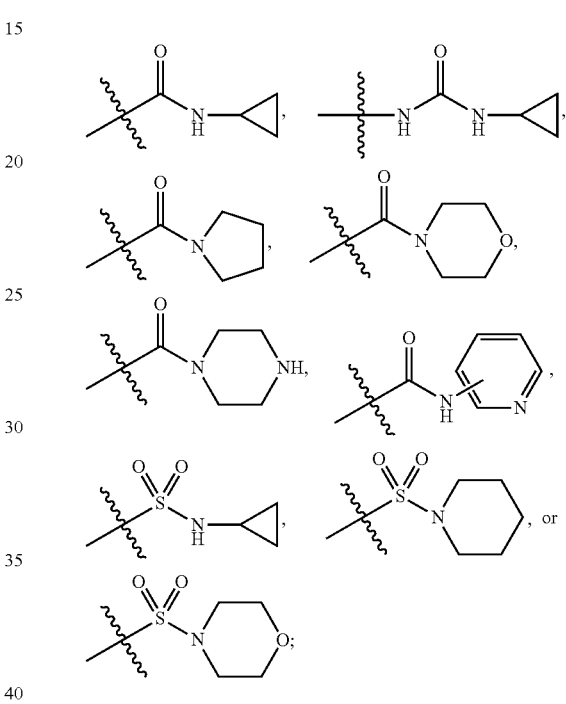

$R^{28}$ is independently hydrogen, halogen, cyano, hydroxyl, $(C_1$-$C_6)$alkyl, or trifluoromethyl;

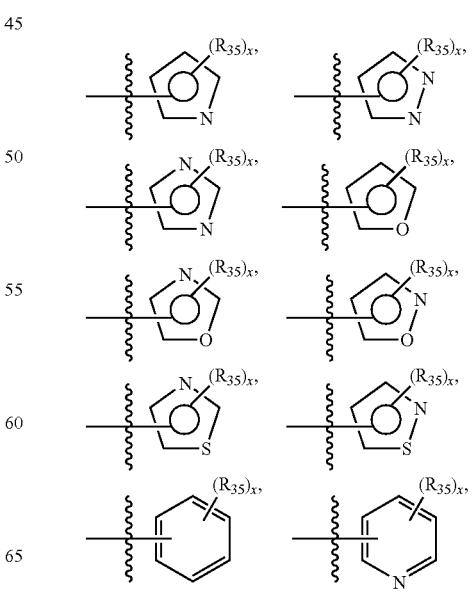

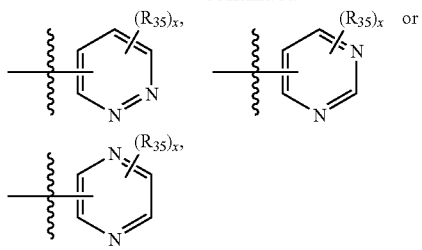 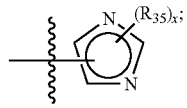

wherein x is independently an integer from 0 to 6;

$R^{28'}$ and $R^{28''}$ are each independently hydrogen, halogen, hydroxyl, alkyl, or perfluoroalkyl; and $R^{35}$ is independently hydrogen, halogen, nitro, cyano, hydroxyl, $(C_1-C_6)$alkyl, cyclo$(C_3-C_{10})$alkyl, perfluoro$(C_1-C_6)$alkyl, —$(CH_2)_j$CN, —$(CH_2)_j$O$(C_1-C_6)$alkyl, —$(CH_2)_j$C(O)$(C_1-C_6)$alkyl, —$(CH_2)_j$C(O)O$(C_1-C_6)$alkyl, —$(CH_2)_j$NH$_2$, —$(CH_2)_j$NH$(C_1-C_6)$alkyl), —$(CH_2)_j$N$((C_1-C_6)$alkyl$)_2$, —$(CH_2)_j$C(O)NH$_2$, —$(CH_2)_j$C(O)NH$(C_1-C_6)$alkyl), —$(CH_2)_j$C(O)N—$((C_1-C_6)$alkyl$)_2$, —$(CH_2)_j$OC(O)NH$_2$, —$(CH_2)_j$OC(O)NH$(C_1-C_6)$alkyl), —$(CH_2)_j$OC(O)N$((C_1-C_6)$-alkyl$)_2$, —$(CH_2)_j$NHC(O)$(C_1-C_6)$alkyl, —$(CH_2)_j$N$((C_1-C_6)$alkyl)C(O)$(C_1-C_6)$alkyl, —$(CH_2)_j$NHC(O)O$(C_1-C_6)$alkyl, —$(CH_2)_j$N$((C_1-C_6)$alkyl)C(O)O$(C_1-C_6)$alkyl, —$(CH_2)_n$NHC(O)NH$_2$, —$(CH_2)_j$NHC(O)NH$(C_1-C_6)$alkyl), —$(CH_2)_j$NHC(O)N$((C_1-C_6)$alkyl$)_2$, —$(CH_2)_j$N$((C_1-C_6)$alkyl)C(O)NH$(C_1-C_6)$alkyl), —$(CH_2)_j$N$((C_1-C_6)$alkyl)C(O)N$((C_1-C_6)$alkyl$)_2$, —$(CH_2)_j$S(O)$_m(C_1-C_6)$alkyl, —$(CH_2)_j$S(O)$_2$NH$_2$, —$(CH_2)_j$S(O)$_2$NH$(C_1-C_6)$alkyl), —$(CH_2)_j$S(O)$_2$N$((C_1-C_6)$alkyl$)_2$, —$(CH_2)_j$NHS(O)$_2(C_1-C_6)$alkyl, —$(CH_2)_j$N$((C_1-C_6)$-alkyl)S(O)$_2(C_1-C_6)$alkyl,

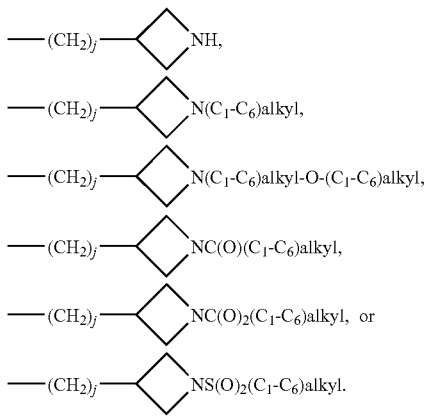

In another aspect, the disclosure provides compounds having formula IV, wherein:

Q is independently substituted or unsubstituted $(C_1-C_6)$ alkyl, —NH$_2$, —NH$(C_1-C_6)$alkyl or —N[$(C_1-C_6)$alkyl]$_2$;

$R^{28}$ is independently

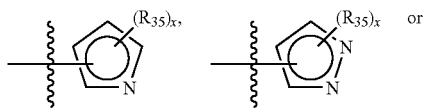

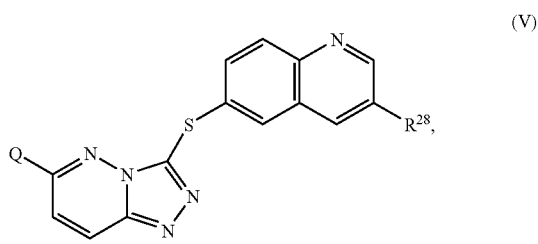

$R^{28'}$ and $R^{28''}$ are each independently hydrogen, halogen, hydroxyl, $(C_1-C_6)$alkyl, or trifluoromethyl; and $R^{35}$ is independently hydrogen, halogen, cyano, hydroxyl, $(C_1-C_6)$alkyl, trifluoromethyl,

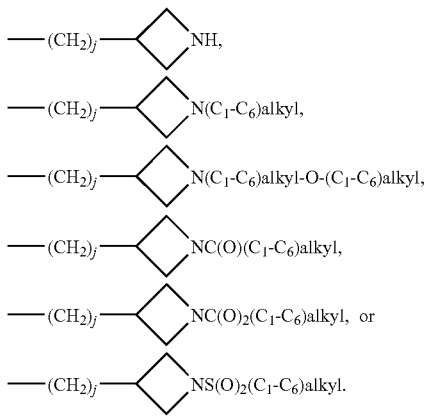

In another aspect, the disclosure provides compounds having formula V:

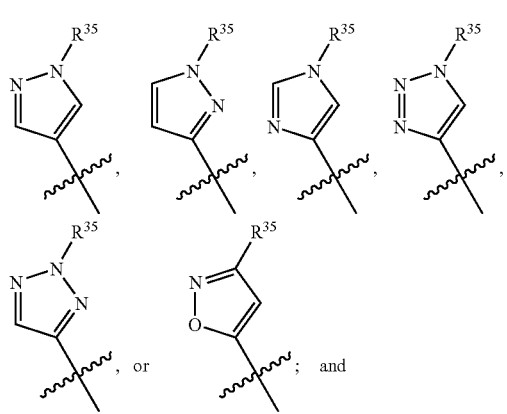

wherein:

Q is methyl, ethyl, cyclopropyl, isopropyl, —NHCH$_3$, or —CH$_2$CF$_3$;

$R^{28}$ is

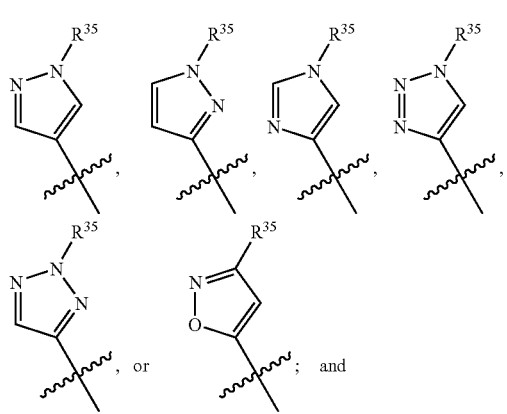

$R^{35}$ is methyl, ethyl, cyclopropyl, or CF$_3$CH$_2$—,

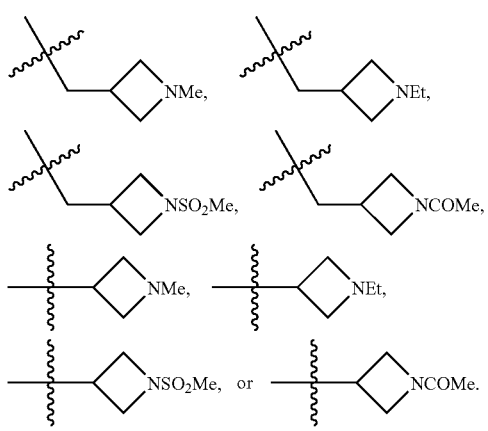
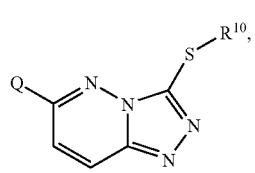
In another aspect, the disclosure provides compounds having formula VI:
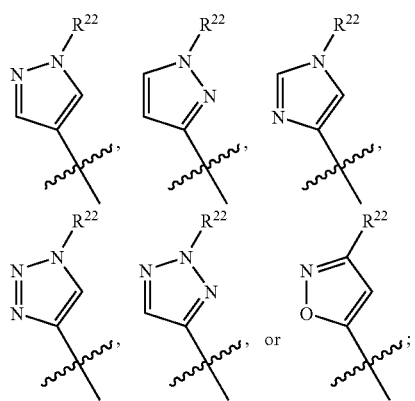
wherein:
Q is
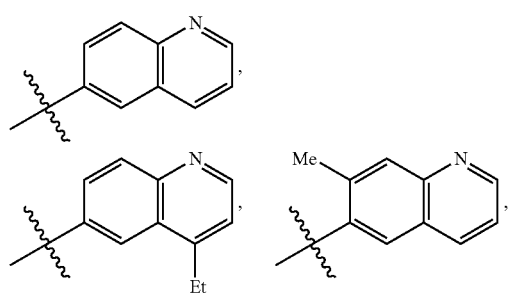
R$^{22}$ is methyl, ethyl, cyclopropyl, or CF$_3$CH$_2$—; and
R$^{10}$ is
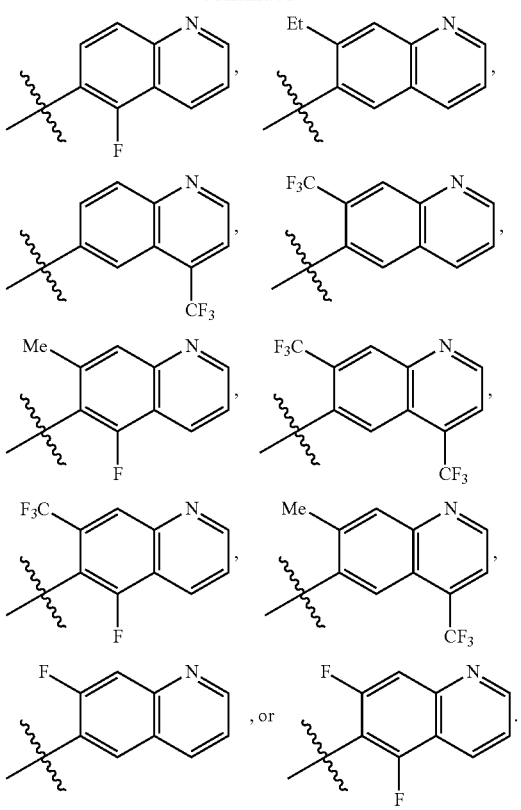
In another aspect, the disclosure provides compounds having formulae:
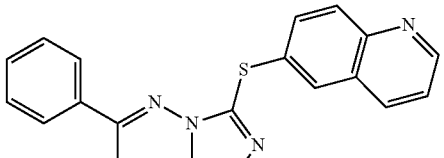
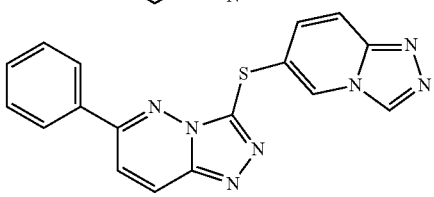
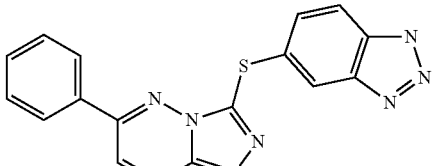
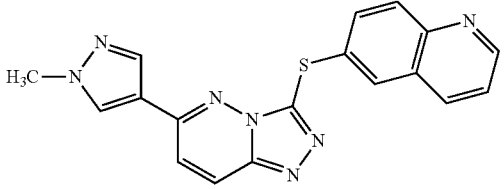

-continued
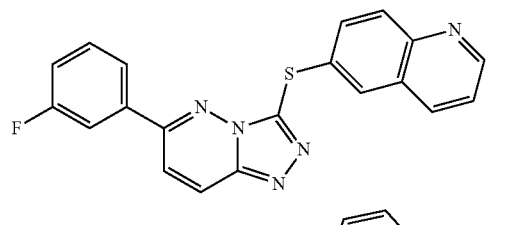
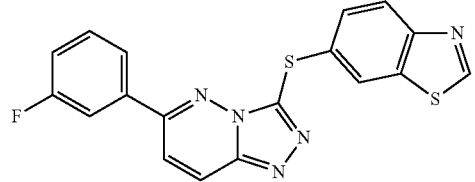
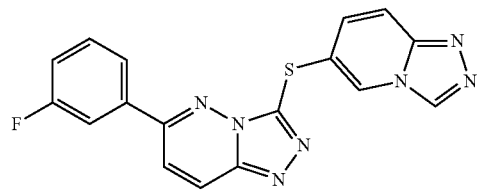
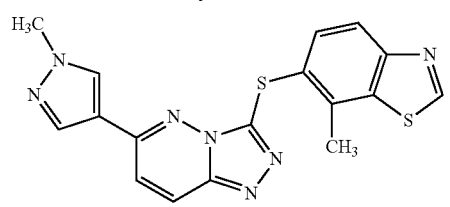
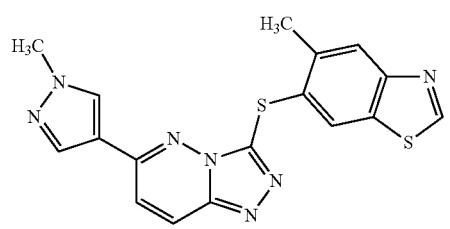
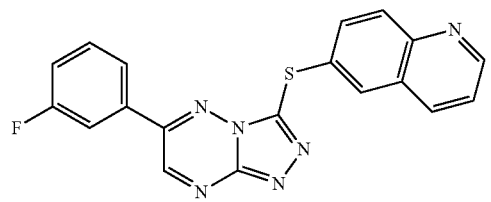
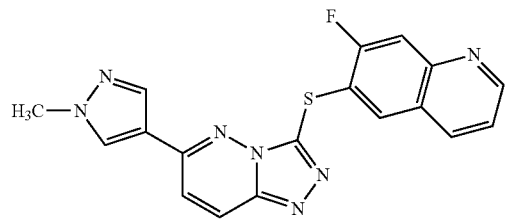
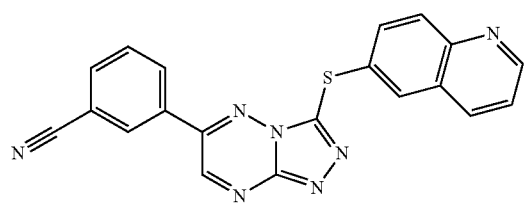
-continued
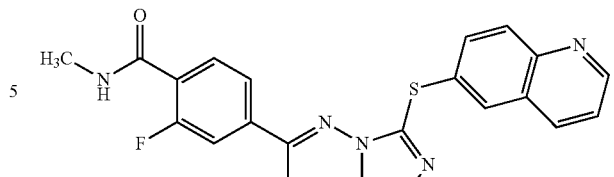
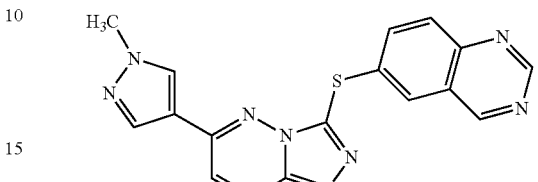
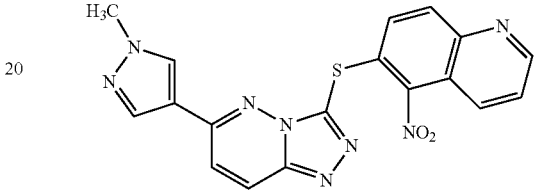
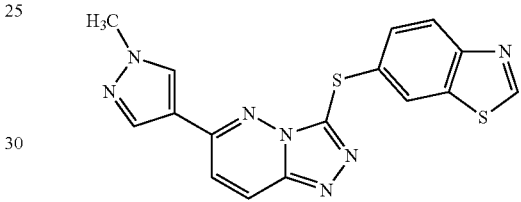
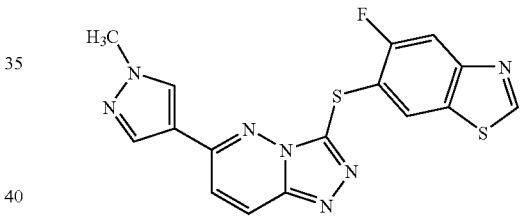
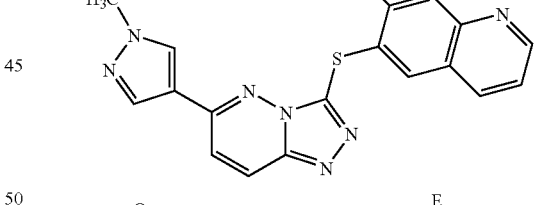
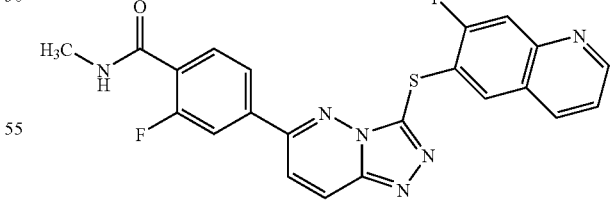
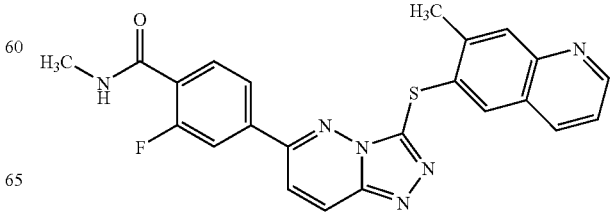

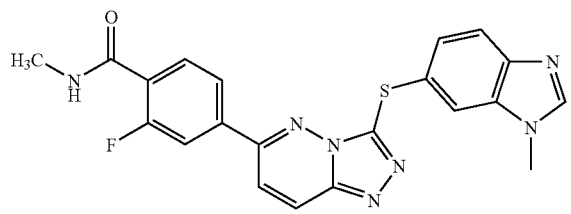
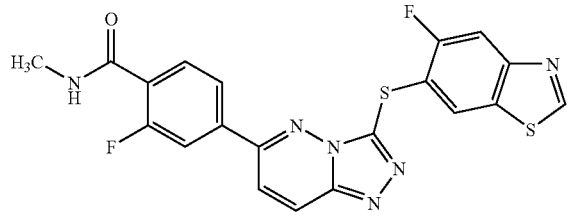
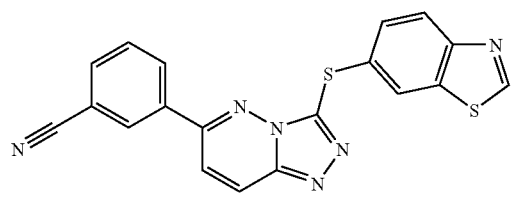
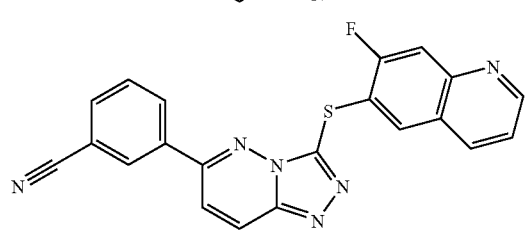
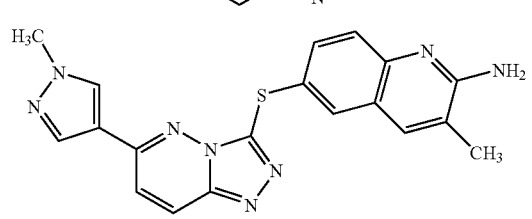
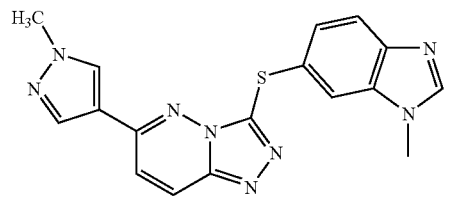
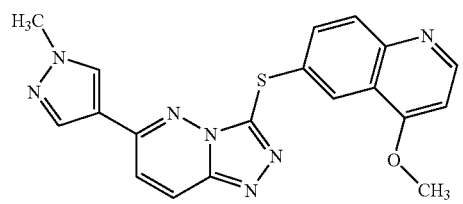
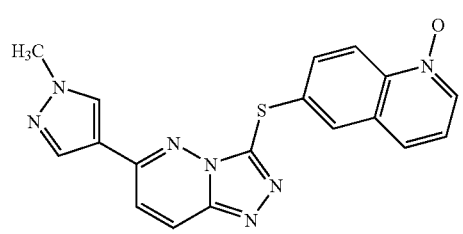
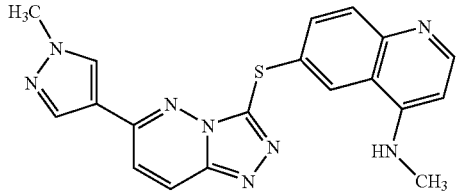
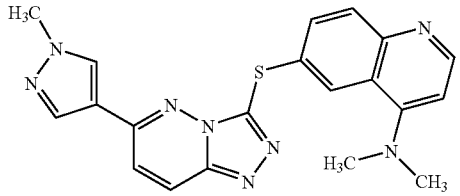
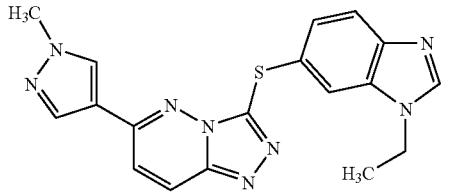
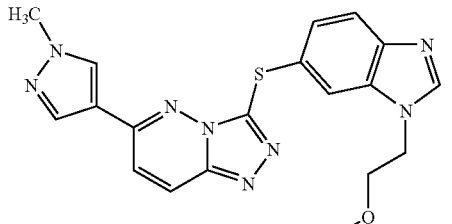
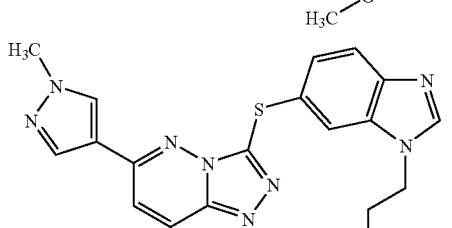
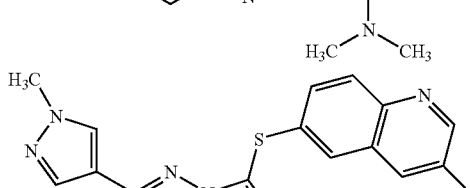
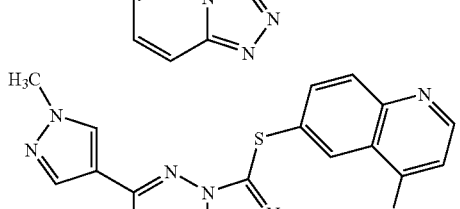
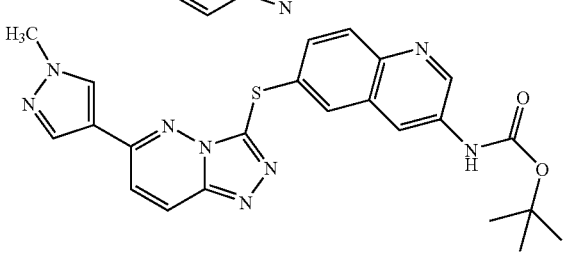

47
-continued
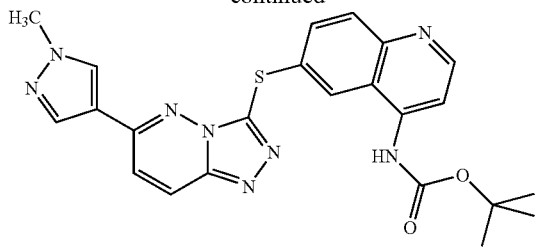
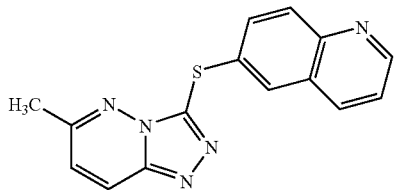
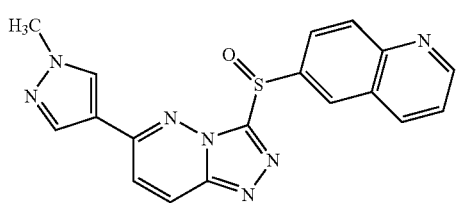
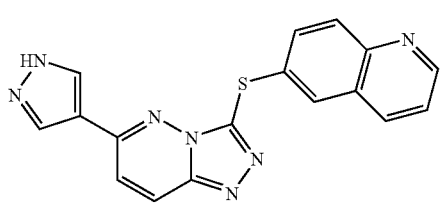
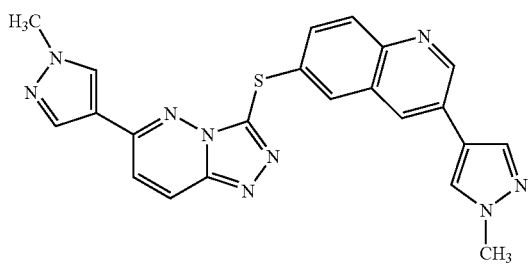
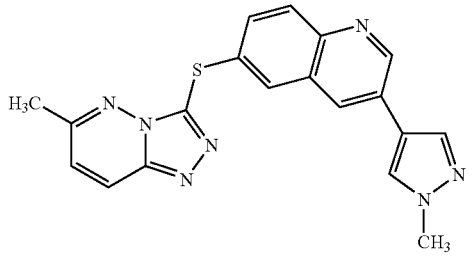
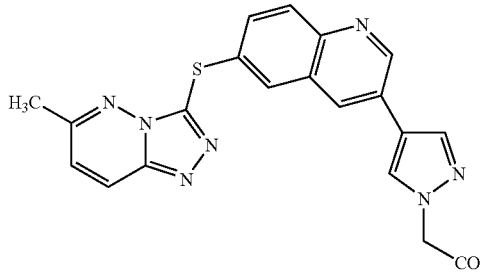
48
-continued
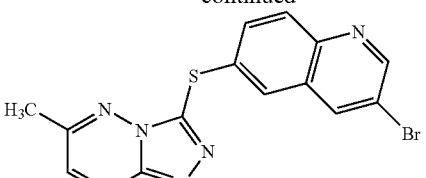
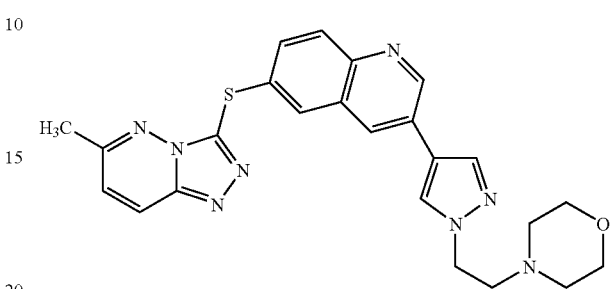
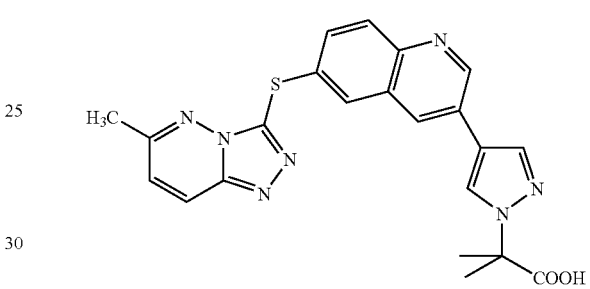
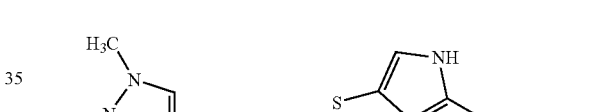
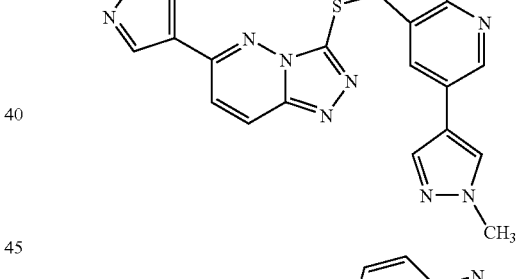
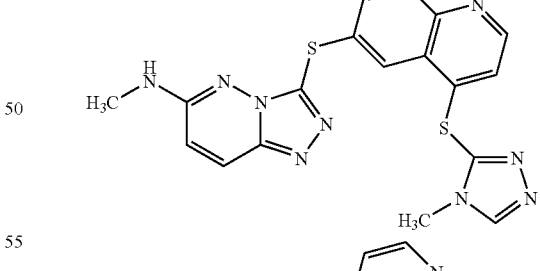
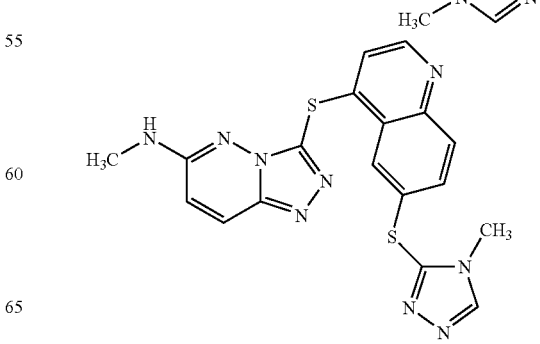

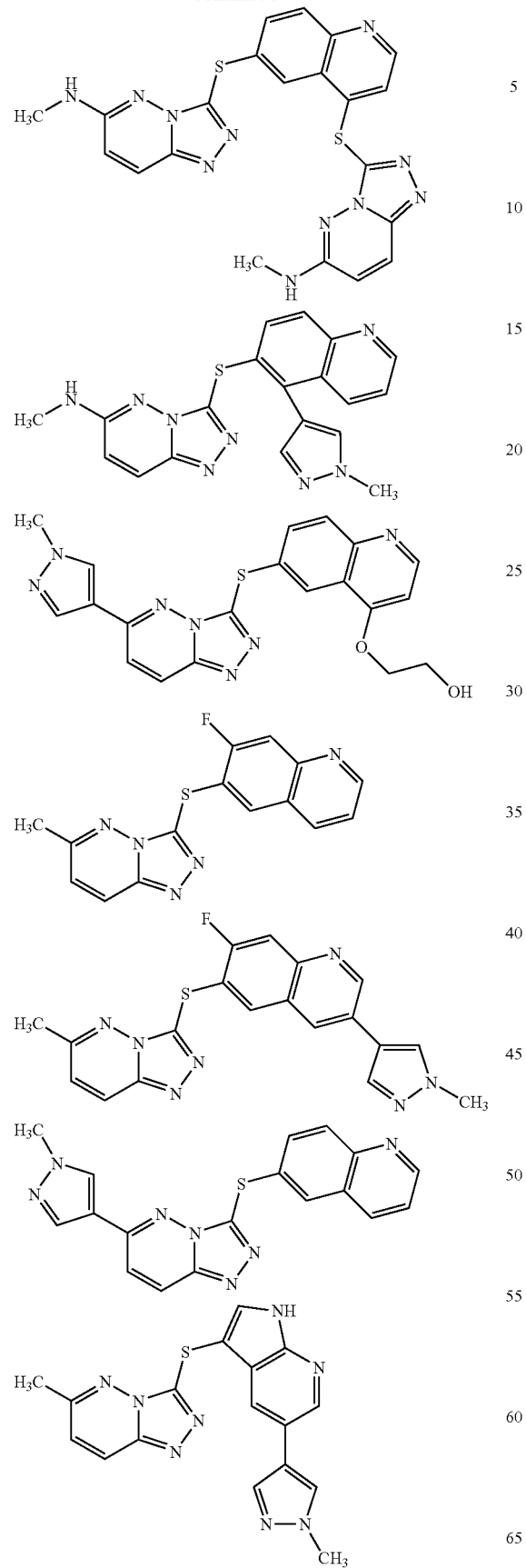
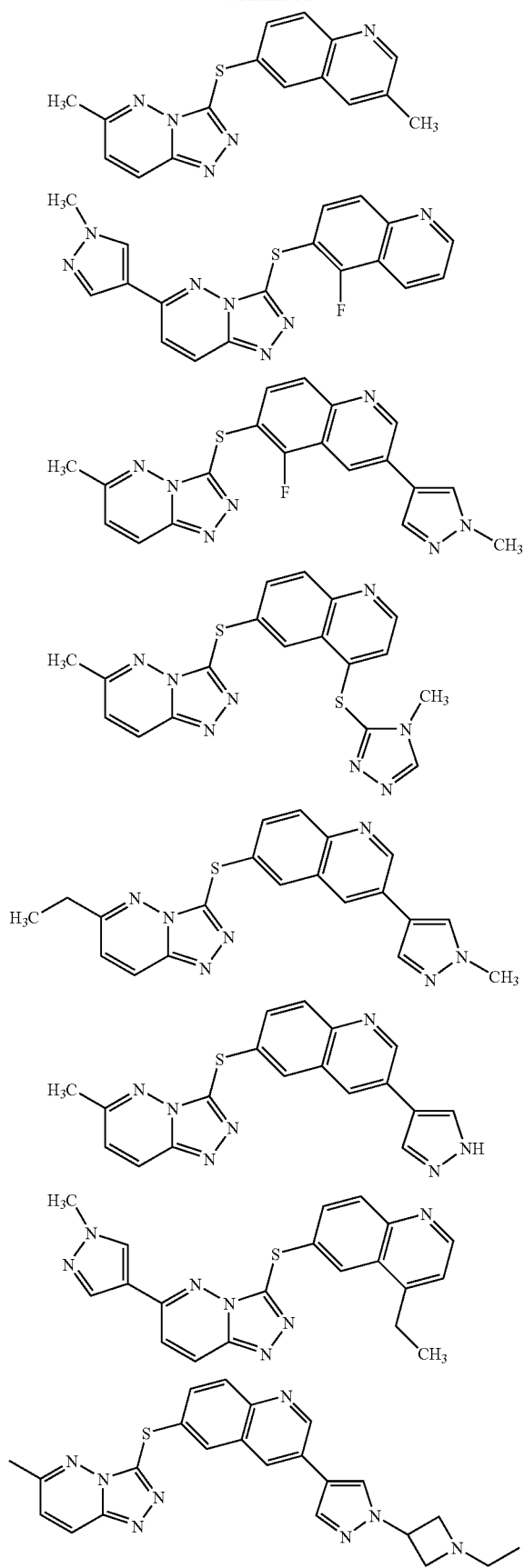

-continued

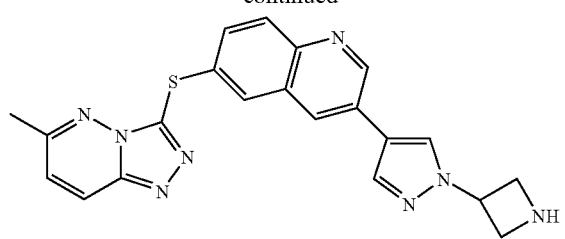
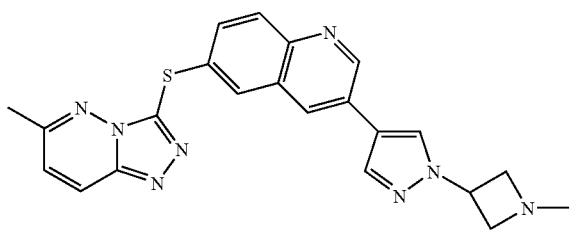
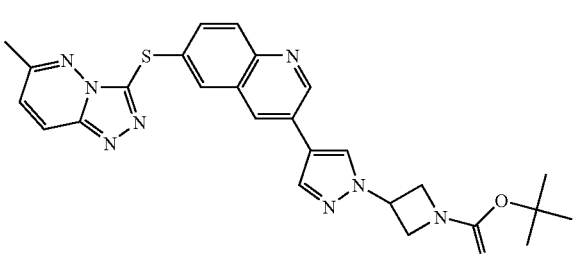
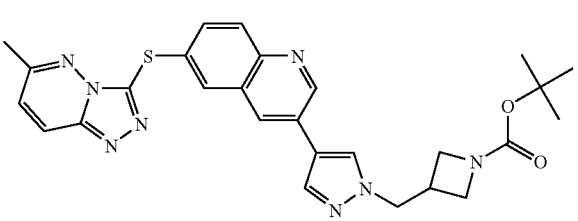
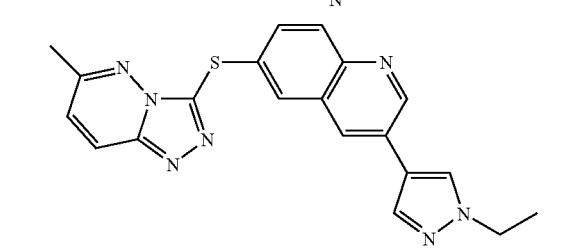

-continued

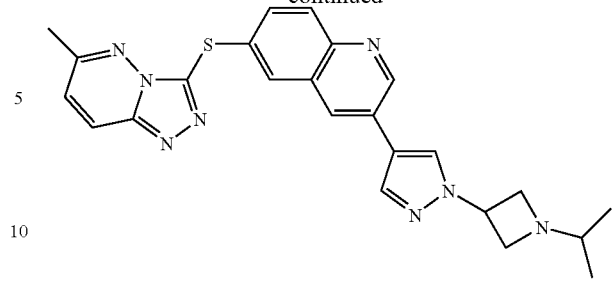

In another aspect, the disclosure provides methods for modulating the activity of a protein kinase by contacting the protein kinase with a compound of formula I.

In another aspect, the disclosure provides methods for modulating the activity of a protein kinase by contacting the protein kinase with a compound of formula I, wherein the protein kinase is Ron receptor tyrosine kinase, Met receptor tyrosine kinase, ALK receptor tyrosine kinase, MER receptor tyrosine kinase, Tyro3/Sky receptor tyrosine kinase, AXL receptor tyrosine kinase, TRKC receptor tyrosine kinase, ROS receptor tyrosine kinase, CSF1R/FMS receptor tyrosine kinase, BRAF kinase, or Raf1 kinase.

In another aspect, the disclosure provides methods for modulating the activity of a protein kinase by contacting the protein kinase with a compound of formula I, wherein the protein kinase is Met receptor tyrosine kinase.

In another aspect, the disclosure provides methods for treating cancer in a human patient in need of such treatment, by administering to the patient a therapeutically effective amount of a compound of formula I.

In another aspect, the disclosure provides methods for treating cancer in a human patient in need of such treatment, by administering to the patient a therapeutically effective amount of a compound of formula I, wherein the cancer is breast cancer, lung cancer, melanoma, colorectal cancer, bladder cancer, ovarian cancer, prostate cancer, renal cancer, squamous cell cancer, glioblastoma, pancreatic cancer, leiomyosarcoma, multiple myeloma, papillary renal cell carcinoma, gastric cancer, liver cancer, head and neck cancer, melanoma, and leukemia (e.g. myeloid, chronic myeloid, acute lymphoblastic, chronic lymphoblastic, Hodgkins, and other leukemias and hematological cancers).

In another aspect, the disclosure provides methods for treating cancer in a human patient in need of such treatment, by administering to the patient a therapeutically effective amount of a compound of formula I, wherein the cancer includes MET mutations, cancers with MET gene amplification, cancers expressing MET protein, cancers expressing phosphorylated MET, cancers with activated MET signaling, cancers expressing HGF, cancers expressing markers for other kinase targets.

In another aspect, the disclosure provides methods for treating Listeria invasion, osteolysis associated with multiple myeloma, malaria infection, diabetic retinopathies, psoriasis, and arthritis, by administering to the patient a therapeutically effective amount of a compound of formula I.

In another aspect, the disclosure provides pharmaceutical compositions containing a compound of formula I in a pharmaceutically acceptable excipient.

In another aspect, the disclosure provides methods for preventing and/or inhibiting metastasis of proliferative cells in a patient in need of such treatment, by administering to the patient a therapeutically effective amount of a compound of formula I.

In another aspect, the disclosure provides methods for preventing and/or inhibiting metastasis of proliferative cells in a patient in need of such treatment, by administering to the patient a therapeutically effective amount of a pharmaceutical composition containing a compound of formula I in a pharmaceutically acceptable excipient.

In another aspect, the disclosure provides methods for preparing compounds having formula I, by the steps of:

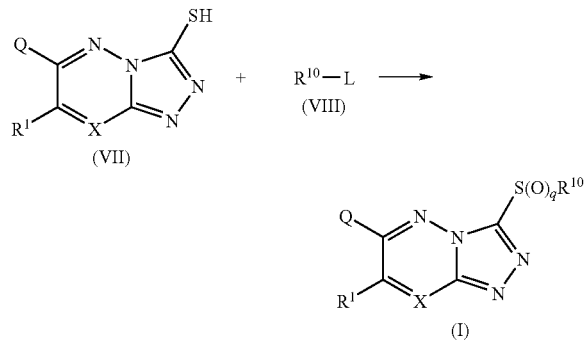

a) reacting the compound of formula VII with the compound of formula VIII, wherein L is Cl, Br, I, $OSO_2CF_3$ or H; and b) optionally oxidizing the compound of formula I.

In another aspect, the disclosure provides methods for preparing compounds having formula I by the steps of a) and b), wherein the reaction occurs in the presence of a solvent, base, metal catalyst, and a ligand.

In another aspect, the disclosure provides methods for preparing compounds having formula I by the steps of a) and b), wherein the solvent is N,N-dimethylformamide, the base is N,N-diisopropylethylamine, the metal catalyst is tris(dibenzylideneacetone)dipalladium (0), and the ligand is 4,5-bis(diphenylphosphino)-9,9-dimethylxanthene.

In another aspect, the disclosure provides methods for preparing compounds having formula I by the steps of a) and b), wherein the compound of formula VI is an aryl halide or heteroaryl halide, and wherein the reaction occurs in the presence of a solvent and a base.

In another aspect, the disclosure provides methods for preparing compounds having formula I by the steps of a) and b), wherein the solvent is methanol, ethanol, n-propanol, sec-propanol or isopropanol, and the base is sodium hydroxide or potassium hydroxide.

Methods of Inhibiting Kinases

In another aspect, the present disclosure provides methods of modulating protein kinase activity using the bicyclic triazole kinase modulators of the present disclosure. The term "modulating kinase activity," as used herein, means that the activity of the protein kinase is increased or decreased when contacted with a bicyclic triazole kinase modulator of the present disclosure relative to the activity in the absence of the bicyclic triazole kinase modulator. Therefore, the present disclosure provides a method of modulating protein kinase activity by contacting the protein kinase with a bicyclic triazole kinase modulator of the present disclosure.

In an exemplary embodiment, the bicyclic triazole kinase modulator inhibits kinase activity. The term "inhibit," as used herein interference to kinase activity, means that the kinase activity is decreased when contacted with a bicyclic triazole kinase modulator relative to the activity in the absence of the bicyclic triazole kinase modulator. Therefore, the present disclosure further provides a method of inhibiting protein kinase activity by contacting the protein kinase with a bicyclic triazole kinase modulator of the present disclosure.

In certain embodiments, the protein kinase is a protein tyrosine kinase. A protein tyrosine kinase, as used herein, refers to an enzyme that catalyzes the phosphorylation of tyrosine residues in proteins with a phosphate donors (e.g. a nucleotide phosphate donor such as ATP). Protein tyrosine kinases include, for example, Abelson tyrosine kinases ("Abl") (e.g. c-Abl and v-Abl), Ron receptor tyrosine kinases ("RON"), Met receptor tyrosine kinases ("MET"), Fms-like tyrosine kinases ("FLT") (e.g. FLT3), src-family tyrosine kinases (e.g. lyn, CSK), and p21-activated kinase-4 ("PAK"), FLT3, aurora-A kinases, B-lymphoid tyrosine kinases ("Blk"), cyclin-dependent kinases ("CDK") (e.g. CDK1 and CDK5), src-family related protein tyrosine kinases (e.g. Fyn kinase), glycogen synthase kinases ("GSK") (e.g. GSK3α and GSK3β), lymphocyte protein tyrosine kinases ("Lck"), ribosomal S6 kinases (e.g. Rsk1, Rsk2, and Rsk3), sperm tyrosine kinases (e.g. Yes), and subtypes and homologs thereof exhibiting tyrosine kinase activity.

In certain embodiments, the protein kinase is a Met receptor tyrosine kinase.

In another embodiment, the kinase is a mutant kinase, such as a mutant MET. Useful mutant MET kinases include, for example, MET kinases having mutations, including insertions and deletions, in the extracellular or transmembrane domains, or in the cytoplasmic domain, including one of more of the following mutations: Ser1058Pro, Val1110Ile, His1112Tyr, His1124Asp, Met1149Thr, Val1206Leu, or Met1268Thr.

MET kinases include, for example, MET kinases having mutations, including insertions and deletions, in the extracellular or transmembrane domains, or in the cytoplasmic domain, including one of more of the following mutations:

Ser1058Pro, Val1110Ile, His1112Tyr, His1124Asp, Met1149Thr, Val1206Leu, or Met1268Thr.

In some embodiments, the kinase is homologous to a known kinase (also referred to herein as a "homologous kinase"). Compounds and compositions useful for inhibiting the biological activity of homologous kinases may be initially screened, for example, in binding assays. Homologous enzymes comprise an amino acid sequence of the same length that is at least 50%, at least 60%, at least 70%, at least 80%, or at least 90% identical to the amino acid sequence of full length known kinase, or 70%, 80%, or 90% homology to the known kinase active domains. Homology may be determined using, for example, a PSI BLAST search, such as, but not limited to that described in Altschul, et al., *Nuc. Acids Rec.* 25:3389-3402 (1997). In certain embodiments, at least 50%, or at least 70% of the sequence is aligned in this analysis. Other tools for performing the alignment include, for example, DbClustal and ESPript, which may be used to generate the PostScript version of the alignment. See Thompson et al, *Nucleic Acids Research,* 28:2919-26, 2000; Gouet, et al., *Bioinformatics,* 15:305-08 (1999). Homologs may, for example, have a BLAST E-value of $1\times10^{-6}$ over at least 100 amino acids (Altschul et al., *Nucleic Acids Res.,* 25:3389-402 (1997) with FLT3, Abl, or another known kinase, or any functional domain of FLT3, Abl, or another known kinase.

Homology may also be determined by comparing the active site binding pocket of the enzyme with the active site binding pockets of a known kinase. For example, in homologous enzymes, at least 50%, 60%, 70%, 80%, or 90% of the amino acids of the molecule or homolog have amino acid structural coordinates of a domain comparable in size to the kinase domain that have a root mean square deviation of the alpha carbon atoms of up to about 1.5 Å, about 1.25 Å, about 1 Å, about 0.75 Å, about 0.5 Å, and or about 0.25 Å.

The compounds and compositions of the present disclosure are useful for inhibiting kinase activity and also for inhibiting other enzymes that bind ATP. They are thus useful for the treatment of diseases and disorders that may be alleviated by inhibiting such ATP-binding enzyme activity. Methods of determining such ATP binding enzymes include those known to those of skill in the art, those discussed herein relating to selecting homologous enzymes, and by the use of the database PROSITE, where enzymes containing signatures, sequence patterns, motifs, or profiles of protein families or domains may be identified.

The compounds of the present disclosure, and their derivatives, may also be used as kinase-binding agents. As binding agents, such compounds and derivatives may be bound to a stable resin as a tethered substrate for affinity chromatography applications. The compounds of this disclosure, and their derivatives, may also be modified (e.g., radiolabelled or affinity labelled, etc.) in order to utilize them in the investigation of enzyme or polypeptide characterization, structure, and/or function.

In an exemplary embodiment, the bicyclic triazole kinase modulator of the present disclosure is a kinase inhibitor. In some embodiments, the kinase inhibitor has an $IC_{50}$ of inhibition constant $(K_i)$ of less than 1 micromolar. In another embodiment, the kinase inhibitor has an $IC_{50}$ or inhibition constant $(K_i)$ of less than 500 micromolar. In another embodiment, the kinase inhibitor has an $IC_{50}$ or $K_i$ of less than 10 micromolar. In another embodiment, the kinase inhibitor has an $IC_{50}$ or $K_i$ of less than 1 micromolar. In another embodiment, the kinase inhibitor has an $IC_{50}$ or $K_i$ of less than 500 nanomolar. In another embodiment, the kinase inhibitor has an $IC_{50}$ or $K_i$ of less than 10 nanomolar. In another embodiment, the kinase inhibitor has an $IC_{50}$ or $K_i$ of less than 1 nanomolar.

Methods of Treatment

In another aspect, the present disclosure provides methods of treating a disease mediated by kinase activity (kinase-mediated disease or disorder) in an organism (e.g. mammals, such as humans). By "kinase-mediated" or "kinase-associated" diseases is meant diseases in which the disease or symptom can be alleviated by inhibiting kinase activity (e.g. where the kinase is involved in signaling, mediation, modulation, or regulation of the disease process). By "diseases" is meant diseases, or disease symptoms.

Examples of kinase associated diseases include cancer (e.g. leukemia, tumors, and metastases), allergy, asthma, inflammation (e.g. inflammatory airways disease), obstructive airways disease, autoimmune diseases, metabolic diseases, infection (e.g. bacterial, viral, yeast, fungal), CNS diseases, brain tumors, degenerative neural diseases, cardiovascular diseases, and diseases associated with angiogenesis, neovascularization, and vasculogenesis. In an exemplary embodiment, the compounds are useful for treating cancer, including leukemia, and other diseases or disorders involving abnormal cell proliferation, myeloproliferative disorders, hematological disorders, asthma, inflammatory diseases or obesity.

More specific examples of cancers treated with the compounds of the present disclosure include breast cancer, lung cancer, melanoma, colorectal cancer, bladder cancer, ovarian cancer, prostate cancer, renal cancer, squamous cell cancer, glioblastoma, pancreatic cancer, leiomyosarcoma, multiple myeloma, papillary renal cell carcinoma, gastric cancer, liver cancer, head and neck cancer, melanoma, and leukemia (e.g. myeloid, chronic myeloid, acute lymphoblastic, chronic lymphoblastic, Hodgkins, and other leukemias and hematological cancers).

Other specific examples of diseases or disorders for which treatment by the compounds or compositions of the disclosure are useful for treatment or prevention include, but are not limited to transplant rejection (for example, kidney, liver, heart, lung, islet cells, pancreas, bone marrow, cornea, small bowel, skin allografts or xenografts and other transplants), graft vs. host disease, osteoarthritis, rheumatoid arthritis, multiple sclerosis, diabetes, diabetic retinopathy, inflammatory bowel disease (for example, Crohn's disease, ulcerative colitis, and other bowel diseases), renal disease, cachexia, septic shock, lupus, myasthenia gravis, psoriasis, dermatitis, eczema, seborrhea, Alzheimer's disease, Parkinson's disease, stem cell protection during chemotherapy, ex vivo selection or ex vivo purging for autologous or allogeneic bone marrow transplantation, ocular disease, retinopathies (for example, macular degeneration, diabetic retinopathy, and other retinopathies), corneal disease, glaucoma, infections (for example bacterial, viral, or fungal), heart disease, including, but not limited to, restenosis.

Combination Therapy

In another aspect, the disclosure provides combination therapies for treating or inhibiting the onset of a cell proliferative disorder or a disorder related to Met in a subject. The combination therapy comprises administering to the subject a therapeutically or prophylactically effective amount of a compound of Formula I, and one or more other anti-cell proliferation therapy including chemotherapy, radiation therapy, gene therapy and immunotherapy.

In another aspect, the compounds of the disclosure may be administered in combination with chemotherapy. As used herein, chemotherapy refers to a therapy involving a chemotherapeutic agent. A variety of chemotherapeutic agents may be used in the combined treatment methods disclosed herein. Chemotherapeutic agents contemplated as exemplary, include, but are not limited to: platinum compounds (e.g., cisplatin, carboplatin, oxaliplatin); taxane compounds (e.g., paclitaxcel, docetaxol); campotothecin compounds (irinotecan, topotecan); vinca alkaloids (e.g., vincristine, vinblastine, vinorelbine); anti-tumor nucleoside derivatives (e.g., 5-fluorouracil, leucovorin, gemcitabine, capecitabine) alkylating agents (e.g., cyclophosphamide, carmustine, lomustine, thiotepa); epipodophyllotoxins/podophyllotoxins (e.g. etoposide, teniposide); aromatase inhibitors (e.g., anastrozole, letrozole, exemestane); anti-estrogen compounds (e.g., tamoxifen, fulvestrant), antifolates (e.g., premetrexed disodium); hypomethylating agents (e.g., azacitidine); biologics (e.g., gemtuzamab, cetuximab, rituximab, pertuzumab, trastuzumab, bevacizumab, erlotinib); antibiotics/anthracylines (e.g. idarubicin, actinomycin D, bleomycin, daunorubicin, doxorubicin, mitomycin C, dactinomycin, caminomycin, daunomycin); antimetabolites (e.g., clofarabine, aminopterin, cytosine arabinoside, methotrexate); tubulin-binding agents (e.g. combretastatin, colchicine, nocodazole); topoisomerase inhibitors (e.g., camptothecin); differentiating agents (e.g., retinoids, vitamin D and retinoic acid); retinoic acid metabolism blocking agents (RAMBA) (e.g., accutane); kinase inhibitors (e.g., flavoperidol, imatinib mesylate, gefitinib, erlotinib, sunitinib, lapatinib, sorafinib, temsirolimus, dasatinib); farnesyltransferase inhibitors (e.g., tipifarnib); histone deacetylase inhibitors; inhibitors of the ubiquitin-proteasome pathway (e.g., bortezomib, Yondelis).

Further useful agents include verapamil, a calcium antagonist found to be useful in combination with antineoplastic agents to establish chemosensitivity in tumor cells resistant to accepted chemotherapeutic agents and to potentiate the efficacy of such compounds in drug-sensitive malignancies. See Simpson W G, The calcium channel blocker verapamil and cancer chemotherapy. Cell Calcium. December 1985; 6(6): 449-67. Additionally, yet to emerge chemotherapeutic agents are contemplated as being useful in combination with the compound of the present disclosure.

In another aspect, the disclosure provides compounds which may be administered in combination with radiation therapy. As used herein, "radiation therapy" refers to a therapy comprising exposing the subject in need thereof to radiation. Such therapy is known to those skilled in the art. The appropriate scheme of radiation therapy will be similar to those already employed in clinical therapies wherein the radiation therapy is used alone or in combination with other chemotherapeutics.

In another aspect, the disclosure provides compounds which may be administered in combination with a gene therapy. As used herein, "gene therapy" refers to a therapy targeting on particular genes involved in tumor development. Possible gene therapy strategies include the restoration of defective cancer-inhibitory genes, cell transduction or transfection with antisense DNA corresponding to genes coding for growth factors and their receptors, RNA-based strategies such as ribozymes, RNA decoys, antisense messenger RNAs and small interfering RNA (siRNA) molecules and the so-called 'suicide genes'.

In other aspect, the disclosure provides compounds which may be administered in combination with an immunotherapy. As used herein, "immunotherapy" refers to a therapy targeting particular protein involved in tumor development via antibodies specific to such protein. For example, monoclonal antibodies against vascular endothelial growth factor have been used in treating cancers.

Where a second pharmaceutical is used in addition to a compound of the disclosure, the two pharmaceuticals may be administered simultaneously (e.g. in separate or unitary compositions) sequentially in either order, at approximately the same time, or on separate dosing schedules. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular chemotherapeutic agent being administered in conjunction with the compound of the present invention, their route of administration, the particular tumor being treated and the particular host being treated.

As will be understood by those of ordinary skill in the art, the appropriate doses of chemotherapeutic agents will be generally similar to or less than those already employed in clinical therapies wherein the chemotherapeutics are administered alone or in combination with other chemotherapeutics.

The optimum method and order of administration and the dosage amounts and regime can be readily determined by those skilled in the art using conventional methods and in view of the information set out herein.

By way of example only, platinum compounds are advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment. Cisplatin is not absorbed orally and must therefore be delivered via injection intravenously, subcutaneously, intratumorally or intraperitoneally.

By way of example only, taxane compounds are advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

By way of example only, camptothecin compounds are advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

By way of example only, vinca alkaloids may be advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

By way of example only, anti-tumor nucleoside derivatives may be advantageously administered in a dosage of 200 to 2500 mg per square meter ($mg/m^2$) of body surface area, for example 700 to 1500 $mg/m^2$. 5-fluorouracil (5-FU) is commonly used via intravenous administration with doses ranging from 200 to 500 $mg/m^2$ (preferably from 3 to 15 mg/kg/day). Gemcitabine is advantageously administered in a dosage of about 800 to 1200 $mg/m^2$ and capecitabine is advantageously administered in about 1000 to 2500 $mg/m^2$ per course of treatment.

By way of example only, alkylating agents may be advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg of body weight, for carmustine in a dosage of about 150 to 200 mg/m², and for lomustine in a dosage of about 100 to 150 mg/m² per course of treatment.

By way of example only, podophyllotoxin derivatives may be advantageously administered in a dosage of 30 to 300 mg per square meter (mg/m2) of body surface area, for example 50 to 250 mg/m², particularly for etoposide in a dosage of about 35 to 100 mg/m² and for teniposide in about 50 to 250 mg/m² per course of treatment.

By way of example only, anthracycline derivatives may be advantageously administered in a dosage of 10 to 75 mg per square meter (mg/m²) of body surface area, for example 15 to 60 mg/m², particularly for doxorubicin in a dosage of about 40 to 75 mg/m², for daunorubicin in a dosage of about 25 to 45 mg/m², and for idarubicin in a dosage of about 10 to 15 mg/m² per course of treatment.

By way of example only, anti-estrogen compounds may be advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

By way of example only, biologics may be advantageously administered in a dosage of about 1 to 5 mg per square meter (mg/m²) of body surface area, or as known in the art, if different. For example, trastuzumab is advantageously administered in a dosage of 1 to 5 mg/m² particularly 2 to 4 mg/m² per course of treatment.

Dosages may be administered, for example once, twice or more per course of treatment, which may be repeated for example every 7, 14, 21 or 28 days.

The compounds of the present disclosure can be administered to a subject systemically, for example, intravenously, orally, subcutaneously, intramuscular, intradermal, or parenterally. The compounds of the present invention can also be administered to a subject locally. Non-limiting examples of local delivery systems include the use of intraluminal medical devices that include intravascular drug delivery catheters, wires, pharmacological stents and endoluminal paving.

The compounds of the present disclosure can further be administered to a subject in combination with a targeting agent to achieve high local concentration of the compound at the target site. In addition, the compounds of the present invention may be Formulated for fast-release or slow-release with the objective of maintaining the drugs or agents in contact with target tissues for a period ranging from hours to weeks.

Pharmaceutical Compositions and Administration

In another aspect, the present disclosure provides a pharmaceutical composition including a bicyclic triazole kinase modulator in admixture with a pharmaceutically acceptable excipient. One of skill in the art will recognize that the pharmaceutical compositions include the pharmaceutically acceptable salts of the bicyclic triazole kinase modulators described above.

In therapeutic and/or diagnostic applications, the compounds of the disclosure can be formulated for a variety of modes of administration, including systemic and topical or localized administration. Techniques and formulations generally may be found in Remington: The Science and Practice of Pharmacy (20$^{th}$ ed.) Lippincott, Williams & Wilkins (2000).

According to another aspect, the disclosure provides pharmaceutical compositions including compounds of formula I, and a pharmaceutically acceptable carrier, adjuvant, or vehicle. The amount of compound in the compositions of the disclosure is such that is effective to detectably inhibit a protein kinase, particularly MET in a biological sample or in a patient.

As used herein, the term "MET" is synonymous with "Met", "c-MET", "c-Met", or other designations known to one skilled in the art. In one aspect, a composition of the present disclosure is formulated for administration to a patient in need of such composition. In another aspect, the composition of the disclosure is formulated for oral administration to a patient.

The compounds according to the disclosure are effective over a wide dosage range. For example, in the treatment of adult humans, dosages from 0.01 to 10,000 mg, from 0.5 to 1000 mg, from 1 to 500 mg per day, and from 5 to 100 mg per day are examples of dosages that may be used. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20$^{th}$ ed.) Lippincott, Williams & Wilkins (2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release forms is known to those skilled in the art. Techniques for formulation and administration may be found in Remington: The Science and Practice of Pharmacy (20$^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articular, intra-sternal, intrasynovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a patient to be treated.

For nasal or inhalation delivery, the agents of the disclosure may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present disclosure include compositions wherein active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with the inhibitors of this disclosure. For example, chemotherapeutic agents or other anti-proliferative agents may be combined with the inhibitors of this disclosure to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents the inhibitors of this disclosure may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and antiviral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the inhibitor-containing composition. Alternatively, these agents may be part of a single dosage form, mixed together with the inhibitor in a single composition.

The present disclosure is not to be limited in scope by the exemplified embodiments, which are intended as illustrations of single aspects of the disclosure. Indeed, various modifications of the disclosure in addition to those described herein will become apparent to those having skill in the art from the foregoing description. Such modifications are intended to fall within the scope of the disclosure. Moreover, any one or more features of any embodiment of the disclosure may be combined with any one or more other features of any other embodiment of the disclosure, without departing from the scope of the disclosure. For example, the bicyclic triazole kinase modulators described in the Bicyclic triazole Kinase Modulators section are equally applicable to the methods of treatment and methods of inhibiting kinases described herein. References cited throughout this application are examples of the level of skill in the art and are hereby incorporated by reference herein in their entirety for all purposes, whether previously specifically incorporated or not.

Assays

The compounds of the present disclosure may be easily assayed to determine their ability to modulate protein kinases, bind protein kinases, and/or prevent cell growth or proliferation. Some examples of useful assays are presented below.

Kinase Inhibition and Binding Assays

Inhibition of various kinases is measured by methods known to those of ordinary skill in the art, such as the various methods presented herein, and those discussed in the Upstate Kinase Profiler Assay Protocols, June 2003 publication.

For example, where in vitro assays are performed, the kinase is typically diluted to the appropriate concentration to form kinase solution. A kinase substrate and phosphate donor, such as ATP, is added to the kinase solution. The kinase is allowed to transfer a phosphate to the kinase substrate to form phosphorylated substrate. The formation of a phosphorylated substrate may be detected directly by any appropriate means, such as radioactivity (e.g. [$\gamma$-$^{32}$P-ATP]), or the use of detectable secondary antibodies (e.g. ELISA). Alternatively, the formation of a phosphorylated substrate may be detected using any appropriate technique, such as the detection of ATP concentration (e.g. Kinase-Glo® assay system (Promega)). Kinase inhibitors are identified by detecting the formation of a phosphorylated substrate in the presence and absence of a test compound (see Examples section below).

The ability of the compound to inhibit a kinase in a cell may also be assayed using methods well known in the art. For example, cells containing a kinase may be contacted with an activating agent (such as a growth factor) that activates the kinase. The amount of intracellular phosphorylated substrate formed in the absence and the presence of the test compound may be determined by lysing the cells and detecting the presence phosphorylated substrate by any appropriate method (e.g. ELISA). Where the amount of phosphorylated substrate produced in the presence of the test compound is decreased relative to the amount produced in the absence of the test compound, kinase inhibition is indicated. More detailed cellular kinase assays are discussed in the Examples section below.

To measure the binding of a compound to a kinase, any method known to those of ordinary skill in the art may be used. For example, a test kit manufactured by Discoverx (Fremont, Calif.), ED-Staurosporine NSIP™ Enzyme Binding Assay Kit (see U.S. Pat. No. 5,643,734) may be used. Kinase activity may also be assayed as in U.S. Pat. No. 6,589,950, issued Jul. 8, 2003.

Suitable kinase inhibitors may be selected from the compounds of the disclosure through protein crystallographic screening, as disclosed in, for example Antonysamy, et al., PCT Publication No. WO03087816A1, which is incorporate herein by reference in its entirety for all purposes.

The compounds of the present disclosure may be computationally screened to assay and visualize their ability to bind to and/or inhibit various kinases. The structure may be computationally screened with a plurality of compounds of the present disclosure to determine their ability to bind to a kinase at various sites. Such compounds can be used as targets or leads in medicinal chemistry efforts to identify, for example, inhibitors of potential therapeutic importance (Travis, Science, 262:1374, 1993). The three dimensional structures of such compounds may be superimposed on a three dimensional representation of kinases or an active site or binding pocket thereof to assess whether the compound fits spatially into the representation and hence the protein. In this screening, the quality of fit of such entities or compounds to the binding pocket may be judged either by shape complementarity or by estimated interaction energy (Meng, et al., J. Comp. Chem. 13:505-24, 1992).

The screening of compounds of the present disclosure that bind to and/or modulate kinases (e.g. inhibit or activate kinases) according to this disclosure generally involves consideration of two factors. First, the compound must be capable of physically and structurally associating, either covalently or non-covalently with kinases. For example, covalent interactions may be important for designing irreversible or suicide inhibitors of a protein. Non-covalent molecular interactions important in the association of kinases with the compound include hydrogen bonding, ionic interactions, van der Waals, and hydrophobic interactions. Second, the compound must be able to assume a conformation and orientation in relation to the binding pocket, that allows it to associate with kinases. Although certain portions of the compound will not directly participate in this association with kinases, those portions may still influence the overall conformation of the molecule and may have a significant impact on potency. Conformational requirements include the overall three-dimensional structure and orientation of the chemical group or compound in relation to all or a portion of the binding pocket, or the spacing between functional groups of a compound comprising several chemical groups that directly interact with kinases.

Docking programs described herein, such as, for example, DOCK, or GOLD, are used to identify compounds that bind to the active site and/or binding pocket. Compounds may be screened against more than one binding pocket of the protein structure, or more than one set of coordinates for the same protein, taking into account different molecular dynamic conformations of the protein. Consensus scoring may then be used to identify the compounds that are the best fit for the protein (Charifson, P. S. et al., J. Med. Chem. 42: 5100-9 (1999)). Data obtained from more than one protein molecule structure may also be scored according to the methods described in Klingler et al., U.S. Utility application, filed May 3, 2002, entitled "Computer Systems and Methods for Virtual Screening of Compounds." Compounds having the best fit are then obtained from the producer of the chemical library, or synthesized, and used in binding assays and bioassays.

Computer modeling techniques may be used to assess the potential modulating or binding effect of a chemical compound on kinases. If computer modeling indicates a strong interaction, the molecule may then be synthesized and tested for its ability to bind to kinases and affect (by inhibiting or activating) its activity.

Modulating or other binding compounds of kinases may be computationally evaluated by means of a series of steps in which chemical groups or fragments are screened and selected for their ability to associate with the individual binding pockets or other areas of kinases. This process may begin by visual inspection of, for example, the active site on the computer screen based on the kinases coordinates. Selected fragments or chemical groups may then be positioned in a variety of orientations, or docked, within an individual binding pocket of kinases (Blaney, J. M. and Dixon, J. S., Perspectives in Drug Discovery and Design, 1:301, 1993). Manual docking may be accomplished using software such as Insight II (Accelrys, San Diego, Calif.) MOE (Chemical Computing Group, Inc., Montreal, Quebec, Canada); and SYBYL (Tripos, Inc., St. Louis, Mo., 1992), followed by energy minimization and/or molecular dynamics with standard molecular mechanics force fields, such as CHARMM (Brooks, et al., J. Comp. Chem. 4:187-217, 1983), AMBER (Weiner, et al., J. Am. Chem. Soc. 106: 765-84, 1984) and C$^2$MMFF (Merck Molecular Force Field; Accelrys, San Diego, Calif.). More automated docking may be accomplished by using programs such as DOCK (Kuntz et al., J. Mol. Biol., 161:269-88, 1982; DOCK is available from University of California, San Francisco, Calif.); AUTODOCK (Goodsell & Olsen, Proteins: Structure, Function, and Genetics 8:195-202, 1990; AUTODOCK is available from Scripps Research Institute, La Jolla, Calif.); GOLD (Cambridge Crystallographic Data Centre (CCDC); Jones et al., J. Mol. Biol. 245:43-53, 1995); and FLEXX (Tripos, St. Louis, Mo.;

Rarey, M., et al., *J. Mol. Biol.* 261:470-89, 1996). Other appropriate programs are described in, for example, Halperin, et al.

During selection of compounds by the above methods, the efficiency with which that compound may bind to kinases may be tested and optimized by computational evaluation. For example, a compound that has been designed or selected to function as a kinases inhibitor may occupy a volume not overlapping the volume occupied by the active site residues when the native substrate is bound, however, those of ordinary skill in the art will recognize that there is some flexibility, allowing for rearrangement of the main chains and the side chains. In addition, one of ordinary skill may design compounds that could exploit protein rearrangement upon binding, such as, for example, resulting in an induced fit. An effective kinase inhibitor may demonstrate a relatively small difference in energy between its bound and free states (i.e., it must have a small deformation energy of binding and/or low conformational strain upon binding). Thus, the most efficient kinase inhibitors should, for example, be designed with a deformation energy of binding of not greater than 10 kcal/mol, not greater than 7 kcal/mol, not greater than 5 kcal/mol, or not greater than 2 kcal/mol. Kinase inhibitors may interact with the protein in more than one conformation that is similar in overall binding energy. In those cases, the deformation energy of binding is taken to be the difference between the energy of the free compound and the average energy of the conformations observed when the inhibitor binds to the enzyme.

Specific computer software is available in the art to evaluate compound deformation energy and electrostatic interaction. Examples of programs designed for such uses include: Gaussian 94, revision C (Frisch, Gaussian, Inc., Pittsburgh, Pa. ©1995); AMBER, version 7. (Kollman, University of California at San Francisco, ©2002); QUANTA/CHARMM (Accelrys, Inc., San Diego, Calif., ©1995); Insight II/Discover (Accelrys, Inc., San Diego, Calif., ©1995); DelPhi (Accelrys, Inc., San Diego, Calif., ©1995); and AMSOL (University of Minnesota) (Quantum Chemistry Program Exchange, Indiana University). These programs may be implemented, for instance, using a computer workstation, as are well known in the art, for example, a LINUX, SGI or Sun workstation. Other hardware systems and software packages will be known to those skilled in the art.

Those of ordinary skill in the art may express kinase protein using methods known in the art, and the methods disclosed herein. The native and mutated kinase polypeptides described herein may be chemically synthesized in whole or part using techniques that are well known in the art (see, e.g., Creighton, Proteins: Structures and Molecular Principles, W.H. Freeman & Co., NY, 1983).

Gene expression systems may be used for the synthesis of native and mutated polypeptides. Expression vectors containing the native or mutated polypeptide coding sequence and appropriate transcriptional/translational control signals, that are known to those skilled in the art may be constructed. These methods include in vitro recombinant DNA techniques, synthetic techniques and in vivo recombination/genetic recombination. See, for example, the techniques described in Sambrook et al., Molecular Cloning: A Laboratory Manual, Cold Spring Harbor Laboratory, NY, 2001, and Ausubel et al., Current Protocols in Molecular Biology, Greene Publishing Associates and Wiley Interscience, NY, 1989.

Host-expression vector systems may be used to express kinase. These include, but are not limited to, microorganisms such as bacteria transformed with recombinant bacteriophage DNA, plasmid DNA or cosmid DNA expression vectors containing the coding sequence; yeast transformed with recombinant yeast expression vectors containing the coding sequence; insect cell systems infected with recombinant virus expression vectors (e.g., baculovirus) containing the coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence; or animal cell systems. The protein may also be expressed in human gene therapy systems, including, for example, expressing the protein to augment the amount of the protein in an individual, or to express an engineered therapeutic protein. The expression elements of these systems vary in their strength and specificities.

Specifically designed vectors allow the shuttling of DNA between hosts such as bacteria-yeast or bacteria-animal cells. An appropriately constructed expression vector may contain: an origin of replication for autonomous replication in host cells, one or more selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency.

The expression vector may also comprise various elements that affect transcription and translation, including, for example, constitutive and inducible promoters. These elements are often host and/or vector dependent. For example, when cloning in bacterial systems, inducible promoters such as the T7 promoter, pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, mammalian promoters (e.g., metallothionein promoter) or mammalian viral promoters, (e.g., adenovirus late promoter; vaccinia virus 7.5K promoter; SV40 promoter; bovine papilloma virus promoter; and Epstein-Barr virus promoter) may be used.

Various methods may be used to introduce the vector into host cells, for example, transformation, transfection, infection, protoplast fusion, and electroporation. The expression vector-containing cells are clonally propagated and individually analyzed to determine whether they produce the appropriate polypeptides. Various selection methods, including, for example, antibiotic resistance, may be used to identify host cells that have been transformed. Identification of polypeptide expressing host cell clones may be done by several means, including but not limited to immunological reactivity with anti-kinase antibodies, and the presence of host cell-associated activity.

Expression of cDNA may also be performed using in vitro produced synthetic mRNA. Synthetic mRNA can be efficiently translated in various cell-free systems, including but not limited to wheat germ extracts and reticulocyte extracts, as well as efficiently translated in cell-based systems, including, but not limited, to microinjection into frog oocytes.

To determine the cDNA sequence(s) that yields optimal levels of activity and/or protein, modified cDNA molecules are constructed. A non-limiting example of a modified cDNA is where the codon usage in the cDNA has been optimized for the host cell in which the cDNA will be expressed. Host cells are transformed with the cDNA molecules and the levels of kinase RNA and/or protein are measured.

Levels of kinase protein in host cells are quantitated by a variety of methods such as immunoaffinity and/or ligand affinity techniques, kinase-specific affinity beads or specific antibodies are used to isolate $^{35}$S-methionine labeled or unlabeled protein. Labeled or unlabeled protein is analyzed by SDS-PAGE. Unlabeled protein is detected by Western blotting, ELISA or RIA employing specific antibodies.

Following expression of kinase in a recombinant host cell, polypeptides may be recovered to provide the protein in active form. Several purification procedures are available and suitable for use. Recombinant kinase may be purified from cell lysates or from conditioned culture media, by various combinations of, or individual application of, fractionation, or chromatography steps that are known in the art.

In addition, recombinant kinase can be separated from other cellular proteins by use of an immuno-affinity column made with monoclonal or polyclonal antibodies specific for full length nascent protein or polypeptide fragments thereof. Other affinity based purification techniques known in the art may also be used.

Alternatively, the polypeptides may be recovered from a host cell in an unfolded, inactive form, e.g., from inclusion bodies of bacteria. Proteins recovered in this form may be solubilized using a denaturant, e.g., guanidinium hydrochloride, and then refolded into an active form using methods known to those skilled in the art, such as dialysis.

Cell Growth Assays

A variety of cell growth assays are known in the art and are useful in identifying bicyclic triazole compounds (i.e. "test compounds") capable of inhibiting (e.g. reducing) cell growth and/or proliferation.

For example, a variety of cells are known to require specific kinases for growth and/or proliferation. The ability of such a cell to grow in the presence of a test compound may be assessed and compared to the growth in the absence of the test compound thereby identifying the anti-proliferative properties of the test compound. One common method of this type is to measure the degree of incorporation of label, such as tritiated thymidine, into the DNA of dividing cells. Alternatively, inhibition of cell proliferation may be assayed by determining the total metabolic activity of cells with a surrogate marker that correlates with cell number. Cells may be treated with a metabolic indicator in the presence and absence of the test compound. Viable cells metabolize the metabolic indicator thereby forming a detectable metabolic product. Where detectable metabolic product levels are decreased in the presence of the test compound relative to the absence of the test compound, inhibition of cell growth and/or proliferation is indicated. Exemplary metabolic indicators include, for example tetrazolium salts and AlamorBlue® (see Examples section below).

An assay for kinases that stimulate cell migration is the scratch assay. This assay is used to evaluate inhibitors of kinases by mimicking events such as wound healing. In one variant of this assay used to test MET inhibitors, a confluent monolayer of cells is allowed to form on a cell plate. After formation of the monolayer, a linear wound on the monolayer is generated by mechanically scraping the monolayer thereby forming a cell-free channel. A growth factor required by the kinase for cell growth is added in the presence or absence of the test compound. The closure of the channel in the presence of the test compound indicates a failure of the test compound to inhibit the kinase thereby allowing cell migration and growth to close the channel. Conversely, the presence of the channel after adding the test compound indicates that test compound inhibited the kinase thereby preventing cell growth. The selection of the appropriate cells, growth conditions, and growth factors are well within the abilities of one skilled in the art (see Examples section below).

Preparation of Protein Kinase Modulator Compounds
Exemplary Synthesis

The compounds of the disclosure are synthesized by an appropriate combination of generally well known synthetic methods. Techniques useful in synthesizing the compounds of the disclosure are both readily apparent and accessible to those of skill in the relevant art. The discussion below is offered to illustrate certain of the diverse methods available for use in assembling the compounds of the disclosure. However, the discussion is not intended to define the scope of reactions or reaction sequences that are useful in preparing the compounds of the present disclosure. The compounds of this disclosure may be made by the procedures and techniques disclosed in the Examples section below, as well as by known organic synthesis techniques.

Protecting Groups

The compounds of the present disclosure may be synthesized using one or more protecting groups generally known in the art of chemical synthesis. The term "protecting group" refers to chemical moieties that block some or all reactive moieties of a compound and prevent such moieties from participating in chemical reactions until the protective group is removed, for example, those moieties listed and described in Greene, et al., Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking or protecting groups include, for example:

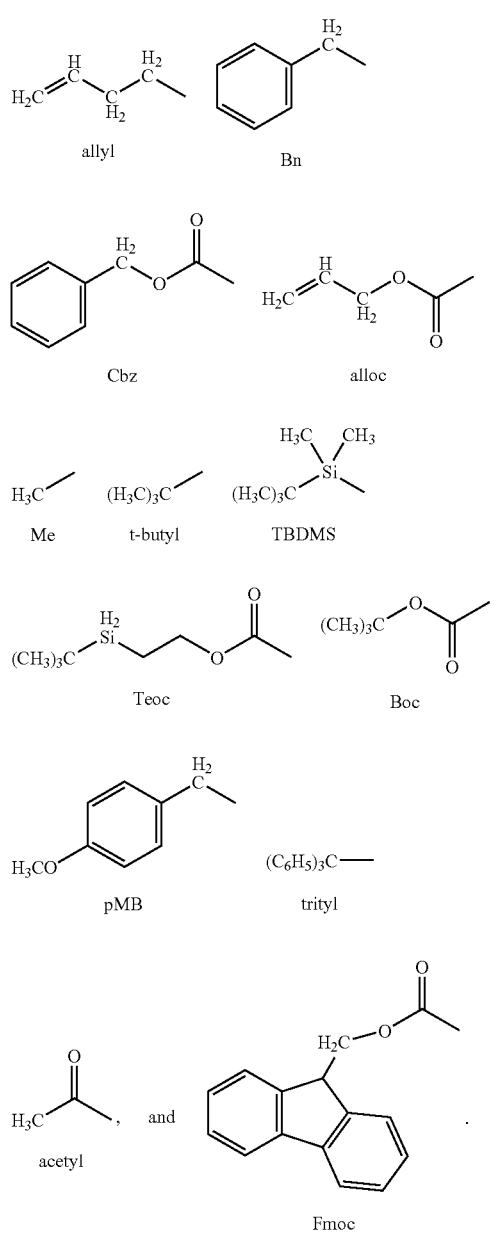

EXAMPLES

The following examples are offered to illustrate, but not to limit the disclosure. The preparation of embodiments of the present disclosure is described in the following examples. Those of ordinary skill in the art will understand that the chemical reactions and synthesis methods provided may be modified to prepare many of the other compounds of the present disclosure. Where compounds of the present disclosure have not been exemplified, those of ordinary skill in the art will recognize that these compounds may be prepared by modifying synthesis methods presented herein, and by using synthesis methods known in the art.

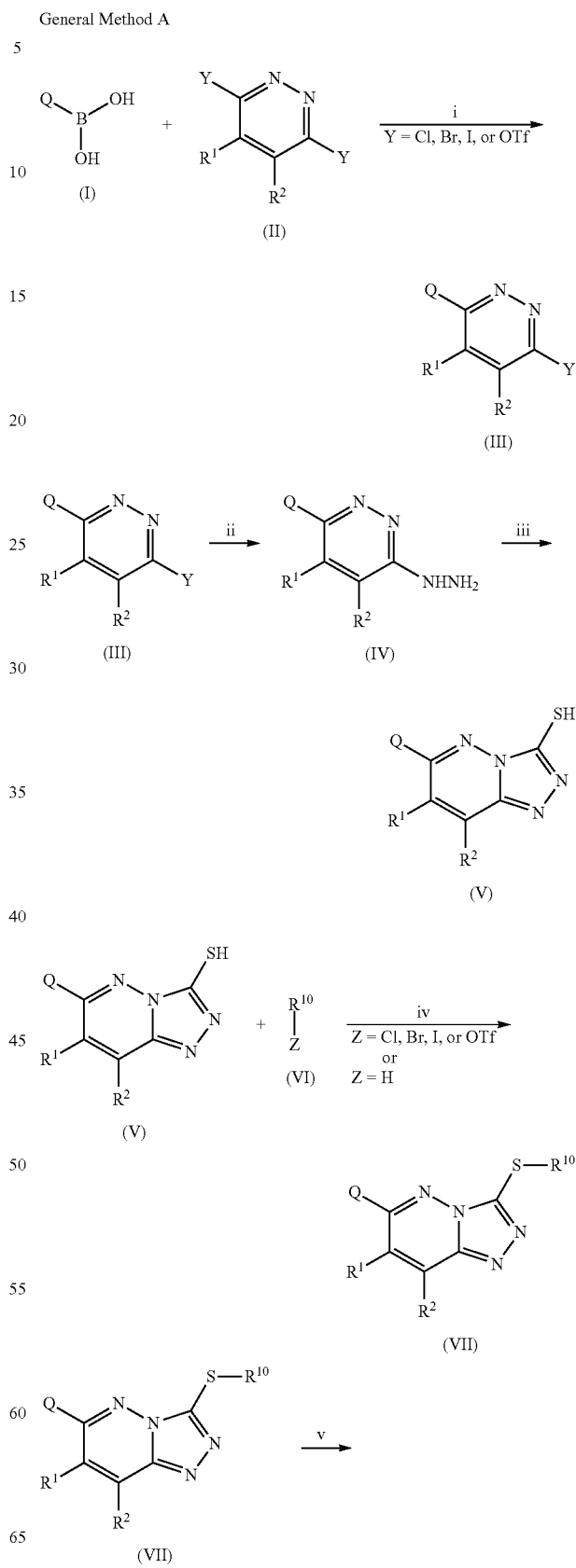

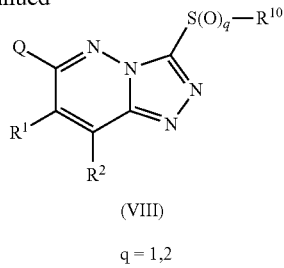

q = 1,2

Compounds of general formula (VII) and (VIII) where Q, $R^1$, $R^2$, and $R^{10}$ are as described herein may be prepared according to general reaction Scheme 1. Compounds of formula (I) and (II) are either available commercially or prepared from commercial compounds using standard chemical reactions and transformations known to those skilled in the art. Compounds of formula (III) may be prepared from compounds of general formula (I) and compounds of general formula (II) by process step (i), which comprises a Suzuki coupling reaction in a suitable solvent, in the presence of a base and a palladium catalyst. The Suzuki coupling reaction can be carried out as described in the literature: Suzuki, A. *Pure & Appli. Chem.* 1985, 57, 1749 and reference contained within; *Angew. Chem. Int. Ed,* 2002, 41, 4176-4211. Typical conditions comprise heating 1-1.5 equivalent of heteroaryl halide or triflate (II), 1 equivalent of boronic acid (I) (or the boronate ester equivalent), 3 equivalents of cesium carbonate, 0.04 equivalents of dichloro[1,1'-bis(diphenylphosphino)ferrocene]palladium(II) dichloromethane adduct in a mixture of DMF and water at 80° C. overnight.

Compounds of formula (IV) may be prepared from compounds of formula (III) by process step (ii), which comprises a substitution reaction with hydrazine in a suitable solvent under heating or microwave conditions. Typical conditions require 1 equivalent of aryl halide (III) and 10 equivalents of hydrazine in ethanol at 80° C. for several hours.

Compounds of formula (V) may be prepared from compounds of formula (IV) by process step (iii), which comprises a cyclization reaction with carbon disulfide in a suitable solvent in the presence of base, as described in the literature: Potts, K. T. et al *J. Org. Chem.* 1969, 34, 3221. Typical conditions comprise 1 equivalent of heteroaryl hydrazine (IV), 2 equivalents of carbon disulfide, and 1 equivalent of potassium hydroxide in a mixture of ethanol and water at 100° C. for several hours. Alternatively, 1,1'-thiocarbonyldiimidazole can be used as a substitute to carbon disulfide. Typical conditions comprise 1 equivalent of heteroaryl hydrazine (IV), 1.1 equivalent of 1,1'-thiocarbonyldiimidazole in DMF at 50° C. for several hours.

Compounds of general formula (VII) may be prepared from compounds of formula (V) and compounds of general formula (VI) by process step (iv), which comprises a S-arylation reaction in a suitable solvent, in the presence of a base, a metal catalyst, and a ligand. Compounds of formula (VI) are either available commercially or prepared from commercial compounds using standard chemical reactions and transformations known to those skilled in the art. The S-arylation reaction can be carried out as described in the literature: Itoh, T. et al *Org. Lett.* 2004, 6, 4587; Schopfer, U. et al *Tetrahedron* 2001, 57, 3069; Buchwald, S. L. et al *Org. Lett.* 2002, 4, 3517; Cheng, C.-H. et al *Org. Lett.* 2006, 8, 5613. Typical conditions comprise 1 equivalent of thiol (V), 1 equivalent of aryl halide or triflate (VI), 2 equivalents of diisopropylethylamine, 0.05 equivalents of tris(dibenzylideneacetone)di-palladium (0), and 0.1 equivalent of 4,5-bis(diphenylphosphino)-9,9-dimethylxanthene (Xantphos) in DMF at 100° C. for several hours. Alternatively, in case of an activated aryl or heteroaryl halide (VI), process step (iv) can proceed via a nucleophilic substitution reaction in presence of a base in a suitable solvent. Typical conditions comprise 1 equivalent of thiol (V), 1.1 equivalent of activated aryl or heteroaryl halide (VI), and 1.2 equivalent of potassium hydroxide in ethanol at 70° C. for several hours. Alternatively, in case of an activated heteroaryl ring (VI, Z=H), such as indole or azaindole rings, process step (iv) can proceed via an oxidative reaction in the presence of an activator such as bromine or iodine in a suitable solvent. Typical conditions comprise 1 equivalent of activated heteroaryl ring (VI), 1.5 equivalent of thiol (V), and 2 equivalents of iodine in DMF at room temperature for several hours.

Compounds of general formula (VIII) may be prepared from compounds of formula (VII) by process step (v), which comprises an oxidation step with an oxidizing agent such as mCPBA or Oxone® in a suitable solvent. Typical conditions comprise 1 equivalent of compound (VII), 1-3 equivalents of mCPBA in DMF at room temperature for several hours.

Scheme 2

General Method B

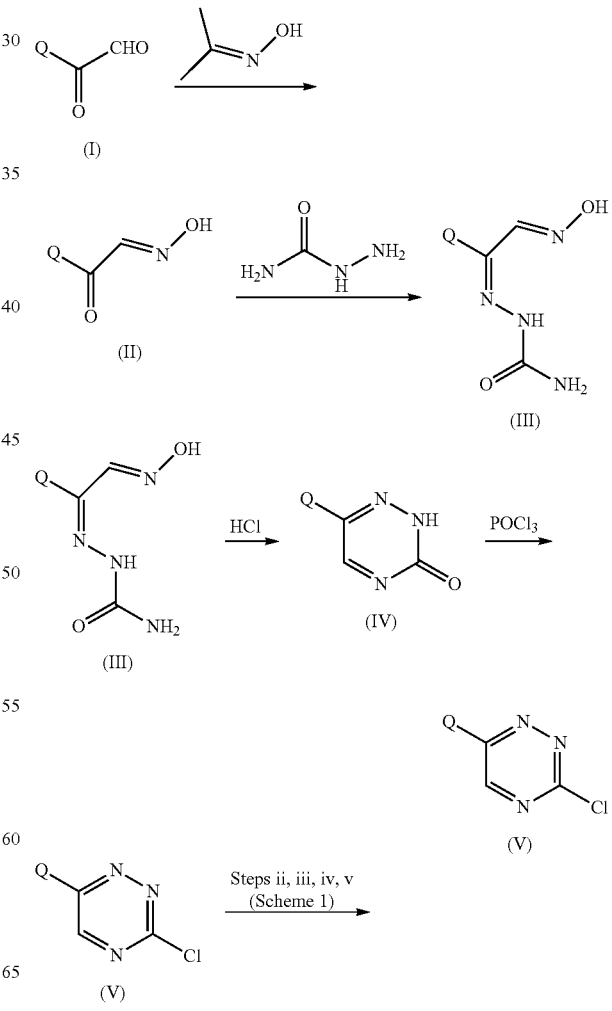

-continued

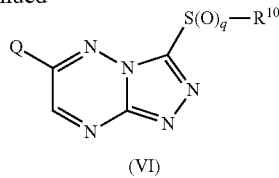

(VI)

Compounds of general formula (VI) where Q, and $R^{10}$ are as described herein may be prepared according to general reaction Scheme 2. Compounds of formula (I) are either available commercially or prepared from commercial compounds using standard chemical reactions and transformations known to those skilled in the art.

Compounds of formula (II) may be prepared from compounds of formula (I) by reacting with acetone oxime in a suitable solvent at temperature ranging from room temperature to 200° C.

Compounds of formula (III) may be prepared from compounds of formula (II) by reacting with semicarbazide in a suitable solvent at temperature ranging from room temperature to 200° C.

Compounds of formula (IV) may be prepared from compounds of formula (III) by treatment with a strong acid in a suitable solvent at temperature ranging from room temperature to 200° C.

Compounds of formula (V) may be prepared from compounds of formula (IV) by reacting with a chlorination agent, such as $POCl_3$ or $PCl_5$, neat or in a suitable solvent at temperature ranging from room temperature to 200° C.

Compounds of general formula (VI) may be prepared from compounds of formula (V) by similar methods described in General Method A and Scheme 1.

Scheme 3

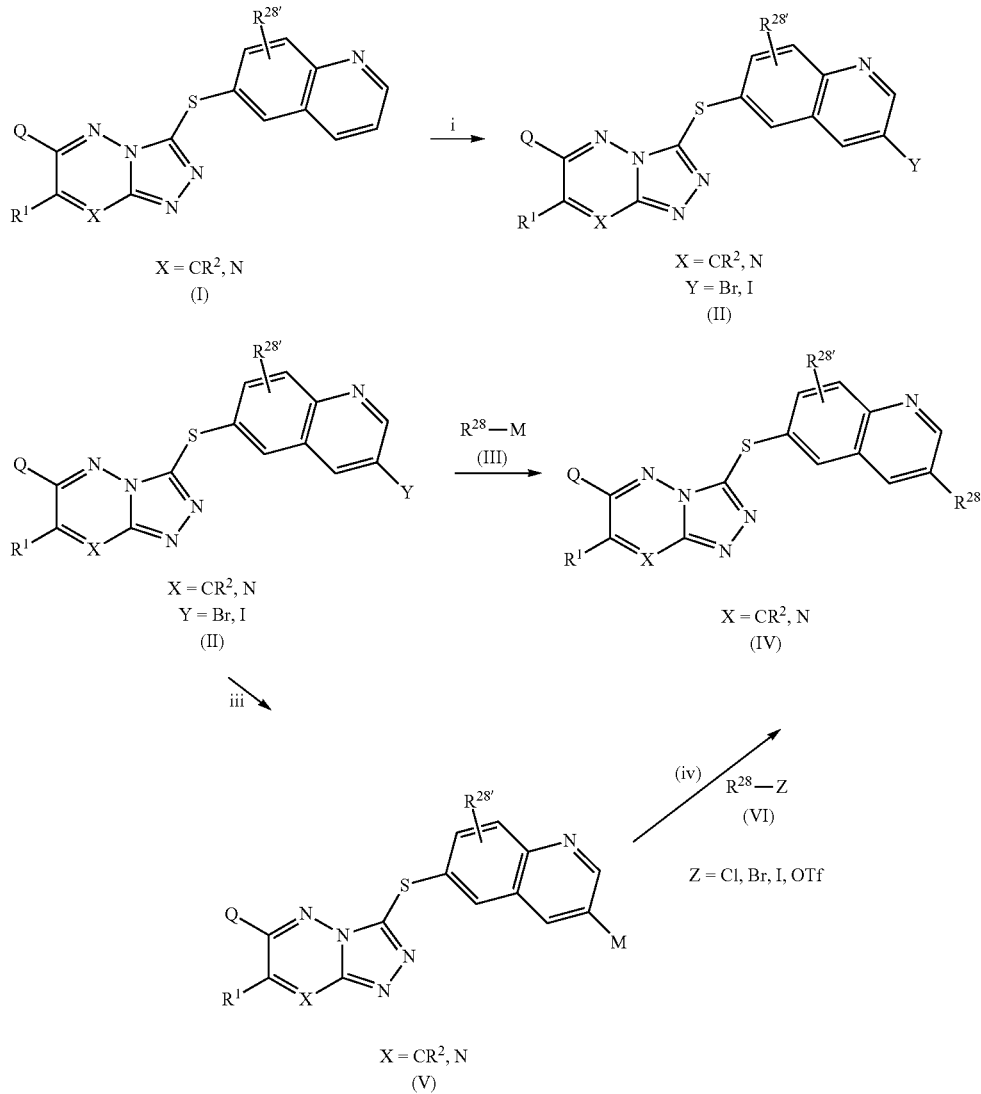

Compounds of general formula (IV) where Q, $R^1$, $R^2$, $R^{28}$ and $R^{28'}$ are as described herein may be prepared according to general reaction Scheme 3. Compounds of formula (III) are either available commercially or prepared from commercial compounds using standard chemical reactions and transformations known to those skilled in the art.

Compounds of formula (II) may be prepared from compounds of general formula (I) by process step (i), which comprises a halogenation reaction in presence of a halogen source, such as bromine, iodine, N-bromo or N-iodosuccinimide, or tetrabutylammonium tribromide, in a suitable solvent at temperatures varying from −20° C. to 200° C. Typical conditions comprise 1 equivalents of compound (I) and 1-5 equivalents of bromine in glacial acetic acid at 100° C. for several hours.

Compounds of formula (IV) may be prepared from compounds of general formula (II) and compounds of general formula (III) by process step (ii), which comprises a catalytic C—C bond coupling reaction between a halogenated species and a metallic species. An array of catalytic C—C bond coupling reactions is available to those skilled in the art, such as Suzuki-Miyaura conditions (M=boron; Miyaura, N.; Suzuki, A. *Chem. Rev.* 1995, 95, 2457), Stille conditions (M=tin; Stille, J. W. *J Org. Chem.* 1990, 55, 3019), or Negishi conditions (M=Zinc, Aluminum; Negishi, E. *Chem. Rev.* 1996, 96, 365). Typical Suzuki-Miyaura conditions comprise 1 equivalent of (I), 1-1.5 equivalent of (II), 1-10 mol % of a palladium catalyst, such as $Pd(dppf)Cl_2$, $Pd(PPh_3)_2Cl_2$, or $Pd(Ph_3)_4$, and an excess of base such as an aqueous solution of sodium or potassium carbonate, in solvents such as 1,2-dimethoxyethane or 1,4-dioxane. Alternatively, the coupling partners can be reversed, where compounds of general formula (II) undergo a metal-halogen exchange reaction (process step iii) to provide compounds of general formula (V). Such step includes, for example, sequential treatment with a strong base, such as nbutyl lithium, tertbutyl lithium, or lithium diisopropylamide, and the desired metal (Li, W. et al. *J. Org. Chem.* 2002, 67, 5394), or a direct treatment with a metallated species (Miyaura, N. et al. *J. Org. Chem.* 1995, 60, 7508; Knochel, P. et al. *Angew. Chem., Int. Ed.* 2003, 42, 4302). Subsequent C—C catalytic coupling reaction (process step iv) with compounds of general formula (VI), as described above, leads to compounds of formula (IV).

Scheme 4

General Method D

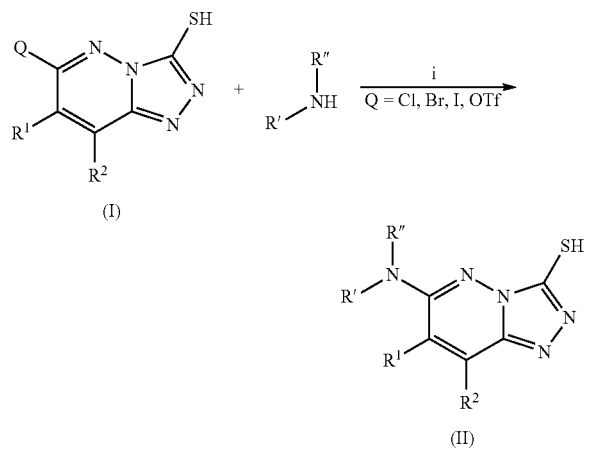

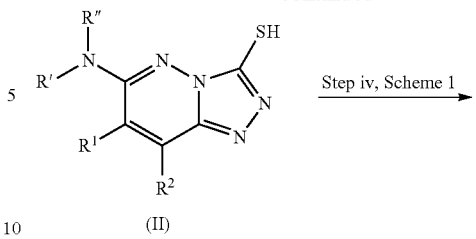

(II)

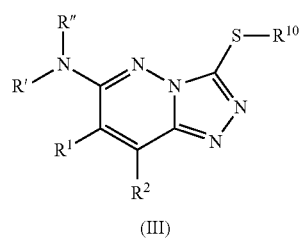

(III)

Compounds of general formula (III) where $R^1$, $R^2$, X, and $R^{10}$ are as described herein may be prepared according to general reaction Scheme 4. Compounds of formula (I) are prepared according to General Method A, steps ii and iii. Compounds of formula (II) may be prepared from compounds of general formula (I) by process step (i), which comprises a nucleophilic substitution reaction in presence of an excess of amine reagent, under neat conditions or in a suitable solvent at temperatures varying from 0° C. to 200° C. Typical conditions comprise 1 equivalent of compound (I) and 5-20 equivalents of amine reagent in water at reflux temperature for several hours.

Example 1

Preparation of Intermediates

Intermediate 1: 6-Bromo-5-nitro-quinoline

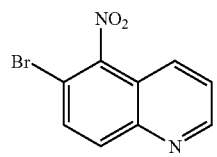

A solution of 6-bromoquinoline (2.0 g, 9.61 mmol) in concentrated sulfuric acid (10 mL) was cooled to 0° C. Sodium nitrite (27 mg, 0.384 mmol) was added, followed by dropwise addition of concentrated nitric acid (0.8 mL). The reaction mixture was stirred at 0° C. for 45 min. then at room temperature for 1 h, before pouring onto ice, resulting into a yellow precipitate. The mixture was neutralized to pH 7 with ammonium hydroxide. The precipitate was filtered, washed with water and dried in vacuo to yield 2.26 g of 6-bromo-5-nitro-quinoline as a light green solid (93% yield):): $^1$H NMR (CDCl$_3$) δ 7.62 (dd, 1H), 7.94 (d, 1H), 8.07 (d, 1H), 8.17 (d, 1H), 9.06 (dd, 1H); MS (m/z) 253, 255 [M+H$^+$]$^+$.

Intermediate 2: 6-Bromo-7-fluoro-quinoline

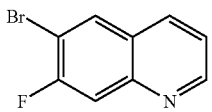

A mixture of 4-bromo-3-fluoroaniline (2.85 g, 15 mmol), ferric sulfate (0.95 g, 6.25 mmol), glycerol (5.66 g, 61 mmol), nitrobenzene (0.93 mL, 9.1 mmol), and concentrated sulfuric acid (2.61 ml) was heated gently. After the first vigorous reaction, the mixture was boiled for 7 h. Nitrobenzene was then evaporated in vacuo. The aqueous solution was acidified with glacial acetic acid, and a dark brown precipitate separated, which was collected and purified by flash chromatography (silica gel, petroleum/ethyl acetate=8/1) to give 1.44 g of 6-bromo-7-fluoro-quinoline as white crystals (42.5% yield).

Intermediate 3: 6-Bromo-5-fluoro-quinoline

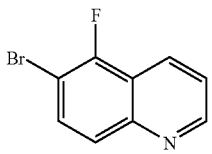 [SMILES: Fc1c(Br)ccc2ncccc12]

A mixture of 4-bromo-3-fluoroaniline (100 g, 526 mmol), 30 g of ferrous sulfate, 200 g of glycerol, 40 g of nitrobenzene and 100 ml of concentrated sulfuric acid was heated gently. After the first vigorous reaction, the mixture was boiled for five hours. Nitrobenzene was removed by distillation in vacuo. The aqueous solution was acidified with glacial acetic acid and dark brown precipitate separated, which was purified by flash chromatography (silica gel, petroleum ether/ethyl acetate=12/1) to give a mixture of 6-bromo-7-fluoro-quinoline and 6-bromo-5-fluoro-quinoline as a white solid (80 g, 68%). The mixture was heated to reflux in petroleum ether. The solution was cooled to room temperature and filtered to collect 6-bromo-7-fluoro-quinoline. To the filtrate was added HCl/methanol, and the resulting white precipitate was filtered. The white solid was basified, collected by filtration and dried to obtain 6-bromo-5-fluoro-quinoline as white solid. $^1$H-NMR (DMSO-d$_6$, 300 MHz): δ 9.0 (d, 1H), 8.5 (d, 1H), 8.0 (m, 1H), 7.8 (d, 1H), 7.7 (m, 1H).

Intermediate 4: 6-Bromo-7-methyl-quinoline

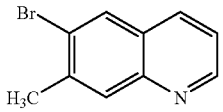

A mixture of 4-bromo-3-methylaniline (20 g, 107.5 mmol), ferric sulfate (6.6 g, 43.4 mmol), glycerol (40.8 g, 440 mmol), nitrobenzene (8.12 g, 66 mmol), and concentrated sulfuric acid (23 ml) was heated gently. After the first vigorous reaction, the mixture was boiled for 3 h and then evaporated to remove the excess nitrobenzene. The solution was added a saturated aqueous solution of sodium bicarbonate until pH=7-8, then the solution was filtered and extracted with dichloromethane. The combined organic layers were dried over Na$_2$SO$_4$, filtered and concentrated in vacuo. The solid was purified by flash column chromatography to give a yellow solid, which was further washed with petroleum ether to give 7.5 g of 6-bromo-7-methyl-quinoline (31% yield): $^1$H NMR (CDCl$_3$): 2.60 (s, 3H), 7.36 (m, 1H), 7.96 (s, 1H), 8.04 (m, 2H), 8.89 (m, 1H).

Intermediate 5: 6-Bromo-5-fluoro-benzothiazole

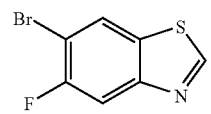

Step 1: 6-Bromo-5-fluoro-benzothiazol-2-ylamine

To a solution of 4-bromo-3-fluoro-aniline (3.68 g, 19.37 mmol) in glacial AcOH (40 mL) was added ammonium thiocyanate (2.95 g, 38.74 mmol). When the reaction mixture was almost clear, it was placed in a cold water bath and a solution of bromine (3.1 g, 19.37 mmol) in glacial AcOH (10 mL) was added dropwise over a 10 min period. The reaction mixture was stirred at room temperature for 1 h, then it was concentrated in vacuo. The residue was partitioned between 1 N aqueous KOH and ethyl acetate. The aqueous layer was further extracted with ethyl acetate, and the combined organic layers were adsorbed on silica gel. Purification by flash chromatography on silica gel using a gradient of 0-70% ethyl acetate/hexane afforded 2.73 g of 6-bromo-5-fluoro-benzothiazol-2-ylamine as a light yellow solid (57% yield): $^1$H NMR (DMSO-d6) δ 7.29 (d, 1H), 7.78 (broad s, 2H), 7.99 (d, 1H); MS (m/z) 247, 249 [M+H$^+$]$^+$.

Step 2: 6-Bromo-5-fluoro-benzothiazole

To a solution of 6-bromo-5-fluoro-benzothiazol-2-ylamine (2.73 g, 11.05 mmol) in DMF (60 mL) was added tert-butylnitrite (1.58 mL, 13.26 mmol) dropwise. The reaction mixture was stirred at 50° C. for 3 h, then it was concentrated in vacuo. The residue was stirred in 1 N aqueous KOH for 10 min, then ethyl acetate was added and the mixture was stirred overnight. The insolubles were filtered, washed with water then ethyl acetate. The resulting filtrate was separated, and the organic layer was washed with brine and directly adsorbed on silica gel. Purification by flash chromatography on silica gel using a gradient of 0-30% ethyl acetate/hexane afforded 1.33 g of 6-bromo-5-fluoro-benzothiazole as a light yellow solid (52% yield): $^1$H NMR (DMSO-d6) δ 8.13 (d, 1H), 8.63 (d, 1H), 9.50 (s, 1H); MS (m/z) 232, 234 [M+H$^+$]$^+$.

Intermediate 6: 6-Bromo-5-methyl-benzothiazole and 6-Bromo-7-methyl-benzothiazole

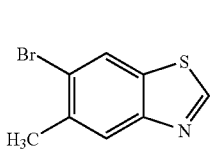 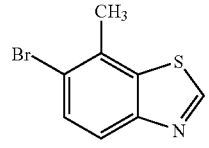

Step 1: 6-Bromo-5-methyl-benzothiazol-2-ylamine and 6-Bromo-7-methyl-benzothiazol-2-ylamine To a solution of 4-bromo-3-methyl-aniline (9.68 g, 52.02 mmol) in glacial AcOH (150 mL) was added ammonium thiocyanate (7.92 g, 104.04 mmol). When the reaction mixture was almost clear, it was placed in a cold water bath and a solution of bromine (2.67 mL, 52.02 mmol) in glacial AcOH (5 mL) was added dropwise. The reaction mixture was stirred at room temperature for 1.5 h. The resulting precipitate was filtered and washed with AcOH. The off-white cake was taken up in water and neutralized to pH 9 with 1 N aqueous NaOH. The resulting solid was filtered, washed with water and dried in vacuo to give 4.83 g of 4:1 mixture of 6-bromo-7-methyl-benzothiazol-2-ylamine and 6-bromo-5-methyl-benzothiazol-2-ylamine respectively (38% yield): MS (m/z) 243, 245 [M+H$^+$]$^+$; 6-Bromo-7-methyl-benzothiazol-2-ylamine: $^1$H NMR (DMSO-d6) δ 2.42 (s, 3H), 7.10 (d, 1H), 7.39 (d, 1H), 7.61 (broad s, 2H). 6-Bromo-5-methyl-benzothiazol-2-ylamine: $^1$H NMR (DMSO-d6) δ 2.35 (s, 3H), 7.31 (s, 1H), 7.57 (broad s, 2H), 7.88 (s, 1H).

Step 2: 6-Bromo-5-methyl-benzothiazole and 6-Bromo-7-methyl-benzothiazole

To a solution of 4:1 mixture of 6-bromo-7-methyl-benzothiazol-2-ylamine and 6-bromo-5-methyl-benzothiazol-2-ylamine respectively (4.5 g, 18.6 mmol) in DMF (100 mL) was added tert-butylnitrite (2.65 mL, 22.3 mmol) dropwise. The reaction mixture was stirred at 50° C. for 1.5 h, then it was concentrated in vacuo. The residue was partitioned between 1 N aqueous potassium carbonate and ethyl acetate. The aqueous layer was extracted with ethyl acetate (3×), and the combined organic layers were adsorbed on silica gel. Purification by flash chromatography on silica gel using a gradient of 0-50% ethyl acetate/hexane afforded 2.1 g of 5:1 mixture of 6-bromo-7-methyl-benzothiazole and 6-bromo-5-methyl-benzothiazole respectively (50% yield): MS (m/z) 228, 230 [M+H$^+$]$^+$; 6-Bromo-7-methyl-benzothiazole: $^1$H NMR (DMSO-d6) δ 2.63 (s, 3H), 7.75 (d, 1H), 7.87 (d, 1H), 9.42 (s, 1H). 6-Bromo-5-methyl-benzothiazole: $^1$H NMR (DMSO-d6) δ 2.63 (s, 3H), 8.09 (s, 1H), 8.48 (s, 1H), 9.37 (s, 1H).

Intermediate 7: 6-Bromo-1-methyl-1H-benzoimidazole

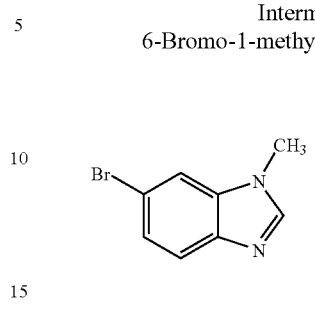

Step 1: 2,4-Dibromo-1-nitro-benzene

To an ice-cold solution of 1,3-dibromobenzene (10 g, 42.4 mmol) in concentrated sulfuric acid (200 mL) was added ammonium nitrate (3.39 g, 42.4 mmol) portionwise. The reaction mixture was stirred at 0° C. for 15 min, then it was poured onto an ice-water mixture. The aqueous mixture was extracted with dichloromethane (2×). The combined organic layers were washed with water then a saturated aqueous solution of sodium bicarbonate (2×), dried over sodium sulfate, filtered, and concentrated in vacuo. The residue was triturated with hexane, filtered, and dried in vacuo to give 7.63 g of 2,4-dibromo-1-nitro-benzene as a yellow solid (64% yield): $^1$H NMR (CDCl$_3$) δ 7.62 (dd, 1H), 7.78 (d, 1H), 7.95 (d, 1H).

Step 2: (5-Bromo-2-nitro-phenyl)-methyl-amine

To a solution of 2,4-dibromo-1-nitro-benzene (2.0 g, 7.14 mmol) in ethanol (50 mL) was added a 40% aqueous solution of methylamine (50 mL). The reaction mixture was stirred at 80° C. in a closed vessel for 3 h, then cooled to 0° C. Water was added and the precipitate was filtered, washed with water, and dried in vacuo to give 1.26 g of (5-bromo-2-nitro-phenyl)-methyl-amine as an orange solid (76% yield): $^1$H NMR (CDCl$_3$) δ 3.04 (s, 3H), 6.79 (dd, 1H), 7.03 (d, 1H), 8.05 (d, 1H), 8.0-8.1 (broad s, 1H); MS (m/z) 231, 233 [M+H$^+$]$^+$.

Step 3: 6-Bromo-1-methyl-1H-benzoimidazole

To a suspension of (5-bromo-2-nitro-phenyl)-methyl-amine (1.2 g, 5.19 mmol) in ethanol (25 mL) was added tin(II) chloride (1.97 g, 10.39 mmol). The reaction mixture was stirred at 80° C. for 4 h, then it was concentrated in vacuo. To the residue was added toluene (12 mL), trimethyl orthoformate (0.625 mL, 5.71 mmol), and para-toluenesulfonic acid (49 mg, 0.26 mmol). The reaction mixture was stirred at 110° C. for 15 h, then it was concentrated in vacuo and the residue was adsorbed on silica gel. Purification by flash chromatography on silica gel using a gradient of 0-8% methanol/dichloromethane afforded 482 mg of 6-bromo-1-methyl-1H-benzoimidazole as a dark orange solid (44% yield): $^1$H NMR (DMSO-d6) δ 3.83 (s, 3H), 7.33 (dd, 1H), 7.59 (d, 1H), 7.86 (d, 1H), 8.21 (s, 1H); MS (m/z) 211, 213 [M+H+]+.

Intermediate 8: Trifluoromethanesulfonic acid 3-methyl-3H-benzoimidazol-5-yl ester

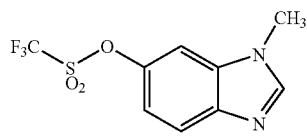

Step 1: 3-Methylamino-4-nitro-phenol

To a pressure vessel was added 3-fluoro-4-nitro-phenol (5.0 g, 31.82 mmol) and a 40% aqueous solution of methylamine (10 mL). The reaction mixture was stirred at 85° C. for 5 h, then it was cooled to room temperature, poured on water, and acidified to pH 1 with 1 N aqueous HCl. The resulting precipitate was filtered, washed with water, and dried in vacuo to give 5.23 g of 3-methylamino-4-nitro-phenol as an orange solid (98% yield): $^1$H NMR (DMSO-d6) δ 2.88 (d, 3H), 6.14 (dd, 1H), 6.17 (d, 1H), 7.96 (d, 1H), 8.25 (q, 1H), 10.8 (broad s, 1H); MS (m/z) 167 [M−H]−.

Step 2: 3-Methyl-3H-benzoimidazol-5-ol

To a suspension of 3-methylamino-4-nitro-phenol (300 mg, 1.786 mmol) in formic acid (4 mL) was added iron powder (1.0 g, 17.86 mmol). The reaction mixture was stirred at 100° C. overnight, then it was cooled to room temperature and diluted with methanol. The insolubles were filtered and washed with methanol. The filtrate was concentrated in vacuo and adsorbed on silica gel. Purification by flash chromatography on silica gel using a gradient of 0-15% methanol/dichloromethane afforded 249 mg of 3-methyl-3H-benzoimidazol-5-ol as a light brown solid (94% yield): $^1$H NMR (DMSO-d6) δ 3.71 (s, 3H), 6.69 (dd, 1H), 6.81 (d, 1H), 7.40 (d, 1H), 7.94 (s, 1H), 9.3 (broad s, 1H); MS (m/z) 149 [M+H]+.

Step 3: Trifluoromethanesulfonic acid 3-methyl-3H-benzoimidazol-5-yl ester

To a suspension of 3-methyl-3H-benzoimidazol-5-ol (245 mg, 1.655 mmol) in THF (5 mL) in a microwave vessel was added potassium carbonate (417 mg, 3.02 mmol) and N-phenyl-bis(trifluoromethanesulfonimide) (1.18 g, 3.31 mmol). The microwave vessel was capped and heated in a microwave reactor at 120° C. for 20 min. The reaction mixture was partitioned between water and ethyl acetate. The aqueous layer was extracted with ethyl acetate and the combined organic layers were adsorbed on silica gel. Purification by flash chromatography on silica gel using a gradient of 0-40% ethyl acetate/hexane afforded 235 mg of trifluoromethanesulfonic acid 3-methyl-3H-benzoimidazol-5-yl ester as a brown oil (51% yield): $^1$H NMR (DMSO-d6) δ3.88 (s, 3H), 7.28 (dd, 1H), 7.80 (d, 1H), 7.87 (d, 1H), 8.37 (s, 1H); MS (m/z) 281 [M+H]+.

Intermediate 9: Trifluoromethanesulfonic acid 7-methyl-quinolin-6-yl ester

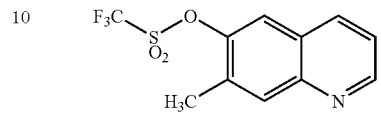

Step 1: 7-Methyl-quinolin-6-ol

A vial was purged with nitrogen and charged with 6-bromo-7-methyl-quinoline (2.0 g, 9 mmol), grounded KOH (2.02 g, 36 mmol), tris(dibenzylideneacetone)dipalladium(0) (165 mg, 0.18 mmol), and X-Phos (Strem ligand, 343 mg, 0.72 mmol). Water (6 mL) and 1,4-dioxane (6 mL) were added, and the reaction mixture was stirred at 100° C. for 2 h. After cooling to room temperature, the reaction mixture was acidified to pH 5 with 1 N aqueous HCl and extracted with ethyl acetate (2×). The combined organic layers were adsorbed on silica gel. Purification by flash chromatography on silica gel using a gradient of 0-100% ethyl acetate/hexane afforded 1.37 g of 7-methyl-quinolin-6-ol as a light yellow solid (95% yield): $^1$H NMR (DMSO-d6) δ 2.34 (s, 3H), 7.12 (s, 1H), 7.32 (dd, 1H), 7.73 (s, 1H), 8.07 (dd, 1H), 8.60 (dd, 1H), 10.1 (broad s, 1H); MS (m/z) 160 [M+H]+.

Step 2: Trifluoromethanesulfonic acid 7-methyl-quinolin-6-yl ester

To a suspension of 7-methyl-quinolin-6-ol (870 mg, 5.47 mmol) in THF (10 mL) in a microwave vessel was added potassium carbonate (2.27 g, 16.41 mmol) and N-phenyl-bis (trifluoromethanesulfonimide) (3.9 g, 10.94 mmol). The microwave vessel was capped and heated in a microwave reactor at 120° C. for 20 min. The reaction mixture was partitioned between water and ethyl acetate. The aqueous layer was extracted with ethyl acetate and the combined organic layers were adsorbed on silica gel. Purification by flash chromatography on silica gel using a gradient of 0-30% ethyl acetate/hexane afforded 1.48 g of trifluoromethanesulfonic acid 7-methyl-quinolin-6-yl ester as a clear oil (93% yield): $^1$H NMR (DMSO-d6) δ 2.53 (s, 3H), 7.60 (dd, 1H), 8.12 (s, 1H), 8.15 (s, 1H), 8.50 (dd, 1H), 8.97 (dd, 1H); MS (m/z) 292 [M+H]+.

Intermediate 10: Trifluoromethanesulfonic acid quinolin-6-yl ester, N-oxide

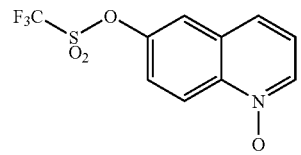

To a solution of trifluoromethanesulfonic acid quinolin-6-yl ester (200 mg, 0.721 mmol) in dichloromethane (3 mL)

was added mCPBA (213 mg, 0.865 mmol). The reaction mixture was stirred for 2 h, then it was diluted with dichloromethane and washed with a saturated aqueous solution of sodium bicarbonate (3×). The organic layer was adsorbed on silica gel. Purification by flash chromatography on silica gel using a gradient of 50-100% ethyl acetate/hexane afforded 185 mg of trifluoromethanesulfonic acid quinolin-6-yl ester, N-oxide as a white solid (87% yield): $^1$H NMR (DMSO-d6) δ 7.60 (dd, 1H), 7.91 (dd, 1H), 8.05 (d, 1H), 8.40 (d, 1H), 8.68 (m, 2H); MS (m/z) 294 [M+H]$^+$.

Intermediate 11: 3-(3-Fluoro-4-nitro-phenylsulfanyl)-6-(1-methyl-1H-pyrazol-4-yl)-[1,2,4]triazolo[4,3-b]pyridazine

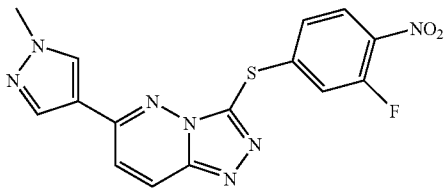 [SMILES: Cn1cc(-c2ccc3nnc(Sc4ccc([N+](=O)[O-])c(F)c4)n3n2)cn1]

A solution of trifluoro-methanesulfonic acid 3-fluoro-4-nitro-phenyl ester (1.51 g, 4.74 mmol), diisopropylethylamine (1.5 mL, 8.62 mmol) in DMF (14 mL) under nitrogen was degassed by bubbling in nitrogen for 10 min. Tris(dibenzylideneacetone)dipalladium (99 mg, 0.108 mmol, Strem catalyst) and Xantphos (125 mg, 0.215 mmol) were added together in one portion, followed by 6-(1-methyl-1H-pyrazol-4-yl)-[1,2,4]triazolo[4,3-b]pyridazine-3-thiol (1.0 g, 4.31 mmol). The reaction mixture was stirred at 100° C. for 3 h, then it was concentrated in vacuo. The residue was partitioned between saturated aqueous ammonium chloride and 10% methanol in dichloromethane. The aqueous layer was extracted with 10% methanol in dichloromethane, and the combined organic layers were directly adsorbed on silica gel. Purification by flash chromatography on silica gel using a gradient of 0-10% methanol/dichloromethane afforded 387 mg of 3-(3-fluoro-4-nitro-phenylsulfanyl)-6-(1-methyl-1H-pyrazol-4-yl)-[1,2,4]triazolo[4,3-b]pyridazine as a yellow solid (24% yield): $^1$H NMR (DMSO-d6) δ 3.90 (s, 3H), 7.20 (dd, 1H), 7.59 (dd, 1H), 7.87 (d, 1H), 8.06 (m, 2H), 8.46 (s, 1H), 8.54 (d, 1H); MS (m/z) 372 [M+H]$^+$.

Intermediate 12: Trifluoro-methanesulfonic acid 3-fluoro-4-nitro-phenyl ester

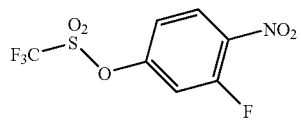

To a microwave vessel was added sequentially 3-fluoro-4-nitrophenol (2.0 g, 12.73 mmol), potassium carbonate (5.28 g, 38.19 mmol), N-phenyl-bis(trifluoromethanesulfonimide) (5.46 g, 15.27 mmol), and THF (10 mL). The microwave vessel was capped and heated in a microwave reactor at 120° C. for 20 min. The reaction mixture was partitioned between water and ethyl acetate. The aqueous layer was extracted with ethyl acetate and the combined organic layers were washed with brine, then directly adsorbed on silica gel. Purification by flash chromatography on silica gel using a gradient of 0-20% ethyl acetate/hexane afforded 2.93 g of trifluoromethanesulfonic acid 3-fluoro-4-nitro-phenyl ester as a light yellow liquid (80% yield): $^1$H NMR (DMSO-d6) δ 7.68 (d, 1H), 8.13 (d, 1H), 8.39 (t, 1H).

Intermediate 13: 2-(6-Bromo-quinolin-4-yloxy)-ethanol

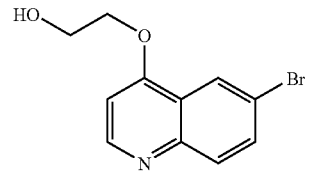 [SMILES: OCCOc1ccnc2ccc(Br)cc12]

To a suspension of sodium hydride (60% suspension, 40 mg, 0.99 mmol) in DMF (3 mL) under nitrogen atmosphere was added ethylene glycol dropwise. The reaction mixture was stirred for 20 min before adding 4-chloro-6-bromoquinoline (200 mg, 0.825 mmol) in one portion. The reaction mixture was stirred at 90° C. for 22 h. Another 20 mg of sodium hydride was added after 16 h. The mixture was cooled to room temperature and concentrated in vacuo. The residue was dissolved in methanol and the solution was adsorbed on silica gel. Purification by flash chromatography on silica gel using a gradient of 0-10% methanol/dichloromethane afforded 127 mg of 2-(6-bromo-quinolin-4-yloxy)-ethanol as a white solid (57% yield): $^1$H NMR (DMSO-d6) δ 3.93 (q, 2H), 4.32 (t, 2H), 5.21 (t, 1H), 7.14 (d, 1H), 7.94 (m, 2H), 8.50 (d, 1H), 8.82 (d, 1H); MS (m/z) 268, 270 [M+H]$^+$.

Intermediate 14: 6-Bromo-4-(4-methyl-4H-[1,2,4] triazol-3-ylsulfanyl)-quinoline

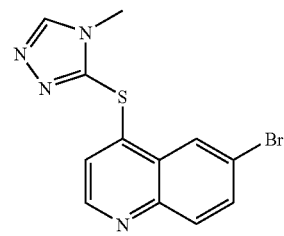 [SMILES: Cn1cnnc1Sc1ccnc2ccc(Br)cc12]

A capped vial was charged with 4-chloro-6-bromoquinoline (500 mg, 2.06 mmol), 4-methyl-4H-[1,2,4]triazole-3-thiol (238 mg, 2.06 mmol), potassium carbonate (427 mg, 3.09 mmol), and DMF (5 mL). The reaction mixture was stirred at 60° C. for 18 h then at 90° C. for another 24 h, and cooled to room temperature. The reaction mixture was poured onto water (50 mL), and the resulting precipitate was filtered, washed with water and dried in a vacuum oven at 70° C. overnight to provide 600 mg of 6-bromo-4-(4-methyl-4H-[1,2,4]triazol-3-ylsulfanyl)-quinoline as a white solid (91% yield): $^1$H NMR (DMSO-d6) δ 3.63 (s, 3H), 6.90 (d, 1H), 8.02 (m, 2H), 8.40 (d, 1H), 8.74 (d, 1H), 8.92 (s, 1H); MS (m/z) 321, 323 [M+H]$^+$.

Intermediate 15: Trifluoromethanesulfonic acid 3-bromo-quinolin-6-yl ester

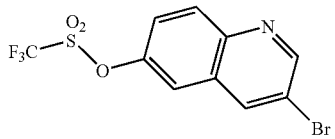

Step 1: Quinolin-6-ol

A mixture of 4-aminophenol (44.7 g, 0.41 mol), ferrous sulfate (14 g, 0.05 mol), glycerol (120 mL, 1.65 mol), p-nitrophenol (33.3 g, 0.24 mol), and concentrated sulfuric acid (20 mL) was heated gently to 70° C. Then a second portion of concentrated sulfuric acid (25 mL) was added dropwise to the reaction mixture and the mixture was stirred at reflux for 8 hours. After cooling down to room temperature, the reaction mixture was basified to pH=5.5 with 15% aqueous sodium hydroxide solution in an ice bath. The resulting precipitate was filtered, dried and 25 g of quinolin-6-ol was obtained as a yellow solid (42% yield).

Step 2: Trifluoromethanesulfonic acid quinolin-6-yl ester

Quinolin-6-ol (2.9 g, 20 mmol) was dissolved in pyridine (30 mL). The mixture was cooled to 0° C. in an ice bath under nitrogen and Tf$_2$O (4 mL, 24 mmol) was added to the reaction mixture slowly. The reaction mixture was stirred at room temperature for 5 hours, before partitioning between dichloromethane (50 mL) and saturated aqueous NaHCO$_3$ (50 mL). The organic phase was separated and washed with brine (5×30 mL). The organic phase was dried over Na$_2$SO$_4$, filtered and concentrated in vacuo. The residue was purified by column chromatography to give 3.9 g of trifluoromethanesulfonic acid quinolin-6-yl ester as a brown oil (70% yield).

Step 3: Trifluoromethanesulfonic acid 3-bromo-quinolin-6-yl ester

To a mixture of trifluoromethanesulfonic acid quinolin-6-yl ester (3.88 g, 14 mmol) and pyridine (2.26 mL, 28 mmol) in CCl$_4$ (50 mL) was added bromine (0.86 mL, 16.8 mmol) dropwise. The mixture was heated to reflux for 2 hrs and cooled to room temperature. The liquid in the flask was decanted and washed with NaHCO$_3$ and water. The dark solid on the bottom of the flask was treated with NaHCO$_3$ and dichloromethane. The combined organic layers were washed with water again and dried before being evaporated to dryness. The crude product was purified by flash column chromatography eluting with petroleum ether/ethyl acetate (10/1~1/1) to give 1.3 g of trifluoromethanesulfonic acid 3-bromo-quinolin-6-yl ester: $^1$H NMR (300 MHz, CDCl$_3$) δ: 7.62 (m, 1H), 7.68 (d, 1H), 8.20 (d, 1H), 8.36 (m, 1H), 8.98 (d, 1H); MS (m/z) 356 [M+H]$^+$.

Intermediate 16: Trifluoromethanesulfonic acid 5-(1-methyl-1H-pyrazol-4-yl)-quinolin-6-yl ester

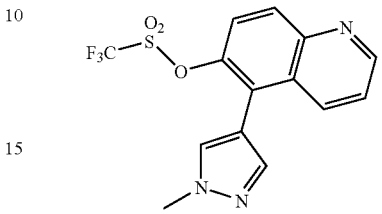

Step 1: 6-Methoxy-quinoline

A mixture of p-methoxyaniline (24.6 g, 0.2 mol), ferrous sulfate (8.34 g, 0.03 mol), glycerol (73.6 g, 60 mL), p-nitrophenol (16.68 g, 0.12 mol), and concentrated sulfuric acid (10 mL) was heated gently to 70° C. Then a second portion of concentrated sulfuric acid (25 mL) was added dropwise to the reaction mixture and it was stirred at reflux for 8 hours. After cooling down to room temperature, the reaction mixture was basified to pH=5.5 with 15% aqueous sodium hydroxide solution in an ice bath. The resulting precipitate was filtered, dried and 16 g of 6-methoxy-quinoline was obtained as a yellow solid (50% yield).

Step 2: 5-Bromo-6-methoxy-quinoline

To a mixture of 6-methoxy-quinoline (13.0 g, 0.082 mol) and pyridine (13.2 mL, 0.164 mol) in CCl$_4$ (130 mL) was added bromine (8.4 mL, 0.164 mol) dropwise. The mixture was heated to reflux for 2 hrs and cooled to room temperature. The liquid in the flask was decanted and washed with saturated aqueous NaHCO$_3$ and water. The dark solid on the bottom of the flask was treated with NaHCO$_3$ and dichloromethane. The combined organic layers were washed with water again and dried before being evaporated to dryness. The crude product was purified by flash column chromatography eluting with petroleum ether/ethyl acetate (10/1~1/1) to give 7 g of 5-bromo-6-methoxy-quinoline as a red solid (36% yield).

Step 3: 6-Methoxy-5-(1-methyl-1H-pyrazol-4-yl)-quinoline

A mixture of 5-bromo-6-methoxy-quinoline (6.5 g, 0.021 mol), 1-methyl-4-pyrazoleboronic acid pinacol ester (8.74 g, 0.042 mol), Na$_2$CO$_3$ (6.687 g, 0.063 mol), Pd(dppf)Cl$_2$ (1.7 g, 0.001 mol), H$_2$O (32 mL) and 1,4-dioxane (80 mL) was heated at 100° C. overnight. After cooling down to room temperature, most of the dioxane was removed under vacuo. The mixture was diluted with ethyl acetate (50 mL) and brine (50 mL). The organic phase was separated and the aqueous phase was extracted with ethyl acetate (2×50 mL). The combined organic phases were dried over Na$_2$SO$_4$, filtered and concentrated. The residue was purified by column chromatography to give compound 7 g of 6-methoxy-5-(1-methyl-1H-pyrazol-4-yl)-quinoline.

Step 4: 5-(1-Methyl-1H-pyrazol-4-yl)-quinolin-6-ol

A flask was charged with compound 6-methoxy-5-(1-methyl-1H-pyrazol-4-yl)-quinoline (5.5 g, 0.023 mol) and dichloromethane (50 mL). A solution of boron tribromide (27.6 mL, 1M solution in dichloromethane, 27.6 mmol) was added at 0° C. The reaction mixture was stirred at 0° C. for 15 minutes, then the cooling bath was removed and the reaction was stirred for 1.5 hours at room temperature. The reaction was quenched by slowly adding excess 10% aqueous hydrochloric acid, then the solution was basified to pH=6 with 20% aqueous sodium hydroxide solution. The mixture was extracted with ethyl acetate and the organic phase was washed with brine, dried over $Na_2SO_4$, and filtered. Removal of the solvent gave 4 g of 5-(1-methyl-1H-pyrazol-4-yl)-quinolin-6-ol as a yellow solid.

Step 5: Trifluoromethanesulfonic acid 5-(1-methyl-1H-pyrazol-4-yl)-quinolin-6-yl ester 5-(1-Methyl-1H-pyrazol-4-yl)-quinolin-6-ol (2.9 g, 12.89 mmol) was dissolved in pyridine (30 mL) and the mixture was cooled to 0° C. in an ice bath under a flow of nitrogen. $Tf_2O$ (2.6 mL, 15.47 mmol) was added slowly. Then the reaction mixture was stirred at room temperature for 5 hours. The mixture was partitioned between dichloromethane (50 mL) and saturated aqueous $NaHCO_3$ (50 mL). The organic phase was separated and washed with brine (5×30 mL). The organic phase was dried over $Na_2SO_4$, filtered and concentrated. The residue was purified by column chromatography to give 3.9 g of Trifluoromethanesulfonic acid 5-(1-methyl-1H-pyrazol-4-yl)-quinolin-6-yl ester (84% yield): $^1$H NMR (300 MHz, $CDCl_3$) δ: 4.05 (s, 3H), 7.48~7.44 (m, 1H), 7.69~7.61 (m, 3H), 8.18 (d, 1H), 8.32 (m, 1H), 8.98 (m, 1H); MS (m/z) 358 $[M+H]^+$.

Intermediate 17: Trifluoro-methanesulfonic acid 3-(1-methyl-1H-pyrazol-4-yl)-quinolin-6-yl ester

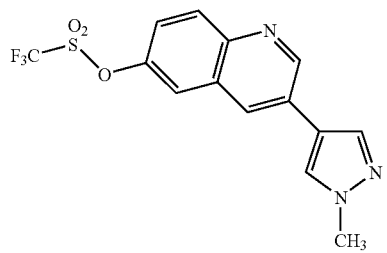 [SMILES: Cn1cc(-c2cnc3ccc(OS(=O)(=O)C(F)(F)F)cc3c2)cn1]

Step 1: Acetic acid quinolin-6-yl ester

Quinolin-6-ol (135 g, 0.93 mol) was dissolved in pyridine (500 mL) and cooled to 0° C. in an ice-bath under a flow of nitrogen. Acetyl chloride (79 mL, 1.16 mol) was added to the reaction mixture slowly. Then it was stirred at room temperature for 3 hours. The mixture was partitioned between ethyl acetate (400 mL) and saturated aqueous $NaHCO_3$ (200 mL). The organic phase was separated and washed with brine (5*200 mL). The organic phase was dried over $Na_2SO_4$, filtered and concentrated in vacuo. The residue was purified by column chromatography to afford 120 g of acetic acid quinolin-6-yl ester as white solid (69% yield).

Step 2: Acetic acid 3-bromo-quinolin-6-yl ester

To a mixture of acetic acid quinolin-6-yl ester (120 g, 0.642 mol) and pyridine (114 mL, 1.41 mol) in 6 L of $CCl_4$ was added $Br_2$ (66 mL, 1.28 mol) dropwise. The mixture was heated to reflux for 2 hours before being cooled to room temperature. The liquid in the flask was decanted and washed with saturated aqueous $NaHCO_3$ and water. The dark solid on the bottom of the flask was partitioned between aqueous $NaHCO_3$ and dichloromethane. The combined organic layers were washed with water again and dried before being evaporated to dryness in vacuo. The crude product was purified through flash column chromatography eluting with Petroleum Ether/ethyl acetate (10/1~1/1) to provide 108 g of acetic acid 3-bromo-quinolin-6-yl ester as a yellow solid (63% yield).

Step 3: 3-(1-Methyl-1H-pyrazol-4-yl)-quinolin-6-ol

A mixture of acetic acid 3-bromo-quinolin-6-yl ester (108 g, 0.406 mol), 1-methyl-4-pyrazoleboronic acid pinacol ester (169 g, 0.752 mol), $Na_2CO_3$ (129 g, 1.28 mol), $Pd(dppf)Cl_2$ (32.8 g, 0.0406 mol), $H_2O$ (607 mL) and 1,4-dioxane (1000 mL) was heated to 100° C. overnight. After cooling down to room temperature, most of the dioxane was removed under vacuo. The mixture was partitioned between ethyl acetate (500 mL) and brine (500 mL). The organic phase was separated and the aqueous phase was extracted with ethyl acetate (2*500 mL). The combined organic phases were dried over $Na_2SO_4$, filtered and concentrated in vacuo. The residue was purified by column chromatography to give 54 g of 3-(1-methyl-1H-pyrazol-4-yl)-quinolin-6-ol as a yellow solid (59% yield).

Step 4: Trifluoro-methanesulfonic acid 3-(1-methyl-1H-pyrazol-4-yl)-quinolin-6-yl ester A solution of 3-(1-methyl-1H-pyrazol-4-yl)-quinolin-6-ol (54 g, 0.24 mol) in Pyridine (400 mL) was cooled to 0° C. in an ice-bath under a flow of nitrogen. Triflic anhydride (48 mL, 0.28 mol) was added to the reaction mixture slowly and stirred at room temperature for 5 hours. The reaction mixture was partitioned between dichloromethane (300 mL) and saturated aqueous $NaHCO_3$ (200 mL). The organic phase was separated and washed by brine (5*300 mL). The organic phase was dried over $Na_2SO_4$, filtered and concentrated in vacuo. The residue was purified by column chromatography to give 58 g of trifluoro-methanesulfonic acid 3-(1-methyl-1H-pyrazol-4-yl)-quinolin-6-yl ester as white solid (70% yield): $^1$H NMR ($CDCl_3$, 300 MHz): 9.30 (d, 1H), 8.62 (d, 1H), 8.43 (s, 1H), 8.16 (d, 1H), 8.11 (s, 1H), 8.10 (d, 1H), 7.76 (m, 1H), 3.92 (s, 3H); MS (m/z) 358 $[M+H]^+$.

Intermediate 18: 2-(4-Iodo-pyrazol-1-yl)-2-methyl-propionic acid ethyl ester

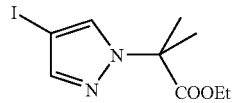

To a solution of iodopyrazole (1.0 g, 5.10 mmol) in DMF (10 mL) was added sodium hydride (60% dispersion in oil, 245 mg, 6.12 mmol). After stirring for 10 min a solution of ethyl-2-bromoisobutyrate (0.681 mL, 4.59 mmol) in DMF (4 mL) was added. The solution was stirred at room temperature for 18 hours. The mixture was diluted with ethyl acetate and the organic layer was washed with water, brine and dried over sodium sulfate to obtain 1.3 g of 2-(4-iodo-pyrazol-1-yl)-2-methyl-propionic acid ethyl ester as a clear oil (83% yield): $^1$H NMR (DMSO-d6) δ 1.11 (t, 3H), 1.73 (s, 6H), 4.08 (q, 2H), 7.57 (s, 1H), 8.11 (s, 1H); MS (m/z) 309 [M+H]$^+$.

Intermediate 19: 4-(4,4,5,5-Tetramethyl-[1,3,2]dioxaborolan-2-yl)-1-(2-trimethylsilanyl-ethoxymethyl)-1H-pyrazole

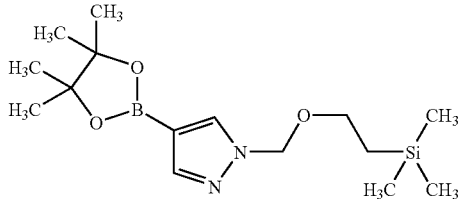

The title compound was prepared according to procedure described in US:2006/0142307A1

Intermediate 20: 1-Methyl-d$_3$-4-(4,4,5,5-tetramethyl-[1,3,2]dioxaborolan-2-yl)-1H-pyrazole

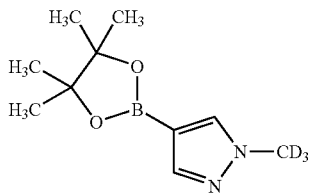 [SMILES: [2H]C([2H])([2H])n1cc(B2OC(C)(C)C(C)(C)O2)cn1]

To a solution of 4-(4,4,5,5-tetramethyl-[1,3,2]dioxaborolan-2-yl)-1H-pyrazole (5.0 g, 25.8 mmol) and Cs$_2$CO$_3$ (10.1 g, 30.96 mmol) in DMF (105 mL) was added CD$_3$I (1.77 mL, 28.38 mmol). The mixture was stirred for 3 hours and then extracted into ethyl acetate and washed with water (3×) and brine (3×) and dried over sodium sulfate. The volatiles were removed to afford 1-methyl-d$_3$-4-(4,4,5,5-tetramethyl-[1,3,2]dioxaborolan-2-yl)-1H-pyrazole (2.7 g, 50% yield): $^1$H NMR (DMSO-d$_6$) δ 1.25 (s, 12H), 7.55 (s, 1H), 7.90 (s, 1H); MS (m/z) 212 [M+H]$^+$.

Intermediate 21: 5-(1-Methyl-1H-pyrazol-4-yl)-1H-pyrrolo[2,3-b]pyridine

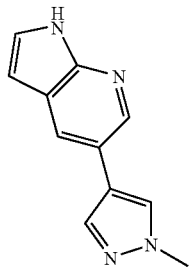

5-Bromo-1H-pyrrolo[2,3-b]pyridine (1.0 g, 5.05 mmol), 1-methyl-4-(4,4,5,5-tetramethyl-[1,3,2]dioxaborolan-2-yl)-1H-pyrazole (1.17 g, 5.55 mmol) and Pd(dppf)Cl$_2$ (37 mg, 0.045 mmol) were placed in a N$_2$ purged round-bottom flask. The reagents were dissolved in DMA (6 ml) and purged with N$_2$. An aqueous solution of K$_2$CO$_3$ (978 mg in 6 ml) was then added slowly to the reaction mixture, while maintaining the temperature below 40° C., and purged for 10 minutes with N$_2$. The solution was then heated to 75° C. overnight. Heating was discontinued and 12 ml of H$_2$O was added. The solution was then heated to 60° C. for 1 h. Next, the solution was transferred to a separatory funnel and extracted with dichloromethane (100 ml×2). The organic layer was dried over Na$_2$SO$_4$ and concentrated down onto silica gel. The reaction mixture was purified by flash chromatography using a gradient of 0-10% methanol/di-chloromethane to afford 780 mg of 5-(1-methyl-1H-pyrazol-4-yl)-1H-pyrrolo[2,3-b]pyridine (78% yield): $^1$H NMR (DMSO-d$_6$) δ 3.94 (3H, s), 6.49 (1H, d), 7.38 (1H, d), 7.84 (1H, s), 7.97 (1H, s), 8.12 (1H, d), 8.38 (1H, d); MS (m/z) 199 [M+H]$^+$.

Intermediate 22: (6-Bromo-quinolin-4-yl)-carbamic acid tert-butyl ester

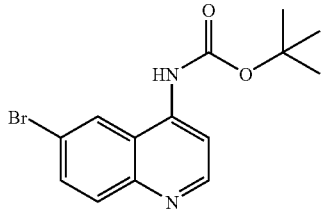 [SMILES: CC(C)(C)OC(=O)Nc1ccnc2ccc(Br)cc12]

To a solution of 6-bromo-quinoline-4-ylamine (100 mg, 0.45 mmol) [prepared according to J. Med. Chem. 1978, 21, 271] and 4-dimethylaminopyridine (5.5 mg, 0.045 mmol) in dichloromethane (2 mL) was added tBOC anhydride (122 mg, 0.56 mmol). The reaction mixture was stirred at room temperature overnight, then it was concentrated in vacuo. The crude was purified by flash chromatography using a gradient of 0-10% methanol/dichloromethane to afford 123 mg of (6-bromo-quinolin-4-yl)-carbamic acid tert-butyl ester (85% yield): $^1$H NMR (DMSO-d$_6$) δ 1.54 (s, 9H), 7.90 (m, 2H), 8.03 (d, 1H), 8.75 (s, 1H), 8.79 (d, 1H), 10.00 (s, 1H); MS (m/z) 325 [M+H]$^+$.

Intermediate 23: (6-Bromo-quinolin-3-yl)-carbamic acid tert-butyl ester

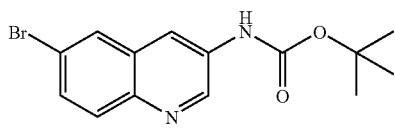 [SMILES: CC(C)(C)OC(=O)Nc1cnc2ccc(Br)cc2c1]

A solution of 6-bromo-quinoline-3-carboxylic acid (500 mg, 1.98 mmol) and triethylamine (3.97 mmol) in tertbutanol (2 mL) was degassed by bubbling nitrogen for 5 min, and DPPA (3.97 mmol, 858 mg) was added. The reaction mixture was stirred at reflux for 4 h. The solvent was removed in vacuo, and the residue was partitioned between water and ethyl acetate. The aqueous layer was extracted with ethyl acetate (2×), and the combined organics were washed sequentially with a saturated aqueous solution of sodium bicarbonate and brine, dried over sodium sulfate, filtered, and concentrated in vacuo. The residue was by flash chromatography using a gradient of 0-10% methanol/dichloromethane to afford 347 mg of (6-bromo-quinolin-3-yl)-carbamic acid tert-butyl ester (54% yield): $^1$H NMR (DMSO-d$_6$) δ 1.53 (s, 9H), 7.69 (dd, 1H), 7.85 (d, 1H), 8.21 (d, 1H), 8.48 (s, 1H), 8.85 (d, 1H), 10.00 (bs, 1H); MS (m/z) 325 [M+H]$^+$.

Intermediate 24: Trifluoro-methanesulfonic acid 4-ethyl-quinolin-6-yl ester

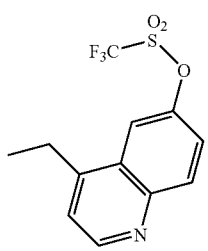

Step 1: 4-Ethyl-quinolin-6-ol

A mixture of toluene (17 mL) and 2 M aqueous sodium carbonate (5 mL) was degassed by bubbling nitrogen for 20 minutes. To the mixture was added 4-chloro-6-methoxy-quinoline (500 mg, 2.58 mmol) and tetrakis(triphenylphosphine)palladium(0) (90 mg, 0.0774 mmol), followed by 1 M triethylborane solution in hexane (15.5 mL, 15.5 mmol). The reaction mixture was stirred at 90° C. for 4 days, periodically adding more palladium catalyst (270 mg total) and triethylborane solution (30 mL total) to drive the reaction. The reaction mixture was cooled to room temperature and partitioned between water and ethyl acetate. The organic layer was separated, dried over sodium sulfate, filtered, and adsorbed on silica gel. Purification by flash chromatography using a gradient of 0-70% ethyl acetate/hexane afforded 579 mg of impure 4-ethyl-6-methoxy-quinoline as a waxy off white solid. The solid was treated with concentrated sulfuric acid (6 mL) and water (4 mL). The reaction mixture was stirred at reflux for 5 h and poured onto ice. Ammonium hydroxide was added until pH 9 and the aqueous layer was extracted with ethyl acetate (2×). Combined organics were adsorbed on silica gel. Purification by flash chromatography using a gradient of 0-80% ethyl acetate/hexane afforded 195 mg of 4-ethyl-quinolin-6-ol as an off white solid (44% yield): $^1$H NMR (DMSO-d$_6$) δ 1.30 (t, 3H), 2.96 (q, 2H), 7.25 (d, 1H), 7.28 (m, 2H), 7.86 (d, 1H), 8.56 (d, 1H), 9.98 (broad s, 1H); MS (m/z) 174 [M+H]$^+$.

Step 2: Trifluoro-methanesulfonic acid 4-ethyl-quinolin-6-yl ester

To a microwave vessel was added sequentially 4-ethyl-quinolin-6-ol (177 mg, 1.022 mmol), potassium carbonate (424 mg, 3.066 mmol), N-phenyl-bis(trifluoromethanesulfonimide) (730 mg, 2.044 mmol), and THF (5 mL). The microwave vessel was capped and heated in a microwave reactor at 120° C. for 20 min. The reaction mixture was partitioned between water and ethyl acetate. The aqueous layer was extracted with ethyl acetate and the combined organic layers were dried over sodium sulfate, filtered and adsorbed on silica gel. Purification by flash chromatography on silica gel using a gradient of 0-50% ethyl acetate/hexane afforded 286 mg of trifluoro-methanesulfonic acid 4-ethyl-quinolin-6-yl ester as a clear oil (92% yield): $^1$H NMR (DMSO-d6) δ 1.31 (t, 3H), 3.13 (q, 2H), 7.53 (d, 1H), 7.86 (dd, 1H), 8.21 (d, 1H), 8.30 (d, 1H), 8.92 (d, 1H); MS (m/z) 306 [M+H]$^+$.

Intermediate 25: 1-Ethyl-4-(4,4,5,5-tetramethyl-[1,3,2]dioxaborolan-2-yl)-1H-pyrazole

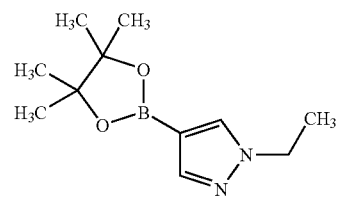 [SMILES: CCn1cc(B2OC(C)(C)C(C)(C)O2)cn1]

The title compound was prepared according to procedure described in Ivachtchenko, A. V. et. al. *J. Heterocyclic Chem.* 2004, 41, 931.

Intermediate 26: 3-[4-(4,4,5,5-Tetramethyl-[1,3]dioxolan-2-yl)-pyrazol-1-ylmethyl]-azetidine-1-carboxylic acid tert-butyl ester

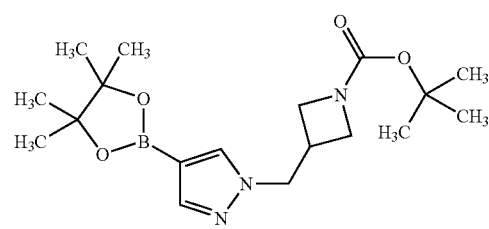 [SMILES: CC(C)(C)OC(=O)N1CC(Cn2cc(B3OC(C)(C)C(C)(C)O3)cn2)C1]

The title compound was prepared according to procedure described in WO 2006/021881.

Intermediate 27: 3-[4-(4,4,5,5-Tetramethyl-[1,3,2]dioxaborolan-2-yl)-pyrazol-1-yl]-azetidine-1-carboxylic acid tert-butyl ester

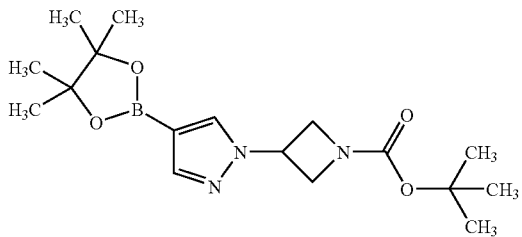 [SMILES: CC(C)(C)OC(=O)N1CC(n2cc(B3OC(C)(C)C(C)(C)O3)cn2)C1]

Title compound was prepared according to procedure described in WO 2006/021881.

Example 2

6-(1-methyl-1H-pyrazol-4-yl)-[1,2,4]triazolo[4,3-b]pyridazine-3-thiol

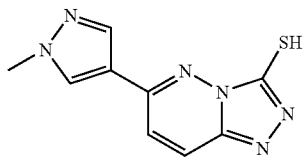 [SMILES: Cn1cc(-c2ccc3nnc(S)n3n2)cn1]

Step 1: 3-Chloro-6-(1-methyl-1H-pyrazol-4-yl)-pyridazine

A mixture of 3,6-dichloropyridazine (20.1 g, 135 mmol), 1-methyl-4-pyrazoleboronic acid pinacol ester (22.46 g, 108 mmol) and $K_2CO_3$ (44.71 g, 324 mmol) in 500 mL of dioxane and 200 mL of $H_2O$ was degassed with nitrogen. To this mixture was added dichloro[1,1'-bis(diphenylphosphino)ferrocene]palladium(II) dichloromethane adduct (5.28 g, 7.2 mmol) and the resulting mixture was bubbled with nitrogen for another 20 min. The reaction mixture was heated at 80° C. for 4 h, then concentrated in vacuo. The residue was purified by flash column chromatography with dichloromethane as eluent to provide 21 g of 3-chloro-6-(1-methyl-1H-pyrazol-4-yl)-pyridazine (76% yield): $^1$H NMR (CDCl$_3$) δ 3.99 (s, 3H), 7.45 (d, 1H), 7.56 (d, 1H), 7.97 (s, 1H), 8.11 (s, 1H).

Step 2: [6-(1-Methyl-1H-pyrazol-4-yl)-pyridazin-3-yl]-hydrazine

To a suspension of 3-chloro-6-(1-methyl-1H-pyrazole-4-yl)-pyridazine (21.0 g, 108 mmol) in ethanol (370 mL) was added hydrazine monohydrate (36 mL). The reaction mixture was stirred at reflux for 18 h, then cooled to room temperature. The precipitate was collected via filtration, washed with cold ethanol and dried in vacuo to provide 18 g of [6-(1-methyl-1H-pyrazol-4-yl)-pyridazin-3-yl]-hydrazine as a beige solid (87% yield): $^1$H NMR (DMSO-d6) δ 3.88 (s, 3H), 4.28 (s, 2H), 7.02 (d, 1H), 7.59 (d, 1H), 7.83 (s, 1H), 7.91 (s, 1H), 8.19 (s, 1H); MS (m/z) 191 [M+H$^+$]$^+$.

Step 3: 6-(1-methyl-1H-pyrazol-4-yl)-[1,2,4]triazolo[4,3-b]pyridazine-3-thiol Method a:

To a solution of [6-(1-methyl-1H-pyrazol-4-yl)-pyridazin-3-yl]-hydrazine (18 g, 94.7 mmol) in ethanol (230 mL) and water (63 mL) was added KOH (5.63 g, 100 mmol), followed by CS$_2$ (12 mL, 198 mmol). The mixture was stirred and heated to reflux for 2 h under nitrogen atmosphere. The mixture was cooled to room temperature and concentrated in vacuo. The residue was dissolved in 1 N aqueous sodium hydroxide and the insolubles were filtered off. The filtrate was acidified to pH 2-3 with 1 N aqueous HCl. The resulting precipitate was collected, washed with water, and dried in vacuo to provide 17.7 g of 6-(1-methyl-1H-pyrazol-4-yl)-[1,2,4]triazolo[4,3-b]pyridazine-3-thiol as a yellow solid (80.5% yield): $^1$H NMR (DMSO-d6) δ 3.95 (s, 3H), 7.73 (d, 1H), 8.13 (s, 1H), 8.16 (d, 1H), 8.53 (s, 1H), 14.7 (s, 1H); MS (m/z) 233 [M+H]$^+$.

Method b:

[6-(1-Methyl-1H-pyrazol-4-yl)-pyridazin-3-yl]-hydrazine (1.0 g, 5.3 mmol) and 1,1'-thiocarbonyldiimidazole (1.08 g, 6.1 mmol) were combined in DMF (10 mL) and heated at 50° C. for 2 h. After such time the mixture was allowed to cool to room temperature. Hexane (10 mL) was added followed by THF (4 mL), stirred for 10 mins then filtered and washed with THF (2 mL then 4 mL). Solid dried in vacuo to return 738 mg of 6-(1-methyl-1H-pyrazol-4-yl)-[1,2,4]triazolo[4,3-b]pyridazine-3-thiol as a yellow solid (60% yield).

The following compounds were prepared according to example 2: 6-Phenyl-[1,2,4]triazolo[4,3-b]pyridazine-3-thiol, 6-(3-Fluoro-phenyl)-[1,2,4]triazolo[4,3-b]pyridazine-3-thiol, 3-(3-Mercapto-[1,2,4]triazolo[4,3-b]pyridazin-6-yl)-benzonitrile, 2-Fluoro-4-(3-mercapto-[1,2,4]triazolo[4,3-b]pyridazin-6-yl)-N-methyl-benzamide.

Example 3

6-(3-Fluoro-phenyl)-[1,2,4]triazolo[4,3-b][1,2,4]triazine-3-thiol

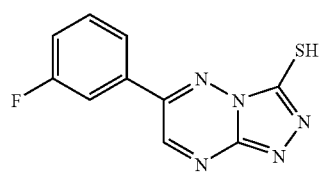 [SMILES: Fc1cccc(-c2cnc3nnc(S)n3n2)c1]

Step 1: (3-Fluoro-phenyl)-oxo-acetaldehyde oxime

To a mixture of selenium dioxide (58.3 g, 525 mmol) in 20 ml of water and 400 ml of 1,4-dioxane was added in one-portion 1-(3-fluoro-phenyl)-ethanone (69.0 g, 500 mmol). The mixture was refluxed overnight, then filtered through diatomaceous earth. The filtrate was added to an equal volume of water and adjusted to pH 4 with 5% aqueous sodium hydroxide. To this mixture was added acetone oxime (40.2 g, 550 mmol) and the mixture was stirred for 24 h. On dilution to 1.5 L with water, the mixture was extracted with ethyl acetate (2×400 ml), and the organic layer was washed with brine, dried with anhydrous sodium sulfate, and concentrated to give a oil residue, which was purified by flash chromatography on silica gel (eluting with pure Petroleum) to return title compound as a pale yellow solid (68.0 g, 81.4%). $^1$H NMR (DMSO-d6): δ 12.78 (s, 1H), 8.02 (s, 1H), 7.82-7.50 (m, 4H).

Step 2: 6-(3-Fluoro-phenyl)-2H-[1,2,4]triazin-3-one

A solution of (3-fluoro-phenyl)-oxo-acetaldehyde oxime (70 g, 419 mmol), semicarbazide hydrochloride (46.7 g, 419 mmol) and sodium acetate trihydrate (57.0 g, 419 mmol) in 560 ml of 50% aqueous ethanol solution was heated to 50-60° C. and maintained at the same temperature overnight. After the reaction mixture cooling down, the resulting white crystalline solid was isolated by filtration, washed well with water, and dried in vacuo to 90.7 g of a white solid (96.6%): $^1$H NMR (DMSO-d6): δ 12.32 (s, 1H), 12.27 (s, 1H), 8.45 (s, 1H), 7.78 (dd, 1H), 7.63 (d, 1H), 7.42 (dd, 1H), 7.19 (dt, 1H), 6.90 (s, 2H).

A suspension of the white solid (22.4 g, 100 mmol) in 630 ml of 5% aqueous hydrochloric acid was heated to reflux and maintained at reflux for 1 hour during which time the suspension solid changed from flurry white solid to a tacky mass which hardened as the mixture cooled. The solid was isolated by filtration, washed well with water and dried, then dissolved in 150 ml of acetic acid. The resulting solution was heated at reflux overnight, and the solvent was removed in vacuo. The residue was triturated with ethanol-hexane (1:3) to give crude title compound (15.1 g, 79.0%) as a yellow amorphous solid.

Step 3: 3-Chloro-6-(3-fluoro-phenyl)-[1,2,4]triazine

A mixture of 6-(3-fluoro-phenyl)-2H-[1,2,4]triazin-3-one (15.2 g, 79.5 mmol, crude) and 2 ml of DMF in 250 ml of 1:1 phosphorous oxychloride-chloroform was maintained at reflux overnight. The mixture was then concentrated at reduced pressure, diluted with methylene chloride and poured onto ice with stirring. When the ice melted the mixture was neutralized with sodium bicarbonate solution, and the layers were separated, the aqueous layer was extracted with dichloromethane once, the combined organic layer was washed with water, dried and concentrated to a brown oil which was purified by column chromatography (eluting with pure petroleum) to give title compound as a pale yellow solid (3.5 g, 21.0%): $^1$H NMR (CDCl$_3$): δ 8.88 (s, 1H), 7.87-7.82 (m, 2H), 7.60-7.52 (m, 1H), 7.32-7.27 (m, 1H).

Step 4: [6-(3-Fluoro-phenyl)-[1,2,4]triazin-3-yl]-hydrazine

A solution of 3-chloro-6-(3-fluoro-phenyl)-[1,2,4]triazine (2.09 g, 10.0 mmol) in 13.6 ml of dry pyridine was cooled to 0° C. with ice bath and 1.7 ml of hydrazine hydrate was added. The mixture was then heated to 65° C. and maintained this temperature for ca. 0.5 hour. After cooling down to room temperature, the mixture was poured into ice-water. The resulting solid was recovered by filtration and washed well with water, dried and scratched with hexane to give title compound (1.85 g, 90.2%) as a yellow crystalline solid: $^1$H NMR (DMSO-d6): δ 8.97 (b, 1H), 8.90 (s, 1H), 7.89-7.82 (m, 2H), 7.59-7.51 (m, 1H), 7.30-~7.24 (m, 1H), 5.47 (b, 2H); MS (m/z) 206 [M+H$^+$]$^+$.

Step 5: 6-(3-Fluoro-phenyl)-[1,2,4]triazolo[4,3-b][1,2,4]triazine-3-thiol

To a suspension of [6-(3-fluoro-phenyl)-[1,2,4]triazin-3-yl]-hydrazine (400 mg, 0.789 mmol) in ethanol (12 mL) was added 2 N aqueous potassium hydroxide (1 mL) followed by carbon disulfide (1 mL). The reaction mixture was stirred at reflux for 1 h, then cooled to room temperature and concentrated in vacuo. The residue was dissolved with 1 N aqueous potassium hydroxide, heated and sonicated then the insolubles were filtered. The filtrate was acidified to pH 2-3 with 1 N aqueous HCl. The resulting precipitate was filtered, washed with water, and dried in vacuo to return title compound as an orange solid (242 mg, 50% yield): $^1$H NMR (DMSO-d6): δ 7.52 (dt, 1H), 7.70 (dt, 1H), 7.97-8.04 (m, 2H), 9.36 (s, 1H), 14.05 (s, 1H); MS (m/z) 248 [M+H$^+$]$^+$.

Example 4

6-[6-(1-Methyl-1H-pyrazol-4-yl)-[1,2,4]triazolo[4,3-b]pyridazin-3-ylsulfanyl]-quinoline (Compound 4)

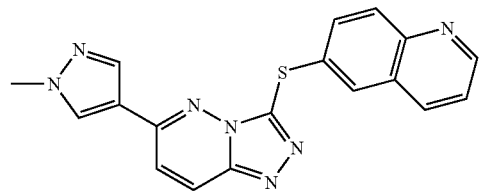 [SMILES: Cn1cc(-c2ccc3nnc(Sc4ccc5ncccc5c4)n3n2)cn1]

Method a:

A solution of 6-bromoquinoline (45 mg, 0.215 mmol), diisopropylethylamine (0.075 mL, 0.43 mmol) in DMF (1 mL) under nitrogen was degassed by bubbling in nitrogen for 5 min. Tris(dibenzylideneacetone)dipalladium (11 mg, 0.011 mmol), Xantphos (13 mg, 0.022 mmol), and 6-(1-methyl-1H-pyrazol-4-yl)-[1,2,4]triazolo[4,3-b]pyridazine-3-thiol (50 mg, 0.215 mmol) were added, and the mixture was degassed for another 5 min. The reaction mixture was stirred at 100° C. for 23 h. More palladium catalyst (11 mg) and ligand (13 mg) were added after 6 h. The reaction mixture was cooled to room temperature, filtered through a 0.45 um filter, and the crude mixture was purified directly by mass-triggered HPLC (5-95% CH$_3$CN/H$_2$O, 0.1% HCOOH modifier) to provide 45 mg of 6-[6-(1-methyl-1H-pyrazol-4-yl)-[1,2,4]triazolo[4,3-b]pyridazin-3-ylsulfanyl]-quinoline as a yellow solid (58% yield).

The following compounds were prepared according to method a: 6-(6-Phenyl-[1,2,4]triazolo[4,3-b]pyridazin-3-ylsulfanyl)-quinoline, 6-Phenyl-3-([1,2,4]triazolo[4,3-a]pyridin-6-ylsulfanyl)-[1,2,4]triazolo[4,3-b]pyridazine, 3-(1H-Benzotriazol-5-yl-sulfanyl)-6-phenyl[1,2,4]triazolo-[4,3-b]pyridazine, 6-[6-(3-Fluoro-phenyl)-[1,2,4]triazolo[4,3-b]pyridazin-3-ylsulfanyl]-quinoline, 3-(Benzothiazol-6-ylsulfanyl)-6-(3-fluoro-phenyl)-[1,2,4]triazolo[4,3-b]pyridazine, 6-(3-Fluoro-phenyl)-3-([1,2,4]triazolo[4,3-a]pyridin-6-ylsulfanyl)-[1,2,4]triazolo[4,3-b]pyridazine, (2:1) mixture of 3-(7-Methyl-benzothiazol-6-ylsulfanyl)-6-(1-methyl-1H-pyrazol-4-yl)-[1,2,4]triazolo[4,3-b]pyridazine and 3-(5-Methyl-benzothiazol-6-ylsulfanyl)-6-(1-methyl-1H-pyrazol-4-yl)-[1,2,4]triazolo[4,3-b]pyridazine, 6-[6-(3-Fluoro-phenyl)-[1,2,4]triazolo[4,3-b][1,2,4]triazin-3-ylsulfanyl]-quinoline, 7-Fluoro-6-[6-(1-methyl-1H-pyrazol-4-yl)-[1,2,4]triazolo[4,3-b]pyridazin-3-ylsulfanyl]-quinoline, 2-Fluoro-N-methyl-4-[3-(quinolin-6-ylsulfanyl)-[1,2,4]triazolo[4,3-b]pyridazin-6-yl]-benzamide, 6-[6-(1-Methyl-1H-pyrazol-4-yl)-[1,2,4]triazolo[4,3-b]pyridazin-3-ylsulfanyl]-quinazoline, 3-(Benzothiazol-6-ylsulfanyl)-6-(1-methyl-1H-pyrazol-4-yl)-[1,2,4]triazolo[4,3-b]pyridazine, 3-(5-Fluorobenzothiazol-6-ylsulfanyl)-6-(1-methyl-1H-pyrazol-4-yl)-[1,2,4]triazolo[4,3-b]pyridazine, 7-Methyl-6-[6-(1-methyl-1H-pyrazol-4-yl)-[1,2,4]triazolo[4,3-b]pyridazin-3-ylsulfanyl]-quinoline, 2-Fluoro-4-[3-(7-fluoro-quinolin-6-ylsulfanyl)-[1,2,4]triazolo[4,3-b]pyridazin-6-yl]-N-methyl-benzamide, 2-Fluoro-N-methyl-4-[3-(7-methyl-quinolin-6-ylsulfanyl)-[1,2,4]triazolo[4,3-b]pyridazin-6-yl]-benzamide, 2-Fluoro-N-methyl-4-[3-(3-methyl-3H-benzoimidazol-5-ylsulfanyl)-[1,2,4]triazolo[4,3-b]pyridazin-6-yl]-benzamide, 3-[3-(Quinolin-6-ylsulfanyl)-[1,2,4]triazolo[4,3-b]pyridazin-6-yl]-benzonitrile, 3-[3-(Benzothiazol-6-ylsulfanyl)-[1,2,4]triazolo[4,3-b]pyridazin-6-yl]-benzonitrile, 3-[3-(7-Fluoro-quinolin-6-ylsulfanyl)-[1,2,4]triazolo[4,3-b]pyridazin-6-yl]-benzonitrile, 3-Methyl-6-[6-(1-methyl-1H-pyrazol-4-yl)-[1,2,4]triazolo[4,3-b]pyridazin-3-ylsulfanyl]-quinolin-2-ylamine, 4-Methoxy-6-[6-(1-methyl-1H-pyrazol-4-yl)-[1,2,4]triazolo[4,3-b]pyridazin-3-ylsulfanyl]-quinoline, Methyl-{6-[6-(1-methyl-1H-pyrazol-4-yl)-[1,2,4]triazolo[4,3-b]pyridazin-3-ylsulfanyl]-quinolin-4-yl}-amine, Dimethyl-{6-[6-(1-methyl-1H-pyrazol-4-yl)-[1,2,4]triazolo[4,3-b]pyridazin-3-ylsulfanyl]-quinolin-4-yl}-amine, 7-Fluoro-6-(6-methyl-[1,2,4]triazolo[4,3-b]pyridazin-3-ylsulfanyl)-quinoline, 2-{6-[6-(1-Methyl-1H-pyrazol-4-yl)-[1,2,4]triazolo[4,3-b]pyridazin-3-ylsulfanyl]-quinolin-4-yloxy}-ethanol, 3-Methyl-6-(6-methyl-[1,2,4]triazolo[4,3-b]pyridazin-3-ylsulfanyl)-quinoline, {6-[6-(1-Methyl-1H-pyrazol-4-yl)-[1,2,4]triazolo[4,3-b]pyridazin-3-ylsulfanyl]-quinolin-3-yl}-carbamic acid tert-butyl ester, {6-[6-(1-Methyl-1H-pyrazol-4-yl)-[1,2,4]triazolo[4,3-b]pyridazin-3-ylsulfanyl]-quinolin-4-yl}-carbamic acid tert-butyl ester, 5-Fluoro-6-[6-(1-methyl-1H-pyrazol-4-yl)-[1,2,4]triazolo[4,3-b]pyridazin-3-ylsulfanyl]-quinoline.

Method b:

A solution of 6-bromoquinoline (550 mg, 2.64 mmol), diisopropylethylamine (1.13 mL, 6.46 mmol) in DMA (4 mL) under nitrogen was degassed by bubbling in nitrogen for 20 min. Tris(dibenzylideneacetone)dipalladium (105 mg, 0.108 mmol, Strem catalyst), Xantphos (125 mg, 0.216 mmol), and 6-(1-methyl-1H-pyrazol-4-yl)-[1,2,4]triazolo[4,3-b]pyridazine-3-thiol (500 mg, 2.155 mmol) were added under a stream of nitrogen. The reaction mixture was stirred at 100° C. for 22 h, with disappearance of the solid suspension. The reaction mixture was cooled to room temperature and filtered through a plug of silica gel, using DMF as eluent. The organics were then directly poured onto ice/water mixture and left standing for 15 min. The precipitate was filtered and washed with water. The resulting cake was grinded in diethyl ether, filtered, and dried in vacuo to yield 770 mg of a yellow solid. The solid was stirred in refluxing isopropanol for 1 h, filtered, washed with isopropanol, and dried in a vacuum oven at 70° C. for 3 days to provide 500 mg of 6-[6-(1-methyl-1H-pyrazol-4-yl)-[1,2,4]triazolo[4,3-b]pyridazin-3-ylsulfanyl]-quinoline as a yellow solid with 8% impurity (64% yield).

Example 5

6-[6-(1-Methyl-1H-pyrazol-4-yl)-[1,2,4]triazolo[4,3-b]pyridazin-3-ylsulfanyl]-5-nitro-quinoline (Compound 13)

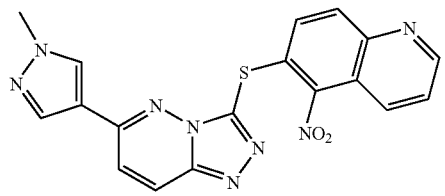 [SMILES: Cn1cc(-c2ccc3nnc(Sc4ccc5ncccc5c4[N+](=O)[O-])n3n2)cn1]

A solution of KOH (146 mg, 2.6 mmol) in ethanol (10 mL) was degassed by bubbling in nitrogen for 15 min. To the solution was added 6-(1-methyl-1H-pyrazol-4-yl)-[1,2,4]triazolo[4,3-b]pyridazine-3-thiol (500 mg, 2.15 mmol) and 6-bromo-5-nitro-quinoline (600 mg, 2.36 mmol). The reaction mixture was stirred at 70° C. for 4 h, then cooled to room temperature, diluted with 10% methanol/dichloromethane and adsorbed on silica gel. Purification by flash chromatography on silica gel using a gradient of 0-7% methanol/dichloromethane afforded 659 mg of 6-[6-(1-methyl-1H-pyrazol-4-yl)-[1,2,4]triazolo[4,3-b]pyridazin-3-ylsulfanyl]-5-nitro-quinoline as a dark yellow solid (76% yield).

Example 6

7-Methyl-6-[6-(1-methyl-1H-pyrazol-4-yl)-[1,2,4]triazolo[4,3-b]pyridazin-3-ylsulfanyl]-quinoline (Compound 16)

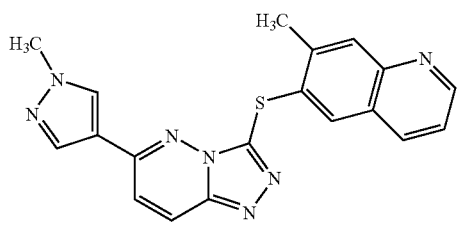 [SMILES: Cc1cc2ncccc2cc1Sc1nnc2ccc(-c3cnn(C)c3)nn12]

A solution of trifluoromethanesulfonic acid 7-methyl-quinolin-6-yl ester (1.38 g, 4.74 mmol), diisopropylethylamine (1.5 mL, 8.61 mmol) in DMF (8 mL) under nitrogen was degassed by bubbling in nitrogen for 20 min. Tris(dibenzylideneacetone)dipalladium (99 mg, 0.11 mmol, Strem catalyst) and Xantphos (125 mg, 0.215 mmol) were added together in one portion, followed by 6-(1-methyl-1H-pyrazol-4-yl)-[1,2,4]triazolo[4,3-b]pyridazine-3-thiol (1 g, 4.36 mmol) under a stream of nitrogen. The reaction mixture was stirred at 100° C. for 1 h. The reaction mixture was cooled to room temperature and poured onto 2 M aqueous NaOH (100 mL). The resulting precipitate was filtered, washed with water, and air-dried for 30 min. The resulting cake was dissolved in MeOH (80 mL) and CHCl$_3$ (80 mL), and 2 g of activated decolorizing charcoal were added. The suspension was stirred at 60° C. for 2.5 h. Celite (10 g) was then added and the warm mixture was filtered over a short silica gel plug.

The filtrate was evaporated in vacuo to give a beige solid. Recrystallization from EtOH and chloroform afforded 1.0 g of 7-methyl-6-[6-(1-methyl-1H-pyrazol-4-yl)-[1,2,4]triazolo[4,3-b]pyridazin-3-ylsulfanyl]-quinoline as white crystals (62% yield).

The following compounds were prepared according to example 6: 6-[6-(1-methyl-1H-pyrazol-4-yl)-[1,2,4]triazolo[4,3-b]pyridazin-3-ylsulfanyl]-quinoline, 3-(3-Methyl-3H-benzoimidazol-5-ylsulfanyl)-6-(1-methyl-1H-pyrazol-4-yl)-[1,2,4]triazolo[4,3-b]pyridazine, 6-[6-(1-Methyl-1H-pyrazol-4-yl)-[1,2,4]triazolo[4,3-b]pyridazin-3-ylsulfanyl]-quinoline, N-oxide, 6-(6-Methyl-[1,2,4]triazolo[4,3-b]pyridazin-3-ylsulfanyl)-quinoline, Methyl-{3-[5-(1-methyl-1H-pyrazol-4-yl)-quinolin-6-ylsulfanyl]-[1,2,4]triazolo[4,3-b]pyridazin-6-yl}-amine, 4-Ethyl-6-[6-(1-methyl-1H-pyrazol-4-yl)-[1,2,4]triazolo[4,3-b]pyridazin-3-ylsulfanyl]-quinoline.

Example 7

3-(3-Ethyl-3H-benzoimidazol-5-ylsulfanyl)-6-(1-methyl-1H-pyrazol-4-yl)-[1,2,4]triazolo[4,3-b]pyridazine (compound 30)

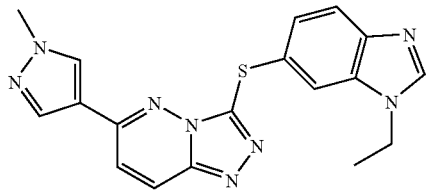 [SMILES: CCn1cnc2ccc(Sc3nnc4ccc(-c5cnn(C)c5)nn34)cc21]

To 3-(3-fluoro-4-nitro-phenylsulfanyl)-6-(1-methyl-1H-pyrazol-4-yl)-[1,2,4]triazolo[4,3-b]pyridazine (50 mg, 0.135 mmol) was added a 2 M solution of ethylamine in THF (1 mL). The reaction mixture was stirred at 70° C. for 1 h, then it was concentrated in vacuo. The residue was suspended in formic acid (1 mL) and iron powder (75 mg, 1.35 mmol) was added. The reaction mixture was stirred at 100° C. for 16 h, then it was cooled to room temperature and the stir bar was removed with most of the iron. The mixture was concentrated in vacuo and the resulting residue was treated with 2 M aqueous sodium hydroxide. The precipitate was filtered, washed with water then diethyl ether. It was then diluted in 2 mL of DMSO, filtered through a 0.45 um filter, and the crude mixture was purified directly by mass-triggered HPLC (5-95% $CH_3CN/H_2O$, 0.1% HCOOH modifier) to provide 25 mg of 3-(3-ethyl-3H-benzoimidazol-5-ylsulfanyl)-6-(1-methyl-1H-pyrazol-4-yl)-[1,2,4]triazolo[4,3-b]pyridazine as a white solid (49% yield).

The following compounds were prepared according to example 7: 3-[3-(2-Methoxy-ethyl)-3H-benzoimidazol-5-ylsulfanyl]-6-(1-methyl-1H-pyrazol-4-yl)-[1,2,4]triazolo[4,3-b]pyridazine, Dimethyl-(2-{6-[6-(1-methyl-1H-pyrazol-4-yl)-[1,2,4]triazolo[4,3-b]pyridazin-3-ylsulfanyl]-benzoimidazol-1-yl}-ethyl)-amine, formic acid salt.

Example 8

6-[6-(1-Methyl-1H-pyrazol-4-yl)-[1,2,4]triazolo[4,3-b]pyridazine-3-sulfinyl]-quinoline (compound 38)

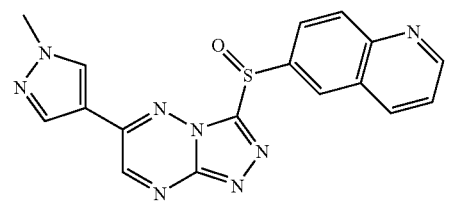 [SMILES: Cn1cc(-c2cnc3nnc(S(=O)c4ccc5ncccc5c4)n3n2)cn1]

To a solution of 6-[6-(1-methyl-1H-pyrazol-4-yl)-[1,2,4]triazolo[4,3-b]pyridazin-3-ylsulfanyl]-quinoline (500 mg, 1.393 mmol) in DMF (10 mL) was added dropwise a solution of 3-chloroperbenzoic acid (70-75% content, 721 mg, 4.178 mmol) in DMF (5 mL) over a period of 20 min. The reaction mixture was stirred for 19 h, and a 10% aqueous solution of NaOH (60 mL) was added. The aqueous layer was extracted with 10% methanol/dichloromethane (3×) and the combined organics were adsorbed on silica gel. Purification by flash chromatography on silica gel using a gradient of 0-8% methanol/dichloromethane afforded 66 mg of a white solid. The solid was dissolved in hot DMSO, and the cooled solution was filtered through a 0.45 um filter. Purification by mass-triggered HPLC (5-95% $CH_3CN/H_2O$, 0.1% HCOOH modifier) provided 5.7 mg of 6-[6-(1-methyl-1H-pyrazol-4-yl)-[1,2,4]triazolo[4,3-b]pyridazine-3-sulfinyl]-quinoline as a white solid (1.1% yield).

Example 9

6-[6-(1H-Pyrazol-4-yl)-[1,2,4]triazolo[4,3-b]pyridazin-3-ylsulfanyl]-quinoline (compound 39)

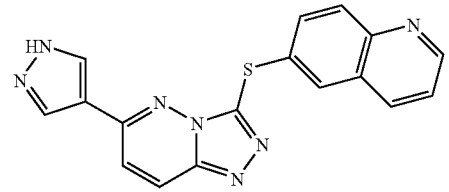 [SMILES: c1cnc2ccc(Sc3nnc4ccc(-c5cn[nH]c5)nn34)cc2c1]

Step 1: 3-Chloro-6-[1-(2-trimethylsilanyl-ethoxymethyl)-1H-pyrazol-4-yl]-pyridazine A mixture of 3,6-dichloropyridazine (505 mg, 3.4 mmol), 4-(4,4,5,5-tetramethyl-dioxaborolan-2-yl)-1-(2-trimethylsilanyl-ethoxymethyl)-1H-pyrazole (1 g, 3.1 mmol) and $K_2CO_3$ (1.3 g, 9.3 mmol) in 10 mL of dioxane and 4 mL of $H_2O$ was degassed with nitrogen. To this mixture was added dichloro[1,1'-bis(diphenylphosphino)ferrocene]palladium (II) dichloromethane adduct (45 mg, 0.06 mmol) and the resulting mixture was bubbled with nitrogen for another 15 min. The reaction mixture was heated at 100° C. for 4 h, then after cooling to room temperature the aqueous phase was removed via pipette. The organic phase was concentrated onto silica gel and purified by flash column chromatography eluting with hexanes:ethyl acetate 100:0 to 60:40 returning title compound as a white solid (640 mg, 2.06 mmol, 66% yield): $^1$H NMR (CDCl$_3$) δ 0.02 (9H, s), 0.96 (2H, t), 3.64 (2H, t), 5.52 (2H, s), 7.52 (1H, d), 7.62 (1H, d), 8.10 (1H, s), 8.34 (1H, s); MS (m/z) 311 [M+H$^+$]$^+$.

Step 2: {6-[1-(2-Trimethylsilanyl-ethoxymethyl)-1H-pyrazol-4-yl]-pyridazin-3-yl}-hydrazine To a suspension of 3-chloro-6-[1-(2-trimethylsilanyl-ethoxymethyl)-1H-pyrazol-4-yl]-pyridazine (640 mg, 2.06 mmol) in ethanol (5 mL) was added hydrazine monohydrate (1.34 mL, 1.4 g, 28 mmol). The reaction mixture was stirred at 50° C. for 18 h, then cooled to room temperature. The precipitate was collected via filtration, washed with cold ethanol and dried in vacuo to provide title compound as a white solid (500 mg, 1.6 mmol, 79% yield): $^1$H NMR (DMSO-d6) δ 0.00 (9H, s), 0.89 (2H, t), 3.61 (2H, t), 4.34 (2H, bs), 5.48 (2H, s), 7.09 (1H, d), 7.69 (1H, d), 7.94 (1H, bs), 8.08 (1H, s), 8.44 (1H, s); MS (m/z) 307 [M+H$^+$]$^+$.

Step 3: 6-[1-(2-Trimethylsilanyl-ethoxymethyl)-1H-pyrazol-4-yl]-[1,2,4]triazolo[4,3-b]pyridazine-3-thiol To a solution of {6-[1-(2-trimethylsilanyl-ethoxymethyl)-1H-pyrazol-4-yl]-pyridazin-3-yl}-hydrazine (490 mg, 1.6 mmol) in ethanol (6.5 mL) and water (1.8 mL) was added K$_2$CO$_3$ (359 mg, 2.6 mmol), followed by CS$_2$ (0.212 mL, 3.5 mmol). The mixture was stirred and heated at 80° C. for 3 h under nitrogen atmosphere. The mixture was cooled to room temperature and concentrated to 50% volume in vacuo and acidified to pH 1 with 1 N aqueous HCl. The resulting precipitate was collected, washed with water, and dried in vacuo to provide title compound as a dark red solid (quantitative yield): $^1$H NMR (DMSO-d$_6$) δ 0.01 (9H, s), 0.90 (2H, t), 3.63 (2H, t), 5.56 (2H, s), 7.82 (1H, d), 8.24 (1H, d), 8.27 (1H, s), 8.80 (1H, s), 15.23 (1H, bs); MS (m/z) 349 [M+H]$^+$.

Step 4: 6-{6-[1-(2-Trimethylsilanyl-ethoxymethyl)-1H-pyrazol-4-yl]-[1,2,4]triazolo[4,3-b]pyridazin-3-ylsulfanyl}-quinoline A solution of 6-quinolinyl trifluoromethanesulfonate (436 mg, 1.57 mmol), diisopropylethylamine (0.746 mL, 4.29 mmol) in DMF (3.8 mL) under nitrogen was degassed by bubbling in nitrogen for 30 min. Tris(dibenzylideneacetone)dipalladium (33 mg, 2.5 mol %, Strem catalyst) and Xantphos (41 mg, 5 mol %) were added together in one portion, followed by 6-[1-(2-trimethylsilanyl-ethoxymethyl)-1H-pyrazol-4-yl]-[1,2,4]triazolo[4,3-b]pyridazine-3-thiol (498 mg, 1.43 mmol) under a stream of nitrogen. The reaction mixture was stirred at 100° C. for 3 h before 500 mg of activated decolorizing charcoal were added. The suspension was stirred at 70° C. for 20, then the warm mixture was directly filtered through a plug of celite, using DMF as eluent. The solvent was evaporated in vacuo and the residue taken up in dichloromethane and washed with 1N aqueous NaOH and concentrated onto silica gel and purified by flash column chromatography eluting with dichloromethane:methanol 100:0 to 92:8 to return title compound as a light yellow foam (250 mg, 0.53 mmol, 37% yield): $^1$H NMR (DMSO-d6) δ 0.00 (9H, s), 0.90 (2H, t), 3.62 (2H, t), 5.54 (2H, s), 7.62 (1H, dd), 7.83 (1H, dd), 7.91 (1H, d), 8.07 (1H, d), 8.18 (1H, s), 8.23 (1H, d), 8.43 (1H, dd), 8.57 (1H, d), 8.75 (1H, d), 8.96 (1H, dd); MS (m/z) 476 [M+H]$^+$.

Step 5: 6-[6-(1H-Pyrazol-4-yl)-[1,2,4]triazolo[4,3-b]pyridazin-3-ylsulfanyl]-quinoline To a solution of 6-{6-[1-(2-trimethylsilanyl-ethoxymethyl)-1H-pyrazol-4-yl]-[1,2,4]triazolo[4,3-b]pyridazin-3-ylsulfanyl}-quinoline (150 mg, 0.32 mmol) in dichloromethane (8 mL) at 0° C. was added trifluoroacetic acid. After 3 hours the mixture was concentrated to dryness and taken Up in dichloromethane and neutralized via the addition of aqueous NaHCO$_3$. To this emulsion was added a chloroform/methanol (95/5) mixture (20 mL) and brine (30 mL). The organic phase was separated and the organic phase filtered and the solid residue washed with water then Et$_2$O and dried to return a yellow solid (64 mg). This solid was taken up in methanol (2 mL) to which ethylenediamine (1 mmol) was added and heated at 50° C. for 1 hour. The mixture was cooled to ambient temperature and the solid collected via filtration and dried to return title compound as a white solid (57 mg, 0.17 mmol, 53% yield).

Example 10

3-(1-Methyl-1H-pyrazol-4-yl)-6-[6-(1-methyl-1H-pyrazol-4-yl)-[1,2,4]triazolo[4,3-b]pyridazin-3-ylsulfanyl]-quinoline (compound 40)

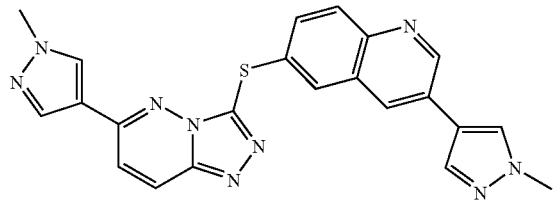 [SMILES: Cn1cc(-c2cnc3ccc(Sc4nnc5ccc(-c6cnn(C)c6)nn45)cc3c2)cn1]

Step 1: 3-Bromo-6-[6-(1-methyl-1H-pyrazol-4-yl)-[1,2,4]triazolo[4,3-b]pyridazin-3-ylsulfanyl]-quinoline To a solution of 6-[6-(1-methyl-1H-pyrazol-4-yl)-[1,2,4]triazolo[4,3-b]pyridazin-3-ylsulfanyl]-quinoline (1 g, 2.785 mmol) in glacial acetic acid (20 mL) was added bromine (0.716 mL, 13.93 mmol) dropwise. The reaction mixture was stirred at room temperature for 5 min then at 100° C. for 3 h. The reaction was cooled to room temperature, and the mixture was concentrated in vacuo. The residue was partitioned between 10% aqueous NaOH and 10% methanol/di-chloromethane. The organic layer was separated, washed with 1 M aqueous Na$_2$S$_2$O$_3$, dried over sodium sulfate, filtered, and adsorbed on silica gel. Purification by flash chromatography on silica gel using a gradient of 0-7% methanol/dichloromethane afforded 381 mg of 3-bromo-6-[6-(1-methyl-1H-pyrazol-4-yl)-[1,2,4]triazolo[4,3-b]pyridazin-3-ylsulfanyl]-quinoline as a beige solid (31% yield): $^1$H NMR (DMSO-d6): δ 3.89 (s, 3H), 7.77 (dd, 1H), 7.80 (d, 1H), 7.99 (d, 1H), 8.00 (s, 1H), 8.43 (s, 1H), 8.48 (d, 1H), 8.68 (d, 1H), 8.92 (d, 1H); MS (m/z) 438, 440 [M+H$^+$]$^+$.

Step 2: 3-(1-Methyl-1H-pyrazol-4-yl)-6-[6-(1-methyl-1H-pyrazol-4-yl)-[1,2,4]triazolo[4,3-b]pyridazin-3-ylsulfanyl]-quinoline A microwave vessel was charged with 3-bromo-6-[6-(1-methyl-1H-pyrazol-4-yl)-[1,2,4]triazolo[4,3-b]pyridazin-3- ylsulfanyl]-quinoline (38 mg, 0.087 mmol), 1-methyl-4-pyrazoleboronic acid pinacol ester (22 mg, 0.104 mmol), and dichlorobis(triphenylphosphine) palladium(0) (3 mg, 0.004 mmol). 1,2-Dimethoxyethane (0.4 mL) and a 2 M aqueous solution of potassium carbonate (0.4 mL) were added. The vessel was capped and microwaved at 120° C. for 20 min. The organic layer was separated, diluted with methanol, and adsorbed on silica gel. Purification by flash chromatography on silica gel using a gradient of 0-10% methanol/di-chloromethane afforded 24 mg of a yellow solid. The solid was further purified sequentially by mass-triggered HPLC (5-95% CH$_3$CN/H$_2$O, 0.1% HCOOH modifier) and by flash chromatography on silica gel using 50% CH$_3$CN/dichloromethane followed by 10% methanol/di-chloromethane to provide 10.5 mg of 3-(1-methyl-1H-pyrazol-4-yl)-6-[6-(1-methyl-1H-pyrazol-4-yl)-[1,2,4]triazolo[4,3-b]pyridazin-3-ylsulfanyl]-quinoline as a yellow solid (28% yield).

Example 11

6-Methyl-[1,2,4]triazolo[4,3-b]pyridazine-3-thiol

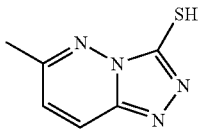

Step 1: (6-Methyl-pyridazin-3-yl)-hydrazine

To a suspension of 3-chloro-6-methyl-pyridazine (3 g, 23.3 mmol) in ethanol (45 mL) was added hydrazine hydrate (45 mL) and the resultant mixture was heated to reflux for 3 hrs. Most of the solvent was removed under reduced pressure and the white solid was collected by filtration and washed with ethanol. Upon drying 2.3 g of (6-methyl-pyridazin-3-yl)-hydrazine was obtained as a white crystalline solid (80% yield).

Step 2:
6-Methyl-[1,2,4]triazolo[4,3-b]pyridazine-3-thiol

To a solution of KOH (11.3 g, 0.202 mol) in methanol (100 mL) was added (6-methyl-pyridazin-3-yl)-hydrazine (25 g, 0.202 mol) at room temperature. The reaction mixture was placed in an ice-water bath and carbon disulfide (98 mL, 1.61 mol) was slowly added. The resultant yellow solution was heated to reflux overnight before removal of solvent. The yellow residue was acidified with 2 N aqueous HCl to pH~4, filtered, and washed with water. Upon drying 33 g of 6-methyl-[1,2,4]triazolo[4,3-b]pyridazine-3-thiol was obtained as a yellow powder (85% yield): $^1$H NMR (DMSO-d6): δ 2.5 (s, 3H), 7.28 (d, 1H), 8.05 (d, 1H), 14.66 (br s, 1H); MS (m/z) 167 [M+H$^+$]$^+$.

Example 12

3-(1-Methyl-1H-pyrazol-4-yl)-6-(6-methyl-[1,2,4]triazolo[4,3-b]pyridazin-3-ylsulfanyl)-quinoline
(compound 41)

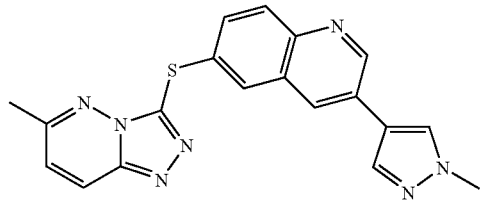

Route 1

Step 1: 3-Bromo-6-(6-methyl-[1,2,4]triazolo[4,3-b]pyridazin-3-ylsulfanyl)-quinoline To a solution of 6-(6-methyl-[1,2,4]triazolo[4,3-b]pyridazin-3-ylsulfanyl)-quinoline (370 mg, 1.26 mmol) in glacial acetic acid (10 mL) was added bromine (0.324 mL, 6.31 mmol) dropwise. The reaction mixture was stirred at room temperature for 5 min then at 100° C. for 2 h. The reaction was cooled to room temperature, and the mixture was concentrated in vacuo. The residue was partitioned between 10% aqueous NaOH and 10% methanol/dichloromethane. The organic layer was separated, washed with 5% aqueous Na$_2$SO$_3$, and adsorbed on silica gel. Purification by flash chromatography on silica gel using a gradient of 0-5% methanol/dichloromethane afforded 422 mg of 3-bromo-6-(6-methyl-[1,2,4]triazolo[4,3-b]pyridazin-3-ylsulfanyl)-quinoline as a beige solid (90% yield): $^1$H NMR (DMSO-d6): δ 2.53 (s, 3H), 7.41 (d, 1H), 7.70 (dd, 1H), 7.87 (d, 1H), 7.99 (d, 1H), 8.41 (d, 1H), 8.66 (d, 1H), 8.93 (d, 1H); MS (m/z) 372, 374 [M+H$^+$]$^+$.

Alternate Route:

A solution of trifluoromethanesulfonic acid 3-bromo-quinolin-6-yl ester (973 mg, 2.74 mmol), diisopropylethylamine (0.87 mL, 4.98 mmol) in DMF (9 mL) under nitrogen was degassed by bubbling in nitrogen for 20 min. Tris(dibenzylideneacetone)dipalladium (114 mg, 0.124 mmol, Strem catalyst) and Xantphos (144 mg, 0.249 mmol) were added together in one portion, followed by 6-methyl-[1,2,4]triazolo[4,3-b]pyridazine-3-thiol (450 mg, 2.49 mmol) under a stream of nitrogen. The reaction mixture was stirred at 100° C. for 1 h. The reaction mixture was cooled to room temperature and 500 mg of activated decolorizing charcoal were added. The suspension was stirred for 2.5 h, and the mixture was directly filtered through a plug of silica gel, using DMF as eluent. The solvent was evaporated in vacuo, and the residue was partitioned between water and 10% methanol/dichloromethane. The organic layer was separated and adsorbed on silica gel. Purification by flash chromatography on silica gel using a gradient of 0-5% methanol/dichloromethane afforded 534 mg of 3-bromo-6-(6-methyl-[1,2,4]triazolo[4,3-b]pyridazin-3-ylsulfanyl)-quinoline as a cream-colored solid (58% yield).

Step 2: 3-(1-Methyl-1H-pyrazol-4-yl)-6-(6-methyl-[1,2,4]triazolo[4,3-b]pyridazin-3-ylsulfanyl)-quinoline A microwave vessel was charged with 3-bromo-6-(6-methyl-[1,2,4]triazolo[4,3-b]pyridazin-3-ylsulfanyl)-quinoline (40 mg, 0.107 mmol), 1-methyl-4-pyrazoleboronic acid pinacol ester (27 mg, 0.129 mmol), and dichlorobis(triphenylphosphine) palladium(0) (4 mg, 0.005 mmol). 1,2-Dimethoxyethane (0.5 mL) and a 2 M aqueous solution of sodium carbonate (0.5 mL) were added. The vessel was capped and microwaved at 120° C. for 30 min. The organic layer was separated, the aqueous layer was extracted with 10% methanol/dichloromethane (2×), and the combined organics were adsorbed on silica gel. Purification by flash chromatography on silica gel using a gradient of 0-6% methanol/dichloromethane afforded 28 mg of an off white solid. The solid was further purified by mass-triggered HPLC (5-95% CH$_3$CN/H$_2$O, 0.1% HCOOH modifier) to provide 11 mg of 3-(1-methyl-1H-pyrazol-4-yl)-6-(6-methyl-[1,2,4]triazolo[4,3-b]pyridazin-3-ylsulfanyl)-quinoline as a white solid (28% yield).

The following compounds were prepared according to example 12, route 1: {4-[6-(6-Methyl-[1,2,4]triazolo[4,3-b]pyridazin-3-ylsulfanyl)-quinolin-3-yl]-pyrazol-1-yl}-acetic acid, 6-(6-Methyl-[1,2,4]triazolo[4,3-b]pyridazin-3-ylsulfanyl)-3-[1-(2-morpholin-4-yl-ethyl)-1H-pyrazol-4-yl]-quinoline, 7-Fluoro-3-(1-methyl-1H-pyrazol-4-yl)-6-(6-methyl-[1,2,4]triazolo[4,3-b]pyridazin-3-ylsulfanyl)-quinoline, 5-Fluoro-3-(1-methyl-1H-pyrazol-4-yl)-6-(6-methyl-[1,2,4]triazolo[4,3-b]pyridazin-3-ylsulfanyl)-quinoline.

Route 2: One Step Procedure

A solution of trifluoro-methanesulfonic acid 3-(1-methyl-1H-pyrazol-4-yl)-quinolin-6-yl ester (15.9 g, 44.79 mmol), diisopropylethylamine (15.5 mL, 89.58 mmol) in DMF (150 mL) under nitrogen was degassed by bubbling with nitrogen for 30 min. Tris(dibenzylideneacetone)dipalladium (2.0 g, 2.24 mmol, Strem catalyst) and Xantphos (2.54 g, 4.48 mmol) were added together in one portion, followed by 6-methyl-[1,2,4]triazolo[4,3-b]pyridazine-3-thiol (7.44 g, 44.79 mmol) under a stream of nitrogen. The reaction mixture was stirred at 100° C. for 4 h. The reaction mixture was filtered while hot and the filtrate was cooled to precipitate. The solid was collected and washed with methanol to give an off-white solid, which was purified via column chromatography to get 13.3 g of 3-(1-methyl-1H-pyrazol-4-yl)-6-(6-methyl-[1,2,4]triazolo[4,3-b]pyridazin-3-ylsulfanyl)-quinoline (79% yield).

The following compounds were prepared according to example 12, route 2: 6-(6-Ethyl-[1,2,4]triazolo[4,3-b]pyridazin-3-ylsulfanyl)-3-(1-methyl-1H-pyrazol-4-yl)-quinoline, Methyl-{3-[3-(1-methyl-1H-pyrazol-4-yl)-quinolin-6-ylsulfanyl]-[1,2,4]triazolo[4,3-b]pyridazin-6-yl}-amine.

Example 13

2-Methyl-2-{4-[6-(6-methyl-[1,2,4]triazolo[4,3-b]pyridazin-3-ylsulfanyl)-quinolin-3-yl]-pyrazol-1-yl}-propionic acid (compound 45)

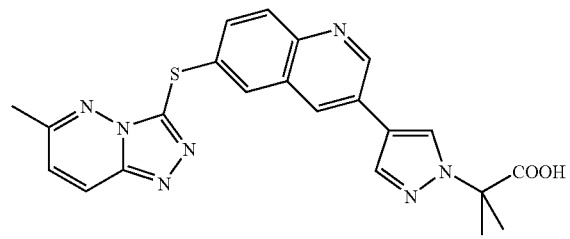 [SMILES: Cc1ccc2nnc(Sc3ccc4ncc(-c5cnn(C(C)(C)C(=O)O)c5)cc4c3)n2n1]

A microwave vessel was charged with 2-(4-iodo-pyrazol-1-yl)-2-methyl-propionic acid ethyl ester (50 mg, 0.162 mmol), bis(pinacolato)diboron (50 mg, 0.195 mmol), potassium acetate (48 mg, 0.486 mmol), [1,1'-bis(diphenylphosphino)ferrocene]palladium(II) chloride dichloromethane adduct (6.6 mg, 0.008 mmol), and DMA (0.6 mL). The vessel was flushed with nitrogen and capped. The reaction mixture was microwaved at 130° C. for 30 min. 3-Bromo-6-(6-methyl-[1,2,4]triazolo[4,3-b]pyridazin-3-ylsulfanyl)-quinoline (48 mg, 0.13 mmol) and dichlorobis(triphenylphosphine) palladium(0) (5.7 mg, 0.008 mmol) were added, followed by DMA (0.4 mL) and a 2 M aqueous solution of potassium carbonate (0.5 mL). The reaction mixture was microwaved at 130° C. for 1 h. Solid sodium sulfate was added to soak up the water, and the liquid layer was filtered through a 0.45 um filter. The crude mixture was diluted to 2 mL with DMSO and purified directly by mass-triggered HPLC (5-95% CH$_3$CN/H$_2$O, 0.1% HCOOH modifier) to provide 11 mg of 2-methyl-2-{4-[6-(6-methyl-[1,2,4]triazolo[4,3-b]pyridazin-3-ylsulfanyl)-quinolin-3-yl]-pyrazol-1-yl}-propionic acid as a cream-colored solid (19% yield).

Example 14

6-Methylamino-[1,2,4]triazolo[4,3-b]pyridazine-3-thiol

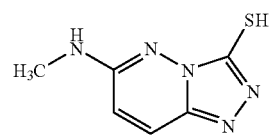

Step 1:
6-Chloro-[1,2,4]triazolo[4,3-b]pyridazine-3-thiol

To a suspension of (6-chloro-pyridazin-3-yl)-hydrazine (1 g, 6.917 mmol) in ethanol (12 mL) was added a solution of KOH (390 mg, 6.917 mmol) in water (12 mL) dropwise. Carbon disulfide (0.84 mL, 13.84 mmol) was added dropwise. The reaction mixture was stirred at room temperature for 48 h. Another 0.84 mL CS$_2$ and 390 mg KOH were added, and the reaction mixture was further stirred for 24 h, before concentrating in vacuo. The residue was treated with 1 M aqueous NaOH and filtered. The filtrate was acidified to pH 3 with 1 N aqueous HCl, and the precipitate was filtered off. The resulting filtrate was extracted with ethyl acetate (3×), and the combined organics were dried over sodium sulfate, filtered, concentrated and dried in vacuo to provide 485 mg of 6-chloro-[1,2,4]triazolo[4,3-b]pyridazine-3-thiol as a yellow solid (38% yield): $^1$H NMR (DMSO-d6): δ 7.48 (d, 1H), 8.24 (d, 1H); MS (m/z) 187 [M+H$^+$]$^+$.

Step 2: 6-Methylamino-[1,2,4]triazolo[4,3-b]pyridazine-3-thiol

6-Chloro-[1,2,4]triazolo[4,3-b]pyridazine-3-thiol (330 mg, 1.77 mmol) was treated with a 40% v/v aqueous solution of methylamine. The reaction mixture was stirred at 100° C. for 17 h, then it was cooled to room temperature and acidified to pH 1-2 with 1 N aqueous HCl. The resulting precipitate was filtered, washed with water, and dried in vacuo to give 185 mg of 6-methylamino-[1,2,4]triazolo[4,3-b]pyridazine-3-thiol as a yellow powder (58% yield): $^1$H NMR (DMSO-d6): δ 2.83 (d, 3H), 6.85 (d, 1H), 7.44 (broad q, 1H), 7.74 (d, 1H), 14.2 (s, 1H); MS (m/z) 182 [M+H$^+$]$^+$.

Example 15

Methyl-{3-[4-(4-methyl-4H-[1,2,4]triazol-3-ylsulfanyl)-quinolin-6-ylsulfanyl]-[1,2,4]triazolo[4,3-b]pyridazin-6-yl}-amine (A), Methyl-{3-[6-(4-methyl-4H-[1,2,4]triazol-3-ylsulfanyl)-quinolin-4-ylsulfanyl]-[1,2,4]triazolo[4,3-b]pyridazin-6-yl}-amine (B), and 4,6-{6-Methylamino-[1,2,4]triazolo[4,3-b]pyridazin-3-ylsulfanyl}-quinoline (C) (Compounds 47 and 48)

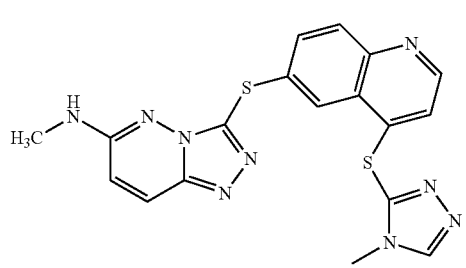

(A)

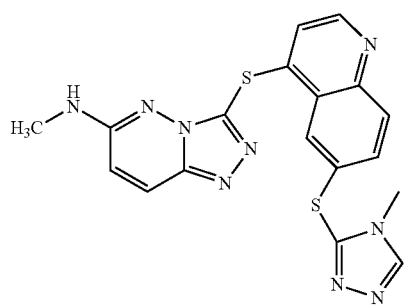

(B)

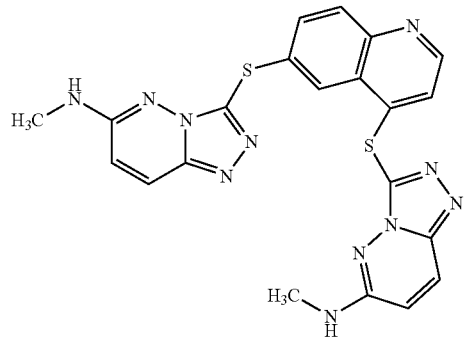

(C)

A solution of 6-bromo-4-(4-methyl-4H-[1,2,4]triazol-3-ylsulfanyl)-quinoline (106 mg, 0.331 mmol), diisopropylethylamine (0.096 mL, 0.552 mmol) in DMF (1 mL) under nitrogen was degassed by bubbling in nitrogen for 15 min. Tris(dibenzylideneacetone) dipalladium (25 mg, 0.028 mmol), Xantphos (32 mg, 0.056 mmol), and 6-methylamino-[1,2,4]triazolo[4,3-b]pyridazine-3-thiol (50 mg, 0.276 mmol) were added. The reaction mixture was stirred at 100° C. for 16 h, cooled to room temperature, concentrated in vacuo, and the residue was dissolved in 10% methanol/dichloromethane and adsorbed on silica gel. First purification by flash chromatography on silica gel using a gradient of 0-20% methanol/dichloromethane afforded 44 mg of a brown solid. A second purification by flash chromatography on amine silica gel using a gradient of 0-8% methanol/dichloromethane afforded 10 mg of (C) as a cream-colored solid and 17 mg of a impure mixture of (A) and (B). The mixture was further purified by mass-triggered HPLC (5-95% CH$_3$CN/H$_2$O, 0.1% HCOOH modifier) to provide 6.7 mg of a (1:1) mixture of (A) and (B) as a white solid (58% yield).

Example 16

6-Methyl-3-[5-(1-methyl-1H-pyrazol-4-yl)-1H-pyrrolo[2,3-b]pyridin-3-ylsulfanyl]-[1,2,4]triazolo[4,3-b]pyridazine (compound 53)

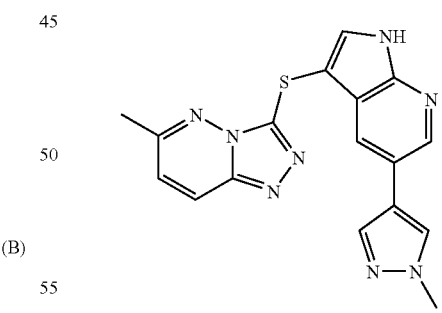

To a solution of 5-(1-methyl-1H-pyrazol-4-yl)-1H-pyrrolo[2,3-b]pyridine (28 mg, 0.141 mmol) and 6-methyl-[1,2,4]triazolo[4,3-b]pyridazine-3-thiol (35.3 mg, 0.212 mmol) in DMF (700 μL) was added iodine (72 μL, 0.283 mmol). The reaction mixture was stirred at room temperature for 3 hours. The reaction mixture was then filtered and purified by mass-triggered HPLC (5-95% CH$_3$CN/H$_2$O, 0.1% HCOOH modifier) to provide 5.7 mg of 6-methyl-3-[5-(1-methyl-1H-pyrazol-4-yl)-1H-pyrrolo[2,3-b]pyridin-3-ylsulfanyl]-[1,2,4]triazolo[4,3-b]pyridazine (11% yield).

The following compound was prepared according to example 16: 6-(1-Methyl-1H-pyrazol-4-yl)-3-[5-(1-methyl-1H-pyrazol-4-yl)-1H-pyrrolo[2,3-b]pyridin-3-ylsulfanyl]-[1,2,4]triazolo[4,3-b]pyridazine.

Example 17

6-[6-(1-Methyl-1H-pyrazol-4-yl)-[1,2,4]triazolo[4,3-b]pyridazin-3-ylsulfanyl]-quinolin-4-ylamine, trifluoroacetic acid salt (compound 34)

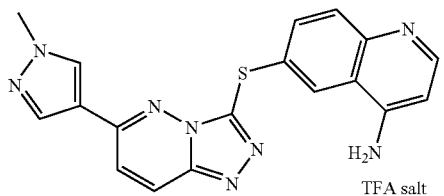 [SMILES: Cn1cc(-c2ccc3nnc(Sc4ccc5nccc(N)c5c4)n3n2)cn1]
TFA salt

To a suspension of {6-[6-(1-methyl-1H-pyrazol-4-yl)-[1,2,4]triazolo[4,3-b]pyridazin-3-ylsulfanyl]-quinolin-4-yl}-carbamic acid tert-butyl ester (15 mg, 0.031 mmol) in dichloromethane (2 mL) was added TFA (1 mL). The reaction mixture was stirred at room temperature for 1 h, and concentrated in vacuo. The residue was dissolved in DMSO, and lyophilized overnight to give 10.4 mg of 6-[6-(1-methyl-1H-pyrazol-4-yl)-[1,2,4]triazolo[4,3-b]pyridazin-3-ylsulfanyl]-quinolin-4-ylamine, trifluoroacetic acid salt (90% yield).

The following compound was prepared according to example 17: 6-[6-(1-Methyl-1H-pyrazol-4-yl)-[1,2,4]triazolo[4,3-b]pyridazin-3-ylsulfanyl]-quinolin-3-ylamine, trifluoroacetic acid salt.

Example 18

6-(6-Methyl-[1,2,4]triazolo[4,3-b]pyridazin-3-ylsulfanyl)-4-(4-methyl-4H-[1,2,4]triazol-3-ylsulfanyl)-quinoline (compound 57)

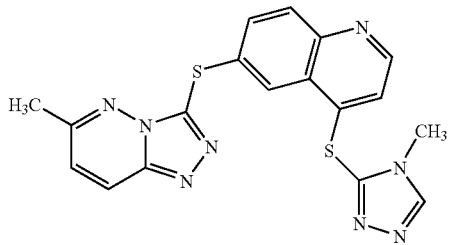 [SMILES: Cc1ccc2nnc(Sc3ccc4nccc(Sc5nncn5C)c4c3)n2n1]

A solution of 4-chloro-6-bromoquinoline (1.6 g, 6.63 mmol), diisopropylethylamine (1.93 mL, 11.05 mmol) in DMF (20 mL) under nitrogen was degassed by bubbling in nitrogen for 30 min. Tris(dibenzylideneacetone)dipalladium (506 mg, 0.552 mmol), Xantphos (640 mg, 1.105 mmol), and 6-methyl-[1,2,4]triazolo[4,3-b]pyridazine-3-thiol (1.0 g, 5.525 mmol) were added. The reaction mixture was stirred at 100° C. for 18 h. The reaction mixture was cooled to room temperature, and partitioned between 1 N aqueous NaOH and 10% methanol/di-chloromethane. The aqueous layer was extracted with 10% methanol/dichloromethane (3×) and the combined organic layers were adsorbed on silica gel. Purification by flash chromatography on silica gel using a gradient of 0-6% methanol/dichloromethane afforded 468 mg of a (1:1) mixture of 4-chloro-6-(6-methyl-[1,2,4]triazolo[4,3-b]pyridazin-3-ylsulfanyl)-quinoline and 6-bromo-4-(6-methyl-[1,2,4]triazolo[4,3-b]pyridazin-3-ylsulfanyl)-quinoline as a beige solid. The (1:1) mixture (70 mg) was dissolved in DMF (0.5 mL), and 4-methyl-4H-[1,2,4]triazole-3-thiol (12 mg, 0.1 mmol) was added. The reaction mixture was stirred at 60° C. for 21 h then at 80° C. for 25 h. The reaction mixture was cooled to room temperature and concentrated in vacuo. The residue was partitioned between 1 N aqueous NaOH and 10% methanol/dichloromethane. The aqueous layer was extracted with 10% methanol/dichloromethane (2×) and the combined organic layers were adsorbed on silica gel. Purification by flash chromatography on silica gel using a gradient of 0-10% methanol/dichloromethane afforded 16 mg of 6-(6-methyl-[1,2,4]triazolo[4,3-b]pyridazin-3-ylsulfanyl)-4-(4-methyl-4H-[1,2,4]triazol-3-ylsulfanyl)-quinoline as a cream color solid (78% yield).

Example 19

6-Ethyl-[1,2,4]triazolo[4,3-b]pyridazine-3-thiol

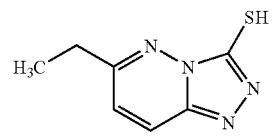

Step 1: 3-Chloro-6-vinyl-pyridazine

A mixture of 3,6-dichloropyridazine (6 g, 40.3 mmol), vinyl boronic acid pinacol ester (6.21 g, 6.83 mL, 40.3 mmol), potassium carbonate (120 mmol, 16.7 g), 1,4-dioxane (60 mL) and water (24 mL) was degassed for 15 min with nitrogen gas. Dichloro[1,1'-bis(diphenylphosphino)ferrocene]palladium(II) dichloromethane adduct (0.4 mmol, 292 mg) was then added and the mixture heated to 80° C. for 4 hours. The aqueous phase was then removed via pipette and the organic phase concentrated onto silica gel and purified via flash column chromatography (SiO$_2$, hexane:ethyl acetate 100:0-60:40) to return 3-chloro-6-vinyl-pyridazine as a white solid (5.2 g, 92% yield). $^1$H NMR (CDCl$_3$) δ 5.75 (1H, d), 6.25 (1H, d), 7.05 (1H, dd), 7.49 (1H, d), 7.59 (1H, d). MS m/z=141 (M+H$^+$)$^+$.

Step 2: 3-Chloro-6-ethyl-pyridazine

A mixture of 3-chloro-6-vinyl-pyridazine (1 g, 7.09 mmol), palladium on carbon (10% wt, 200 mg) in ethyl acetate (14 mL) under a hydrogen atmosphere was stirred vigorously at ambient temperature for 4 hours. The mixture was then filtered through a pad of celite and the filtrate concentrated onto silica gel and purified via flash column chromatography (SiO$_2$, hexane:ethyl acetate 90:10-50:50) to return 3-chloro-6-ethyl-pyridazine as a white solid (627 mg, 63% yield). $^1$H NMR (CDCl$_3$) δ 1.27 (3H, t), 2.93 (2H, q), 7.72 (1H, d), 7.83 (1H, d). MS m/z=143 (M+H$^+$)$^+$.

Step 3: (4-Ethyl-phenyl)-hydrazine, hydrochloride salt

To a solution of 3-chloro-6-ethyl-pyridazine (1.0 g, 7.01 mmol) in ethanol (14 mL) was added hydrazine monohydrate (14 mL). The reaction mixture was stirred at 80° C. for 18 h, before concentrating in vacuo. The residue was partitioned between brine and ethyl acetate. The organic layer was washed with brine (3×), dried over sodium sulfate and filtered. The aqueous layer was saturated with solid sodium chloride and further extracted with ethyl acetate (3×). The combined organic layers was dried over sodium sulfate and filtered. Both filtrates were adsorbed on silica gel and purified by flash chromatography on silica gel using a gradient of 0-10% methanol/di-chloromethane to afford 476 mg of N-(4-ethyl-phenyl)-N'-isopropylidene-hydrazine as a yellow waxy solid. The solid (450 mg) was dissolved in ethanol (3 mL) and concentrated HCl (2 mL) was added. The reaction mixture was stirred at 80° C. for 48 h, before concentrated in vacuo to dryness. The resulting solid was triturated with diethyl ether, azeotroped with toluene and dried in vacuo to give a brown solid used in the next step without further purification.

Step 4:
6-Ethyl-[1,2,4]triazolo[4,3-b]pyridazine-3-thiol

The brown solid was suspended in ethanol (3.8 mL), and KOH (425 mg, 7.59 mmol) was added. The reaction vessel was flushed with nitrogen and carbon disulfide (1.2 mL, 20.24 mmol) was added. The reaction mixture was stirred at 80° C. for 19 h, before concentrating in vacuo. The residue was treated with 1 N aqueous NaOH and filtered. The filtrate was treated with 1 N aqueous HCl to pH 2 and extracted with ethyl acetate (3×). The combined organics were concentrated in vacuo to give 258 mg of a dark yellow solid. The solid was triturated with ethyl acetate and hexane, filtered and dried in vacuo to give 192 mg of 6-ethyl-[1,2,4]triazolo[4,3-b]pyridazine-3-thiol as a beige solid (42% yield from N-(4-ethyl-phenyl)-N'-isopropylidene-hydrazine): $^1$H NMR (DMSO-d6): δ 1.26 (t, 3H), 2.82 (q, 2H), 7.35 (d, 1H), 8.07 (d, 1H), 14.2 (broad s, 1H); MS (m/z) 181 [M+H$^+$]$^+$.

Example 20

6-(6-Methyl-[1,2,4]triazolo[4,3-b]pyridazin-3-ylsulfanyl)-3-(1H-pyrazol-4-yl)-quinoline (Compound 59)

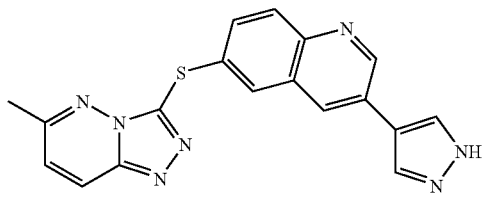 [SMILES: Cc1ccc2nnc(Sc3ccc4ncc(-c5cn[nH]c5)cc4c3)n2n1]

A microwave vessel was charged with 3-bromo-6-(6-methyl-[1,2,4]triazolo[4,3-b]pyridazin-3-ylsulfanyl)-quinoline (970 mg, 2.606 mmol), 4-(4,4,5,5-tetramethyl-[1,3,2]dioxaborolan-2-yl)-1-(2-trimethylsilanyl-ethoxymethyl)-1H-pyrazole (930 mg, 2.866 mmol), and dichlorobis(triphenylphosphine) palladium(0) (92 mg, 0.13 mmol). 1,4-Dioxane (10 mL) and a 2 M aqueous solution of sodium carbonate (5 mL) were added. The vessel was capped and microwaved at 130° C. for 30 min. The reaction mixture was partitioned between water and 10% methanol/dichloromethane. The aqueous layer was extracted with 10% methanol/dichloromethane, and the combined organics were adsorbed on silica gel. Purification by flash chromatography on silica gel using a gradient of 0-8% methanol/dichloromethane afforded 1.073 g of the crude coupling product as a light brown oil. The oil was treated with TFA (10 mL). The reaction mixture was stirred at room temperature for 2 h, before concentrating in vacuo. The residue was treated with 1 N aqueous NaOH, and the precipitate was filtered, washed sequentially with water and ethyl acetate. The resulting yellow solid was dissolved in 10% methanol/dichloromethane and adsorbed on silica gel. Purification by flash chromatography on silica gel using a gradient of 0-10% methanol/dichloromethane afforded 417 mg of impure 6-(6-methyl-[1,2,4]triazolo[4,3-b]pyridazin-3-ylsulfanyl)-3-(1H-pyrazol-4-yl)-quinoline. Purification of 30 mg of material by mass-triggered HPLC (5-95% CH$_3$CN/H$_2$O, 0.1% HCOOH modifier) provided 12 mg of pure 6-(6-methyl-[1,2,4]triazolo[4,3-b]pyridazin-3-ylsulfanyl)-3-(1H-pyrazol-4-yl)-quinoline.

Example 21

3-(1-Ethyl-1H-pyrazol-4-yl)-6-(6-methyl-[1,2,4]triazolo[4,3-b]pyridazin-3-ylsulfanyl)-quinoline (Compound 66)

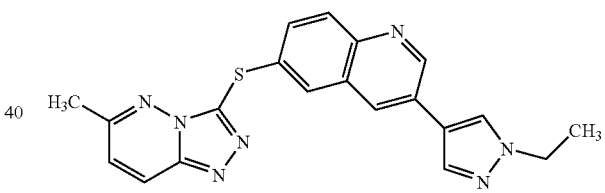

To a microwave vessel was added 3-bromo-6-(6-methyl-[1,2,4]triazolo[4,3-b]pyridazin-3-ylsulfanyl)-quinoline (200 mg, 0.54 mmol), 1-ethyl-4-(4,4,5,5-tetramethyl-[1,3,2]dioxaborolan-2-yl)-1H-pyrazole (149 mg, 0.67 mmol), K$_2$CO$_3$ (186 mg, 1.34 mmol), 1,4-dioxane (7 mL) and water (3.5 mL). The solution was degassed by bubbling nitrogen for 10 min and then Pd(dppf)$_2$Cl$_2$ dichloromethane (20 mg, 0.0269 mmol) was added. The microwave vessel was capped and reacted in a microwave reactor at 120° C. for 20 min. The microwave vessel was cooled and then the mixture was extracted into dichloromethane and washed with water. The volatiles were removed in vacuo and the residue absorbed onto silica gel and purified by flash chromatography (SiO$_2$, dichloromethane:CH$_3$OH 100:0-80:20) to obtain 3-(1-ethyl-1H-pyrazol-4-yl)-6-(6-methyl-[1,2,4]triazolo[4,3-b]pyridazin-3-ylsulfanyl)-quinoline as a brown oil (7% yield).

The following compounds were prepared according to example 21: 3-{4-[6-(6-Methyl-[1,2,4]triazolo[4,3-b]pyridazin-3-ylsulfanyl)-quinolin-3-yl]-pyrazol-1-yl}-azetidine-1-carboxylic acid tert-butyl ester, 3-{4-[6-(6-Methyl-[1,2,4]triazolo[4,3-b]pyridazin-3-ylsulfanyl)-quinolin-3-yl]-pyrazol-1-ylmethyl}-azetidine-1-carboxylic acid tert-butyl ester.

Example 22

3-(1-Azetidin-3-yl-1H-pyrazol-4-yl)-6-(6-methyl-[1,2,4]triazolo[4,3-b]pyridazin-3-ylsulfanyl)-quinoline (Compound 62)

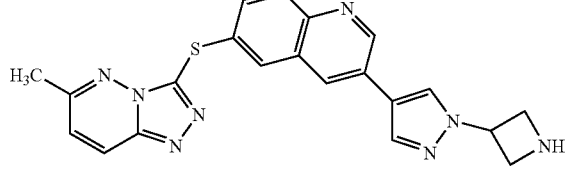

To 3-{4-[6-(6-methyl-[1,2,4]triazolo[4,3-b]pyridazin-3-ylsulfanyl)-quinolin-3-yl]-pyrazol-1-yl}-azetidine-1-carboxylic acid tert-butyl ester (65 mg, 0.126 mmol) was added 6 mL of (1:1) TFA:dichloromethane. The mixture was allowed to sit for 2 hours. The volatiles were removed by rotary evaporation and then methanol (6 mL) and MP-carbonate (500 mg, 3.18 mmol/g) were added. The resin was filtered and the volatiles were removed in vacuo to provide 3-(1-azetidin-3-yl-1H-pyrazol-4-yl)-6-(6-methyl-[1,2,4]triazolo[4,3-b]pyridazin-3-ylsulfanyl)-quinoline as a yellow solid (quantitative yield).

The following compounds were prepared according to example 22: 3-(1-Azetidin-3-ylmethyl-1H-pyrazol-4-yl)-6-(6-methyl-[1,2,4]triazolo[4,3-b]pyridazin-3-ylsulfanyl)-quinoline, 3-(1-Azetidin-3-yl-1H-pyrazol-4-yl)-6-(6-ethyl-[1,2,4]triazolo[4,3-b]pyridazin-3-ylsulfanyl)-quinoline, 3-(1-Azetidin-3-ylmethyl-1H-pyrazol-4-yl)-6-(6-ethyl-[1,2,4]triazolo[4,3-b]pyridazin-3-ylsulfanyl)-quinoline.

Example 23

3-[1-(1-Ethyl-azetidin-3-yl)-1H-pyrazol-4-yl]-6-(6-methyl-[1,2,4]triazolo[4,3-b]pyridazin-3-ylsulfanyl)-quinoline (Compound 61)

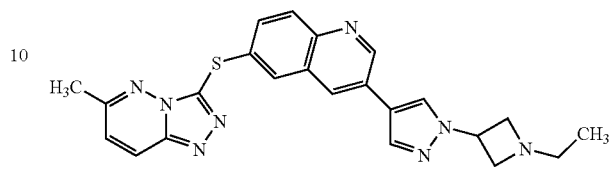

To 3-(1-azetidin-3-yl-1H-pyrazol-4-yl)-6-(6-methyl-[1,2,4]triazolo[4,3-b]pyridazin-3-ylsulfanyl)-quinoline (63 mg, 0.152 mmol) in dichloromethane (3.0 mL) was added acetaldehyde (34 uL, 0.608 mmol). The solution was stirred at room temperature for 15 minutes and then sodium triacetoxyborohydride (80 mg, 0.380) was added. After 1 hour the solution was diluted with dichloromethane (3.0 mL) and washed with sodium bicarbonate (3.0 mL). The aqueous layer was extracted further with dichloromethane (3.0 mL). The combined dichloromethane layers were washed with brine (6 mL), dried over $Na_2SO_4$ and filtered. The filtrate was concentrated in vacuo onto silica gel and purified by flash chromatography ($SiO_2$, dichloromethane:$CH_3OH$:$NH_4OH$, 95:4.995:0.005-80:19.98:0.02) to return 23 mg of 3-[1-(1-ethyl-azetidin-3-yl)-1H-pyrazol-4-yl]-6-(6-methyl-[1,2,4]triazolo[4,3-b]pyridazin-3-ylsulfanyl)-quinoline (34% yield).

The following compounds were prepared according to example 23: 3-[1-(1-Methyl-azetidin-3-yl)-1H-pyrazol-4-yl]-6-(6-methyl-[1,2,4]triazolo[4,3-b]pyridazin-3-ylsulfanyl)-quinoline, 3-[1-(1-Ethyl-azetidin-3-ylmethyl)-1H-pyrazol-4-yl]-6-(6-methyl-[1,2,4]triazolo[4,3-b]pyridazin-3-ylsulfanyl)-quinoline, 3-[1-(1-Isopropyl-azetidin-3-yl)-1H-pyrazol-4-yl]-6-(6-methyl-[1,2,4]triazolo[4,3-b]pyridazin-3-ylsulfanyl)-quinoline, 3-[1-(1-Ethyl-azetidin-3-yl)-1H-pyrazol-4-yl]-6-(6-ethyl-[1,2,4]triazolo[4,3-b]pyridazin-3-ylsulfanyl)-quinoline.

The structure, name, physical and biological data of the compounds are further described in Table I.

TABLE I

| Compounds | Enzyme Assay c-MET $IC_{50}$ | XTT Assay (GTL16) $IC_{50}$ | Structure | $^1$H NMR (500 MHz) | MS (m/z) $[M + H^+]^+$ |
|---|---|---|---|---|---|
| 1 | I | I | 6-(6-Phenyl-[1,2,4]triazolo[4,3-b]pyridazin-3-ylsulfanyl)-quinoline | (DMSO-d6) δ: 7.50(m, 2H), 7.55(m, 2H), 7.74 (dd, 1H), 7.93(m, 2H), 7.99(d, 1H), 8.05(d, 1H), 8.15(d, 1H), 8.35 (dd, 1H), 8.57(d, 1H), 8.89(dd, 1H) | 356 |

TABLE I-continued

| Compounds | Enzyme Assay c-MET IC50 | XTT Assay (GTL16) IC50 | Structure | 1H NMR (500 MHz) | MS (m/z) [M + H+]+ |
|---|---|---|---|---|---|
| 2 | III | | 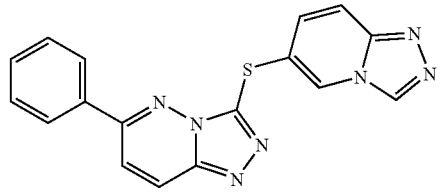<br>6-Phenyl-3-([1,2,4]triazolo[4,3-a]pyridin-6-ylsulfanyl)-[1,2,4]triazolo[4,3-b]pyridazine | (DMSO-d6) δ: 7.42(dd, 1H), 7.47-7.51(m, 3H), 7.84(d, 1H), 7.92-7.94 (m, 2H), 7.98(d, 1H), 8.04(s, 1H), 8.48(d, 1H) | 346 |
| 3 | III | | 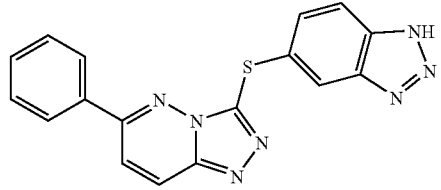<br>3-(1H-Benzotriazol-5-yl-sulfanyl)-6-phenyl[1,2,4]triazolo-[4,3-b]pyridazine | (DMSO-d6) δ: 7.48(dd, 1H), 7.58(m, 3H), 7.81 (d, 1H), 8.04-8.07(m, 3H), 8.54(d, 1H), 9.02 (s, 1H), 9.25(s, 1H) | 346 |
| 4 | I | I | 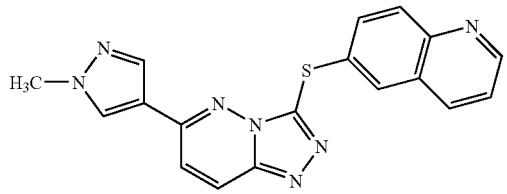<br>6-[6-(1-Methyl-1H-pyrazol-4-yl)-[1,2,4]triazolo-[4,3-b]pyridazin-3-ylsulfanyl]quinoline | (DMSO-d6) δ: 3.95(s, 3H), 7.57(dd, 1H), 7.74 (d, 1H), 7.82(dd, 1H), 7.99(s, 1H,), 8.01(d, 1H), 8.17(d, 1H), 8.24 (d, 1H), 8.25(s, 1H), 8.34(dd, 1H), 8.86(dd, 1H) | 360 |
| 5 | I | I | 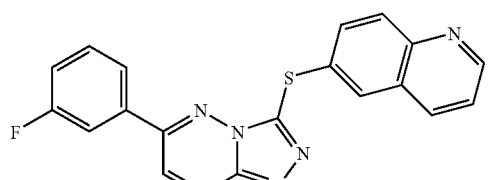<br>6-[6-(3-Fluoro-phenyl)-[1,2,4]triazolo[4,3-b]pyridazin-3-ylsulfanyl]-quinoline | (DMSO-d6) δ: 7.41(dt, 1H), 7.54(m, 2H), 7.70 (dt, 1H), 7.74(dd, 1H,), 7.80(d, 1H), 7.99(d, 1H), 8.09(d, 1H), 8.16 (d, 1H), 8.35(dd, 1H), 8.61(d, 1H), 8.89(dd, 1H) | 374 |
| 6 | II | II | 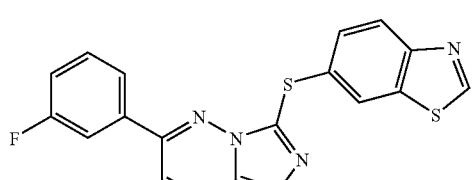<br>3-(Benzothiazol-6-ylsulfanyl)-6-(3-fluoro-phenyl)-[1,2,4]triazolo[4,3-b]pyridazine | (DMSO-d6) δ: 7.42(dt, 1H), 7.61(m, 1H), 7.63 (dd, 1H), 7.75(dt, 1H), 7.83(d, 1H), 8.07(d, 1H), 8.08(d, 1H), 8.38 (d, 1H), 8.59(d, 1H), 9.41(s, 1H) | 380 |

TABLE I-continued

| Compounds | Enzyme Assay c-MET IC$_{50}$ | XTT Assay (GTL16) IC$_{50}$ | Structure | $^1$H NMR (500 MHz) | MS (m/z) [M + H$^+$]$^+$ |
|---|---|---|---|---|---|
| 7 | III | III | 6-(3-Fluoro-phenyl)-3-([1,2,4]triazolo[4,3-a]pyridin-6-ylsulfanyl)-[1,2,4]triazolo[4,3-b]pyridazine | (DMSO-d6) δ: 7.47(m, 2H), 7.64(m, 1H), 7.80 (d, 1H), 7.87(dt, 1H), 7.92(d, 1H,), 8.09(d, 1H), 8.58(d, 1H), 9.02 (s, 1H), 9.23(s, 1H) | 364 |
| 8 | I | I | 3-(7-Methyl-benzothiazol-6-ylsulfanyl)-6-(1-methyl-1H-pyrazol-4-yl)-[1,2,4]triazolo[4,3-b]pyridazine (66%) | (DMSO-d6) δ: 2.75(s, 3H), 3.86(s, 3H), 7.62 (d, 1H), 7.68(d, 1H), 7.85(d, 1H), 7.99(s, 1H), 8.33(d, 1H), 8.39 (s, 1H), 9.39(s, 1H) | 380 |
|  |  |  | 3-(5-Methyl-benzothiazol-6-ylsulfanyl)-6-(1-methyl-1H-pyrazol-4-yl)-[1,2,4]triazolo[4,3-b]pyridazine (34%) | (DMSO-d6) δ: 2.55(s, 3H), 3.85(s, 3H), 7.69 (d, 1H), 7.98(m, 2H), 8.25(s, 1H), 8.34(d, 1H), 8.40(s, 1H), 9.30 (s, 1H) |  |
| 9 | I | I | 6-{6-(3-Fluoro-phenyl)-[1,2,4]triazolo[4,3-b][1,2,4]triazin-3-ylsulfanyl]-quinoline | (DMSO-d6) δ: 7.47(dt, 1H), 7.56(dd, 1H), 7.61 (dt, 1H), 7.79(dd, 1H), 7.83(dt, 1H), 7.89(d, 1H), 7.99(d, 1H), 8.17 (d, 1H), 8.33(dd, 1H), 8.90(dd, 1H), 9.48(s, 1H) | 375 |
| 10 | I | I | 7-Fluoro-6-[6-(1-methyl-1H-pyrazol-4-yl)-[1,2,4]triazolo[4,3-b]pyridazin-3-ylsulfanyl]-quinoline | (DMSO-d6) δ: 3.88 (s, 3H), 7.53(dd, 1H), 7.78(d, 1H), 7.91(d, 1H), 7.99(s, 1H), 8.22 (d, 1H), 8.38(dd, 1H), 8.40(s, 1H), 8.45(d, 1H), 8.92(dd, 1H) | 378 |

TABLE I-continued

| Compounds | Enzyme Assay c-MET IC$_{50}$ | XTT Assay (GTL16) IC$_{50}$ | Structure | $^1$H NMR (500 MHz) | MS (m/z) [M + H$^+$]$^+$ |
|---|---|---|---|---|---|
| 11 | I | II | 2-Fluoro-N-methyl-4-[3-(quinolin-6-ylsulfanyl)-[1,2,4]triazolo[4,3-b]pyridazin-6-yl]-benzamide | (CD$_3$OD) δ: 2.95(s, 3H), 7.56-7.59(m, 1H), 7.70-7.72(d, 1H), 7.81-7.85(m, 3H), 8.01(d, 2H), 8.21(d, 1H), 8.34(d, 1H), 8.40(d, 1H), 8.86(d, 1H) | 431 |
| 12 | II | II | 6-[6-(1-Methyl-1H-pyrazol-4-yl)-[1,2,4]triazolo[4,3-b]pyridazin-3-ylsulfanyl]-quinazoline | (DMSO-d6) δ: 3.90(s, 3H), 7.74(d, 1H), 7.77(dd, 1H), 7.95(s, 1H), 7.97(d, 1H), 8.20(d, 1H), 8.38(s, 1H), 8.41(d, 1H), 8.84(broad s, 1H), 9.20(d, 1H) | 361 |
| 13 | II | II | 6-[6-(1-Methyl-1H-pyrazol-4-yl)-[1,2,4]triazolo[4,3-b]pyridazin-3-ylsulfonyl]-5-nitro-quinoline | (DMSO-d6) δ: 3.85(s, 3H), 7.44(d, 1H), 7.81(d, 1H), 7.82(dd, 1H), 7.86(s, 1H), 8.10(d, 1H), 8.38(s, 1H), 8.52(d, 1H), 8.53(d, 1H), 9.05(dd, 1H) | 405 |
| 14 | I | I | 3-(Benzothiazol-6-ylsulfanyl)-6-(1-methyl-1H-pyrazol-4-yl)-[1,2,4]triazolo[4,3-b]pyridazine | (DMSO-d6) δ: 3.91(s, 3H), 7.63(dd, 1H), 7.77(d, 1H), 8.05-8.07(m, 2H), 8.40-8.47(m, 3H), 9.41(s, 1H) | 366 |
| 15 | I | I | 3-(5-Fluoro-benzothiazo-6-ylsulfanyl)-6-(1-methyl-1H-pyrazol-4-yl)-[1,2,4]triazolo[4,3-b]pyridazine | (DMSO-d6) δ: 3.84(s, 3H), 7.70(d, 1H), 7.98(s, 1H), 8.03(d, 1H), 8.36-8.39(m, 3H), 9.43(s, 1H) | 384 |

TABLE I-continued

| Compounds | Enzyme Assay c-MET IC$_{50}$ | XTT Assay (GTL16) IC$_{50}$ | Structure | $^1$H NMR (500 MHz) | MS (m/z) [M + H$^+$]$^+$ |
|---|---|---|---|---|---|
| 16 | I | I | 7-Methyl-6-[6-[1-methyl-1H-pyrazol-4-yl)-[1,2,4]triazolo[4,3-b]pyridazin-3-ylsulfanyl]-quinoline | (DMSO-d6) δ: 2.65(s, 3H), 3.89(s, 3H), 7.45 (dd, 1H), 7.75(d, 1H), 7.97(s, 1H), 8.02(s, 1H), 8.04(s, 1H), 8.27 (dd, 1H), 8.43(d, 1H), 8.44(s, 1H), 8.85(dd, 1H) | 374 |
| 17 | I | I | 2-Fluoro-4-[3-(7-fluoro-quinolin-6-ylsulfanyl)-[1,2,4]triazolo[4,3-b]pyridazin-6-yl]-N-methyl-benzamide | (DMSO-d6) δ: 2.79(d, 3H), 7.54-7.57(m, 1H), 7.72(t, 1H), 7.81(dd, 1H), 7.85(dd, 1H), 7.93 (d, 1H), 8.12(d, 1H), 8.29(d, 1H), 8.39(m, 2H), 8.63(d, 1H), 8.93-8.95(m, 1H) | 449 |
| 18 | I | I | 2-Fluoro-N-methyl-4-[3-(7-methyl-quinolin-6-ylsulfanyl)-[1,2,4]triazolo[4,3-b]pyridazin-6-yl]-benzamide | (DMSO-d6) δ: 2.64(s, 3H), 2.79(d, 3H), 7.46-7.49(m, 1H), 7.74(t, 1H), 7.82-7.85(m, 1H), 7.87(m, 1H), 8.00(s, 1H), 8.08(d, 1H), 8.11 (s, 1H), 8.27(m, 1H), 8.39(broad m, 1H), 8.60(d, 1H), 8.87(m, 1H) | 445 |
| 19 | I | I (BaF3) | 2-Fluoro-N-methyl-4-[3-(3-methyl-3H-benzoimidazol-5-ylsulfanyl)-[1,2,4]triazolo[4,3-b]pyridazin-6-yl]-benzamide | (DMSO-d6) δ: 2.80(d, 3H), 3.82(s, 3H), 7.38 (dd, 1H), 7.65(d, 1H), 7.78(t, 1H), 7.86-7.89 (m, 1H), 7.94-7.97(m, 2H), 8.08(d, 1H), 8.24 (s, 1H) | 434 |
| 20 | I | I (BaF3) | 2-Fluoro-4-[3-(5-fluoro-benzothiazol-6-ylsulfanyl)-[1,2,4]triazolo[4,3-b]pyridazin-6-yl]-N-methyl-benzamide | (DMSO-d6) δ: 3.11(d, 3H), 8.06(t, 1H), 8.15-8.21(m, 2H) 8.42(s, 1H), 8.44(s, 1H), 8.70-8.74(broad m, 1H), 8.77(d, 1H), 8.92(d, 1H), 9.83(s, 1H) | 455 |

TABLE I-continued

| Compounds | Enzyme Assay c-MET IC$_{50}$ | XTT Assay (GTL16) IC$_{50}$ | Structure | $^1$H NMR (500 MHz) | MS (m/z) [M + H$^+$]$^+$ |
|---|---|---|---|---|---|
| 21 | I | I (BaF3) | 3-[3-(Quinolin-6-ylsulfanyl)-[1,2,4]triazolo[4,3-b]pyridazin-6-yl]-benzonitrile | (DMSO-d6) δ: 7.48(dd, 1H), 7.65(t, 1H), 7.68 (dd, 1H), 7.93(d, 1H), 7.96(dt, 1H), 8.08(d, 1H), 8.12(d, 1H), 8.18 (dt, 1H), 8.28(dd, 1H), 8.33(t, 1H), 8.58(d, 1H), 8.83(dd, 1H) | 381 |
| 22 | I | II (BaF3) | 3-[3-(Benzothiazol-6-ylsulfanyl)-[1,2,4]triazolo[4,3-b]pyridazin-6-yl]-benzonitrile | (DMSO-d6) δ: 7.65(dd, 1H), 7.76(t, 1H), 8.05 (dt, 1H), 8.08(d, 1H), 8.15d, 1H), 8.28(dt, 1H), 8.39(d, 1H), 8.44 (t, 1H), 8.64(d, 1H), 9.42(s, 1H) | 387 |
| 23 | I | I (BaF3) | 3-[3-(7-Fluoro-quinolin-6-ylsulfanyl)-[1,2,4]triazolo[4,3-b]pyridazin-6-yl]-benzonitrile | (DMSO-d6) δ: 7.48(dd, 1H), 7.65(t, 1H), 7.85 (d, 1H), 7.98(dd, 1H), 8.08(d, 1H), 8.18(dt, 1H), 8.23(d, 1H), 8.32-8.36(m, 2H), 8.58(d, 1H), 8.86(dd, 1H) | 399 |
| 24 | II | | 3-Methyl-6-[6-(1-methyl-1H-pyrazol-4-yl)-[1,2,4]triazolo[4,3-b]pyridazin-3-ylsulfanyl}-quinolin-2-ylamine | (DMSO-d6) δ: 2.18(s, 3H), 3.92(s, 3H), 6.46 (broad s, 2H), 7.41(d, 1H), 7.53(dd, 1H), 7.73 (d, 1H), 7.75(s, 1H), 7.90(d, 1H), 8.07(s, 1H), 8.38(d, 1H), 8.47 (s, 1H) | 389 |
| 25 | I | I | 3-(3-Methyl-3H-benzoimidazol-5-ylsulfanyl)-6-(1-methyl-1H-pyrazol-4-yl)-[1,2,4]triazolo[4,3-b]pyridazine | (DMSO-d6) δ: 3.81(s, 3H), 3.92(s, 3H), 7.39 (d, 1H), 7.41(d, 1H), 7.63(d, 1H), 7.74(d, 1H), 7.96(d, 1H), 8.11 (s, 1H), 8.23(s, 1H), 8.39(d, 1H), 8.51(s, 1H) | 363 |

TABLE I-continued

| Compounds | Enzyme Assay c-MET IC$_{50}$ | XTT Assay (GTL16) IC$_{50}$ | Structure | $^1$H NMR (500 MHz) | MS (m/z) [M + H$^+$]$^+$ |
|---|---|---|---|---|---|
| 26 | I | I | 4-Methoxy-6-[6-(1-methyl-1H-pyrazol-4-yl)-[1,2,4]triazolo[4,3-b]pyridazin-3-ylsulfanyl]-quinoline | (DMSO-d6) δ: 3.90(s, 3H), 4.02(s, 3H), 7.06 (d, 1H), 7.76-7.78(m, 2H), 7.91(d, 1H), 8.05 (s, 1H), 8.32(d, 1H), 8.43(d, 1H), 8.46(s, 1H), 8.73(d, 1H) | 390 |
| 27 | III | | 6-[6-(1-methyl-1H-pyrazol-4-yl)-[1,2,4]triazolo[4,3-b]pyridazin-3-ylsulfanyl]-quinoline, N-oxide | (DMSO-d6) δ: 3.89(s, 3H), 7.47(dd, 1H), 7.75 (dd, 1H), 7.81(d, 1H), 7.87(d, 1H), 8.00(s, 1H), 8.16(d, 1H), 8.44 (s, 1H), 8.46(d, 1H), 8.49(d, 1H), 8.55(d, 1H) | 376 |
| 28 | III | | Methyl-{6-[6-(1-methyl-1H-pyrazol-4-yl)-[1,2,4]triazolo[4,3-b]pyridazin-3-ylsulfanyl]-quinolin-4-yl}-amine | (DMSO-d6) δ: 2.96(d, 3H), 3.98(s, 3H), 6.48 (d, 1H), 7.60(broad q, 1H), 7.72(dd, 1H), 7.80 (d, 1H), 7.83(d, 1H), 8.54(s, 1H), 8.60(d, 1H) | 389 |
| 29 | II | | Dimethyl-{6-[6-(1-methyl-1H-pyrazol-4-yl)-[1,2,4]triazolo[4,3-b]pyridazin-3-ylsulfanyl]-quinolin-4-yl}-amine | (DMSO-d6) δ: 2.96(s, 6H), 3.98(s, 3H), 6.95 (d, 1H), 7.79(dd, 1H), 7.86(d, 1H), 7.96(d, 1H), 8.10(s, 1H), 8.16 (d, 1H), 8.53(s, 1H), 8.54(d, 1H), 8.65(d, 1H) | 403 |
| 30 | I | I | 3-(3-Ethyl-3H-benzoimidazol-5-ylsulfanyl)-6-(1-methyl-1H-pyrazol-4-yl)-[1,2,4]triazolo[4,3-b]pyridazine | (DMSO-d6) δ: 1.27(t, 3H), 3.86(s, 3H), 4.20 (q, 2H), 7.31(d, 1H), 7.57(d, 1H), 7.68(d, 1H), 7.97(s, 1H), 8.03 (s, 1H), 8.24(s, 1H), 8.33(d, 1H), 8.47(s, 1H) | 377 |

TABLE I-continued

| Compounds | Enzyme Assay c-MET IC$_{50}$ | XTT Assay (GTL16) IC$_{50}$ | Structure | $^1$H NMR (500 MHz) | MS (m/z) [M + H$^+$]$^+$ |
|---|---|---|---|---|---|
| 31 | I | II | 3-{3-(2-Methoxy-ethyl)-3H-benzoimidazol-5-ylsulfanyl]-6-(1-methyl-1H-pyrazol-4-yl)-[1,2,4]triazolo[4,3-b]pyridazine | (DMSO-d60 δ: 3.05(s, 3H), 3.51(t, 2H), 3.86 (s, 3H), 4.34(t, 2H), 7.32(dd, 1H), 7.57(d, 1H), 7.68(d, 1H), 7.94 (s, 1H), 8.03(s, 1H), 8.15(s, 1H), 8.33(d, 1H), 8.45(s, 1H) | 407 |
| 32 | II | III | Dimethyl-(2-(6-[6-(1-methyl-1H-pyrazol-4-yl)-[1,2,4]triazolo[4,3-b]pyridazin-3-ylsulfanyl]-benzoimidazol-1-yl)-ethyl)-amine, formic acid salt | (DMSO-d6) δ: 2.06(s, 6H), 2.52(t, 2H), 3.93 (s, 3H), 4.30(t, 2H), 7.38(dd, 1H), 7.63(d, 1H), 7.75(d, 1H), 7.97 (d, 1H), 8.10(s, 1H), 8.20(broad s, 1H), 8.25 (s, 1H), 8.40(d, 1H), 8.52(s, 1H) | 420 |
| 33 | I | I | 6-[6-(1-Methyl-1H-pyrazol-4-yl)-[1,2,4]triazolo[4,3-b]pyridazin-3-ylsulfanyl]-quinolin-3-ylamine, trifluoroacetic acid salt | (DMSO-d6) δ: 3.89(s, 3H), 7.30(bs, 1H), 7.35 (dd, 1H), 7.75(d, 1H), 7.82(d, 1H), 7.87(d, 1H), 8.02(s, 1H), 8.4 (dd, 3H) | 375 |
| 34 | II | | 6-[6-(1-Methyl-1H-pyrazol-4-yl)-[1,2,4]triazolo[4,3-b]pyridazin-3-ylsulfanyl]-quinolin-4-ylamine, trifluoroacetic acid salt | (DMSO-d6) δ: 3.90(s, 3H), 6.76(d, 1H), 7.78 (d, 1H), 7.83(d, 1H), 7.95(dd, 1H), 8.01(s, 1H), 8.41(t, 1H), 8.47 (d, 2H), 8.62(d, 1H), 9.04(d, 2H) | 375 |

TABLE I-continued

| Compounds | Enzyme Assay c-MET IC$_{50}$ | XTT Assay (GTL16) IC$_{50}$ | Structure | $^1$H NMR (500 MHz) | MS (m/z) [M + H$^+$]$^+$ |
|---|---|---|---|---|---|
| 35 | I | I | {6-[6-(1-Methyl-1H-pyrazol-4-yl)-[1,2,4]triazolo[4,3-b]pyridazin-3-ylsulfanyl]-quinolin-3-yl}-carbamic acid tert-butyl ester | (DMSO-d6) δ: 1.50(s, 9H), 3.89(s, 3H), 7.52 (dd, 1H), 7.78(d, 1H), 7.86(d, 1H), 8.01(d, 2H), 8.45(m, 3H), 8.79 (d, 1H), 9.95(bs, 1H) | 475 |
| 36 | III |  | {6-[6-(1-Methyl-1H-pyrazol-4-yl)-[1,2,4]triazolo[4,3-b]pyridazin-3-ylsulfanyl]-quinolin-4-yl}-carbamic acid tert-butyl ester | (DMSO-d6) δ: 1.52(s, 9H), 3.88(s, 3H), 7.76 (d, 1H), 7.78(d, 1H), 7.95(d, 1H), 8.01(s, 1H), 8.08(d, 1H), 8.44 (s, 1H), 8.46(d, 1H), 8.76(s, 1H), 8.81(d, 1H), 10.21(s, 1H) | 475 |
| 37 | II |  | 6-(6-Methyl-[1,2,4]triazolo[4,3-b]pyridazin-3-ylsulfanyl)-quinoline | (DMSO-d6) δ: 2.53(s, 3H), 7.39(d, 1H), 7.55(dd, 1H), 7.65(dd, 1H), 7.98(d, 1H), 8.00 (d, 1H), 8.32(dd, 1H), 8.39(d, 1H), 8.89(d, 1H) | 294 |
| 38 | III |  | 6-[6-(1-Methyl-1H-pyrazol-4-yl)-[1,2,4]triazolo[4,3-b]pyridazine-3-sulfinyl]-quinoline | (DMSO0-d6) δ: 3.86(s, 3H), 7.62(dd, 1H), 7.79 (d, 1H), 7.99(s, 1H), 8.00(dd, 1H), 8.11(d, 1H), 8.43(s, 1H), 8.44 (d, 1H), 8.63(dd, 1H), 8.71(d, 1H), 8.96(dd, 1H) | 376 |

TABLE I-continued

| Compounds | Enzyme Assay c-MET IC$_{50}$ | XTT Assay (GTL16) IC$_{50}$ | Structure | $^1$H NMR (500 MHz) | MS (m/z) [M + H$^+$]$^+$ |
|---|---|---|---|---|---|
| 39 | I | II | 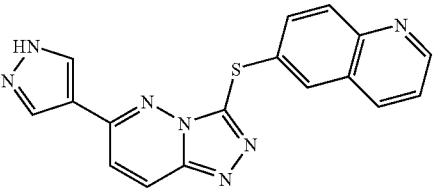<br>6-[6-(1H-Pyrazol-4-yl)-[1,2,4]triazolo[4,3-b]pyridazin-3-ylsulfanyl]-quinoline | (DMSO-d6) δ: 7.55(1H, d), 7.75(1H, dd), 7.83 (1H, d), 7.98(1H, d), 8.01(1H, s), 8.16(1H, d), 8.35(1H, d), 8.46 (1H, d), 8.47(1H, s), 8.90(1H, dd), 13.40 (1H, bs) | 346 |
| 40 | I | I | 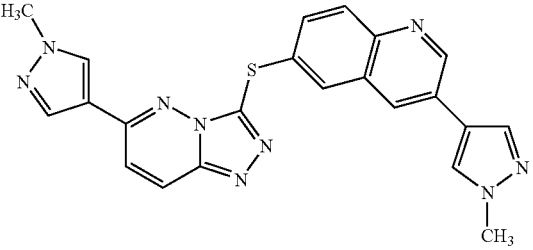<br>3-(1-Methyl-1H-pyrazol-4-yl)-6-[6-(1-methyl-1H-pyrazol-4-yl)-[1,2,4]triazolo[4,3-b]pyridazin-3-ylsulfanyl]-quinoline | (DMSO-d6) δ: 3.88(s, 3H), 3.90(s, 3H), 7.67 (dd, 1H), 7.80(d, 1H), 7.95(m, 2H), 8.03(s, 1H), 8.06(s, 1H), 8.37 (s, 1H), 8.43(d, 1H), 8.45(s, 1H), 8.48(d, 1H), 9.17(d, 1H) | 440 |
| 41 | I | I | 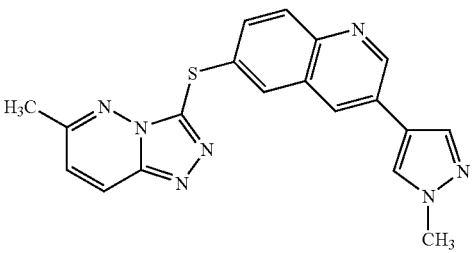<br>3-(1-Methyl-1H-pyrazol-4-yl)-6-(6-methyl-[1,2,4]triazolo[4,3-b]pyridazin-3-ylsulfanyl)-quinoline | (DMSO-d6) δ: 2.47(s, 3H), 3.83(s, 3H), 7.33 (d, 1H), 7.51(dd, 1H), 7.74(d, 1H), 7.87(d, 1H), 7.99(s, 1H), 8.31 (s, 1H), 8.33(m, 2H), 9.10(d, 1H) | 374 |
| 42 | I | III | 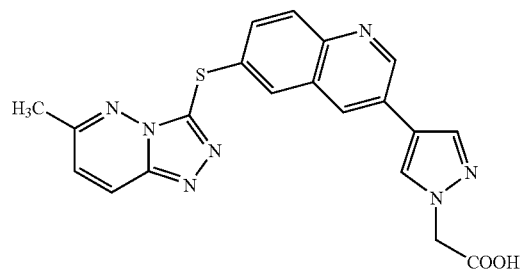<br>{4-[6-(6-Methyl-[1,2,4]triazolo[4,3-b]pyridazin-3-ylsulfanyl)-quinolin-3-yl]-pyrazol-1-yl}-acetic acid | (DMSO-d6) δ: 2.47(s, 3H), 4.90(s, 2H), 7.33 (d, 1H), 7.52(dd, 1H), 7.76(d, 1H), 7.88(d, 1H), 8.03(s, 1H), 8.33 (m, 2H), 8.37(d, 1H), 9.11(d, 1H), 16.0(s, 1H) | 418 |

TABLE I-continued

| Compounds | Enzyme Assay c-MET IC$_{50}$ | XTT Assay (GTL16) IC$_{50}$ | Structure | $^1$H NMR (500 MHz) | MS (m/z) [M + H$^+$]$^+$ |
|---|---|---|---|---|---|
| 43 | II | | 3-Bromo-6-(6-methyl-[1,2,4]triazolo[4,3-b]pyridazin-3-ylsulfanyl)-quinoline | (DMSO-d6) δ: 2.53(s, 3H), 7.41(d, 1H), 7.70(dd, 1H), 7.87(d, 1H), 7.99(d, 1H), 8.41(d, 1H), 8.66(d, 1H), 8.93(d, 1H) | 372, 374 |
| 44 | I | I | 6-(6-Methyl-[1,2,4]triazolo[4,3-b]pyridazin-3-ylsulfanyl)-3-[1-(2-morpholin-4-yl-ethyl)-1H-pyrazol-4-yl]-quinoline | (DMSO-d6) δ: 2.35(m, 4H), 2.46(s, 3H), 2.68(t, 2H), 3.48(t, 4H), 4.20(t, 2H), 7.33(d, 1H), 7.52(dd, 1H), 7.75(d, 1H), 7.87(d, 1H), 8.01(s, 1H), 8.33(m, 2H), 8.37(s, 1H), 9.10(d, 1H) | 473 |
| 45 | I | III | 2-Methyl-2-{4-[6-(6-methyl-[1,2,4]triazolo]4,3-b]pyridazin-3-ylsulfanyl)-quinolin-3-yl]-pyrazol-1-yl}-propionic acid | (DMSO-d6) δ: 1.70(s, 6H), 2.44(s, 3H), 7.33(d, 1H), 7.52(dd, 1H), 7.69(d, 1H), 7.88(d, 1H), 8.03(s, 1H), 8.34(d, 1H), 8.38(d, 1H), 8.54(s, 1H), 9.17(d, 1H) | 446 |
| 46 | I | I | 6-(1-Methyl-1H-pyrazol-4-yl)-3-[5-(1-methyl-1H-pyrazol-4-yl)-1H-pyrrolo[2,3-b]pyridin-3-ylsulfanyl]-[1,2,4]triazolo[4,3-b]pyridazine | (DMSO-d6) δ: 3.85(3H, s), 3.92(3H, s), 7.73(1H, d), 7.88(1H, d), 8.08(1H, d), 8.14(1H, d), 8.16(1H, s), 8.19(1H, s), 8.34(1H, d), 8.53(1H, s), 8.56(1H, d), 12.26(1H, s) | 429 |

TABLE I-continued

| Compounds | Enzyme Assay c-MET IC$_{50}$ | XTT Assay (GTL16) IC$_{50}$ | Structure | $^1$H NMR (500 MHz) | MS (m/z) [M + H$^+$]$^+$ |
|---|---|---|---|---|---|
| 47 | III | | 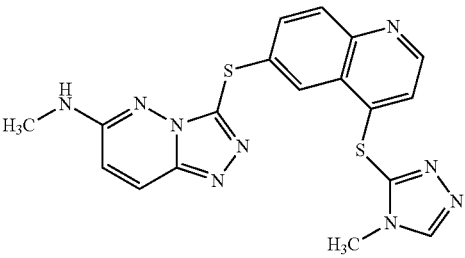<br>Methyl-{3-[4-(4-methyl-4H-[1,2,4]triazol-3-ylsulfanyl)-quinolin-6-ylsulfanyl]-[1,2,4]triazolo[4,3-b]pyridazin-6-yl}-amine<br>+<br>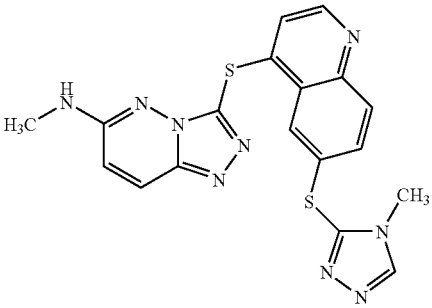<br>Methyl-{3-[6-(4-methyl-4H-[1,2,4]triazol-3-ylsulfanyl)-quinolin-4-ylsulfanyl]-[1,2,4]triazolo[4,3-b]pyridazin-6-yl}-amine | (DMSO-d6) δ: 2.45(d, 3H), 2.59(d, 3H), 3.51 (s, 3H), 3.55(s, 3H), 6.73(d, 1H), 6.79(m, 2H), 7.00(d, 1H), 7.48 (q, 2H), 7.55(dd, 1H), 7.66(dd, 1H), 7.93-7.98 (m, 4H), 8.04(d, 1H), 8.10(d, 1H), 8.59(m, 2H), 8.74(s, 1H), 8.83 (s, 1H) | 422 |
| 48 | IV | | 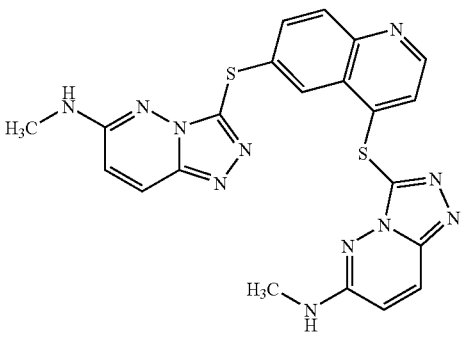<br>4,6-{6-Methylamino-[1,2,4]triazolo[4,3-b]pyridazin-3-ylsulfanyl}-quinoline | (DMSO-d6) δ: 2.58(d, 3H), 2.75(d, 3H), 6.94 (m, 2H), 7.08(d, 1H), 7.61(m, 2H), 7.79(dd, 1H), 8.10(m, 3H), 8.39 (s, 1H), 8.72(d, 1H) | 488 |

TABLE I-continued

| Compounds | Enzyme Assay c-MET IC$_{50}$ | XTT Assay (GTL16) IC$_{50}$ | Structure | $^1$H NMR (500 MHz) | MS (m/z) [M + H$^+$]$^+$ |
|---|---|---|---|---|---|
| 49 | IV | | 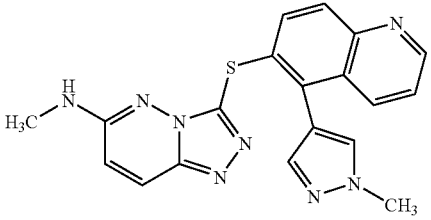<br>Methyl-{3-[5-(1-methyl-1H-pyrazol-4-yl)-quinolin-6-ylsulfanyl]-[1,2,4]triazolo[4,3-b]pyridazin-6-yl}-amine | (DMSO-d6) δ: 2.56(d, 3H), 3.99(s, 3H), 6.82 (d, 1H), 7.21(d, 1H), 7.46(q, 1H), 7.52(dd, 1H), 7.67(s, 1H), 7.85 (d, 1H), 7.98(d, 1H), 8.04(s, 1H), 8.09(dd, 1H), 8.87(dd, 1H) | 389 |
| 50 | I | I | 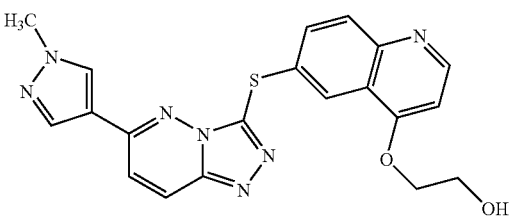<br>2-{6-(6-(1-Methyl-1H-pyrazol-4-yl)-[1,2,4]triazolo[4,3-b]pyridazin-3-ylsulfanyl]-quinolin-4-yloxy}-ethanol | (DMSO-d6) δ: 3.86(q, 2H), 3.91(s, 3H), 4.26 (t, 2H), 5.12(t, 1H), 7.06 (d, 1H), 7.72(dd, 1H), 7.77(d, 1H), 7.89(d, 1H), 8.06(s, 1H), 8.43 (d, 1H), 8.46(s, 1H), 8.51(d, 1H), 8.72(d, 1H) | 420 |
| 51 | II | | 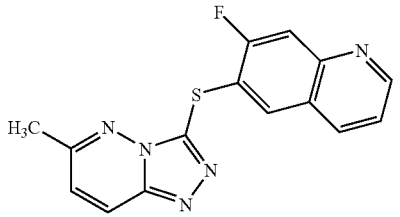<br>7-Fluoro-6-(6-methyl-[1,2,4]triazolo[4,3-b]pyridazin-3-ylsulfanyl)-quinoline | (DMSO-d6) δ: 2.53(s, 3H), 7.38(d, 1H), 7.54 (dd, 1H), 7.92(d, 1H), 8.03(d, 1H), 8.34(dd, 1H), 8.38(d, 1H), 8.93 (dd, 1H) | 312 |
| 52 | I | I | 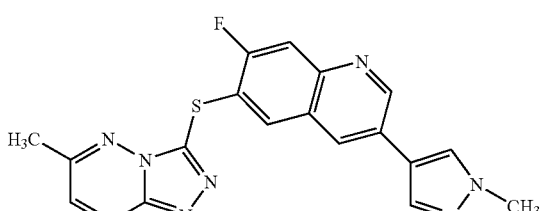<br>7-Fluoro-3-(1-methyl-1H-pyrazol-4-yl)-6-(6-methyl-[1,2,4]triazolo[4,3-b]pyridazin-3-ylsulfanyl)-quinoline | (DMSO-d6) δ: 2.54(s, 3H), 3.89(s, 3H), 7.41 (d, 1H), 7.79(d, 1H), 7.89(d, 1H), 8.03(s, 1H), 8.35(s, 1H), 8.41 (d, 1H), 8.43(d, 1H), 9.20(d, 1H) | 392 |

TABLE I-continued

| Compounds | Enzyme Assay c-MET IC$_{50}$ | XTT Assay (GTL16) IC$_{50}$ | Structure | $^1$H NMR (500 MHz) | MS (m/z) [M + H$^+$]$^+$ |
|---|---|---|---|---|---|
| 53 | I | II | 6-Methyl-3-[5-(1-methyl-1H-pyrazol-4-yl)-1H-pyrrolo[2,3-b]pyridin-3-ylsulfanyl]-[1,2,4]triazolo[4,3-b]pyridazine | (DMSO-d6) δ: 2.57(3H, s), 3.86(3H, s), 7.28 (1H, d), 7.90(1H, d), 8.00(1H, d), 8.14(1H, d), 8.20(1H, s), 8.21 (1H, d), 8.56(1H, d), 12.27(1H, s) | 363 |
| 54 | II | | 3-Methyl-6-(6-methyl-[1,2,4]triazolo[4,3-b]pyridazin-3-ylsulfanyl)-quinoline | (DMSO-d6) δ: 2.45(s, 3H), 2.53(s, 3H), 7.39 (d, 1H), 7.57(dd, 1H), 7.88(d, 1H), 7.93(d, 1H), 8.07(s, 1H), 8.38 (d, 1H), 8.76(d, 1H) | 308 |
| 55 | I | I | 5-Fluoro-6-[6-(1-methyl-1H-pyrazol-4-yl)-[1,2,4]triazolo[4,3-b]pyridazin-3-yl sulfanyl]-quinoline | (DMSO-d6) δ: 3.83(s, 3H), 7.62(dd, 1H), 7.65 (t, 1H), 7.69(d, 1H), 7.79(d, 1H), 7.92(s, 1H), 8.36(s, 1H), 8.37 (d, 1H), 8.48(d, 1H), 8.94(dd, 1H) | 378 |
| 56 | I | I | 5-Fluoro-3-(1-methyl-1H-pyrazol-4-yl)-6-(6-methyl-[1,2,4]triazolo[4,3-b]pyridazin-3-ylsulfanyl)-quinoline | (DMSO-d6) δ: 2.45(s, 3H), 3.85(s, 3H), 7.31 (d, 1H), 7.41(dd, 1H), 7.73(d, 1H), 8.16(s, 1H), 8.30(d, 1H), 8.46 (s, 1H), 8.50(d, 1H), 9.22(d, 1H) | 392 |

TABLE I-continued

| Compounds | Enzyme Assay c-MET IC$_{50}$ | XTT Assay (GTL16) IC$_{50}$ | Structure | $^1$H NMR (500 MHz) | MS (m/z) [M + H$^+$]$^+$ |
|---|---|---|---|---|---|
| 57 | IV | | 6-(6-Methyl-[1,2,4]triazolo[4,3-b]pyridazin-3-ylsulfanyl)-4-(4-methyl-4H-[1,2,4]triazol-3-ylsulfanyl)-quinoline | (DMSO-d6) δ: 2.56(s, 3H), 3.59(s, 3H), 6.85 (d, 1H), 7.41(d, 1H), 7.73(dd, 1H), 8.03(d, 1H), 8.19(d, 1H), 8.40 (d, 1H), 8.68(d, 1H), 8.89(s, 1H) | 407 |
| 58 | I | I | 6-(6-Ethyl-[1,2,4]triazolo[4,3-b]pyridazin-3-ylsulfanyl)-3-(1-methyl-1H-pyrazol-4-yl)-quinoline | (DMSO-d6) δ: 0.98(t, 3H), 2.67(m, 2H), 3.71 (s, 3H), 7.26(d, 1H), 7.42(m, 1H), 7.68(d, 1H), 7.76(d, 1H), 7.88 (s, 1H), 8.19(s, 1H), 8.23(m, 2H), 8.99(d, 1H) | 388 |
| 59 | I | II | 6-(6-Methyl-[1,2,4]triazolo[4,3-b]pyridazin-3-ylsulfanyl)-3-(1H-pyrazol-4-yl)-quinoline | (DMSO-d6) δ: 2.35(s, 3H), 7.32(d, 1H), 7.41 (m, 1H), 7.62(d, 1H), 7.77(d, 1H), 7.95(s, 1H), 8.23(d, 1H), 8.27 (m, 2H), 9.05(d, 1H) | 360 |
| 60 | I | I | 4-Ethyl-6-[6-(1-methyl-1H-pyrazol-4-yl)-[1,2,4]triazolo[4,3-b]pyridazin-3-ylsulfanyl]-quinoline | (DMSO-d6) δ: 1.21(t, 3H), 3.03(q, 2H), 3.89 (s, 3H), 7.40(d, 1H), 7.69(dd, 1H), 7.78(d, 1H), 7.96(d, 1H), 8.01 (s, 1H), 8.28(d, 1H), 8.45(m, 2H), 8.78(d, 1H) | 388 |
| 61 | I | I | 3-[1-(1-Ethyl-azetidin-3-yl)-1H-pyrazol-4-yl]-6-(6-methyl-[1,2,4]triazolo[4,3-b]pyridazin-3-ylsulfanyl)-quinoline | (DMSO-d60) δ: 2.53(s, 3H), 3.35(m, 2H), 3.71 (m, 2H), 4.99(m, 1H), 5.71(s, 2H), 7.39(d, 1H), 7.59(dd, 1H), 7.78 (d, 1H), 7.94(d, 1H), 8.14(s, 1H), 8.41(d, 1H), 8.43(1H, d), 8.60 (1H, s), 9.19(1H, d) | 443 |

TABLE I-continued

| Compounds | Enzyme Assay c-MET IC$_{50}$ | XTT Assay (GTL16) IC$_{50}$ | Structure | $^1$H NMR (500 MHz) | MS (m/z) [M + H$^+$]$^+$ |
|---|---|---|---|---|---|
| 62 | I | I | 3-(1-Azetidin-3-yl-1H-pyrazol-4-yl)-6-(6-methyl-[1,2,4]triazolo[4,3-b]pyridazin-3-ylsulfanyl)-quinoline | (DMSO-d6) δ: 2.50(s, 3H), 3.84(m, 2H), 3.98(m, 2H), 5.23(quintet, 1H), 7.40(d, 1H), 7.61(dd, 1H), 7.81(d, 1H), 7.95(d, 1H), 8.18(s, 1H), 8.40(d, 1H), 8.44(d, 1H), 8.59(s, 1H), 9.20(d, 1H) | 415 |
| 63 | I | I | 3-[1-(1-Methyl-azetidin-3-yl)-1H-pyrazol-4-yl]-6-(6-methyl-[1,2,4]triazolo[4,3-b]pyridazin-3-ylsulfanyl)-quinoline | (DMSO-d6) δ: 2.34(s, 3H), 2.53(s, 3H), 3.41(m, 2H), 3.72(m, 2H), 4.98(quintet, 1H), 7.40(d, 1H), 7.60(dd, 1H), 7.79(d, 1H), 7.95(d, 1H), 8.15(s, 1H), 8.40(d, 1H), 8.44(d, 1H), 8.60(s, 1H), 9.20(d, 1H) | 429 |
| 64 | I | I | 3-{4-[6-(6-Methyl-[1,2,4]triazolo[4,3-b]pyridazin-3-ylsulfanyl)-quinolin-3-yl]-pyrazol-1-yl}-azetidine-1-carboxylic acid tert-butyl ester | (DMSO-d6) δ: 1.42(s, 9H), 2.54(s, 3H), 4.17(br m, 2H), 4.34(br m, 2H), 5.26(m, 1H), 7.40(d,1H), 7.60(dd, 1H), 7.80(d, 1H), 7.95(d, 1H), 8.22(s, 1H), 8.40(d, 1H), 8.45(d, 1H), 8.63(s, 1H), 9.21(1H, d) | 515 |
| 65 | I | I | 3-{4-[6-(6-Methyl-[1,2,4]triazolo[4,3-b]pyridazin-3-ylsulfanyl)-quinolin-3-yl]-pyrazol-1-ylmethyl}-azetidine-1-carboxylic acid tert-butyl ester | (DMSO-d6) δ: 1.35(s, 9H), 2.52(s, 3H), 3.00(m, 1H), 3.70(br m, 2H), 3.90(br m, 2H), 4.37(d, 2H), 7.39(d, 1H), 7.60(dd, 1H), 7.80(d, 1H), 7.94(d, 1H), 8.10(s, 1H), 8.39(d, 1H), 8.40(s, 1H), 9.16(d, 1H) | 529 |

TABLE I-continued

| Compounds | Enzyme Assay c-MET IC$_{50}$ | XTT Assay (GTL16) IC$_{50}$ | Structure | $^1$H NMR (500 MHz) | MS (m/z) [M + H$^+$]$^+$ |
|---|---|---|---|---|---|
| 66 | I | I | 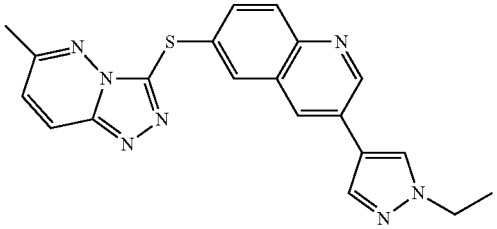<br>3-(1-Ethyl-1H-pyraozl-4-yl)-6-(6-methyl-[1,2,4]triazolo[4,3-b]pyridazin-3-ylsulfanyl)-quinoline | (DMSO-d6) δ: 1.42(t, 3H), 2.53(s, 3H), 4.18 (q, 2H), 7.39(d, 1H), 7.58(dd, 1H), 7.79(d, 1H), 7.93(d, 1H), 8.07 (s, 1H), 8.38(d, 1H), 3.39(s, 1H), 8.43(s, 1H), 9.17(d, 1H) | 388 |
| 67 | I | I | 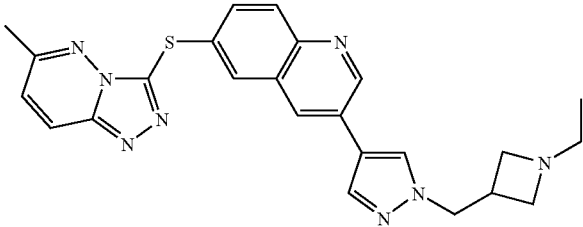<br>3-[1-(1-Ethyl-azetidin-3-ylmethyl)-1H-pyrazol-4-yl]-6-(6-methyl-[1,2,4]triazolo[4,3-b]pyridazin-3-ylsulfanyl)-quinoline | (DMSO-d6) δ: 0.84(t, 3H), 2.37(q, 2H), 2.52 (s, 3H), 2.81(m, 1H), 2.93-3.00(m, 2H), 3.19-3.25(m, 2H), 4.32(d, 2H), 7.40(d, 1H), 7.59 (dd, 1H), 7.79(d, 1H), 7.93(d, 1H), 8.07(d, 1H), 8.38-8.43(m, 3H), 9.17(d, 1H) | 457 |
| 68 | I | I | 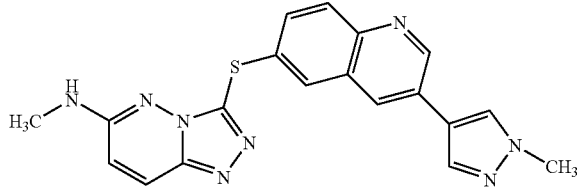<br>Methyl-{3-[3-(1-methyl-1H-pyrazol-4-yl)-quinolin-6-ylsulfanyl]-[1,2,4]triazolo[4,3-b]pyridazin-6-yl}-amine | (CD$_3$OD) δ: 2.72(s, 3H), 3.96(s, 3H), 6.83 (d, 1H), 7.65(m, 1H), 7.81(d, 1H), 7.92(d, 1H), 7.95(d, 1H), 8.02 (s, 1H), 8.19(s, 1H), 8.35(s, 1H), 9.06(d, 1H) | 389 |
| 69 | I | I | 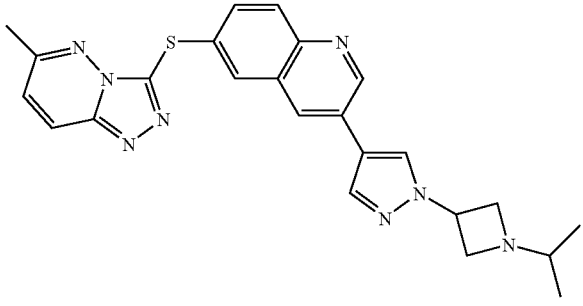<br>3-[1-(1-Isopropyl-azetidin-3-yl)-1H-pyrazol-4-yl]-6-(6-methyl-[1,2,4]triazolo[4,3-b]pyridazin-3-ylsulfanyl)-quinoline | (DMSO-d6) δ: 0.91(d, 6H), 2.44(m, 1H), 2.54 (s, 3H), 3.36(m, 2H), 3.69(m, 2H), 4.94 (quintet, 1H), 7.40(d, 1H), 7.60(dd, 1H), 7.79 (d, 1H), 7.95(d, 1H), 8.15(s, 1H), 8.40(d, 1H), 8.44(d, 1H), 8.61 (s, 1H), 9.21(d, 1H) | 457 |

TABLE I-continued

| Compounds | Enzyme Assay c-MET IC$_{50}$ | XTT Assay (GTL16) IC$_{50}$ | Structure | $^1$H NMR (500 MHz) | MS (m/z) [M + H$^+$]$^+$ |
|---|---|---|---|---|---|
| 70 | I | I | 3-[1-(1-Ethyl-azetidin-3-yl)-1H-pyrazol-4-yl]-6-(6-ethyl-[1,2,4]triazolo[4,3-b]pyridazin-3-ylsulfanyl)-quinoline | (DMSO-d6) δ: 0.86(t, 3H), 1.09(t, 3H), 2.77 (q, 2H), under DMSO peak(q, 2H), under H2O peak(m, 2H), 3.63 (m, 3), 4.93(quintet, 1H), 7.37(d, 1H), 7.54 (dd, 1H), 7.78(d, 1H), 7.88(d, 1H), 8.08(s, 1H), 8.34(d, 1H), 8.38 (d, 1H), 8.54(s, 1H), 9.14(d, 1H) | 457 |
| 71 | | | 3-(1-Azetidin-3-yl-1H-pyraozl-4-yl)-6-(6-ethyl-[1,2,4]triazolo[4,3-b]pyridazin-3-ylsulfanyl)-quinoline | | 429 |
| 72 | | | 3-(1-Azetidin-3-ylmethyl-1H-pyrazol-4-yl)-6-(6-ethyl-[1,2,4]triazolo[4,3-b]pyridazin-3-yl sulfanyl)-quinoline | | 443 | wherein:

I    IC$_{50}$ ≦ 100 nM;

II   100 nM < IC$_{50}$ ≦ 1 μM;

III  1 μM < IC$_{50}$ ≦ 10 μM; and

IV   IC$_{50}$ > 10 μM.

Example 24

In Vitro Assays

Kinase assays known to those of skill in the art may be used to assay the inhibitory activities of the compounds and compositions of the present disclosure. Kinase assays include, but are not limited to, the following examples.

Screening data was evaluated using the equation: $Z'=1-[3*(\sigma_+ +\sigma_-)/|\mu_+ -\mu_-|]$ (Zhang, et al., 1999 J Biomol Screening 4(2) 67-73), where t denotes the mean and C the standard deviation. The subscript designates positive or negative controls. The Z' score for a robust screening assay should be $\geq 0.50$. The typical threshold$=\mu_+ -3*\sigma_+$. Any value that falls below the threshold was designated a "hit". Dose response was analyzed using the equation: $y=min+\{(max-min)/(1+10^{[compound]-logIC50})\}$, where y is the observed initial slope, max=the slope in the absence of inhibitor, min=the slope at infinite inhibitor, and the $IC_{50}$ is the concentration of compound that corresponds to ½ the total observed amplitude (Amplitude=max-min).

MET Luminescence-Based Enzyme Assay

Materials: Poly Glu-Tyr (4:1) substrate (Sigma Cat# P-0275), ATP (Sigma Cat#A-3377, FW=551), HEPES buffer, pH 7.5, Bovine serum albumin (BSA) (Roche 92423420), $MgCl_2$, Staurosporine (*Streptomyces* sp. Sigma Cat#85660-1MG), white Costar 384-well flat-bottom plate (VWR Cat#29444-088). MET kinase (see below), Kinase-Glo™ (Promega Cat#V6712).

Stock Solutions: 10 mg/ml poly Glu-Tyr in water, stored at −20° C.; 100 mM HEPES buffer, pH 7.5 (5 ml IM stock+45 ml miliQH₂O); 10 mM ATP (5.51 mg/ml in dH₂O) stored at −20° C. (diluted 50 µl into total of 10 ml miliQH₂O daily=50 µM ATP working stock); 1% BSA (1 g BSA in 100 ml 0.1M HEPES, pH 7.5, stored at −20° C.), 100 mM $MgCl_2$; 200 µM Staurosporine, 2× Kinase-Glo™ reagent (made fresh or stored at −20° C.).

Standard Assay Setup for 384-well format (20 µl kinase reaction, 40 µl detection reaction): 10 mM $MgCl_2$; 0.3 mg/ml poly Glu-Tyr; 0.1% BSA; 1 µl test compound (in DMSO); 0.4 µg/ml MET kinase; 10 µM ATP; 100 mM HEPES buffer. Positive controls contained DMSO with no test compound. Negative controls contained 10 µM staurosporine. The kinase reactions were initiated at time t=0 by the addition of ATP. Kinase reactions were incubated at 21° C. for 60 min, then 20 µl of Kinase-Glo™ reagent were added to each well to quench the kinase reaction and initiate the luminescence reaction. After a 20 min incubation at 21° C., the luminescence was detected in a plate-reading luminometer.

Purification of Met

The cell pellets produced from half of a 12 L Sf9 insect cell culture expressing the kinase domain of human Met were resuspended in a buffer containing 50 mM Tris-HCl pH 7.7 and 250 mM NaCl, in a volume of approximately 40 ml per 1 L of original culture. One tablet of Roche Complete, EDTA-free protease inhibitor cocktail (Cat#1873580) was added per 1 L of original culture. The suspension was stirred for 1 hour at 4° C. Debris was removed by centrifugation for 30 minutes at 39,800×g at 4° C. The supernatant was decanted into a 500 ml beaker and 10 ml of 50% slurry of Qiagen Ni-NTA Agarose (Cat#30250) that had been pre-equilibrated in 50 mM Tris-HCl pH 7.8, 50 mM NaCl, 10% Glycerol, 10 mM Imidazole, and 10 mM Methionine, were added and stirred for 30 minutes at 4° C. The sample was then poured into a drip column at 4° C. and washed with 10 column volumes of 50 mM Tris-HCl pH 7.8, 500 mM NaCl, 10% Glycerol, 10 mM Imidazole, and 10 mM Methionine. The protein was eluted using a step gradient with two column volumes each of the same buffer containing 50 mM, 200 mM, and 500 mM Imidazole, sequentially. The 6× Histidine tag was cleaved overnight using 40 units of TEV protease (Invitrogen Cat#10127017) per 1 mg of protein while dialyzing in 50 mM Tris-HCl pH 7.8, 500 mM NaCl, 10% Glycerol, 10 mM Imidazole, and 10 mM Methionine at 4° C. The 6× Histidine tag was removed by passing the sample over a Pharmacia 5 ml IMAC column (Cat#17-0409-01) charged with Nickel and equilibrated in 50 mM Tris-HCl pH 7.8, 500 mM NaCl, 10% Glycerol, 10 mM Imidazole, and 10 mM Methionine. The cleaved protein bound to the Nickel column at a low affinity and was eluted with a step gradient. The step gradient was run with 15% and then 80% of the B-side (A-side=50 mM Tris-HCl pH 7.8, 500 mM NaCl, 10% Glycerol, 10 mM Imidazole, and 10 mM Methionine; B-side=50 mM Tris-HCl pH 7.8, 500 mM NaCl, 10% Glycerol, 500 mM Imidazole, and 10 mM Methionine) for 4 column volumes each. The Met protein eluted in the first step (15%), whereas the non-cleaved Met and the cleaved Histidine tag eluted in the 80% fractions. The 15% fractions were pooled after SDS-PAGE gel analysis confirmed the presence of cleaved Met; further purification was done by gel filtration chromatography on an Amersham Biosciences HiLoad 16/60 Superdex 200 prep grade (Cat#17-1069-01) equilibrated in 50 mM Tris-HCl pH 8.5, 150 mM NaCl, 10% Glycerol and 5 mM DTT. The cleanest fractions were combined and concentrated to ~10.4 mg/ml by centrifugation in an Amicon Ultra-15 10,000 Da MWCO centrifugal filter unit (Cat# UFC901024).

SelectScreen™ Kinase Profiling (Invitrogen Corp.)

SelectScreen™ is a trademark screening assay protocol for kinases developed by Invitrogen Corporation, Madison, Wis. Details on assay conditions can be found on the company's website.

Table II summarizes % inhibition of compounds 4 and 41 against a panel of kinases at 1 µM concentration.

TABLE II

| | % Inhibition@1 µM | |
|---|---|---|
| Kinase Tested | Compound 4 | Compound 41 |
| ABL1 T315I | 11 | 47 |
| ABL1 Y253F | 20 | 30 |
| AKT1 (PKB alpha) | 5 | −1 |
| ALK | −10 | 23 |
| AURKA (Aurora A) | 18 | 49 |
| AURKB (Aurora B) | 7 | 61 |
| BRAF V599E | 36 | 7 |
| CDK1/cyclin B | 5 | 17 |
| CSF1R (FMS) | 19 | 79 |
| EGFR (ErbB1) | −2 | 0 |
| EPHA2 | −23 | 2 |
| FES (FPS) | 5 | 1 |
| FGFR3 | −4 | 26 |
| FLT3 D835Y | 8 | 35 |
| FRAP1 (mTOR) | | 0 |
| GRK4 | 2 | −4 |
| GSK3B (GSK3 beta) | 5 | 1 |
| HCK | 8 | 9 |
| IGF1R | −3 | 6 |
| IKBKB (IKK beta) | −5 | 1 |
| JAK2 JH1 JH2 V617F | −11 | 9 |
| KDR (VEGFR2) | 5 | 16 |
| KIT T670I | −12 | 4 |
| MAP2K1 (MEK1) | 16 | 3 |
| MAP4K4 (HGK) | −1 | 27 |
| MAPK1 (ERK2) | 9 | 0 |
| MERTK (cMER) | 7 | 10 |
| MET (cMet) | 92 | 98 |
| MET M1250T | 64 | 89 |
| MST1R (RON) | 9 | 53 |

TABLE II-continued

| | % Inhibition@1 µM | |
|---|---|---|
| Kinase Tested | Compound 4 | Compound 41 |
| NTRK3 (TRKC) | 7 | 85 |
| PDGFRA T674I | −9 | −1 |
| PDK1 | 7 | 6 |
| PIM1 | 4 | 0 |
| PLK1 | 0 | 0 |
| PRKCD (PKC delta) | 4 | 5 |
| PTK2B (FAK2) | 6 | 12 |
| RET | 5 | 21 |
| ROS1 | 7 | 41 |
| RPS6KB1 (p70S6K) | 3 | 5 |
| TEK (Tie2) | 8 | 4 |
| TYRO3 (RSE) | 19 | 22 |

Cell Assays

GTL16 cells were maintained in DMEM Medium supplemented with 10% fetal bovine serum (FBS) 2 mM L-Glutamine and 100 units penicillin/100 µg streptomycin, at 37° C. in 5% $CO_2$.

TPR-MET Ba/F3 cells were created by stably transducing the human TPR-MET gene into Ba/F3 cells using a retroviral system. All cell lines were grown in RPMI-1640 supplemented with 1× penicillin/streptomycin and 10% fetal bovine (Invitrogen, Carlsbad, Calif.). The cells were maintained in a 5% $CO_2$ humidified incubator at 37° C.

Cell Survival Assays

Compounds were tested in the following assays in duplicate.

96-well XTT assay (GTL16 cells): One day prior to assay the growth media was aspirated off and assay media was added to cells. On the day of the assay, the cells were grown in assay media containing various concentrations of compounds (duplicates) on a 96-well flat bottom plate for 72 hours at 37° C. in 5% $CO_2$. The starting cell number was 5000 cells per well and volume was 120 µl. At the end of the 72-hour incubation, 40 µl of XTT labeling mixture (50:1 solution of sodium 3'-[1-(phenylaminocarbonyl)-3,4-tetrazolium]-bis (4-methoxy-6-nitro) benzene sulfonic acid hydrate and Electron-coupling reagent: PMS (N-methyl dibenzopyrazine methyl sulfate) were added to each well of the plate. After an additional 5 hours of incubation at 37° C., the absorbance reading at 450 nm with a background correction of 650 nm was measured with a spectrophotometer.

96-well XTT assay (Ba/F3 cells): Cells were grown in growth media containing various concentrations of compounds (duplicates) on a 96-well plate for 72 hours at 37° C. The starting cell number was 5000-8000 cells per well and volume was 120 µl. At the end of the 72-hour incubation, 40 µl of XTT labeling mixture (50:1 solution of sodium 3'-[1-(phenylamino-carbonyl)-3,4-tetrazolium]-bis(4-methoxy-6-nitro) benzene sulfonic acid hydrate and Electron-coupling reagent: PMS (N-methyl dibenzopyrazine methyl sulfate) were added to each well of the plate. After an additional 2-6 hours of incubation at 37° C., the absorbance reading at 405 nm with background correction at 650 nm was measured with a spectrophotometer.

Phosphorylation Assays

Met phosphorylation assay: GTL16 cells were plated out at $1\times10^6$ cells per 60×15 mm dish (Falcon) in 3 mL of assay media. The following day compound at various concentrations were added in assay media and incubated for 1 hour at 37° C. 5% $CO_2$. After 1 hour the media was aspirated, and the cells were washed once with 1×PBS. The PBS was aspirated and the cells were harvested in 100 µL of modified RIPA lysis buffer (Tris.Cl pH 7.4, 1% NP-40, 5 mM EDTA, 5 mM NaPP, 5 mM NaF, 150 mM NaCl, Protease inhibitor cocktail (Sigma), 1 mM PMSF, 2 mM $NaVO_4$) and transferred to a 1.7 mL eppendorf tube and incubated on ice for 15 minutes. After lysis, the tubes were centrifuged (10 minutes, 14,000 g, 4° C.). Lysates were then transferred to a fresh eppendorf tube. The samples were diluted 1:2 (250,000 cells/tube) with 2×SDS PAGE loading buffer and heated for 5 minutes at 98° C. The lysates were separated on a NuPage 4-12% Bis-Tris Gel 1.0 mm×12 well (Invitrogen), at 200V, 400 mA for approximately 40 minutes. The samples were then transferred to a 0.45 micron Nitrocellulose membrane Filter Paper Sandwich (Invitrogen) for 1 hour at 75V, 400 mA. After transferring, the membranes were placed in blocking buffer for 1 hour at room temperature with gentle rocking. The blocking buffer was removed and a 1:500 dilution of anti-Phospho-Met (Tyr1234/1235) antibody (Cell Signaling Technologies Cat. #3126L) in 5% BSA, 0.05% Tween® 20 in 1×PBS was added and the blots were incubated overnight at room temperature. The following day the blots were washed three times with 1×PBS, 0.1% Tween® 20. A 1:3000 dilution of HRP conjugated goat anti-rabbit antibody (Jackson ImmunoResearch Laboratories Cat. #111-035-003) in blocking buffer, was added and incubated for 1 hr at room temperature with gentle rocking. The blot was wash 3 times in PBS, 0.1% Tween® 20 and visualized by chemiluminescence with SuperSignal West Pico Chemiluminescent Substrate (Pierce #34078).

Example 25

GTL16 Tumor Xenograft Model

Materials and Methods

Female athymic nude mice (nu/nu from Harlan) were 6-8 weeks old with a body weight range of 18-22 g at the beginning of the study. The animals had free access to food and water throughout the study. The mice were housed on irradiated Alpha-Dri® Bed-O-Cobs® Laboratory Animal Bedding in static micro isolator caging on a 12-hour light cycle at 70-74° F. and 40-60% humidity. All procedures involving animals were conducted in compliance with the NIH *Guide for the Care and Use of Laboratory Animals* and all protocols were approved by an Internal Animal Care and Use Committee (IACUC).

Tumor Implantation

Xenografts were initiated from GTL-16 tumor cells cultured and maintained by an internal Cell Biology Department. Each test mouse received a subcutaneous injection of $4\times10^6$ cells suspended in 100 µL of serum free RPMI media. Tumors were randomized into treatment groups on Day 5 when the average tumor size reached approximately 150 mm³. Each dose groups contained n=5 mice. Tumor volume was calculated using the formula:

$$\text{Tumor Volume} = \frac{w^2 \times l}{2}$$

where w=width and l=length in mm of the tumor. Tumor weight may be estimated with the assumption that 1 mg is equivalent to 1 mm³ of tumor volume.

Tumor Growth Inhibition (TGI) Analysis

TGI was calculated from the difference between the mean tumor volumes of vehicle-treated and drug-treated mice, expressed as a percentage.

% TGI=Mean Tumor Volume$_{control}$−Mean Tumor Volume$_{drug-treated}$×100 Median Tumor Volume$_{control}$ The MTV is defined as the mean tumor volume (MTV) for the number of animals, n, remaining in the study on that day.

Results

Figure 2:
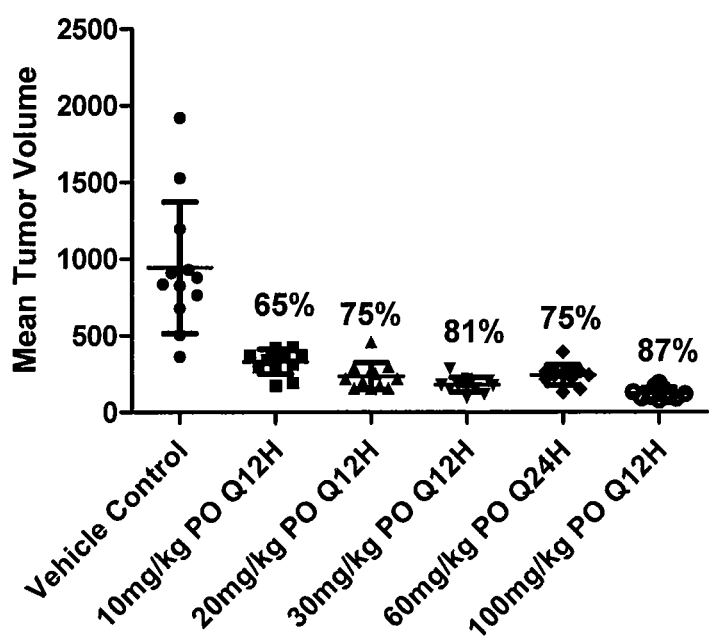
FIG. 2 illustrates the tumor growth inhibition (TGI) after administration of compound 4 compared to the mean tumor volumes of vehicle treated group.
Figure 3:
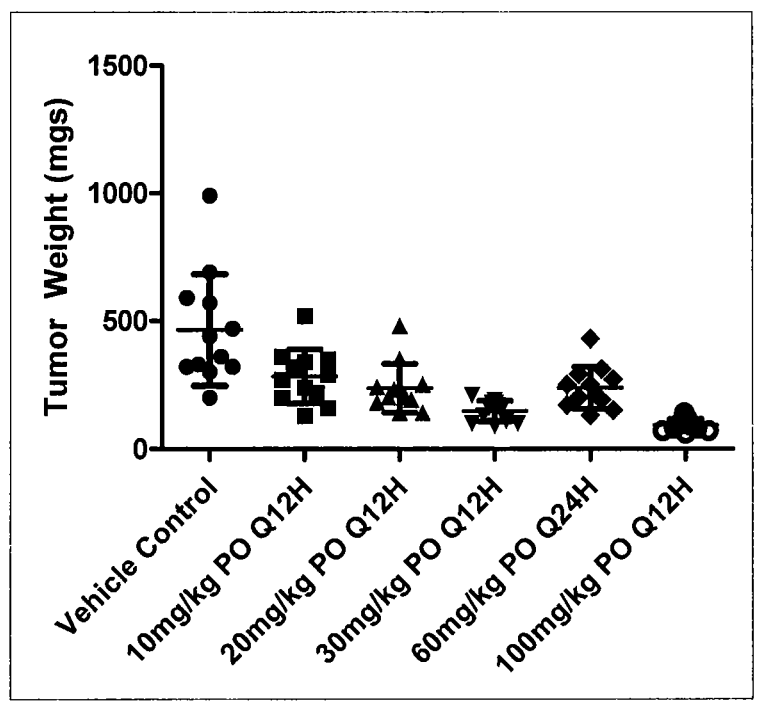
FIG. 3 illustrates the decrease in tumor weight after administration of compound 4 compared to the mean tumor weight of the vehicle treated group.

Results of the GTL16 tumor growth study for compound 4 are shown in FIG. 1, FIG. 2, and FIG. 3.

In FIG. 1, compound 4 was administered orally (PO) at 10, 20, 30, and 100 mg/kg twice a day (Q12H) and 60 mg/kg once a day (Q24H) for 14 consecutive days. Treatment began on Day 4. On the last day of treatment the 10, 20, 30, 100 mg/kg PO Q12H and 60 mg/kg PO Q24H doses decreased mean tumor volume by 65% (p<0.0001), 75% (p<0.0001), 81% (p<0.0001), 87% (p<0.0001) and 75% (p<0.0001) respectively compared to the mean tumor volume of the vehicle-treated group. Compound 4 was shown to have inhibited MET autophosphorylation by greater than 90% in tumors from mice treated at these doses. On the last day of treatment MET autophosphorylation in excised tumors was evaluated by Western Blot at various timepoints (1, 2, 6, 12 hours post terminal dose) and compared to vehicle controls. From the tumors of mice treated at 10, 30 and 100 mg/kg PO Q12H phospho-MET levels were less than 10% of vehicle controls at all timepoints.

FIG. 2 shows the effects of oral and intraperitoneal administration of compound 4 on tumor growth inhibition (TGI) in GTL16 tumors in nude mice. All treatments began on Day 4 after tumor cell implant. At the end of the 14-day dosing regime, final TGI % was calculated from the difference between the mean tumor volumes of vehicle-treated and drug-treated mice, expressed as a percentage of the mean tumor volume of the vehicle-treated control group.

FIG. 3 shows the effects of oral and intraperitoneal administration of compound 4 on the growth of GTL16 tumors. Female athymic nude mice were inoculated subcutaneously on the right flank with 4×10$^6$ GTL16 cells in a delivery volume of 100 μL. Tumors were allowed to grow for four days. Mice were dosed orally at 10, 20, 30, and 100 mg/kg twice per day and orally at 60 mg/kg once per day for 14 consecutive days. On the day of study termination, tumors were immediately excised intact and weighed, with final tumor wet weight (milligrams) serving as a primary efficacy endpoint.

Figure 4:
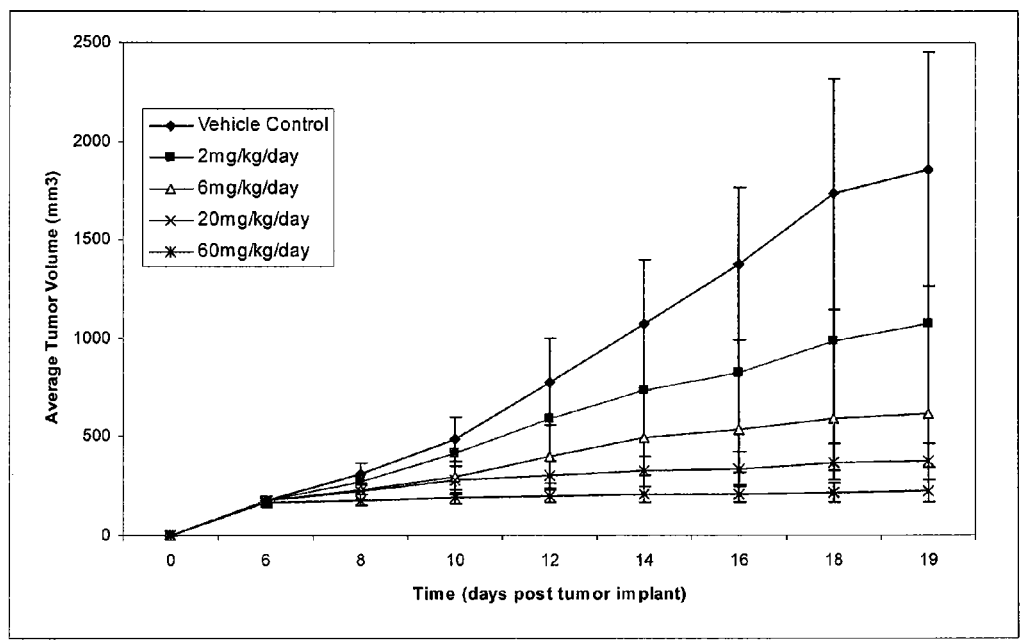
FIG. 4 illustrates the decrease in mean tumor volume after administration of compound 41 compared to the mean tumor volume of the vehicle treated group
Figure 5:
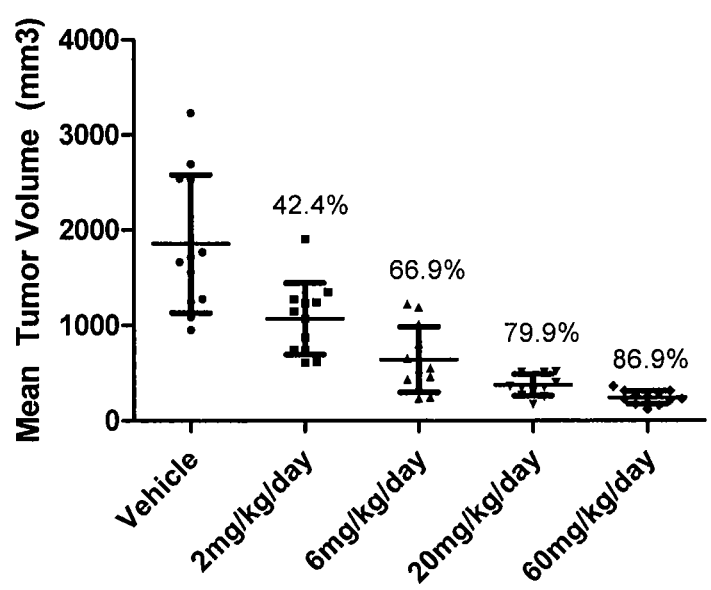
FIG. 5 illustrates the tumor growth inhibition (TGI) after administration of compound 41 compared to the mean tumor volumes of vehicle treated group.
Figure 6:
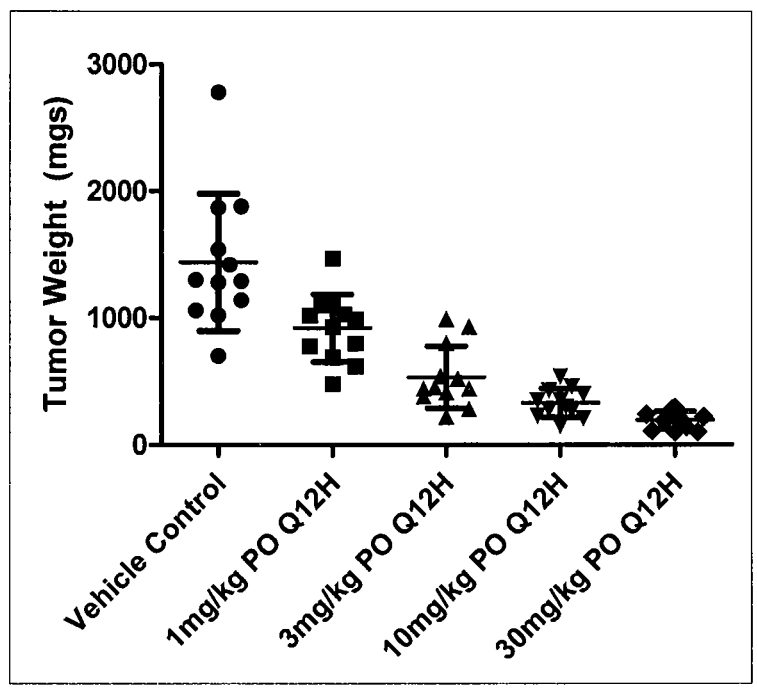
FIG. 6 illustrates the decrease in tumor weight after administration of compound 41 compared to the mean tumor weight of the vehicle treated group.

Results of the GTL16 tumor growth study for compound 41 are shown in FIG. 4, FIG. 5, and FIG. 6.

In FIG. 4, compound 41 was administered orally (PO) at 1, 3, 10, and 30 mg/kg twice a day (Q12H) for 13 consecutive days. Treatment began on Day 6. On the last day of treatment the 1, 3, 10, 30 mg/kg PO Q12H and doses decreased mean tumor volume by 42% (p=0.0030), 67% (p<0.0001), 80% (p<0.0001), and 87% (p<0.0001) respectively compared to the mean tumor volume of the vehicle-treated group.

FIG. 5 shows the effects of oral and intraperitoneal administration of Compound 41 on tumor growth inhibition (TGI) in GTL16 tumors in nude mice. All treatments began on Day 6 after tumor cell implant. At the end of the 13-day dosing regime, final TGI % was calculated from the difference between the mean tumor volumes of vehicle-treated and drug-treated mice, expressed as a percentage of the mean tumor volume of the vehicle-treated control group.

FIG. 6 shows the effects of oral administration of Compound 41 on the growth of GTL16 tumors. Female athymic nude mice were inoculated subcutaneously on the right flank with 4×10$^6$ GTL16 cells in a delivery volume of 100 μL. Tumors were allowed to grow for six days. Mice were dosed orally at 1, 3, 10, and 30 mg/kg twice per day for 13 consecutive days. On the day of study termination, tumors were immediately excised intact and weighed, with final tumor wet weight (milligrams) serving as a primary efficacy endpoint.

ABBREVIATIONS

IP Intraperitoneal
PO Per Oral
BID Twice per day
Q12H Every 12 hours
Q24H Every 24 hours
RPMI Roswell Park Memorial Institute
NIH National Institute of Health
IACUC Animal Care and Use Committee
TGI Tumor Growth Inhibition
MTV Mean Tumor Volume It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound selected from the group consisting of:

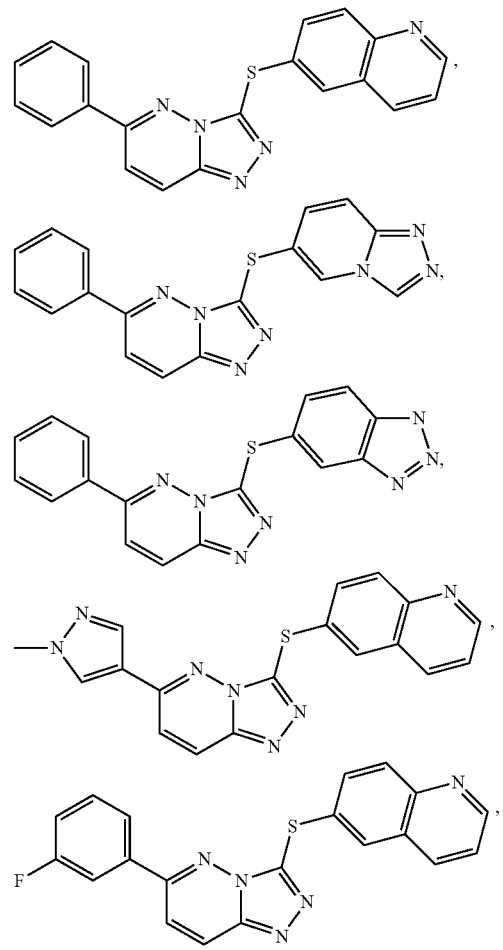

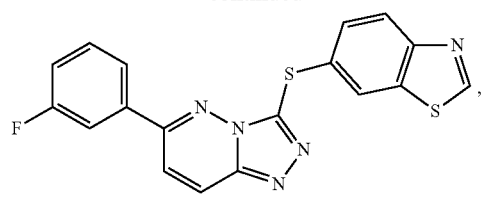
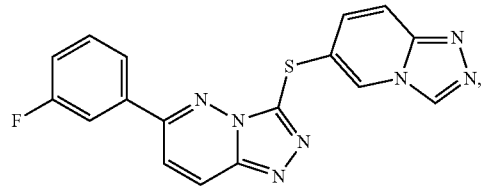
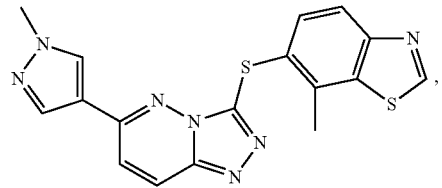
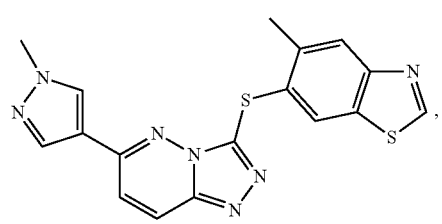
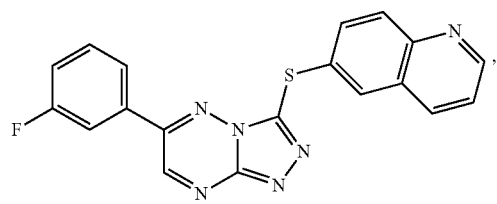
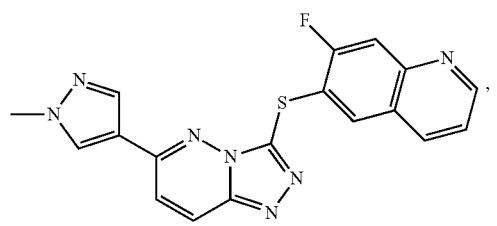
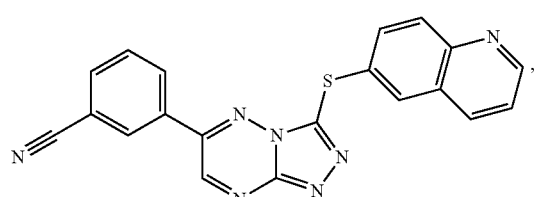
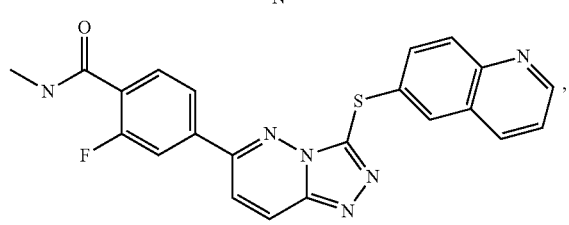
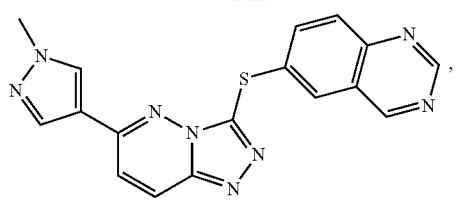
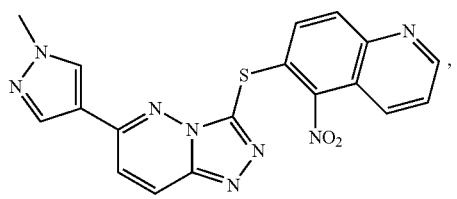
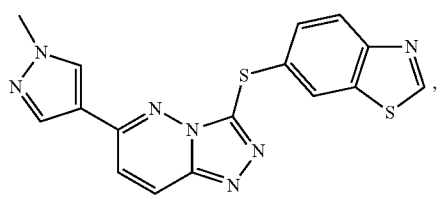
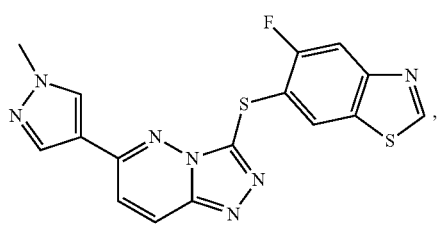
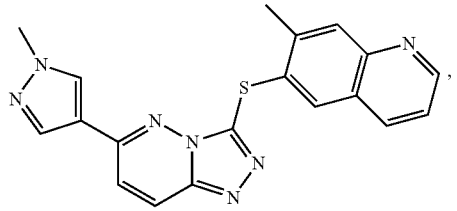
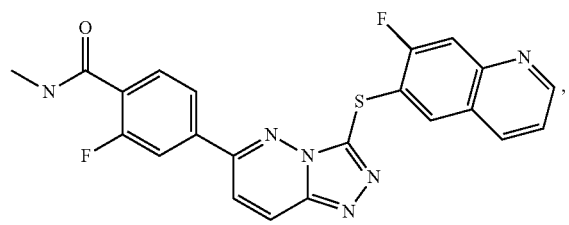
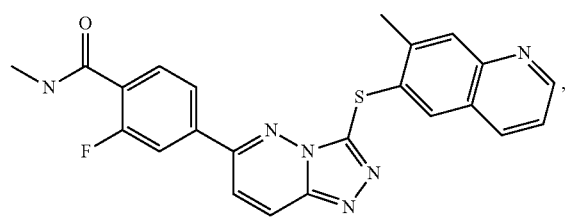
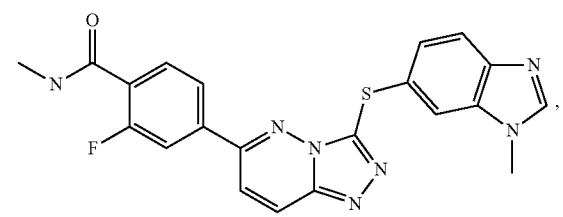

157
-continued
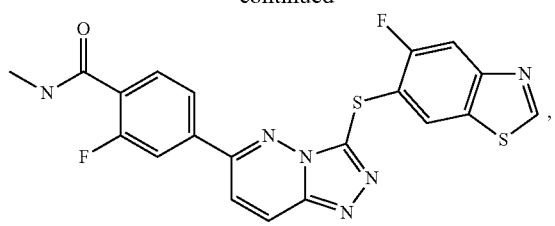
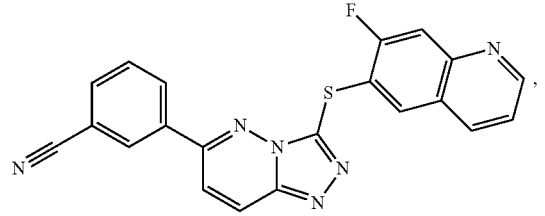
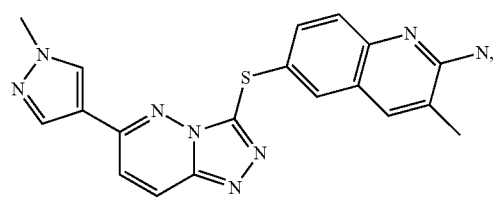
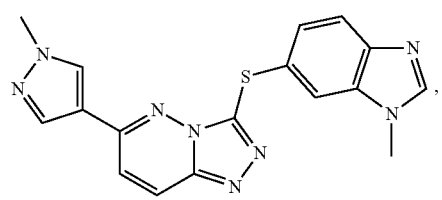
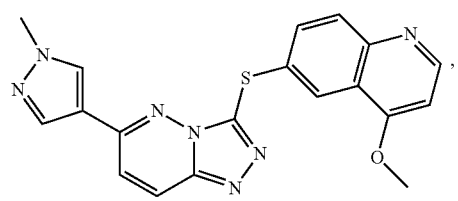
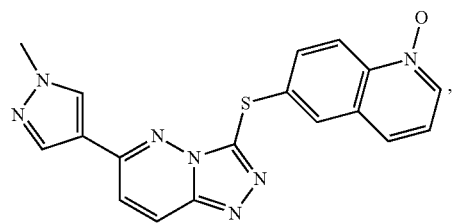
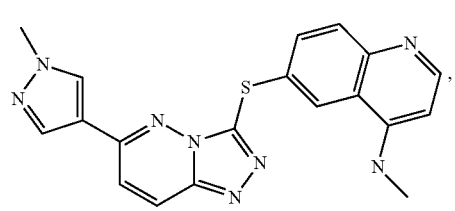
158
-continued
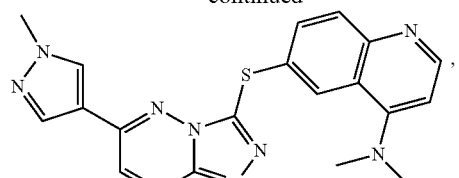
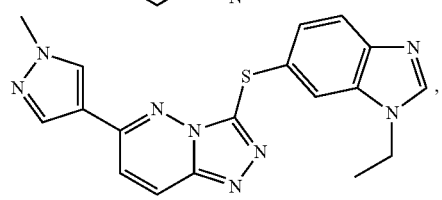
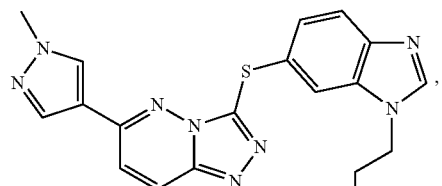
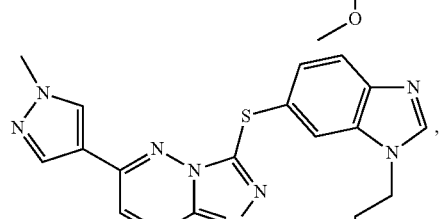
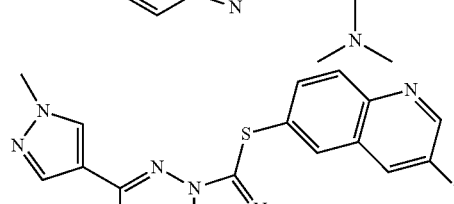
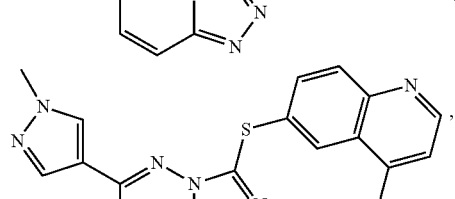
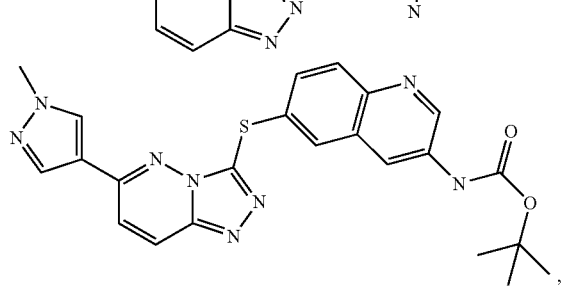
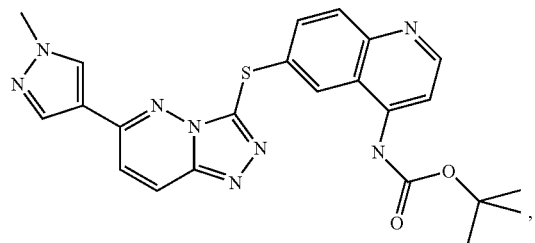

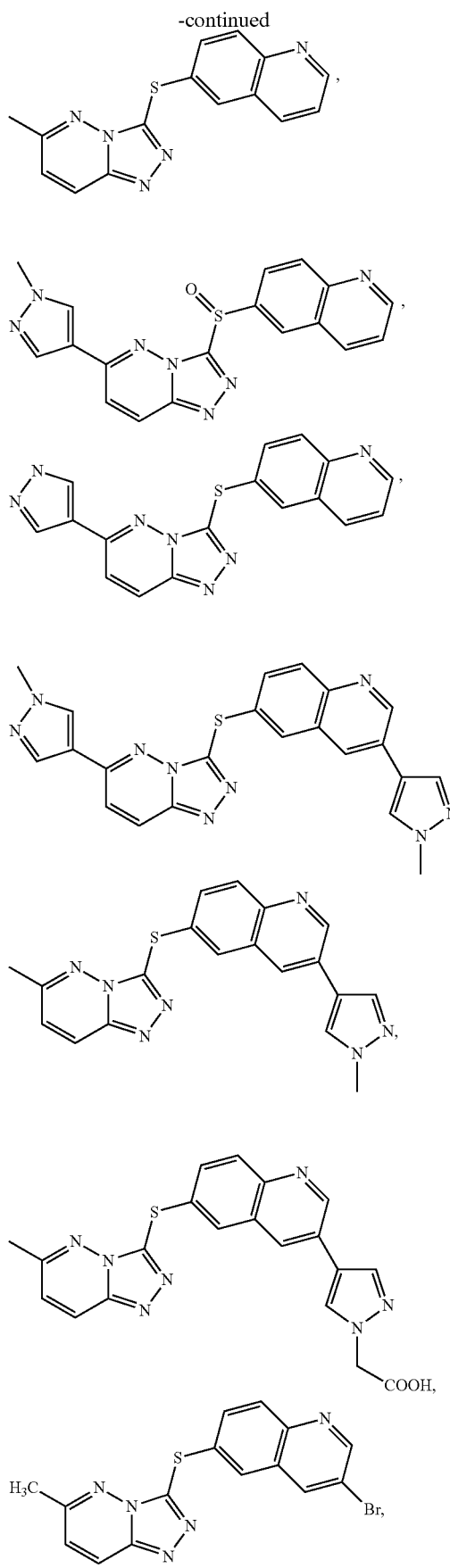
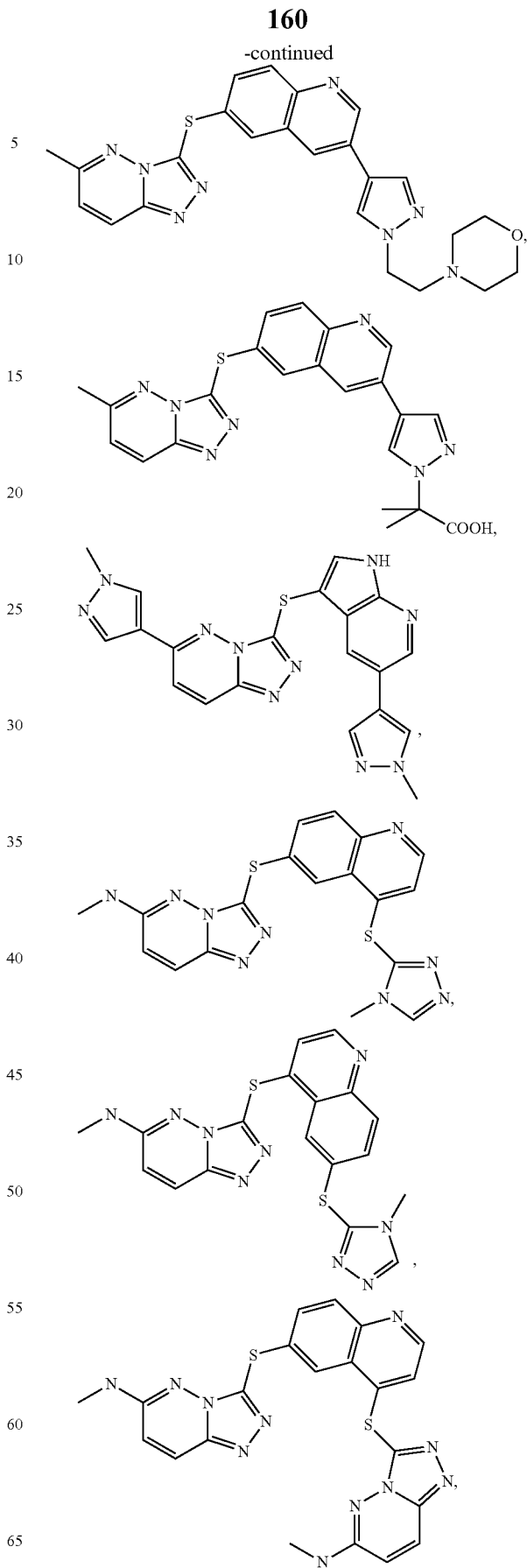

161
-continued
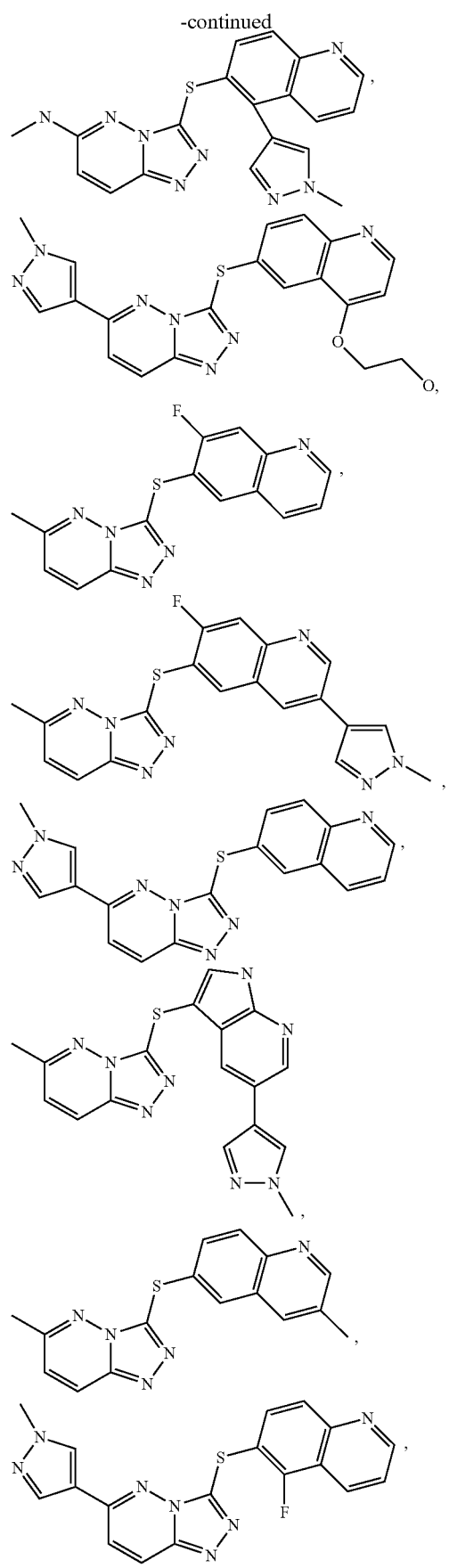
162
-continued
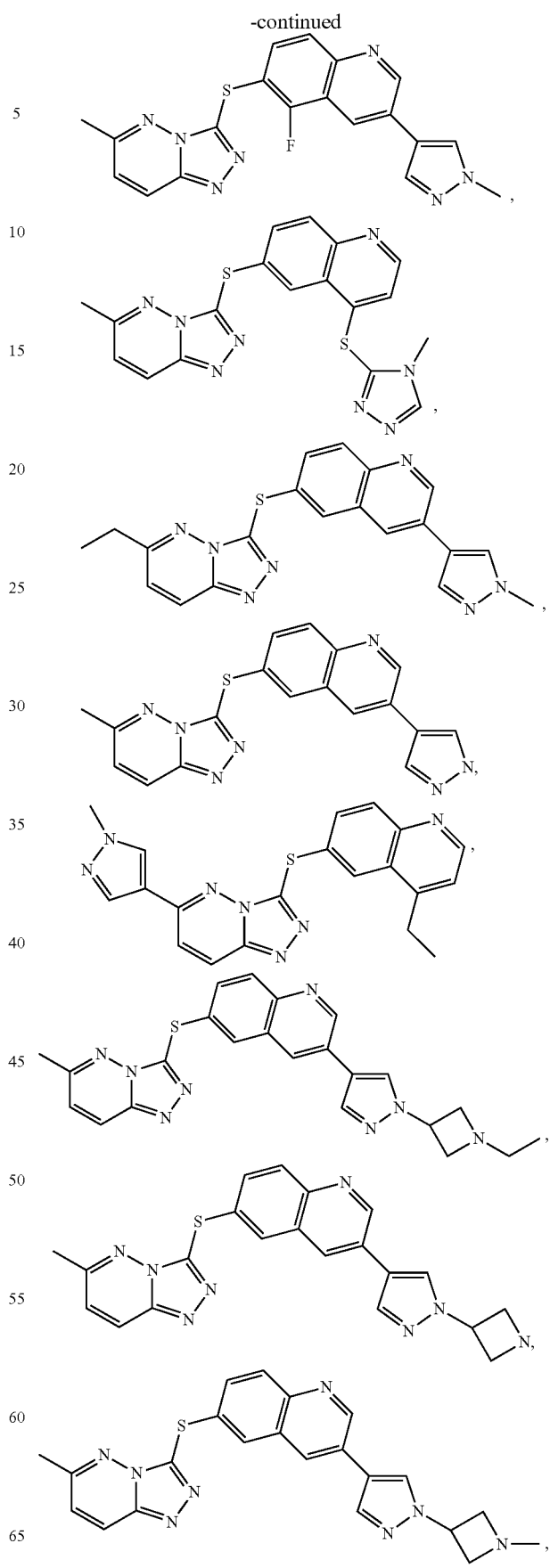

-continued

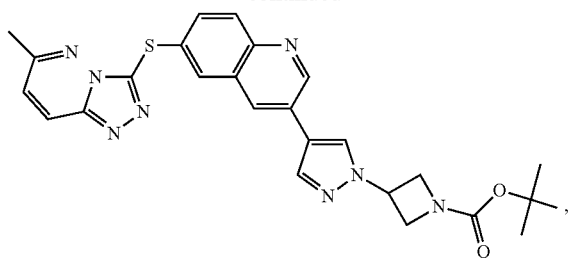

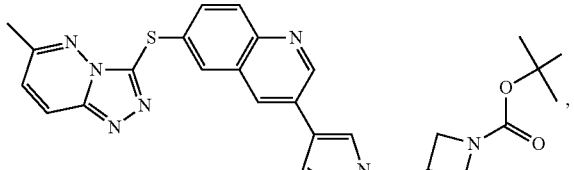

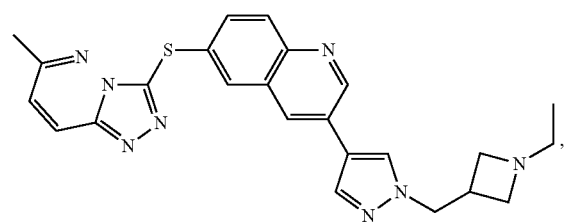

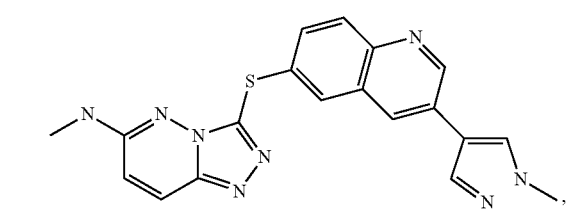

-continued

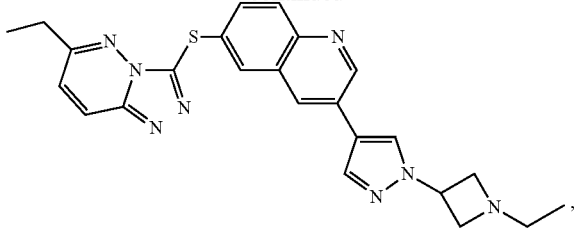

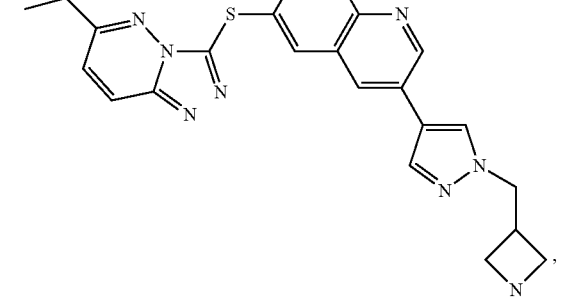

or a pharmaceutically acceptable salt thereof.

2. A pharmaceutical composition comprising a compound according to claim 1 and a pharmaceutically acceptable excipient or solvent.

3. The compound of claim 1 where it is

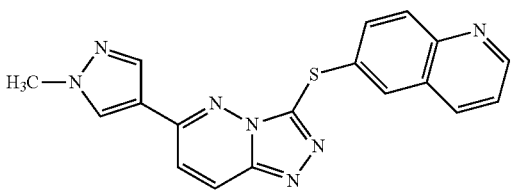 [SMILES: Cn1cc(-c2ccc3nnc(Sc4ccc5ncccc5c4)n3n2)cn1]

or a pharmaceutically acceptable salt thereof.

4. A pharmaceutical composition comprising a compound according to claim 3 and a pharmaceutically acceptable excipient.

5. The compound of claim 1 where it is

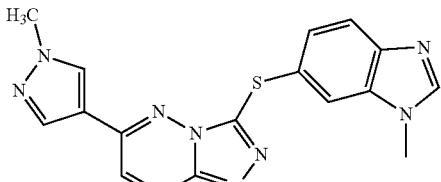

or a pharmaceutically acceptable salt thereof.

6. A pharmaceutical composition comprising a compound according to claim 5 and a pharmaceutically acceptable excipient.

7. The compound of claim 1 where it is

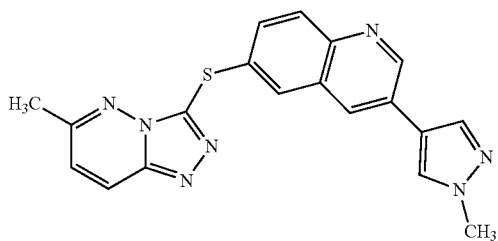 [SMILES: Cc1ccc2nnc(Sc3ccc4ncc(-c5cnn(C)c5)cc4c3)n2n1]

or a pharmaceutically acceptable salt thereof.

8. A pharmaceutical composition comprising a compound according to claim 7 and a pharmaceutically acceptable excipient.

9. The compound of claim 1 where it is

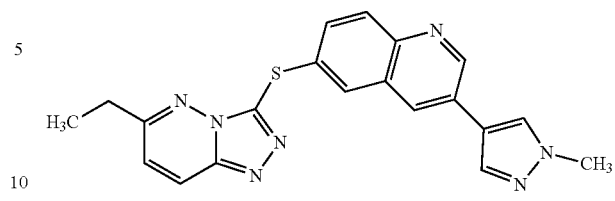

or a pharmaceutically acceptable salt thereof.

10. A pharmaceutical composition comprising a compound according to claim 9 and a pharmaceutically acceptable excipient.

* * * * *